United States Patent
Claremon et al.

(10) Patent No.: US 11,008,340 B2
(45) Date of Patent: May 18, 2021

(54) MODULATORS OF ROR-GAMMA

(71) Applicant: Vitae Pharmaceuticals, LLC, Madison, NJ (US)

(72) Inventors: David A. Claremon, Maple Glen, PA (US); Lawrence Wayne Dillard, Yardley, PA (US); Yi Fan, Doylestown, PA (US); Lanqi Jia, Horsham, PA (US); Suresh B. Singh, Kendall Park, NJ (US); Colin M. Tice, Maple Glen, PA (US); Zhenrong Xu, Chalfont, PA (US); Jing Yuan, Lansdale, PA (US); Linghang Zhuang, Chalfont, PA (US)

(73) Assignee: Vitae Pharmaceuticals, LLC, Madison, NJ (US)

( * ) Notice: Subject to any disclaimer, the term of this patent is extended or adjusted under 35 U.S.C. 154(b) by 65 days.

(21) Appl. No.: 15/776,836

(22) PCT Filed: Nov. 17, 2016

(86) PCT No.: PCT/US2016/062422
§ 371 (c)(1),
(2) Date: May 17, 2018

(87) PCT Pub. No.: WO2017/087608
PCT Pub. Date: May 26, 2017

(65) Prior Publication Data
US 2019/0322687 A1 Oct. 24, 2019

Related U.S. Application Data

(60) Provisional application No. 62/320,805, filed on Apr. 11, 2016, provisional application No. 62/257,964, filed on Nov. 20, 2015.

(51) Int. Cl.

| | | |
|---|---|---|
| *C07D 513/04* | (2006.01) | |
| *C07D 217/04* | (2006.01) | |
| *C07D 217/24* | (2006.01) | |
| *C07D 231/56* | (2006.01) | |
| *C07D 239/88* | (2006.01) | |
| *C07D 401/06* | (2006.01) | |
| *C07D 401/12* | (2006.01) | |
| *C07D 401/14* | (2006.01) | |
| *C07D 405/12* | (2006.01) | |
| *C07D 471/04* | (2006.01) | |

(52) U.S. Cl.
CPC ......... *C07D 513/04* (2013.01); *C07D 217/04* (2013.01); *C07D 217/24* (2013.01); *C07D 231/56* (2013.01); *C07D 239/88* (2013.01); *C07D 401/06* (2013.01); *C07D 401/12* (2013.01); *C07D 401/14* (2013.01); *C07D 405/12* (2013.01); *C07D 471/04* (2013.01)

(58) Field of Classification Search
CPC .. C07D 513/04; C07D 217/04; C07D 217/24; C07D 231/56; C07D 239/88; C07D 401/06; C07D 401/12; C07D 405/12; C07D 471/04
See application file for complete search history.

(56) References Cited

U.S. PATENT DOCUMENTS

| | | |
|---|---|---|
| 5,238,950 A | 8/1993 | Clader et al. |
| 5,272,158 A | 12/1993 | Hartman et al. |
| 5,326,760 A | 7/1994 | McElroy et al. |
| 5,364,869 A | 11/1994 | De |
| 5,389,631 A | 2/1995 | Claremon et al. |
| 5,571,774 A | 11/1996 | Hamprecht et al. |
| 5,719,144 A | 2/1998 | Hartman et al. |
| 5,770,590 A | 6/1998 | Natsugari et al. |
| 5,786,352 A | 7/1998 | Natsugari et al. |
| 5,959,116 A | 9/1999 | Hamprecht et al. |
| 6,103,659 A | 8/2000 | Pasenok et al. |
| 6,166,219 A | 12/2000 | Yamasaki et al. |
| 6,177,443 B1 | 1/2001 | Madsen et al. |

(Continued)

FOREIGN PATENT DOCUMENTS

| | | |
|---|---|---|
| CA | 2031684 A1 | 6/1991 |
| CA | 2134192 A1 | 5/1995 |

(Continued)

OTHER PUBLICATIONS

STN Registry database entry for CAS RN 1030136-78-7, entry date of Jun. 24, 20082, Accessed Feb. 26, 2020.*
Ito et al. in Cancer Science 94(1), 3-8 (2003).*
STN Registry Entry for CAS RN 434289-52-8, Entry date Jun. 27, 2002, Accessed via STN Next Sep. 14, 2020.*
Babu et al., Emerging therapeutic strategies in COPD. Drug Discov Today. Mar. 2015;20(3):371-9.

(Continued)

*Primary Examiner* — Alicia L Otton
(74) *Attorney, Agent, or Firm* — McCarter & English, LLP; Steven G. Davis; Michael J. DeGrazia

(57) ABSTRACT

Provided are novel compounds of Formula I: pharmaceutically acceptable salts thereof, and pharmaceutical compositions thereof, which are useful in the treatment of diseases and disorders mediated by RORγ. Also provided are pharmaceutical compositions comprising the novel compounds of Formula I and methods for their use in treating one or more inflammatory, metabolic, autoimmune and other diseases or disorders.

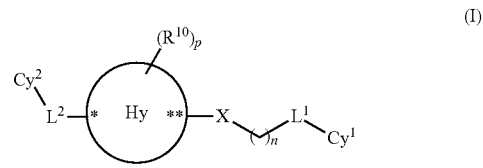

(I)

14 Claims, No Drawings

Specification includes a Sequence Listing.

(56) References Cited

U.S. PATENT DOCUMENTS

| | | |
|---|---|---|
| 6,348,032 B1 | 2/2002 | Sperl et al. |
| 6,358,978 B1 | 3/2002 | Ritzeler et al. |
| 6,417,207 B1 | 7/2002 | Garvey et al. |
| 6,444,617 B1 | 9/2002 | Takaishi et al. |
| 6,489,315 B1 | 12/2002 | Natsugari et al. |
| 6,512,117 B1 | 1/2003 | Harclerode et al. |
| 6,627,646 B2 | 9/2003 | Bakale et al. |
| 6,770,666 B2 | 8/2004 | Hashimoto et al. |
| 7,112,600 B1 | 9/2006 | Hashimoto et al. |
| 7,115,752 B2 | 10/2006 | Lesieur et al. |
| 7,183,318 B2 | 2/2007 | Lesieur et al. |
| 7,244,730 B2 | 7/2007 | Suzuki et al. |
| 7,732,616 B2 | 6/2010 | Marlow et al. |
| 7,750,021 B2 | 7/2010 | Mi et al. |
| 8,389,739 B1 | 3/2013 | Thacher et al. |
| 8,399,477 B2 | 3/2013 | Alisi et al. |
| 8,415,351 B2 | 4/2013 | Wagner et al. |
| 9,266,886 B2 | 2/2016 | Lotesta et al. |
| 9,481,674 B1 | 11/2016 | Claremon et al. |
| 9,624,217 B2 | 4/2017 | Claremon et al. |
| 9,663,515 B2 | 5/2017 | Claremon et al. |
| 9,796,710 B2 | 10/2017 | Claremon et al. |
| 9,868,748 B2 | 1/2018 | Claremon et al. |
| 10,047,085 B2 | 8/2018 | Claremon et al. |
| 10,087,184 B2 | 10/2018 | Claremon et al. |
| 10,399,976 B2 | 9/2019 | Claremon et al. |
| 10,807,980 B2 | 10/2020 | Claremon et al. |
| 2002/0132817 A1 | 9/2002 | Natsugari et al. |
| 2003/0050320 A1 | 3/2003 | Hashimoto et al. |
| 2004/0002424 A1 | 1/2004 | Minn et al. |
| 2004/0038973 A1 | 2/2004 | Nahra et al. |
| 2005/0004204 A1 | 1/2005 | Suzuki et al. |
| 2005/0020593 A1 | 1/2005 | Mailliet et al. |
| 2005/0234065 A1 | 10/2005 | Hulin et al. |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |
| 2016/0122345 A1 | 5/2016 | Claremon et al. |
| 2017/0081327 A1 | 3/2017 | Claremon et al. |
| 2017/0260180 A1 | 9/2017 | Claremon et al. |
| 2018/0222860 A1 | 8/2018 | Claremon et al. |
| 2018/0222902 A1 | 8/2018 | Claremon et al. |
| 2019/0352286 A1 | 11/2019 | Claremon et al. |
| 2020/0062707 A1 | 2/2020 | Claremon et al. |
| 2020/0079767 A1 | 3/2020 | Claremon et al. |
| 2020/0148677 A1 | 5/2020 | Duguid et al. |
| 2020/0165245 A1 | 5/2020 | Deng et al. |
| 2020/0339566 A1 | 10/2020 | Claremon et al. |

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| CN | 104024239 A | 9/2014 |
| DE | 4343922 A1 | 6/1995 |
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| EP | 2327704 A1 | 6/2011 |
| FR | 2725946 A1 | 4/1996 |
| FR | 2926554 A1 | 7/2009 |
| GB | 2276384 A | 9/1994 |
| JP | H06-236056 A | 8/1994 |
| JP | H11-43489 A | 2/1999 |
| JP | 2000-007661 A | 1/2000 |
| JP | 2003-171380 A | 6/2003 |
| JP | 2003-531894 A | 10/2003 |
| JP | 2004-203791 A | 7/2004 |
| JP | 2004-535404 A | 11/2004 |
| JP | 2015-124178 A | 7/2015 |
| WO | 1990/09787 A1 | 9/1990 |
| WO | 1994/00119 A1 | 1/1994 |
| WO | 1994/24712 A1 | 10/1994 |
| WO | 1995/11680 A1 | 5/1995 |
| WO | 1995/17397 A1 | 6/1995 |
| WO | 1996/26187 A1 | 8/1996 |
| WO | 1997/32832 A1 | 9/1997 |
| WO | 1998/40385 A1 | 9/1998 |
| WO | 1998/42666 A1 | 10/1998 |
| WO | 1999/47132 A2 | 9/1999 |
| WO | 1999/58495 A1 | 11/1999 |
| WO | 1999/58496 A1 | 11/1999 |
| WO | 2000/032192 A1 | 6/2000 |
| WO | 2000/067754 A1 | 11/2000 |
| WO | 2001/005790 A1 | 1/2001 |
| WO | 2001/09076 A2 | 2/2001 |
| WO | 2001/047883 A1 | 7/2001 |
| WO | 2001/051128 A1 | 7/2001 |
| WO | 2001/83438 A2 | 11/2001 |
| WO | 2001/083445 A1 | 11/2001 |
| WO | 2001/85722 A1 | 11/2001 |
| WO | 2002/024650 A2 | 3/2002 |
| WO | 2002/38107 A2 | 5/2002 |
| WO | 2002/081443 A1 | 10/2002 |
| WO | 2002/081447 A1 | 10/2002 |
| WO | 2002/081463 A1 | 10/2002 |
| WO | 2002/085855 A1 | 10/2002 |
| WO | 2002/094833 A1 | 11/2002 |
| WO | 2003/008421 A1 | 1/2003 |
| WO | 2003/029252 A1 | 4/2003 |
| WO | 2003/029254 A1 | 4/2003 |
| WO | 2003/043991 A1 | 5/2003 |
| WO | 2003/062241 A1 | 7/2003 |
| WO | 2003/066055 A1 | 8/2003 |
| WO | 2003/070710 A1 | 8/2003 |
| WO | 2003/076440 A1 | 9/2003 |
| WO | 2003/104216 A1 | 12/2003 |
| WO | 2004/014365 A1 | 2/2004 |
| WO | 2004/026871 A1 | 4/2004 |
| WO | 2004/042029 A2 | 5/2004 |
| WO | 2004/065351 A1 | 8/2004 |
| WO | 2004/089897 A1 | 10/2004 |
| WO | 2004/103309 A2 | 12/2004 |
| WO | 2004/108133 A2 | 12/2004 |
| WO | 2004/111010 A1 | 12/2004 |
| WO | 2004/113330 A1 | 12/2004 |
| WO | 2005/005392 A1 | 1/2005 |
| WO | 2005/011601 A2 | 2/2005 |
| WO | 2005/023806 A2 | 3/2005 |
| WO | 2005/025504 A2 | 3/2005 |
| WO | 2005/028480 A2 | 3/2005 |
| WO | 2005/039564 A1 | 5/2005 |

(56) References Cited

FOREIGN PATENT DOCUMENTS

| | | |
|---|---|---|
| WO | 2005/051301 A2 | 6/2005 |
| WO | 2005/060958 A1 | 7/2005 |
| WO | 2005/063296 A2 | 7/2005 |
| WO | 2005/097129 A2 | 10/2005 |
| WO | 2005/100334 A1 | 10/2005 |
| WO | 2005/117890 A2 | 12/2005 |
| WO | 2006/032631 A1 | 3/2006 |
| WO | 2006/062981 A2 | 6/2006 |
| WO | 2006/065842 A2 | 6/2006 |
| WO | 2006/074428 A2 | 7/2006 |
| WO | 2006/082001 A1 | 8/2006 |
| WO | 2006/092731 A1 | 9/2006 |
| WO | 2006/109085 A1 | 10/2006 |
| WO | 2007/007054 A1 | 1/2007 |
| WO | 2007/022280 A1 | 2/2007 |
| WO | 2007/036733 A1 | 4/2007 |
| WO | 2007/036734 A1 | 4/2007 |
| WO | 2007/050124 A1 | 5/2007 |
| WO | 2007/084451 A1 | 7/2007 |
| WO | 2007/084455 A1 | 7/2007 |
| WO | 2007/084815 A2 | 7/2007 |
| WO | 2007/087231 A2 | 8/2007 |
| WO | 2007/097931 A2 | 8/2007 |
| WO | 2007/101224 A2 | 9/2007 |
| WO | 2007/107545 A1 | 9/2007 |
| WO | 2007/109596 A2 | 9/2007 |
| WO | 2007/131982 A2 | 11/2007 |
| WO | 2008/006479 A1 | 1/2008 |
| WO | 2008/010964 A1 | 1/2008 |
| WO | 2008/013963 A2 | 1/2008 |
| WO | 2008/044027 A2 | 4/2008 |
| WO | 2008/044029 A1 | 4/2008 |
| WO | 2008/044041 A1 | 4/2008 |
| WO | 2008/044045 A1 | 4/2008 |
| WO | 2008/044054 A2 | 4/2008 |
| WO | 2008/048991 A1 | 4/2008 |
| WO | 2008/073865 A2 | 6/2008 |
| WO | 2008/083070 A1 | 7/2008 |
| WO | 2008/086161 A1 | 7/2008 |
| WO | 2008/132155 A2 | 11/2008 |
| WO | 2008/135524 A2 | 11/2008 |
| WO | 2008/135526 A1 | 11/2008 |
| WO | 2008/149163 A2 | 12/2008 |
| WO | 2009/004496 A2 | 1/2009 |
| WO | 2009/013299 A2 | 1/2009 |
| WO | 2009/026248 A2 | 2/2009 |
| WO | 2009/049154 A1 | 4/2009 |
| WO | 2009/050228 A2 | 4/2009 |
| WO | 2009/052319 A1 | 4/2009 |
| WO | 2009/052320 A1 | 4/2009 |
| WO | 2009/068463 A2 | 6/2009 |
| WO | 2009/073788 A1 | 6/2009 |
| WO | 2009/083526 A1 | 7/2009 |
| WO | 2009/097972 A1 | 8/2009 |
| WO | 2009/112445 A1 | 9/2009 |
| WO | 2009/112678 A2 | 9/2009 |
| WO | 2009/112826 A1 | 9/2009 |
| WO | 2009/112839 A1 | 9/2009 |
| WO | 2009/124755 A1 | 10/2009 |
| WO | 2009/131926 A1 | 10/2009 |
| WO | 2009/144450 A1 | 12/2009 |
| WO | 2010/003022 A1 | 1/2010 |
| WO | 2010/021878 A1 | 2/2010 |
| WO | 2010/033350 A1 | 3/2010 |
| WO | 2010/056194 A1 | 5/2010 |
| WO | 2010/056195 A1 | 5/2010 |
| WO | 2010/077680 A2 | 7/2010 |
| WO | 2010/086311 A1 | 8/2010 |
| WO | 2011/078143 A1 | 6/2011 |
| WO | 2011/090473 A1 | 7/2011 |
| WO | 2011/094545 A2 | 8/2011 |
| WO | 2011/107248 A1 | 9/2011 |
| WO | 2011/140936 A1 | 11/2011 |
| WO | 2011/146358 A1 | 11/2011 |
| WO | 2011/159297 A1 | 12/2011 |
| WO | 2012/019015 A2 | 2/2012 |
| WO | 2012/027965 A1 | 3/2012 |
| WO | 2012/028100 A1 | 3/2012 |
| WO | 2012/031197 A1 | 3/2012 |
| WO | 2012/043505 A1 | 4/2012 |
| WO | 2012/062462 A1 | 5/2012 |
| WO | 2012/064744 A2 | 5/2012 |
| WO | 2012/100732 A1 | 8/2012 |
| WO | 2012/100734 A1 | 8/2012 |
| WO | 2012/106995 A1 | 8/2012 |
| WO | 2012/125521 A1 | 9/2012 |
| WO | 2012/136296 A1 | 10/2012 |
| WO | 2012/139775 A1 | 10/2012 |
| WO | 2013/000994 A1 | 1/2013 |
| WO | 2013/019621 A1 | 2/2013 |
| WO | 2013/019626 A1 | 2/2013 |
| WO | 2013/019635 A1 | 2/2013 |
| WO | 2013/019653 A1 | 2/2013 |
| WO | 2013/019682 A1 | 2/2013 |
| WO | 2013/029338 A1 | 3/2013 |
| WO | 2013/045431 A1 | 4/2013 |
| WO | 2013/064231 A1 | 5/2013 |
| WO | 2013/067036 A1 | 5/2013 |
| WO | 2013/078233 A1 | 5/2013 |
| WO | 2013/078240 A1 | 5/2013 |
| WO | 2013/079223 A1 | 6/2013 |
| WO | 2013/083741 A1 | 6/2013 |
| WO | 2013/087739 A1 | 6/2013 |
| WO | 2013/092460 A1 | 6/2013 |
| WO | 2013/092939 A1 | 6/2013 |
| WO | 2013/092941 A1 | 6/2013 |
| WO | 2013/096496 A2 | 6/2013 |
| WO | 2013/100027 A1 | 7/2013 |
| WO | 2013/159095 A1 | 10/2013 |
| WO | 2013/160418 A1 | 10/2013 |
| WO | 2013/160419 A1 | 10/2013 |
| WO | 2013/166013 A1 | 11/2013 |
| WO | 2013/169588 A1 | 11/2013 |
| WO | 2013/169704 A2 | 11/2013 |
| WO | 2013/169864 A2 | 11/2013 |
| WO | 2013/171729 A2 | 11/2013 |
| WO | 2013/178362 A1 | 12/2013 |
| WO | 2014/008214 A1 | 1/2014 |
| WO | 2014/009447 A1 | 1/2014 |
| WO | 2014/026327 A1 | 2/2014 |
| WO | 2014/026328 A1 | 2/2014 |
| WO | 2014/026329 A1 | 2/2014 |
| WO | 2014/026330 A1 | 2/2014 |
| WO | 2014/028589 A2 | 2/2014 |
| WO | 2014/028591 A2 | 2/2014 |
| WO | 2014/028597 A2 | 2/2014 |
| WO | 2014/028600 A2 | 2/2014 |
| WO | 2014/028669 A1 | 2/2014 |
| WO | 2014/044738 A1 | 3/2014 |
| WO | 2014/062938 A1 | 4/2014 |
| WO | 2014/086894 A1 | 6/2014 |
| WO | 2014/110442 A1 | 7/2014 |
| WO | 2014/179564 A1 | 11/2014 |
| WO | 2015/017335 A1 | 2/2015 |
| WO | 2015/035032 A1 | 3/2015 |
| WO | 2015/038503 A1 | 3/2015 |
| WO | 2015/067575 A1 | 5/2015 |
| WO | 2015/083130 A1 | 6/2015 |
| WO | 2015/100420 A1 | 7/2015 |
| WO | 2015/101928 A1 | 7/2015 |
| WO | 2015/114157 A1 | 8/2015 |
| WO | 2015/116904 A1 | 8/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/159233 A1 | 10/2015 |
| WO | 2016/061160 A1 | 4/2016 |
| WO | 2016/064970 A1 | 4/2016 |
| WO | 2016/144351 A1 | 9/2016 |
| WO | 2017/024018 A1 | 2/2017 |

(56) References Cited

FOREIGN PATENT DOCUMENTS

| | | |
|---|---|---|
| WO | 2017/087608 A1 | 5/2017 |
| WO | 2017/132432 A1 | 8/2017 |

OTHER PUBLICATIONS

Bendele et al., Animal models of arthritis: relevance to human disease. Toxicol Pathol. Jan.-Feb. 1999;27(1):134-42.
Bendele, Animal models of rheumatoid arthritis. J Musculoskelet Neuronal Interact. Jun. 2001;1(4):377-85.
Campochiaro, The complexity of animal model generation for complex diseases. JAMA. Feb. 17, 2000;303(7):657-8.
Center for Disease Control, Classification of Diseases and Injuries. ICD-9-CM Tabular List of Diseases (FY03). 748 pages, accessed online Sep. 10, 2015.
Chaichian et al., Targeted Therapies in Systemic Lupus Erythematosus: A State-of-the-Art Review. J Clin Cell Immunol. 2013;S6:8 pages.
Chiba, Emerging Therapeutic Strategies in Alzheimer's Disease. InTech, retrieved online at: http://dx.doi.org/10.5772/55293. Chapter 9, pp. 181-225, (2013).
Cyr et al., Recent progress on nuclear receptor RORgamma modulators. Bioorganic & Medicinal Chemistry Letters. 2016;26:4387-4393.
Damia et al., Contemporary pre-clinical development of anticancer agents—What are the optimal preclinical models? European Journal of Cancer. 2009;45:2768-2781.
Edwards et al., Molecular genetics of AMD and current animal models. Angiogenesis. 2007;10(2):119-32.
Elborn, Cystic fibrosis. The Lancet. Retrieved online at: http://dx.doi.org/10.1016/S0140-6736(16)00576-6. 13 pages. Apr. 29, 2016.
Flowers et al., How we treat chronic graft-versus-host disease. Blood. Jan. 22, 2015;125(4):606-15.
Fries et al., O-divinylbenzene and naphthalene. Ber Dtsch Chem Ges B. 1936;69:715-22.
Galiéet al., Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J. Oct. 2009;30(20):2493-537.
Hackam et al., Translation of research evidence from animals to humans. JAMA. Oct. 11, 2006;296(14):1731-2.
Healthline, Overview. Retrieved online at: http://www.healthline.com/health/inflammatory-bowel-disease. 7 pages. (2005-2015).
Hynes et al., The discovery of (R)-2-(sec-butylamino)-N-(2-methyl-5-(methylcarbamoyl)phenyl) thiazole-5-carboxamide (BMS-640994)—A potent and efficacious p38alpha MAP kinase inhibitor. Bioorg Med Chem Lett. Mar. 15, 2008;18(6):1762-7.
Johnson et al., Relationships between drug activity in NCI preclinical in vitro and in vivo models and early clinical trials. Br J Cancer. May 18, 2001;84(10)1424-31.
Jordan, Tamoxifen: a most unlikely pioneering medicine. Nat Rev Drug Discov. Mar. 2003;2(3):205-13.
Lamotte et al., Discovery of novel indazole derivatives as dual angiotensin II antagonists and partial PPAR? agonists. Bioorg Med Chem Lett. Feb. 15, 2014;24(4):1098-103.
Ledford, US cancer institute to overhaul tumour cell lines. Nature. Feb. 25, 2016;530(7591):391.
Lim et al., Age-related macular degeneration. Lancet. May 5, 2012;379(9827):1728-38.
Lutz et al., Overview of Animal Models of Obesity. Curr Protoc Pharmacol. Sep. 2012. Chapter: Unit 5.61. 22 pages.
Maddur et al., Th17 cells: biology, pathogenesis of autoimmune and inflammatory diseases, and therapeutic strategies. Am J Pathol. Jul. 2012;181(1):8-18.
Makrilakis, Pathophysiology of Type 2 diabetes. Diabetes in Clinical Practice: Questions and Answers from Case Studies. John Wiley & Sons, Ltd. Chapter 3, pp. 43-58, (2006).
Marcoux et al., Annulation of ketones with vinamidinium hexafluorophosphate salts: an efficient preparation of trisubstituted pyridines. Org Lett. Jul. 27, 2000;2(15):2339-41.
Ocana et al., Preclinical development of molecular-targeted agents for cancer. Nat Rev Clin Oncol. 2011;8:200-209.
Pilz et al., Modern multiple sclerosis treatment—what is approved, what is on the horizon. Drug Discov Today. Dec. 2008;13(23-24):1013-25.
Quinby, Conventional Therapy. Psoriasis and Psoriatic Arthritis. An Integrated Approach. Kenneth B. Gordon (Ed.), Springer-Verlag, Berlin Heidelberg. Chapter 9, pp. 134-184, (2005).
Sangshetti et al., Antileishmanial drug discovery: comprehensive review of the last 10 years. RSC Adv. 2015;5:32376-32415.
Schlecker et al., Regioselective Metalation of Pyridinylcarbamates and Pyridinecarboxamides with (2,2,6,6-Tetra methyl-piperidino)magnesium Chloride. J Org Chem. 1995;60:8414-8416.
Schlecker et al., Regioselective Monometalation of 2,5-Pyridinedicarboxamides with (2,2,6,6-Tetra- methylpi-peridino)magnesium Chloride (TMPMgCl). Liebigs Ann. 1995;8:1441-1446.
Sharma et al., Cell line-based platforms to evaluate the therapeutic efficacy of candidate anticancer agents. Nat Rev Cancer. Apr. 2010;10(4):241-53.
Sime et al., Discovery of GSK1997132B a novel centrally penetrant benzimidazole PPAR? partial agonist. Bioorg Med Chem Lett. Sep. 15, 2011;21(18):5568-72.
Co-pending U.S. Appl. No. 15/776,836, filed May 17, 2018.
Co-pending U.S. Appl. No. 16/025,155, filed Jul. 2, 2018.
Co-pending U.S. Appl. No. 16/073,503, filed Jul. 27, 2018
Co-pending U.S. Appl. No. 16/115,860, filed Aug. 29, 2018.
University of Cambridge, Alzheimer's disease and tauopathy. John van Geest Centre for Brain Repair, School of Clinical Medicine. 1 page, (2016).
Vickers et al., The utility of animal models to evaluate novel anti-obesity agents. Br J Pharmacol. Oct. 2011;164(4):1248-62.
Vourloumis et al., Solid-phase synthesis of benzimidazole libraries biased for RNA targets. Tetrahedron Letters. 2003;44:2807-2811.
Wang et al., Structure-Based Design of Tetrahydroisoquinoline-7-carboxamides as Selective Discoidin Domain Receptor 1 (DDR1) Inhibitors. J Med Chem. Jun. 23, 2016;59(12):5911-6.
Yan et al., Quality control in combinatorial chemistry: determination of the quantity, purity, and quantitative purity of compounds in combinatorial libraries. J Comb Chem. Sep.-Oct. 2003;5(5):547-59.
Co-pending U.S. Appl. No. 16/110,224, filed Aug. 23, 2018.
Fries at al., o-Divinylbenzol und Naphtalin. Annalen der Chemie. 1937;533:72-92.
European Office Action for Application No. 16816023.2, dated Jun. 27, 2019, 6 pages.
Schonherr et al., Profound Methyl Effects in Drug Discovery and a Call for New C—H Methylation Reactions. Angew Chem Int Ed. 2013;52:12256-67.
STN Registry No. 1030136-78-7. 2H-Indazole-6-carboxamide, N-[(4-chlorophenyl)methyl]-2-[{4-methoxyphenyl}methyl]. Jun. 24, 2008.
STN Registry No. 1115530-36-3, Thieno[2,3-d]pyrimidine-6-carboxamide, N-[(2-bromophenyl)methyl]-4-(4-ethyl-1-piperazinyl)-5-methyl. Mar. 4, 2009.
STN Registry No. 1141899-39-9, 6-Isoquinolinecarboxamide, N-((2,4-dichlorophenyl)methyl)-1,2,3,4-tetrahydro-2-(4-(methylamino)-6-phenyl-1,3,5-triazine-2-yl). May 1, 2009.
STN Registry No. 1346976-76-8, 2H-Indazole-6-carboxamide, 2-[2-[5-(aminocarbonyl)-1H-pyrazol-1-yl]ethyl]-N-[(3-chlorophenyl)methyl]. Dec. 1, 2011.
STN Registry No. 926926-48-9, 6-Isoquinolinecarboxamide, N-(cyclopropylmethyl)-2-(6,7-dimethoxy-4-quinazolinyl)-1,2,3,4-tetrahydro. Mar. 18, 2007.
Copending U.S. Appl. No. 16/506,518, filed Jul. 9, 2019.
Copending U.S. Appl. No. 16/751,739, filed Jan. 24, 2020.
Bernstein, Polymorphism in Molecular Crystals. Clarendon Press, Oxford. pp. 115-118, 272, (2002).
Braga et al., Making crystals from crystals: a green route to crystal engineering and polymorphism. Chem Commun (Camb). Aug. 7, 2005;(29):3635-45.

(56) References Cited

OTHER PUBLICATIONS

Brittain, Polymorphism in Pharmaceutical Solids. Marcel Dekker, Inc., New York. pp. 1-2, 125-181, 183-226, (1999).
Carnegie Mellon, CMU Seed Fund Project on Detection and Control of Pharmaceutical Polymorphism. Carnegie Mellon, The Department of Physics. Retrieved online at: http://andrew.crnu/edu/user/suter/polymorph.html. 3 pages. (2002).
Chauhan et al., Autoimmunity in Dry Eye is due to Resistance of Th17 to Treg Suppression. J Immunol. Feb. 1, 2009;182(3)1247-52.
Chauhan et al., Role of Th17 Cells in the Immunopathogenesis of Dry Eye Disease. Mucosal Immunol. 2009;2(4):375-6.
Davidovich et al., Detection of polymorphism by powder X-ray diffraction: Interference by preferred orientation. Am Pharm Rev. 2004;2(1):10, 12, 14, 16, 100.
De Gruyter, Concise Encyclopedia Chemistry. Bibliographisches Institut & F.A. Brockhaus AG, Mannheim. Dr. Hans-Dieter Jakubke (Ed.). pp. 872-873, (1993).
Dean, Analytical Chemistry Handbook. McGraw-Hill, Inc., New York. Section 10, pp. 10.24-10.26, (1995).
Doelker, Crystalline modifications and polymorphism changes during drug manufacture. Ann Pharm Fr. May 2002;60(3):161-76.
Doelker, Physicochemical behavior of active substances. Consequences for the feasibility of pharmaceutical forms. S.T.P. Pharma Pratiques. 1999;9(5):399-409, including CAPLUS abstract, AN:2000:10870.
Guillory, Generation of Polymorphs, Hydrates, Solvates, and Amorphous Solids. Materials Science. Chapter 5, pp. 183-226, (1999).
Ivanisevic et al., Uses of X-Ray Powder Diffraction in the Pharmaceutical Industry. Pharmaceutical Sciences Encyclopedia: Drug Discovery, Development, and Manufacturing. Shayne C. Gad (Ed.), John Wiley & Sons, Inc. pp. 1-42, Jun. 25, 2010.
Jain, Polymorphism in Pharmacy. Indian Drugs. 1986:23(6):315-29.
Kirk-Othmer, Crystallization. Encyclopedia of Chemistry Technology. Chapter 8, pp. 95-147, (2002).
Muzaffar et al., Polymorphism and Drug Availability. Journal of Pharmacy (Lahore). 1979;1(1):59-66.
Otsuka et al., Effect of Polymorphic Forms of Bulk Powders on Pharmaceutical Properties of Carbamazepine Granules. Chem Pharm Bull. 1999;47(6):852-6.
Rodriguez-Spong et al., General principles of pharmaceutical solid polymorphism: a supramolecular perspective. Adv Drug Deliv Rev. Feb. 23, 2004;56(3):241-74.
Seddon, Pseudopolymorph: A Polemic. Crystal Growth & Design. 2004;4(6):1087.
Singhal et al., Drug polymorphism and dosage form design: a practical perspective. Adv Drug Deliv Rev. Feb. 23, 2004;56(3):335-47.
Taday et al., Using Terahertz pulse spectroscopy to study the crystalline structure of a drug: a case study of the polymorphs of ranitidine hydrochloride. J Pharm Sci. Apr. 2003;92(4):831-8.
U.S. Pharmacopia #23, National Formulary #18. X-Ray Diffraction. (941), pp. 1843-4, (1995).
Vippagunta et al., Crystalline solids. Adv Drug Deliv Rev. May 16, 2001;48(1):3-26.
Co-pending U.S. Appl. No. 17/015,825, filed Sep. 9, 2020.
Co-pending U.S. Appl. No. 17/032,428, filed Sep. 25, 2020.
Co-pending U.S. Appl. No. 17/023,871, filed Sep. 17, 2020.

\* cited by examiner

MODULATORS OF ROR-GAMMA

RELATED APPLICATIONS

This application is a 35 U.S.C. § 371 national stage filing of International Application No. PCT/US2016/062422, filed Nov. 17, 2016, which claims priority to U.S. Provisional Application No. 62/320,805, filed Apr. 11, 2016, and U.S. Provisional Application No. 62/257,964, filed Nov. 20, 2015. The entire contents of each of the aforementioned applications are incorporated herein by reference.

SEQUENCE LISTING

The instant application contains a Sequence Listing which has been filed electronically in ASCII format and is hereby incorporated by reference in its entirety. Said ASCII copy, created on Aug. 28, 2018, is named 121374-01803 SL.txt and is 582 bytes in size.

TECHNICAL FIELD

The present disclosure is directed to novel retinoic acid receptor-related orphan receptor gamma ("RORγ" or "ROR-gamma") modulators, processes for their preparation, pharmaceutical compositions containing these modulators, and their use in the treatment of inflammatory, metabolic, autoimmune and other diseases mediated by RORγ.

BACKGROUND

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal, 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1): 113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Recently, IL-17-producing neutrophils have been identified as promoting inflammation leading to both microbial clearance and IL-17-associated tissue damage in the cornea and other tissues (Taylor et al., 2014, J. Immunol, 192:3319-3327; Taylor et al., 2014, Nat. Immunol., 15:143-151), supporting a role for compounds that inhibit RORγ activity in the treatment of corneal ulcers and other diseases and disorders associated with IL-17 expressing neutrophils.

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6). Recent evidence also shows that RORγ is overexpressed and amplified in metastatic castration-resistant prostate cancer tumors, and that RORγ antagonists suppressed tumor growth in multiple androgen receptor-expressing xenograft prostate cancer models. See e.g., Nature Medicine, Mar. 28, 2016, advance online publication, doi: 10.1038/nm.4070.

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY

It has now been found that compounds described herein, and pharmaceutically acceptable compositions thereof, are effective modulators of RORγ (see e.g., Tables 11-20). Such compounds include those of Formula I:

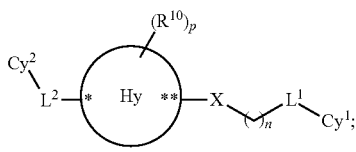

(I)

or a pharmaceutically acceptable salt thereof, wherein each of $Cy^2$, $L^2$, Hy, *, **, $R^{10}$, p, X, n, $L^1$, and $Cy^1$ are as defined and described herein.

The provided compounds, and pharmaceutically acceptable compositions thereof, are modulators of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds

In certain embodiments, the present disclosure provides a compound of Formula I:

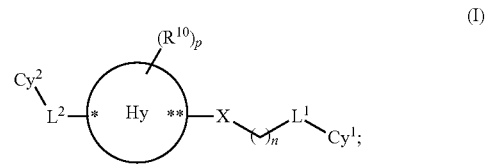

(I)

or a pharmaceutically acceptable salt thereof, wherein
Hy is

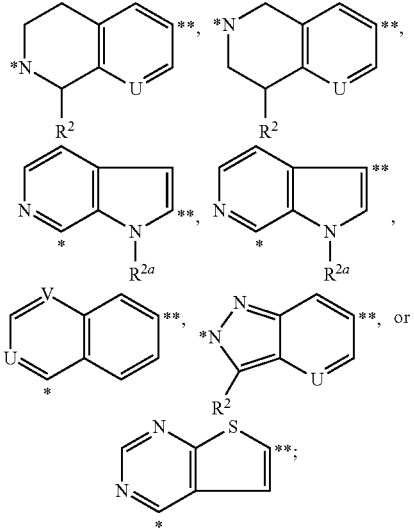

U and V are each independently $CR^9$ or N, provided that both are not $CR^9$;

X is —C(O)NH— or —NHC(O)—;

n is 0, 1, 2, or 3;

p is 0, 1, 2, or 3;

* designates the attachment to $L^2$;

** designates the attachment to X;

$L^2$ is a bond or is selected from $CH_2$, $CH_2CH_2$, CHMe, O, C(=O), CH(OH), and $CH_2O$, wherein the oxygen atom in $CH_2O$ can either be attached to $Cy^2$ or Hy, provided that attachment to Hy occurs at a carbon atom on Hy;

$L^1$ is absent or is $CR^7R^8$;

$Cy^1$ is selected from aryl, heteroaryl, heterocyclyl, and cycloalkyl, wherein the aryl, heteroaryl, heterocyclyl, and cycloalkyl are each substituted with 1 to 3 groups independently selected from $R^5$;

$Cy^2$ is selected from aryl, heteroaryl, monocyclic cycloalkyl, and monocyclic heterocyclyl, wherein the aryl, heteroaryl, monocyclic cycloalkyl, and monocyclic heterocyclyl are each optionally substituted with 1 to 3 groups independently selected from $R^6$;

$R^2$ is $(C_1-C_4)$alkyl, $(C_2-C_4)$alkenyl, $(C_1-C_4)$haloalkyl, or monocyclic cycloalkyl;

$R^{2a}$ is H, $(C_1-C_4)$alkyl, $(C_2-C_4)$alkenyl, $(C_1-C_4)$haloalkyl, or monocyclic cycloalkyl;

$R^5$ and $R^6$ are each independently selected from halogen, —CN, —$OR^c$, —$NR^dR^e$, —$S(O)_kR^c$, —$NR^cS(O)_2R^c$, —$S(O)_2NR^dR^e$, —C(=O)$OR^c$, —OC(=O)$OR^c$, —OC(=O)$R^c$, —OC(=S)$OR^c$, —C(=S)$OR^c$, —OC(=S)$R^c$, —C(=O)$NR^dR^e$, —$NR^cC$(=O)$R^c$, —C(=S)$NR^dR^e$, —$NR^cC$(=S)$R^c$, —$NR^cC$(=O)$OR^c$, —OC(=O)$NR^dR^e$, —$NR^cC$(=S)$OR^c$, —OC(=S)$NR^dR^e$, —$NR^cC$(=O)

$NR^dR^e$, —$NR^c(C=S)NR^dR^e$, —$C(=S)R^c$, —$C(=O)R^c$, ($C_1$-$C_6$)alkyl, cycloalkyl, —$(CH_2)_{1-4}$-cycloalkyl, heterocyclyl, —$(CH_2)_{1-4}$-heterocyclyl, aryl, —NHC(=O)-heterocyclyl, —NHC(=O)-cycloalkyl, —$(CH_2)_{1-4}$-aryl, heteroaryl and —$(CH_2)_{1-4}$-heteroaryl, wherein the alkyl, cycloalkyl, heterocyclyl, aryl or heteroaryl portion present in each of said ($C_1$-$C_6$)alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl substituent for $R^6$ are optionally substituted with halogen, $OR^c$, —$NO_2$, —CN, —$NR^cC(=O)R^c$, —$NR^dR^e$, —$S(O)_kR^c$, —$C(=O)OR^c$, —$C(=O)NR^dR^e$, —$C(=O)R^c$, ($C_1$-$C_3$)alkyl, halo($C_1$-$C_3$)alkyl, ($C_1$-$C_3$)alkoxy($C_1$-$C_3$)alkyl, ($C_1$-$C_3$)alkoxy, or halo($C_1$-$C_3$)alkoxy;

each $R^c$ is independently selected from hydrogen and ($C_1$-$C_6$)alkyl optionally substituted with hydroxy, ($C_1$-$C_2$)alkoxy, —$C(O)NH_2$, —$C(O)O(C_1$-$C_3)$alkyl, or 1 to 3 halogen;

each $R^d$ and $R^e$ is independently selected from hydrogen and ($C_1$-$C_6$)alkyl;

k is 0, 1 or 2;

any heterocyclyl or heteroaryl portion of $Cy^1$ or $Cy^2$ is further optionally substituted with =O;

$R^7$ and $R^8$ are each independently hydrogen, $OR^c$, —$C(=O)OR^c$, monocyclic heterocyclyl, halophenyl, quinolin-2(1H)one-4yl-methyl, or ($C_1$-$C_3$)alkyl, wherein the ($C_1$-$C_3$)alkyl is optionally substituted with $OR^c$, —$NR^dR^e$, —$C(=O)OR^c$, —$C(=O)NR^dR^e$, or halophenyl;

$R^9$ is hydrogen, ($C_1$-$C_4$)alkyl, ($C_1$-$C_4$)haloalkyl, ($C_1$-$C_4$)alkoxy, ($C_1$-$C_4$)haloalkoxy, halo, cyano, or monocyclic cycloalkyl; and $R^{10}$ is ($C_1$-$C_4$)alkyl, ($C_1$-$C_4$)haloalkyl, ($C_1$-$C_4$)alkoxy, ($C_1$-$C_4$)haloalkoxy, halo, cyano, or monocyclic cycloalkyl.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, and bromine.

The terms "cycloalkyl" and "cycloaliphatic", used alone or as part of a larger moiety, refer to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl or cycloaliphatic group is attached.

The term "carbocycle", "carbocyclyl", "carbocyclo", or "carbocyclic" used alone or as part of a larger moiety refer to saturated, partially saturated, or aromatic ring systems comprising all carbon atoms having, unless otherwise specified, a total of 3 to 10 ring members. It will be understood that when specified, optional substituents on a carbocycle, carbocyclyl, carbocyclo, or carbocyclic may be present on any substitutable position and, include, e.g., the position at which the cycloalkyl is attached.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring", "aryl group", "aryl moiety," or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group may be present on any substitutable position and, include, e.g., the position at which the aryl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl or heteroaryl rings. Nonlimiting examples include indolyl, indazolyl, benzimidazolyl, benzthiazolyl, quinolyl, quinazolinyl, quinoxalinyl, pyrrolopyridinyl, pyrrolopyrimidinyl, thienopyridinyl, and thienopyrimidinyl. A heteroaryl group may be mono- or bicyclic. It will be understood that when specified, optional substituents on a heteroaryl group may be present on any substitutable position and, include, e.g., the position at which the heteroaryl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated heterocyclic radicals fused to another unsaturated heterocyclic radical or aromatic or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

As used herein, a hyphen ("-") at the beginning or end of a recited group designates the point at which a recited group is attached to a defined group. For example, $-SO_2-(C_1-C_3)$alkyl-$(C_2-C_6)$cycloalkyl means that the group is attached via the sulfonyl.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or all geometric isomers.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g., the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

The compounds of the herein may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present disclosure provides a compound of Formula I:

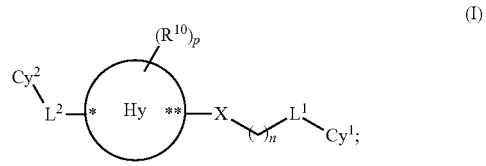

or a pharmaceutically acceptable salt thereof, wherein the variables are as described above.

In a second embodiment, the compound of Formula I is of the Formula II:

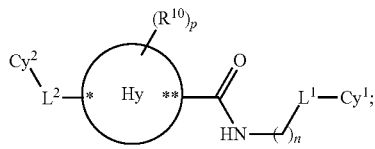

or a pharmaceutically acceptable salt thereof, wherein the variables are as described above for Formula I.

In a third embodiment, p in Formula I or II is 0, 1, or 2; and $R^{10}$ is $(C_1-C_4)$alkyl or halo, wherein the remaining variables are as described above for Formula I and the second embodiment.

In a fourth embodiment, $L^2$ in Formula I or II is a bond or is selected from $CH_2$, O, and $CH_2O$, wherein the oxygen atom in $CH_2O$ is attached to a carbon atom on Hy, wherein the remaining variables are as described above for Formula I and the second or third embodiment.

In a fifth embodiment, the compound of Formula I is of the Formula III or IV:

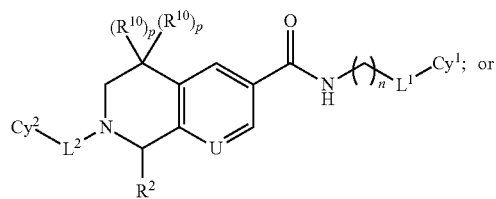

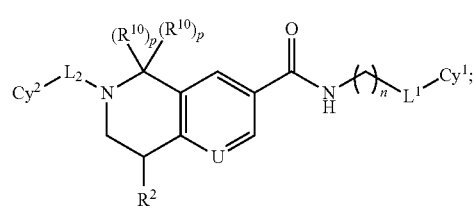

or a pharmaceutically acceptable salt thereof, wherein each p is independently 0 or 1, and wherein the remaining variables in Formula III and IV are as described above for Formula I and the second, third, or fourth embodiment.

In a sixth embodiment, the compound of Formula I is of the Formula IIIa or IVa:

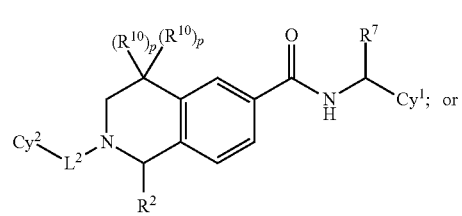

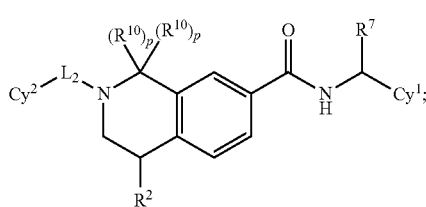

or a pharmaceutically acceptable salt thereof, wherein each p is independently 0 or 1, and wherein the remaining variables in Formula IIIa and IVa are as described above for Formula I and the second, third, fourth, or fifth embodiment.

In a seventh embodiment, $R^{10}$ in Formula I, II, III, IIIa, IV, and IVa is $(C_1-C_4)$alkyl; and $L^2$ is a bond or $CH_2$, wherein the remaining variables in Formula I, II, III, IIIa, IV, and IVa are as described above for Formula I and the second, third, fourth, fifth, or sixth embodiment.

In an eighth embodiment, the compound of Formula I is of the Formula V or VI:

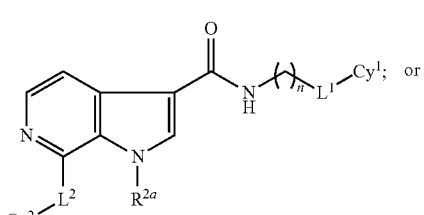

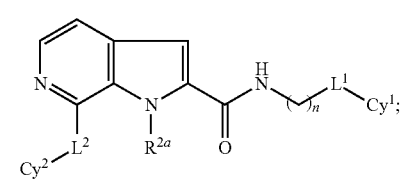

or a pharmaceutically acceptable salt thereof, wherein the variables in structural Formula V and VI are as described above for Formula I and the second, third, or fourth embodiment.

In a ninth embodiment, the compound of Formula I is of the Formula Va or VIa:

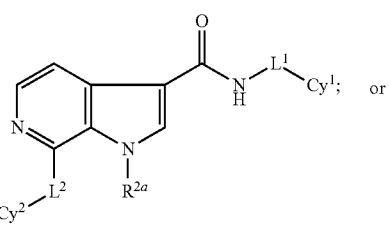

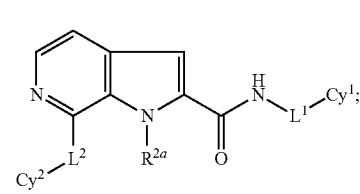

or a pharmaceutically acceptable salt thereof, wherein the variables in structural Formula Va and VIa are as described above for Formula I and the second, third, fourth, or eighth embodiment.

In a tenth embodiment, the compound of Formula I is of Formula Va' or VIa':

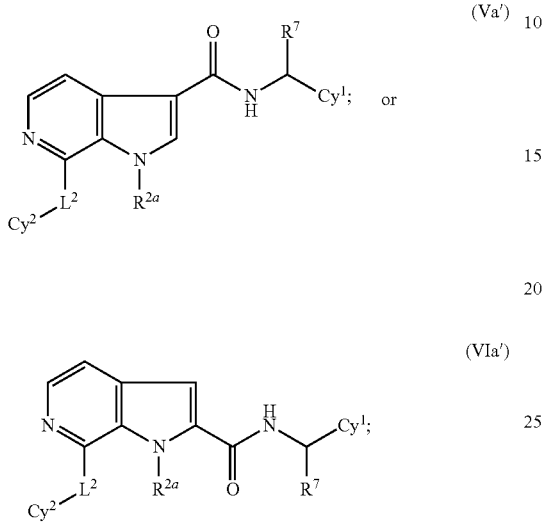

or a pharmaceutically acceptable salt thereof, wherein the variables in structural Formula Va' and VIa' are as described for Formula I and the second, third, fourth, eighth, or ninth embodiment.

In an eleventh embodiment, $R^{2a}$ is hydrogen or $(C_1-C_4)$ alkyl, wherein the variables in structural Formula Va' and VIa' are as described for Formula I and the second, third, fourth, eighth, ninth, or tenth embodiment.

In a twelfth embodiment, $L^2$ in Formula V, VI, Va, VIa, Va', and VIa' is O or $CH_2O$, wherein the methylene portion of $CH_2O$ is attached to $Cy^2$, and wherein the variables in Formula V, VI, Va, VIa, Va', and VIa' are as described above for Formula I and the second, third, fourth, eighth, ninth, tenth, or eleventh embodiment.

In a thirteenth embodiment, the compound of Formula I is of the Formula VII:

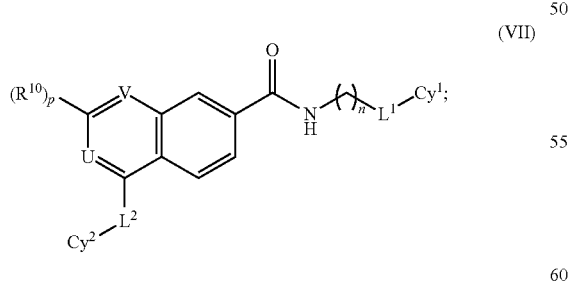

or a pharmaceutically acceptable salt thereof, wherein p is 0 or 1, and wherein the remaining variables in Formula VII are as described above for Formula I and the second, third, or fourth embodiment.

In a fourteenth embodiment, the compound of Formula I is of the Formula VIIa, VIIb, or VIIc:

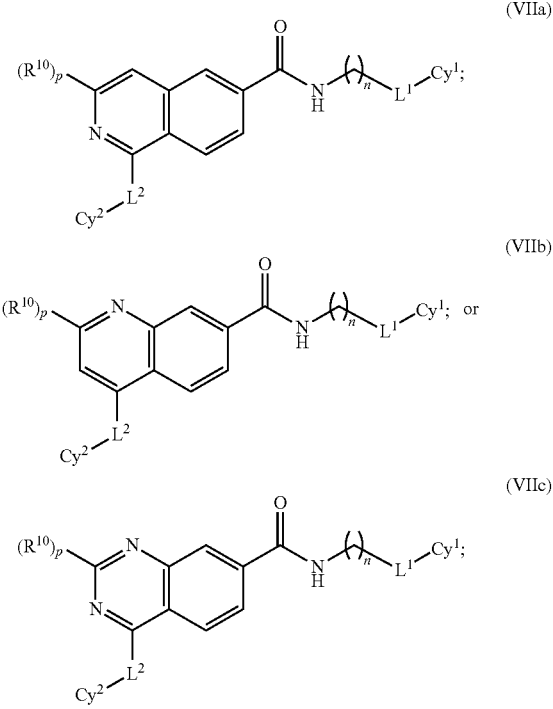

or a pharmaceutically acceptable salt thereof, wherein p is 0 or 1, and wherein the remaining variables in Formula VIIa, VIIb, and VIIc are as described above for Formula I and the second, third, fourth, fifth, or thirteenth embodiment.

In a fifteenth embodiment, the compound of Formula I is of the Formula VIIa', VIIb', or VIIc':

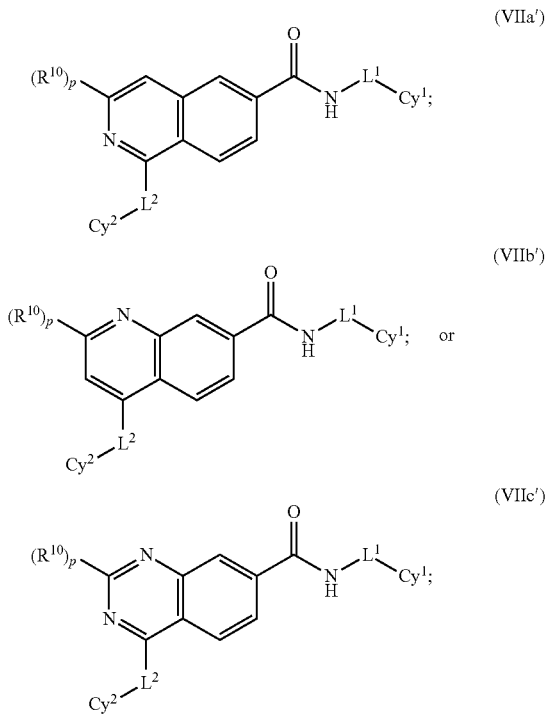

or a pharmaceutically acceptable salt thereof, wherein p is 0 or 1, and wherein the remaining variables in Formula VIIa', VIIb', and VIIc' are as described above for Formula I and the second, third, fourth, thirteenth, or fourteenth embodiment.

In a sixteenth embodiment, the compound of Formula I is of the Formula VIIa", VIIb", or VIIc":

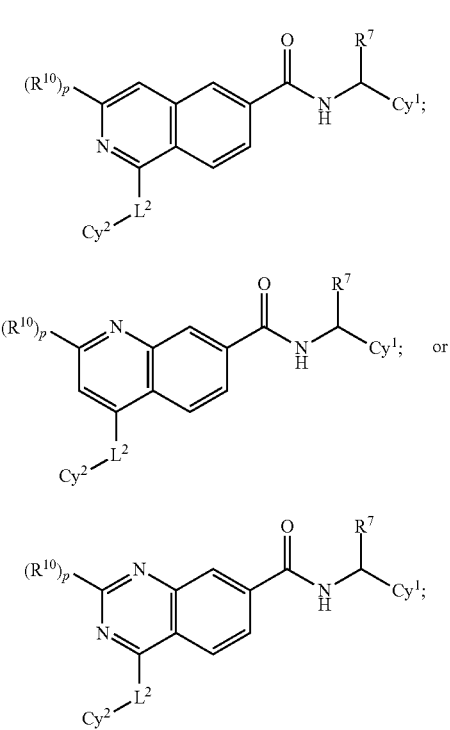

or a pharmaceutically acceptable salt thereof, wherein p is 0 or 1, and wherein the remaining variables in Formula VIIa", VIIb", and VIIc" are as described above for Formula I and the second, third, fourth, thirteenth, fourteenth, or fifteenth embodiment.

In a seventeenth embodiment, $L^2$ in Formula VII, VIIa, VIIb, VIIc, VIIa', VIIb', VIIc', VIIa", VIIb", and VIIc" is O or CH$_2$O, wherein the methylene portion of CH$_2$O is attached to Cy$^2$, wherein the remaining variables in Formula VII, VIIa, VIIb, VIIc, VIIa', VIIb', VIIc', VIIa", VIIb", and VIIc" are as described above for Formula I and the second, third, fourth, thirteenth, fourteenth, fifteenth, or sixteenth embodiment.

In an eighteenth embodiment, the compound of Formula I is of the Formula VIII:

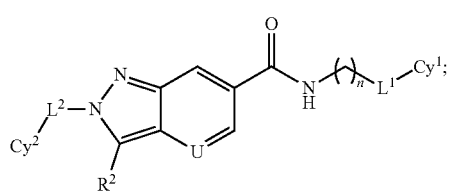

or a pharmaceutically acceptable salt thereof, wherein the variables in Formula VIII are as described above for Formula I and the second, third, or fourth embodiment.

In a nineteenth embodiment, the compound of Formula I is of the Formula VIIIa or VIIIb:

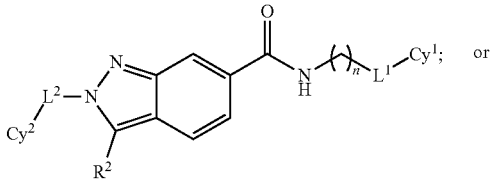

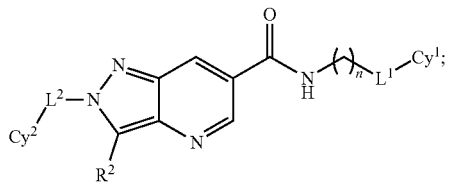

or a pharmaceutically acceptable salt thereof, wherein the variables in Formula VIIIa and VIIIb are as described above for Formula I and the second, third, fourth, or eighteenth embodiment.

In a twentieth embodiment, the compound of Formula I is of the Formula VIIIa' or VIIIb':

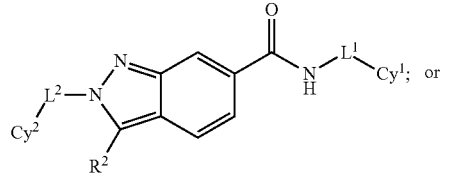

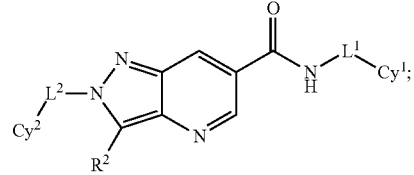

or a pharmaceutically acceptable salt thereof, wherein the variables in Formula VIIIa' and VIIIb' are as described above for Formula I and the second, third, fourth, eighteenth, or nineteenth embodiment.

In a twenty-first embodiment, the compound of Formula I is of the Formula VIIIa" or VIIIb":

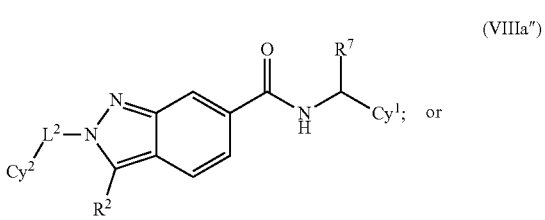

-continued

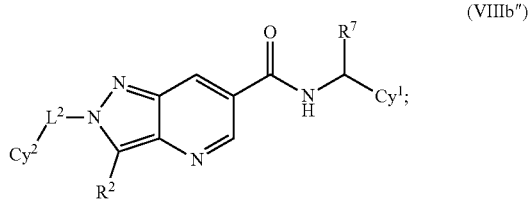
(VIIIb")

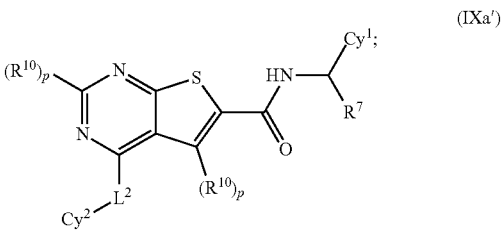
(IXa')

or a pharmaceutically acceptable salt thereof, wherein the variables in Formula VIIIa" and VIIIb" are as described above for Formula I and the second, third, fourth, eighteenth, nineteenth, or twentieth embodiment.

In a twenty-second embodiment, $L^2$ in Formula VIII, VIIIa, VIIIb, VIIIa', VIIIb', VIIIa", and VIIIb" is $CH_2$, wherein the variables in Formula VIII, VIIa, VIIIb, VIIIa', VIIIb', VIIIa", and VIIb" are as described above for Formula I and the second, third, fourth, eighteenth, nineteenth, twentieth, or twenty-first embodiment.

In a twenty-third embodiment, the compound of Formula I is of the Formula IX:

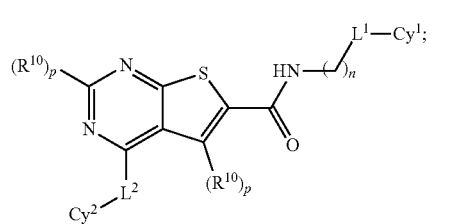
(IX)

or a pharmaceutically acceptable salt thereof, wherein p is 0 or 1, and wherein the remaining variables are as described above for Formula I and the second, third, or fourth embodiment.

In a twenty-fourth embodiment, the compound of Formula I is of the Formula IXa:

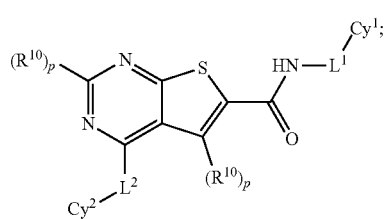
(IXa)

or a pharmaceutically acceptable salt thereof, wherein p is 0 or 1, and wherein the variables are as described above for Formula I and the second, third, fourth, or twenty-third embodiment.

In a twenty-fifth embodiment, the compound of Formula I is of the Formula IXa':

or a pharmaceutically acceptable salt thereof, wherein p is 0 or 1, and wherein the variables are as described above for Formula I and the second, third, fourth, twenty-third, or twenty-fourth embodiment.

In a twenty-sixth embodiment, $R^{10}$ in Formula IX, IXa, and IXa' is $(C_1-C_4)$alkyl; and $L^2$ is $CH_2O$, wherein the methylene portion of $CH_2O$ is attached to $Cy^2$, and wherein the remaining variables are as described above for Formula I and the second, third, fourth, twenty-third, twenty-fourth, or twenty-fifth embodiment.

In a twenty-seventh embodiment, $R^2$ in Formula I, II, III, IIIa, IV, IVa, VIII, VIIIa, VIIIb, VIIIa', VIIIb', VIIIa" and VIIIb" is $(C_1-C_4)$alkyl or cyclopropyl, wherein the remaining variables are as described above for Formula I and the second, third, fourth, fifth, sixth, seventh, eighteenth, nineteenth, twentieth, twenty-first, or twenty-second embodiment.

In a twenty-eighth embodiment, $R^7$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is hydrogen, $OR^e$, or $(C_1-C_3)$alkyl, wherein the $(C_1-C_3)$alkyl is optionally substituted with $OR^e$ or $—NR^dR^e$; and $R^8$ is hydrogen, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, or twenty-seventh embodiment.

In a twenty-eighth embodiment, $R^7$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is hydrogen, $—O(C_1-C_3)$alkyl, or $(C_1-C_3)$alkyl, wherein the $(C_1-C_3)$alkyl is optionally substituted with OH, $NH_2$ or $—N(C_1-C_3$ alkyl$)_2$; and $R^8$ is hydrogen, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, or twenty-eighth embodiment.

In a thirteenth embodiment, $R^7$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIa', VIIIb', VIIIa", VIIIb", IX, IXa, and IXa' is hydrogen or hydroxy$(C_1-C_3)$alkyl; and $R^8$ is hydrogen, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, or twenty-ninth.

In a thirty-first embodiment, $Cy^1$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIa', VIIIb', VIIa", VIIIb", IX, IXa, and IXa' is aryl or heteroaryl, each substituted with 1 to 3 groups independently selected from $R^5$, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth embodiment or thirteenth.

In a thirty-second embodiment, $Cy^1$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is phenyl or pyridinyl, each substituted with 1 to 3 groups independently selected from $R^5$, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, or thirty-first embodiment.

In a thirty-third embodiment, at least one $R^5$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is $-SO_2-(C_1-C_3)$alkyl, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, or thirty-second embodiment.

In a thirty-fourth embodiment, $Cy^2$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is phenyl, pyrimidinyl, cyclohexyl, pyridinyl, tetrahydropyranyl, or piperidinyl, each optionally substituted with 1 to 3 groups independently selected from $R^6$, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, thirty-second, or thirty-third embodiment.

In a thirty-fifth embodiment, $Cy^2$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIIa', VIIIb', VIIIa", VIIIb", IX, IXa, and IXa' is phenyl or cyclohexyl, each optionally substituted with 1 to 3 groups independently selected from $R^6$, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, or thirty-second, thirty-third, or thirty-fourth embodiment.

In a thirty-sixth embodiment, $R^5$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIIa, VIIIb, VIIa', VIIIb', VIIa", VIIIb", IX, IXa, and IXa' is selected from halogen, $-CN$, $-OR^c$, $-NR^dR^e$, $-NR^cS(O)_2R^c$, $-S(O)_2NR^dR^e$, $-C(=O)OR^c$, $-C(=O)NR^dR^e$, $-NR^cC(=O)R^c$, $-NR^cC(=O)OR^c$, $-OC(=S)NR^dR^e$, $-C(=O)R^c$, $-SO_2-(C_1-C_3)$alkyl, and $(C_1-C_4)$alkyl optionally substituted with halogen; and $R^6$ is selected from halogen, $-CN$, $-OR^c$, $-NR^dR^e$, $-NR^cS(O)_2R^c$, $-S(O)_2NR^dR^e$, $-C(=O)OR^c$, $-OC(=O)OR^c$, $-OC(=O)R^c$, $-C(=O)NR^dR^e$, $-NR^cC(=O)R^c$, $-C(=S)NR^dR^e$, $-NR^cC(=S)R^c$, $-NR^cC(=O)OR^c$, $-OC(=O)NR^dR^e$, $-NR(C=S)OR^c$, $-OC(=S)NR^dR^e$, $-NR^cC(=O)NR^dR^e$, $-NR^c(C=S)NR^dR^e$, $-C(=S)R^c$, $-C(=O)R^c$, $-SO_2-(C_1-C_3)$alkyl, and $(C_1-C_4)$alkyl optionally substituted with halogen, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, or thirty-second, thirty-third, thirty-fourth, or thirty-fifth embodiment.

In a thirty-seventh embodiment, $R^5$ in Formula I, II, III, IIIa, IV, IVa, V, VI, Va, VIa, Va', VIa, VII, VIIa, VIIb, VIIc, VIIa', VIIb', VIIc', VIIa", VIIb", VIc", VIII, VIIa, VIIIb, VIIa', VIIIb', VIIIa", VIIIb", IX, IXa, and IXa' is $-SO_2-(C_1-C_3)$alkyl; $R^6$ is selected from $-CN$, halo, $-C(=O)OR^c$, $OR^c$, and $(C_1-C_4)$alkyl optionally substituted with halogen; and $R^c$ is $(C_1-C_4)$alkyl optionally substituted with halogen, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, or thirty-second, thirty-third, thirty-fourth, thirty-fifth, or thirty-sixth embodiment.

In a thirty-eighth embodiment, $R^6$ in Formula I, II, III, IIIa, IV, IVa, V, VI, Va, VIa, Va', VIa, VII, VIIa, VIIb, VIIc, VIIa', VIIb', VIIc', VIIa", VIIb", VIIc", VIII, VIIa, VIIIb, VIIIa', VIIIb', VIIIa", VIIIb", IX, IXa, and IXa' is $CF_3$, wherein the remaining variables are as described above for Formula I and the second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eight, twenty-ninth, thirtieth, thirty-first, or thirty-second, thirty-third, thirty-fourth, thirty-fifth, thirty-sixth, or thirty-seventh embodiment.

Specific examples of compounds are provided in the EXEMPLIFICATION. Pharmaceutically acceptable salts as well as the neutral forms of these compounds are included herein.

In certain embodiments, the present disclosure provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present disclosure provides a method of treating a subject (e.g., a human) with a disorder mediated by RORγ using a composition comprising a compound of Formula I and a pharmaceutically acceptable carrier, adjuvant, or vehicle. In certain embodiments, the amount of compound of Formula I in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharma+ceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope herein. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for modulating RORγ. Thus, in some embodiments, the present disclosure provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Modulation of RORγ (or to modulate RORγ), means that a change or alteration in the activity of RORγ has occurred from the administration of one or more of the compounds described herein. Modulation may be an upregulation (increase) or a downregulation (decrease) in the magnitude of the activity or function of RORγ. Exemplary activities and functions include e.g., binding characteristics, enzymatic activity, cell receptor activation, transcriptional activity, and signal transduction. In one aspect, the compounds described herein inhibit RORγ. In further aspects, the compounds described herein act as agonists, antagonists, or inverse agonists of RORγ.

In another aspect, compounds and compositions described herein are useful for reducing the amount of IL-17 in a subject. Thus, in some embodiments, provided herein are methods of reducing the amount of IL-17 in a subject comprising administering an effective amount of a provided compound or composition. RORγ modulators disclosed in WO 2014/179564, WO 2015/116904, WO 2016/061160, PCT/US2016/045318, and U.S. patent application Ser. Nos. 14/933,468 and 14/933,524 can also be used in such methods.

In another aspect, compounds and compositions described herein are useful for inhibiting the synthesis of IL-17 in a subject. Thus, in some embodiments, provided herein are methods of inhibiting the synthesis of IL-17 in a subject comprising administering an effective amount of a provided compound or composition. RORγ modulators disclosed in WO 2014/179564, WO 2015/116904, WO 2016/061160, PCT/US2016/045318, and U.S. patent application Ser. Nos. 14/933,468 and 14/933,524 can also be used in such methods.

Diseases and conditions treatable according to the methods herein include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, urticaria, hives, angioedema, cystic fibrosis, allograft rejection, multiple sclerosis, Balo's concentric (circular) sclerosis, Balo disease, leukoencephalitis periaxialis concentrica, encephalitis periaxialis concentrica, scleroderma, limited scleroderma, CREST syndrome, arthritis, rheumatoid arthritis, juvenile rheumatoid arthritis, reactive arthritis, Reiter's syndrome, osteoarthritis, ankylosing spondylitis, systemic lupus erythematosus (SLE), psoriasis, plaque psoriasis, guttate psoriasis, inverse psoriasis, pustular psoriasis, erythrodermic psoriasis, psoriatic epidermal hyperplasia, epidermal hyperplasia, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barre syndrome, psoriatic arthritis (PsA), steroid resistant asthma, Graves' disease, scleritis, endometriosis, obstructive sleep apnea syndrome (OSAS), Behçet's disease, dermatomyositis, polymyocitis, graft versus host disease, chronic graft versus host disease, acute graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, celiac sprue, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer. In one aspect, an exemplified form of cancer treatable according to the methods herein also includes prostate cancer e.g., (metastatic castration-resistant prostate cancer tumors). In another aspect, an exemplified form of cancer treatable according to the methods herein includes e.g., malignant tumor, angiogenesis glaucoma, infantile hemangioma, multiple myeloma, acute myeloblastic leukemia, chronic sarcoma, chronic myelogenous leukemia, metastasis melanoma, Kaposi's sacroma, vascular proliferation, cachexia, colorectal cancer (e.g., familial colorectal cancer, hereditary nonpolyposis colorectal cancer, and gastrointestinal stromal tumor), lung cancer (e.g., non-small cell lung cancer, small cell lung cancer and malignant mesothelioma), mesothelioma, pancreatic cancer (e.g., pancreatic duct cancer), gastric cancer (e.g., papillary adenocarcinoma, mucinous adenocarcinoma and adenosquamous carcinoma), breast cancer (e.g., invasive ductal carcinoma, ductal carcinoma in situ, inflammatory breast cancer and metastatic breast cancer), ovarian cancer (e.g., ovarian epithelial carcinoma, extragonadal germ cell tumor, ovarian germ cell tumor, and ovarian low malignant potential tumor), hormone-dependent prostate cancer, non-hormone dependent prostate cancer, liver cancer (e.g., primary liver cancer and extrahepatic bile duct cancer), thyroid cancer (e.g., medullary thyroid carcinoma), kidney cancer (e.g., renal cell carcinoma, and transitional cell carcinoma in kidney and urinary duct), uterine cancer, endometrial cancer, brain tumor (e.g., pineal astrocytoma, pilocytic astrocytoma, diffuse astrocytoma and anaplastic astrocytoma), melanoma, sarcoma, urinary bladder cancer, hematologic cancer, hypophyseal adenoma, glioma, acoustic neurinoma, retinoblastoma, head and neck cancer, head and neck squamous cell carcinoma, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervical cancer, endometrial cancer, uterus sarcoma, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, chronic myelocytic leukemia, malignant myeloma, adult T cell leukemia, chronic bone marrow proliferative disease, pancreatic endocrine tumor, fibrous histiocytoma, leiomyosarcoma, rhabdomyosarcoma, cancer of unknown primary, cancer-driven myelopoiesis, tumor growth, and metastasis.

Diseases and disorders mediated by IL-17 expression, and which are treatable using the compounds described herein also include, e.g., emphysema, lung fibrosis, idiopathic pulmonary fibrosis, retroperitoneal fibrosis, giant cell arteritis, giant cell myocarditis, arteriosclerosis, hepatitis, chronic active hepatitis, alcoholic hepatitis, alcoholic liver fibrosis, alcoholic cirrhosis, viral hepatitis, hepatitis B viral liver disorder, autoimmune hepatitis, cartilage inflammation, bone degradation, juvenile arthritis, pauciarticular juvenile rheumatoid arthritis, polyarticular juvenile rheumatoid arthritis, systemic onset juvenile rheumatoid arthritis, spondyloarthritis, juvenile ankylosing spondylitis, juvenile enteropathic arthritis, juvenile reactive arthritis, juvenile Reiter's syndrome, seronegative enthesopathy and arthropathy (SEA) syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, vasculitis, leukocytoclastic vasculitis, myositis, juvenile myositis, polymyositis, autoimmune myositis, osteoarthritis, polyarteritis nodosa, arteritis, Takayasu's arteritis, temporal arteritis, giant cell arterististesticular autoimmunity, polymyalgia rheumatica, rheumatic fever, sclerosis, primary biliary sclerosis, primary biliary cirrhosis, sclerosing cholangitis, primary sclerosing cholangitis, enthesitis, enthesopathy, dermatitis, dermatitis herpetiformis, progesterone dermatitis, atopic eczema, contact eczema, eczema, atherosclerosis, Still's disease, Addison's disease, Raynaud's phenomenon, erythrodermic psoriasis, noninfectious uveitis, peripheral uveitis, Dressler's syndrome, eosinophilic esophagitis, eosinophilic fasciitis, erythema nodosum, experimental allergic encephalomyelitis, Evans syndrome, fibrosing alveolitis, Vogt-Koyanagi-Harada syndrome, mucosal leishmaniasis, Kawasaki disease or syndrome, Hashimoto's encephalitis, Hashimoto's thyroiditis, thrombocytopenic purpura, immune thrombocytopenic purpura (also known as immune thrombocytopenia, idiopathic immune thrombocytopenia, idiopathic thrombocytopenic thrombotic purpura, primary immune thrombocytopenia, idiopathic thrombocytopenic purpura (ITP), primary immune thrombocytopenic purpura, or autoimmune thrombocytopenic purpura), agammaglobulinemia, kidney inflammation, interstitial kidney inflammation, kidney disease, chronic kidney disease, renal failure, acute renal failure, end stage kidney disease, acute kidney injury, cisplatin induced acute renal failure, sepsis induced acute renal failure, antiglomerular basement membrane (GBM) nephritis, anti-tubular basement membrane (TBM) nephritis, antiphospholipid syndrome (APS), nephritis, nephrotoxic nephritis, glomerulonephritis, acute glomerulonephritis, antineutrophil cytoplasmic autoantibody (ANCA) associated vasculitis, microscopic polyangiitis, granulomatosis with polyangiitis (GPA), Wegener's granulomatosis, amyotrophic lateral sclerosis, lupus nephritis, allergic eczema, transplant rejection, non-radiographic spondyloarthropathy, ophthalmic disorders, organ allograft rejection, fibroid lung, renal insufficiency, diabetic complications, diabetic nephropathy, diabetic retinopathy, diabetic retinitis, diabetic microangiopathy, insulitis, tuberculosis, invasive staphylococcia, invasive *Staphylococcus aureus* infection, inflammation after cataract surgery, allergic conjunctivitis, alopecia, alopecia areata, chronic urticaria, allergic asthma, neutrophilic asthma, periodontal diseases, periodontis, gingivitis, gum disease, cardiomyopathy, diastolic cardiomyopathies, cardiac infarction, myocarditis, chronic heart failure, congenital heart block, coxsackie myocarditis, postmyocardial infarction syndrome, postpericardiotomy syndrome, endocarditis, subacute bacterial endocarditis (SBE), angiostenosis, restenosis, reperfusion disorders, autoimmune pancreatitis, acute pancreatitis, chronic pancreatitis, asthma, bronchial asthma, acute respiratory distress syndrome, adult respiratory distress syndrome, inflammatory bone disease, inflammatory pulmonary disease, ischemic attack, transient ischemic attack, systemic inflammatory response syndrome, glaucoma, orbital cellulitis, sudden orbital inflammation, postoperative inflammation, posttraumatic inflammation, allergic inflammation, intestinal inflammation, mucosal inflammation, prostate inflammation, prostatitis, chronic pelvic pain syndrome, testicular inflammation, chronic testicular inflammation, orchitis, orchitis mediated infertility, liver disorder, liver injury, hepatoxicity, pneumonia, meningitis, cystitis, interstitial cystitis, pharyngolaryngitis, gastric mucosal injury, chronic pneumonia, pulmonary infarction, silicosis, sarcoidosis, pulmonary sarcoidosis, autoimmune angioedema, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune aplastic anemia, autoimmune anemia, autoimmune hemolytic anemia, hemolytic anemia, autoimmune retinopathy, autoimmune thrombocytopenic purpura (ATP), autoimmune thyroid disease, autoimmune urticaria, Goodpasture's syndrome, sinusitis, chronic hypertrophic rhinitis, chronic inflammatory demyelinating polyneuropathy, mixed connective tissue disease, undifferentiated connective tissue disease (UCTD), cognitive impairment, cognitive impairment in Alzheimer's disease, Parkinson's disease, spinal muscular atrophy, spinal cerebellar atrophy, progressive supranuclear palsy, Fisher syndrome, dicoid lupus, central nervous system lupus, neuromyelitis optica (NMO; also known as Devic's disease or Devic's syndrome), encephalomyelitis, acute disseminated encephalomyelitis (ADEM), transverse myelitis, acute necrotizing hemorrhagic leukoencephalitis, multiple system atrophy, Huntington's disease, cerebrovascular dementia, diffuse Lewy body disease, amyloidosis, cerebrovascular disorder, cerebral infarction, transient ischemic attack, intracerebral hemorrhage, vascular disease of the spinal cord, spinal cord infarction, Lambert-Eaton syndrome, muscular dystrophy, metabolic myopathy, inflammatory myopathy, Chagas disease, chronic inflammatory demyelinating polyneuropathy (CIDP), chronic recurrent multifocal ostomyelitis (CRMO), Churg-Strauss syndrome, Cogan's syndrome, cold agglutinin disease, essential mixed cryoglobulinemia, demyelinating neuropathies, inclusion body myositis, encephalitis, pemphigoid, bullous pemphigoid, pemphigus, pemphigus vulgaris, pemphigus foliaceus, cicatricial pemphigoid, ocular cicatricial pemphigoid, benign mucosal pemphigoid, Castleman disease (also known as giant or angiofollicular lymph node hyperplasia, lymphoid hamartoma, and angiofollicular lymph node hyperplasia), profundus lupus erythematosus, chronic thyroiditis, autoimmune gastritis, sepsis, burn injury, axonal and neuronal neuropathies, pain, neuropathy, peripheral neuropathy, chronic pain, optic neuritis, optic neuropathy, traumatic optic neuropathy, ischemic brain injury, deep venous thrombosis, neutropenia, autoimmune neutropenia, thrombocytopenia, abnormal immunoresponse, radiodermatitis, osteoporosis, parasitic infection, clonorchiasis, *Cryptosporidium* infection, *Streptococcus pneumoniae* carriage, chronic pneumococcal carriage, an immune disorder associated with or arising from activity of pathogenic lymphocytes, Henoch-Schonlein purpura, herpes gestationis, hypogammaglobulinemia, IgA nephropathy, IgG4-related sclerosing disease, immunoregulatory lipoproteins, Lambert-Eaton syndrome, lichen planus, lichen sclerosus, ligneous conjunctivitis, linear IgA disease (LAD), chronic Lyme disease, Meniere's disease, microscopic polyangiitis, mixed connective tissue disease (MCTD), Mooren's ulcer, Mucha-Habermann disease, narcolepsy, palindromic rheumatism, pediatric autoimmune neuropsychiatric disorders associated with *Streptococcus* (PANDAS), paraneoplastic cerebellar degeneration, paroxysmal nocturnal hemoglobinuria (PNH), Parry-Romberg syndrome, Parsonnage-Turner syndrome, pars planitis, perivenous encephalomyelitis, pernicious anemia, POEMS syndrome, type I autoimmune polyglandular syndrome, type II autoimmune polyglandular syndrome, type III autoimmune polyglandular syndrome, pyoderma gangrenosum, pure red cell aplasia, reflex sympathetic dystrophy, relapsing polychondritis, restless legs syndrome, Schmidt syndrome, sperm autoimmunity, stiff person syndrome, Susac's syndrome, sympathetic ophthalmia, Tolosa-Hunt syndrome, vesiculobullous dermatosis, and vitiligo.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's disease and other central nervous system (CNS) disorders associated with altered sleep and/or circadian rhythms.

Further included are diseases and disorders mediated by IL-17 expression, including STAT3-mediated IL-17 expression, in neutrophils, and include, e.g., corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; and histoplasmosis, including, systemic histoplasmosis. In particular embodiments, the fungus or fungal infection meditating the disease or disorder described above includes one or more of *Aspergillus, Fusarium, Alternaria, Candida, Curvularia* or *Histoplasma*.

Compounds described herein can also be used to treat or reduce the risk of abnormal cortical development or psychiatric disorder, e.g., autism spectrum disorder (ASD), schizophrenia, and/or depression, in a fetus. Compounds described herein can also be used to treat a pregnant female having a hyper-inflammatory condition associated with an infection, such as a viral or bacterial infection, or associated with exposure to an inflammatory or environmental toxin during pregnancy. In particular embodiments, a fetus is treated in utero in a pregnant female with a compound disclosed herein to decrease the risk of the fetus developing a psychiatric disorder, to reduce inflammation in the pregnant female, to reduce the risk of abnormal cortical development in the fetus, and/or to decrease symptoms of a psychiatric disorder in offspring of a pregnant female.

In one embodiment, a human patient is treated with a compound of Formula I and a pharmaceutically acceptable carrier, adjuvant, or vehicle, wherein said compound is present in an amount to treat or ameliorate one or more of the diseases and conditions recited above. In an alternative embodiment, the diseases and conditions treated or ameliorated by a compound of Formula I include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient.

The present disclosure further relates to a combination therapy for treating or ameliorating a disease or a disorder described herein. In some embodiments, the combination therapy comprises administering at least one compound represented by Structural Formula I in combination with one or more agents for treating or ameliorating inflammatory, metabolic and autoimmune diseases or disorders mediated by RORγ. In some embodiments, the combination therapy comprises administering at least one compound represented by Structural Formula I in combination with one or more agents for the treatment of diseases including asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barre syndrome, psoriasis, psoriatic arthritis (PsA), steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to, lung cancer, gastric cancer, breast cancer and colon cancer.

The compounds herein may also be used in combination with immunotherapies for the treatment of a disease or disorder disclosed herein.

Combination therapy includes, e.g., co-administration of a compound described herein and one or more other agents, sequential administration of a compound described herein and one or more other agents, administration of a composition containing a compound described herein and one or more other agents, or simultaneous administration of separate compositions containing a compound described herein and one or more other agents.

The present disclosure further provides a method of treating a subject, such as a human, suffering from one of the abovementioned disorders or diseases.

In one aspect, RORγ modulators disclosed in WO 2014/179564, WO 2015/116904, WO 2016/061160, PCT/US2016/045318, and U.S. patent application Ser. Nos. 14/933,468 and 14/933,524 can also be used in the methods disclosed herein to treat or ameliorate, in a subject, one or more of the diseases and/or disorders and/or conditions recited herein. In one embodiment, a subject is treated with one or more RORγ modulators disclosed in WO 2014/179564, WO 2015/116904, WO 2016/061160, PCT/US2016/045318, and U.S. patent application Nos. U.S. Ser. No. 14/933,468 or U.S. Ser. No. 14/933,524 and a pharmaceutically acceptable carrier, adjuvant, or vehicle, wherein said RORγ modulator is present in an amount to treat or ameliorate a disease or disorder selected from corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; histoplasmosis, including, systemic histoplasmosis; and prostate cancer. In some embodiments, the one or more RORγ modulator disclosed in WO 2014/179564, WO 2015/116904, WO 2016/061160, PCT/US2016/045318, and U.S. patent application Ser. Nos. 14/933,468 and 14/933,524 is administered in combination with one or more additional agent for treating the disease or disorder.

The present disclosure further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds and subclasses and species of each of these compounds, as described herein.

General Description of Synthesis

The compounds described herein can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds described herein will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
| --- | --- |
| ACN, MeCN, $CH_3CN$ | acetonitrile |
| AIBN | azobisisobutyronitrile |
| aq | aqueous |
| Boc | tert-butoxycarbonyl or t-butoxycarbonyl |
| brine | saturated aqueous NaCl |
| c-Bu | cyclobutyl |
| Cbz | benzyloxy carbonyl |
| $CeCl_3$ | ceric chloride |
| $Cs_2CO_3$ | cesium carbonate |
| CuI | cuprous iodide |
| c-Pr | cyclopropyl |
| DCM or $CH_2Cl_2$ | methylene chloride |
| dcpp.2$HBF_4$ | 1,3-Bis(dicyclohexylphosphino)propane bis(tetrafluoroborate) |
| DIEA | diisopropyl ethyl amine |
| DMF | dimethyl formamide |
| DMS/$Me_2S$ | dimethyl sulfide |
| DMSO | dimethyl sulfoxide |
| EDCI | 1-(3-dimethylaminopropyl)-3-ethylcarbodiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |

| Abbreviation | Meaning |
| --- | --- |
| HCl | hydrochloric acid |
| $H_2O$ | water |
| $H_2O_2$ | hydrogen peroxide |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diiisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $MgSO_4$ | magnesium sulfate (anhydrous) |
| min | minute(s) |
| mL | milliliters |
| mmol | millimoles |
| mp, m.p. | melting point |
| MS | mass spectrometry |
| MW, uwave | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |

| Abbreviation | Meaning |
| --- | --- |
| $NH_4Cl$ | ammonium chloride |
| $Na_2CO_3$ | sodium carbonate |
| $NaHCO_3$ | sodium bicarbonate |
| NaH | sodium hydride |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| $PdCl_2dppf$ | [1,1-bis(diphenylphosphino)ferrocene]dichloropalladium(ii) |
| $Pd_2(dba)_3$ | tris(dibenzylideneacetone)dipalladium(0) |
| PE | petroleum ether |
| rt | room temperature |
| sat. | saturated |
| SEM | 2-trimethylsilylethyoxymethyl |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| tR | retention time |
| Zn | zinc |
| $Zn(CN)_2$ | zinc cyanide |

Preparation of Compounds of Formula I

Compounds of Formula I were prepared according to the general procedures outlined below.

Compounds Names[a]

| Cpd No | Name |
| --- | --- |
| Hy1A-1 | (R)-N-(1-(4-(ethylsulfonyl)phenyl)-2-hydroxyethyl)-3-methyl-1-((tetrahydro-2H-pyran-4-yl)methoxy)isoquinoline-6-carboxamide |
| Hy1A-2 | N-(4-(ethylsulfonyl)benzyl)-1-(4-(trifluoromethyl)phenoxy)isoquinoline-6-carboxamide |
| Hy1A-3.1[a] | N-(4-(ethylsulfonyl)benzyl)-1-(((1s,4s)-4-(trifluoromethyl)cyclohexyl)oxy)isoquinoline-6-carboxamide |
| Hy1A-3.2[a] | N-(4-(ethylsulfonyl)benzyl)-1-(((1r,4r)-4-(trifluoromethyl)cyclohexyl)oxy)isoquinoline-6-carboxamide |
| Hy1A-4 | N-(4-(ethylsulfonyl)benzyl)-1-((4-(trifluoromethyl)benzyl)oxy)isoquinoline-6-carboxamide |
| Hy1A-5 | N-(4-(ethylsulfonyl)benzyl)-1-(((1r,4r)-4-(trifluoromethyl)cyclohexyl)methoxy)isoquinoline-6-carboxamide |
| Hy1A-6 | N-(4-(ethylsulfonyl)benzyl)-3-methyl-1-(((1r,4r)-4-(trifluoromethyl)cyclohexyl)methoxy)isoquinoline-6-carboxamide |
| Hy1A-7 | (R)-N-(1-(4-(ethylsulfonyl)phenyl)-2-hydroxyethyl)-1-((4-(trifluoromethyl)benzyl)oxy)isoquinoline-6-carboxamide |
| Hy1A-8 | N-((R)-1-(4-(ethylsulfonyl)phenyl)-2-hydroxyethyl)-1-(((1r,4R)-4-(trifluoromethyl)cyclohexyl)methoxy)isoquinoline-6-carboxamide |
| Hy1A-9 | 3-chloro-N-(4-(ethylsulfonyl)benzyl)-1-(((1r,4r)-4-(trifluoromethyl)cyclohexyl)methoxy)isoquinoline-6-carboxamide |
| Hy1A-10 | N-((R)-1-(4-(ethylsulfonyl)phenyl)-2-hydroxyethyl)-3-methyl-1-(((1r,4R)-4-(trifluoromethyl)cyclohexyl)methoxy)isoquinoline-6-carboxamide |
| Hy1A-11 | 3-chloro-N-((R)-1-(4-(ethylsulfonyl)phenyl)-2-hydroxyethyl)-1-(((1r,4R)-4-(trifluoromethyl)cyclohexyl)methoxy)isoquinoline-6-carboxamide |
| Hy1A-12 | (R)-1-((3,3-difluorocyclobutyl)methoxy)-N-(1-(4-(ethylsulfonyl)phenyl)-2-hydroxyethyl)-3-methylisoquinoline-6-carboxamide |
| Hy1A-13 | (R)-N-(1-(4-(ethylsulfonyl)phenyl)-2-hydroxyethyl)-1-((4-fluorobenzyl)oxy)-3-methylisoquinoline-6-carboxamide |
| Hy1A-14 | (R)-1-((4,4-difluorocyclohexyl)methoxy)-N-(1-(4-(ethylsulfonyl)phenyl)-2-hydroxyethyl)-3-methylisoquinoline-6-carboxamide |
| Hy1A-15 | (R)-N-(1-(4-(ethylsulfonyl)phenyl)-2-hydroxyethyl)-3-methyl-1-(4-(trifluoromethoxy)phenoxy)isoquinoline-6-carboxamide |
| Hy1A-16 | N-((S)-1-(4-(ethylsulfonyl)phenyl)-2-hydroxyethyl)-3-methyl-1-(((1r,4S)-4-(trifluoromethyl)cyclohexyl)methoxy)isoquinoline-6-carboxamide |

-continued

Compounds Names[a]

| Cpd No | Name |
| --- | --- |
| Hy1A-17 | (R)-N-(1-(4-(ethylsulfonyl)phenyl)-2-hydroxyethyl)-3-methyl-1-((1-(2,2,2-trifluoroethyl)piperidin-4-yl)oxy)isoquinoline-6-carboxamide |
| Hy1A-18[b] | N-((R)-1-(4-(ethylsulfonyl)phenyl)-2-hydroxyethyl)-3-methyl-1-(((3S,6R)-6-(trifluoromethyl)tetrahydro-2H-pyran-3-yl)methoxy)isoquinoline-6-carboxamide |
| Hy1A-18.2[b] | N-((R)-1-(4-(ethylsulfonyl)phenyl)-2-hydroxyethyl)-3-methyl-1-(((3R,6S)-6-(trifluoromethyl)tetrahydro-2H-pyran-3-yl)methoxy)isoquinoline-6-carboxamide |
| Hy1A-18.3[b] | Mixture of N-((R)-1-(4-(ethylsulfonyl)phenyl)-2-hydroxyethyl)-3-methyl-1-(((3S,6S)-6-(trifluoromethyl)tetrahydro-2H-pyran-3-yl)methoxy)isoquinoline-6-carboxamide and N-((R)-1-(4-(ethylsulfonyl)phenyl)-2-hydroxyethyl)-3-methyl-1-(((3R,6R)-6-(trifluoromethyl)tetrahydro-2H-pyran-3-yl)methoxy)isoquinoline-6-carboxamide |
| Hy1A-19 | (R)-N-(1-(4-(ethylsulfonyl)phenyl)-2-hydroxyethyl)-3-methyl-1-((1-(2,2,2-trifluoroethyl)piperidin-4-yl)methoxy)isoquinoline-6-carboxamide |
| Hy1A-20 | 3-ethyl-N-(4-(ethylsulfonyl)benzyl)-1-(((1r,4r)-4-(trifluoromethyl)cyclohexyl)methoxy)isoquinoline-6-carboxamide |
| Hy1A-21 | 3-cyclopropyl-N-((R)-1-(4-(ethylsulfonyl)phenyl)-2-hydroxyethyl)-1-(((1r,4R)-4-(trifluoromethyl)cyclohexyl)methoxy)isoquinoline-6-carboxamide |
| Hy1A-22.1[c] | N-((R)-1-(5-(ethylsulfonyl)pyridin-2-yl)-2-hydroxyethyl)-3-methyl-1-(((1r,4R)-4-(trifluoromethyl)cyclohexyl)methoxy)isoquinoline-6-carboxamide |
| Hy1A-22.2[c] | N-((S)-1-(5-(ethylsulfonyl)pyridin-2-yl)-2-hydroxyethyl)-3-methyl-1-(((1r,4S)-4-(trifluoromethyl)cyclohexyl)methoxy)isoquinoline-6-carboxamide |
| Hy1A-23 | N-((R)-1-(4-(ethylsulfonyl)phenyl)-2-hydroxyethyl)-3-methoxy-1-(((1r,4R)-4-(trifluoromethyl)cyclohexyl)methoxy)isoquinoline-6-carboxamide |
| Hy1A-24 | (R)-N-(1-(4-(ethylsulfonyl)phenyl)-2-hydroxyethyl)-1-((4-(trifluoromethyl)phenoxy)methyl)isoquinoline-6-carboxamide |
| Hy1B-1 | N-(4-(ethylsulfonyl)benzyl)-2-methyl-4-((4-(trifluoromethyl)benzyl)oxy)quinoline-7-carboxamide |
| Hy1B-2 | N-(4-(ethylsulfonyl)benzyl)-2-methyl-4-(((1r,4r)-4-(trifluoromethyl)cyclohexyl)methoxy)quinoline-7-carboxamide |
| Hy1B-3 | (R)-N-(1-(4-(ethylsulfonyl)phenyl)-2-hydroxyethyl)-2-methyl-4-((4-(trifluoromethyl)benzyl)oxy)quinoline-7-carboxamide |
| Hy1B-4 | N-((R)-1-(4-(ethylsulfonyl)phenyl)-2-hydroxyethyl)-2-methyl-4-(((1r,4R)-4-(trifluoromethyl)cyclohexyl)methoxy)quinoline-7-carboxamide |
| Hy1C-1 | N-((R)-1-(4-(ethylsulfonyl)phenyl)-2-hydroxyethyl)-4-(((1r,4R)-4-(trifluoromethyl)cyclohexyl)methoxy)quinazoline-7-carboxamide |
| Hy1C-2 | N-(4-(ethylsulfonyl)benzyl)-4-(((1r,4r)-4-(trifluoromethyl)cyclohexyl)methoxy)quinazoline-7-carboxamide |
| Hy2A-1.1[d] | (R)-2-(5-cyanopyrimidin-2-yl)-N-(4-(ethylsulfonyl)benzyl)-1-isopropyl-1,2,3,4-tetrahydroisoquinoline-6-carboxamide |
| Hy2A-1.2[d] | (S)-2-(5-cyanopyrimidin-2-yl)-N-(4-(ethylsulfonyl)benzyl)-1-isopropyl-1,2,3,4-tetrahydroisoquinoline-6-carboxamide |
| Hy2A-2 | N-(4-(ethylsulfonyl)benzyl)-1-isopropyl-2-(5-(trifluoromethyl)pyrimidin-2-yl)-1,2,3,4-tetrahydroisoquinoline-6-carboxamide |
| Hy2A-3 | N-(4-(ethylsulfonyl)benzyl)-1-isopropyl-2-(4-(trifluoromethyl)pyrimidin-2-yl)-1,2,3,4-tetrahydroisoquinoline-6-carboxamide |
| Hy2A-4.1[e] | ethyl (S)-2-(6-((4-(ethylsulfonyl)benzyl)carbamoyl)-1-isopropyl-3,4-dihydroisoquinolin-2(1H)-yl)pyrimidine-5-carboxylate |
| Hy2A-4.2[e] | ethyl (R)-2-(6-((4-(ethylsulfonyl)benzyl)carbamoyl)-1-isopropyl-3,4-dihydroisoquinolin-2(1H)-yl)pyrimidine-5-carboxylate |
| Hy2A-5 | ethyl 2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate |
| Hy2A-5.1[f] | ethyl (S)-2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate |
| Hy2A-5.2[f] | ethyl (R)-2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate |
| Hy2A-6 | 2-(4-fluorobenzyl)-1-methyl-N-(4-(methylsulfonyl)benzyl)-1,2,3,4-tetrahydroisoquinoline-6-carboxamide |
| Hy2A-7 | 2-(4-cyanobenzyl)-1-methyl-N-(4-(methylsulfonyl)benzyl)-1,2,3,4-tetrahydroisoquinoline-6-carboxamide |
| Hy2A-8 | N-(4-(ethylsulfonyl)benzyl)-2-(4-fluorobenzyl)-1-methyl-1,2,3,4-tetrahydroisoquinoline-6-carboxamide |
| Hy2A-9 | 2-(4-chlorobenzyl)-1-methyl-N-(4-(methylsulfonyl)benzyl)-1,2,3,4-tetrahydroisoquinoline-6-carboxamide |
| Hy2A-10 | 2-(4-cyanobenzyl)-N-(4-(ethylsulfonyl)benzyl)-1-methyl-1,2,3,4-tetrahydroisoquinoline-6-carboxamide |
| Hy2A-11 | 2-(4-chlorobenzyl)-N-(4-(ethylsulfonyl)benzyl)-1-methyl-1,2,3,4-tetrahydroisoquinoline-6-carboxamide |

-continued

Compounds Names[a]

| Cpd No | Name |
|---|---|
| Hy2A-12.1[g] | (S)-N-(4-(ethylsulfonyl)benzyl)-1-isopropyl-2-((5-methylpyrimidin-2-yl)methyl)-1,2,3,4-tetrahydroisoquinoline-6-carboxamide |
| Hy2A-12.2[g] | (R)-N-(4-(ethylsulfonyl)benzyl)-1-isopropyl-2-((5-methylpyrimidin-2-yl)methyl)-1,2,3,4-tetrahydroisoquinoline-6-carboxamide |
| Hy2A-13 | N-(4-(ethylsulfonyl)benzyl)-2-(4-fluorobenzyl)-1-isopropyl-1,2,3,4-tetrahydroisoquinoline-6-carboxamide |
| Hy2A-14 | 2-(4-cyanobenzyl)-N-(4-(ethylsulfonyl)benzyl)-1-isopropyl-1,2,3,4-tetrahydroisoquinoline-6-carboxamide |
| Hy2A-15.1[h] | (S)-2-(4-cyanobenzyl)-N-(4-(ethylsulfonyl)benzyl)-1-isopropyl-1,2,3,4-tetrahydroisoquinoline-6-carboxamide |
| Hy2A-15.2[h] | (R)-2-(4-cyanobenzyl)-N-(4-(ethylsulfonyl)benzyl)-1-isopropyl-1,2,3,4-tetrahydroisoquinoline-6-carboxamide |
| Hy2A-16.1[i] | (S)-2-((5-cyanopyridin-2-yl)methyl)-N-(4-(ethylsulfonyl)benzyl)-1-isopropyl-1,2,3,4-tetrahydroisoquinoline-6-carboxamide |
| Hy2A-16.2[i] | (R)-2-((5-cyanopyridin-2-yl)methyl)-N-(4-(ethylsulfonyl)benzyl)-1-isopropyl-1,2,3,4-tetrahydroisoquinoline-6-carboxamide |
| Hy2A-17.1[j] | (S)-2-((6-cyanopyridin-3-yl)methyl)-N-(4-(ethylsulfonyl)benzyl)-1-isopropyl-1,2,3,4-tetrahydroisoquinoline-6-carboxamide |
| Hy2A-17.2[j] | (R)-2-((6-cyanopyridin-3-yl)methyl)-N-(4-(ethylsulfonyl)benzyl)-1-isopropyl-1,2,3,4-tetrahydroisoquinoline-6-carboxamide |
| Hy2A-18 | N-(1-(4-(ethylsulfonyl)phenyl)ethyl)-1-isopropyl-2-((5-methylpyrazin-2-yl)methyl)-1,2,3,4-tetrahydroisoquinoline-6-carboxamide |
| Hy2A-19 | 2-(4-chlorobenzyl)-N-(4-(ethylsulfonyl)benzyl)-1-isopropyl-1,2,3,4-tetrahydroisoquinoline-6-carboxamide |
| Hy2A-20.1[k] | (S)-2-(4-chlorobenzyl)-N-(4-(ethylsulfonyl)benzyl)-1-isopropyl-1,2,3,4-tetrahydroisoquinoline-6-carboxamide |
| Hy2A-20.2[k] | (R)-2-(4-chlorobenzyl)-N-(4-(ethylsulfonyl)benzyl)-1-isopropyl-1,2,3,4-tetrahydroisoquinoline-6-carboxamide |
| Hy2A-21 | 2-((5-chloropyridin-2-yl)methyl)-N-(4-(ethylsulfonyl)benzyl)-1-isopropyl-1,2,3,4-tetrahydroisoquinoline-6-carboxamide |
| Hy2A-22.1[l] | (S)-N-(4-(ethylsulfonyl)benzyl)-1-isopropyl-4,4-dimethyl-2-((5-methylpyrazin-2-yl)methyl)-1,2,3,4-tetrahydroisoquinoline-6-carboxamide |
| Hy2A-22.2[l] | (R)-N-(4-(ethylsulfonyl)benzyl)-1-isopropyl-4,4-dimethyl-2-((5-methylpyrazin-2-yl)methyl)-1,2,3,4-tetrahydroisoquinoline-6-carboxamide |
| Hy2A-23.1[m] | (S)-2-(4-cyanobenzyl)-N-(4-(ethylsulfonyl)benzyl)-1-isopropyl-4,4-dimethyl-1,2,3,4-tetrahydroisoquinoline-6-carboxamide |
| Hy2A-23.2[m] | (R)-2-(4-cyanobenzyl)-N-(4-(ethylsulfonyl)benzyl)-1-isopropyl-4,4-dimethyl-1,2,3,4-tetrahydroisoquinoline-6-carboxamide |
| Hy2A-24 | methyl (S)-4-((6-((4-(ethylsulfonyl)benzyl)carbamoyl)-1-isopropyl-3,4-dihydroisoquinolin-2(1H)-yl)methyl)piperidine-1-carboxylate |
| Hy2A-25.1[n] | (S)-2-((6-(difluoromethoxy)pyridin-3-yl)methyl)-N-(4-(ethylsulfonyl)benzyl)-1-isopropyl-1,2,3,4-tetrahydroisoquinoline-6-carboxamide |
| Hy2A-25.2[n] | (R)-2-((6-(difluoromethoxy)pyridin-3-yl)methyl)-N-(4-(ethylsulfonyl)benzyl)-1-isopropyl-1,2,3,4-tetrahydroisoquinoline-6-carboxamide |
| Hy2A-26.1[o] | (S)-2-((5-bromopyrimidin-2-yl)methyl)-N-(4-(ethylsulfonyl)benzyl)-1-isopropyl-1,2,3,4-tetrahydroisoquinoline-6-carboxamide |
| Hy2A-26.2[o] | (R)-2-((5-bromopyrimidin-2-yl)methyl)-N-(4-(ethylsulfonyl)benzyl)-1-isopropyl-1,2,3,4-tetrahydroisoquinoline-6-carboxamide |
| Hy2A-27 | (S)-1-ethyl-N-(4-(ethylsulfonyl)benzyl)-2-(((1r,4S)-4-(trifluoromethyl)cyclohexyl)methyl)-1,2,3,4-tetrahydroisoquinoline-6-carboxamide |
| Hy2A-28.1[p] | (S)-1-ethyl-N-((R)-1-(4-(ethylsulfonyl)phenyl)-2-hydroxyethyl)-2-(((1r,4S)-4-(trifluoromethyl)cyclohexyl)methyl)-1,2,3,4-tetrahydroisoquinoline-6-carboxamide |
| Hy2A-28.2[p] | (S)-1-ethyl-N-((S)-1-(4-(ethylsulfonyl)phenyl)-2-hydroxyethyl)-2-(((1r,4S)-4-(trifluoromethyl)cyclohexyl)methyl)-1,2,3,4-tetrahydroisoquinoline-6-carboxamide |
| Hy2A-28.3[p] | (R)-1-ethyl-N-((R)-1-(4-(ethylsulfonyl)phenyl)-2-hydroxyethyl)-2-(((1r,4R)-4-(trifluoromethyl)cyclohexyl)methyl)-1,2,3,4-tetrahydroisoquinoline-6-carboxamide |
| Hy2A-29.1[q] | (S)-1-ethyl-N-((R)-1-(5-(ethylsulfonyl)pyridin-2-yl)-2-hydroxyethyl)-2-(((1r,4S)-4-(trifluoromethyl)cyclohexyl)methyl)-1,2,3,4-tetrahydroisoquinoline-6-carboxamide |
| Hy2A-29.2[q] | (S)-1-ethyl-N-((S)-1-(5-(ethylsulfonyl)pyridin-2-yl)-2-hydroxyethyl)-2-(((1r,4R)-4-(trifluoromethyl)cyclohexyl)methyl)-1,2,3,4-tetrahydroisoquinoline-6-carboxamide |
| Hy2A-29.3[q] | (R)-1-ethyl-N-((R)-1-(5-(ethylsulfonyl)pyridin-2-yl)-2-hydroxyethyl)-2-(((1r,4R)-4-(trifluoromethyl)cyclohexyl)methyl)-1,2,3,4-tetrahydroisoquinoline-6-carboxamide |
| Hy2B-1.1[r] | (S)-7-(5-cyanopyrimidin-2-yl)-N-(4-(ethylsulfonyl)benzyl)-8-isopropyl-5,6,7,8-tetrahydro-1,7-naphthyridine-3-carboxamide |
| Hy2B-1.2[r] | (R)-7-(5-cyanopyrimidin-2-yl)-N-(4-(ethylsulfonyl)benzyl)-8-isopropyl-5,6,7,8-tetrahydro-1,7-naphthyridine-3-carboxamide |

-continued

Compounds Names[a]

| Cpd No | Name |
|---|---|
| Hy2B-2.1[s] | (S)-7-(5-chloropyrimidin-2-yl)-N-(4-(ethylsulfonyl)benzyl)-8-isopropyl-5,6,7,8-tetrahydro-1,7-naphthyridine-3-carboxamide |
| Hy2B-2.2[s] | (R)-7-(5-chloropyrimidin-2-yl)-N-(4-(ethylsulfonyl)benzyl)-8-isopropyl-5,6,7,8-tetrahydro-1,7-naphthyridine-3-carboxamide |
| Hy2B-3.1[t] | (S)-N-(4-(ethylsulfonyl)benzyl)-8-isopropyl-7-(5-(trifluoromethyl)pyrimidin-2-yl)-5,6,7,8-tetrahydro-1,7-naphthyridine-3-carboxamide |
| Hy2B-3.2[t] | (R)-N-(4-(ethylsulfonyl)benzyl)-8-isopropyl-7-(5-(trifluoromethyl)pyrimidin-2-yl)-5,6,7,8-tetrahydro-1,7-naphthyridine-3-carboxamide |
| Hy2B-4.1[u] | ethyl (R)-2-(3-((4-(ethylsulfonyl)benzyl)carbamoyl)-8-isopropyl-5,8-dihydro-1,7-naphthyridin-7(6H)-yl)pyrimidine-5-carboxylate |
| Hy2B-4.2[u] | ethyl (S)-2-(3-((4-(ethylsulfonyl)benzyl)carbamoyl)-8-isopropyl-5,8-dihydro-1,7-naphthyridin-7(6H)-yl)pyrimidine-5-carboxylate |
| Hy2B-5.1[v] | ethyl (R)-2-(3-((4-(ethylsulfonyl)benzyl)carbamoyl)-8-isopropyl-5,8-dihydro-1,7-naphthyridin-7(6H)-yl)-4-(trifluoromethyl)pyrimidine-5-carboxylate |
| Hy2B-5.2[v] | ethyl (S)-2-(3-((4-(ethylsulfonyl)benzyl)carbamoyl)-8-isopropyl-5,8-dihydro-1,7-naphthyridin-7(6H)-yl)-4-(trifluoromethyl)pyrimidine-5-carboxylate |
| Hy2B-6.1[w] | rel-(R)-N-(4-(ethylsulfonyl)benzyl)-7-(4-fluorobenzyl)-8-isopropyl-5,6,7,8-tetrahydro-1,7-naphthyridine-3-carboxamide |
| Hy2B-6.2[w] | rel-(R)-N-(4-(ethylsulfonyl)benzyl)-7-(4-fluorobenzyl)-8-isopropyl-5,6,7,8-tetrahydro-1,7-naphthyridine-3-carboxamide |
| Hy2B-7.1[x] | rel-(R)-7-(4-cyanobenzyl)-N-(4-(ethylsulfonyl)benzyl)-8-isopropyl-5,6,7,8-tetrahydro-1,7-naphthyridine-3-carboxamide |
| Hy2B-7.2[x] | rel-(R)-7-(4-cyanobenzyl)-N-(4-(ethylsulfonyl)benzyl)-8-isopropyl-5,6,7,8-tetrahydro-1,7-naphthyridine-3-carboxamide |
| Hy2B-8.1[y] | rel-(R)-7-(4-chlorobenzyl)-N-(4-(ethylsulfonyl)benzyl)-8-isopropyl-5,6,7,8-tetrahydro-1,7-naphthyridine-3-carboxamide |
| Hy2B-8.2[y] | rel-(R)-7-(4-chlorobenzyl)-N-(4-(ethylsulfonyl)benzyl)-8-isopropyl-5,6,7,8-tetrahydro-1,7-naphthyridine-3-carboxamide |
| Hy2B-9.1[z] | (S)-N-(4-(ethylsulfonyl)benzyl)-8-isopropyl-7-(((1r,4S)-4-(trifluoromethyl)cyclohexyl)methyl)-5,6,7,8-tetrahydro-1,7-naphthyridine-3-carboxamide |
| Hy2B-9.2[z] | (R)-N-(4-(ethylsulfonyl)benzyl)-8-isopropyl-7-(((1r,4R)-4-(trifluoromethyl)cyclohexyl)methyl)-5,6,7,8-tetrahydro-1,7-naphthyridine-3-carboxamide |
| Hy2B-10.1[aa] | (S)-N-((5-(ethylsulfonyl)pyridin-2-yl)methyl)-8-isopropyl-7-(((1r,4S)-4-(trifluoromethyl)cyclohexyl)methyl)-5,6,7,8-tetrahydro-1,7-naphthyridine-3-carboxamide |
| Hy2B-10.2[aa] | (R)-N-((5-(ethylsulfonyl)pyridin-2-yl)methyl)-8-isopropyl-7-(((1r,4R)-4-(trifluoromethyl)cyclohexyl)methyl)-5,6,7,8-tetrahydro-1,7-naphthyridine-3-carboxamide |
| Hy3A-1 | 3-cyclopropyl-N-((R)-1-(4-(ethylsulfonyl)phenyl)-2-hydroxyethyl)-2-(((1r,4R)-4-(trifluoromethyl)cyclohexyl)methyl)-2H-indazole-6-carboxamide |
| Hy3A-2 | 3-cyclopropyl-N-(4-(ethylsulfonyl)benzyl)-2-(((1r,4r)-4-(trifluoromethyl)cyclohexyl)methyl)-2H-indazole-6-carboxamide |
| Hy3A-3 | 3-cyclopropyl-N-((5-(ethylsulfonyl)pyridin-2-yl)methyl)-2-(((1r,4r)-4-(trifluoromethyl)cyclohexyl)methyl)-2H-indazole-6-carboxamide |
| Hy3A-4 | (R)-3-cyclopropyl-N-(1-(4-(ethylsulfonyl)phenyl)-2-hydroxyethyl)-2-(4-(trifluoromethyl)benzyl)-2H-indazole-6-carboxamide |
| Hy3A-5 | 3-ethyl-N-((R)-1-(4-(ethylsulfonyl)phenyl)-2-hydroxyethyl)-2-(((1r,4R)-4-(trifluoromethyl)cyclohexyl)methyl)-2H-indazole-6-carboxamide |
| Hy3A-6 | 3-cyclopropyl-N-((R)-1-(5-(ethylsulfonyl)pyridin-2-yl)-2-hydroxyethyl)-2-(((1r,4R)-4-(trifluoromethyl)cyclohexyl)methyl)-2H-indazole-6-carboxamide |
| Hy3A-7 | (R)-3-cyclopropyl-N-(1-(5-(ethylsulfonyl)pyridin-2-yl)-2-hydroxyethyl)-2-(4-(trifluoromethyl)benzyl)-2H-indazole-6-carboxamide |
| Hy3B-1 | 3-cyclopropyl-N-((R)-1-(4-(ethylsulfonyl)phenyl)-2-hydroxyethyl)-2-(((1r,4R)-4-(trifluoromethyl)cyclohexyl)methyl)-2H-pyrazolo[4,3-b]pyridine-6-carboxamide |
| Hy3B-2 | 3-cyclopropyl-N-(4-(ethylsulfonyl)benzyl)-2-(((1r,4r)-4-(trifluoromethyl)cyclohexyl)methyl)-2H-pyrazolo[4,3-b]pyridine-6-carboxamide |
| Hy3B-3 | 3-cyclopropyl-N-((5-(ethylsulfonyl)pyridin-2-yl)methyl)-2-(((1r,4r)-4-(trifluoromethyl)cyclohexyl)methyl)-2H-pyrazolo[4,3-b]pyridine-6-carboxamide |
| Hy3B-4 | 3-cyclopropyl-N-((R)-1-(5-(ethylsulfonyl)pyridin-2-yl)-2-hydroxyethyl)-2-(((1r,4R)-4-(trifluoromethyl)cyclohexyl)methyl)-2H-pyrazolo[4,3-b]pyridine-6-carboxamide |
| Hy4-1 | N-(4-(ethylsulfonyl)benzyl)-1-methyl-7-(((1r,4r)-4-(trifluoromethyl)cyclohexyl)methoxy)-1H-pyrrolo[2,3-c]pyridine-2-carboxamide |

-continued

Compounds Names[a]

| Cpd No | Name |
|---|---|
| Hy4-2 | N-((R)-1-(4-(ethylsulfonyl)phenyl)-2-hydroxyethyl)-1-methyl-7-(((1r,4R)-4-(trifluoromethyl)cyclohexyl)methoxy)-1H-pyrrolo[2,3-c]pyridine-2-carboxamide |
| Hy4-3 | N-(4-(ethylsulfonyl)benzyl)-1-methyl-7-((4-(trifluoromethyl)benzyl)oxy)-1H-pyrrolo[2,3-c]pyridine-2-carboxamide |
| Hy4-4 | (R)-N-(1-(4-(ethylsulfonyl)phenyl)-2-hydroxyethyl)-1-methyl-7-((4-(trifluoromethyl)benzyl)oxy)-1H-pyrrolo[2,3-c]pyridine-2-carboxamide |
| Hy4-5 | N-(4-(ethylsulfonyl)benzyl)-7-(((1r,4r)-4-(trifluoromethyl)cyclohexyl)methoxy)-1H-pyrrolo[2,3-c]pyridine-2-carboxamide |
| Hy5-1 | N-(4-(ethylsulfonyl)benzyl)-1-methyl-7-(4-(trifluoromethyl)phenoxy)-1H-pyrrolo[2,3-c]pyridine-3-carboxamide |
| Hy5-2 | N-(4-(ethylsulfonyl)benzyl)-7-(((1r,4r)-4-(trifluoromethyl)cyclohexyl)methoxy)-1H-pyrrolo[2,3-c]pyridine-3-carboxamide |
| Hy5-3 | N-(4-(ethylsulfonyl)benzyl)-1-methyl-7-((4-(trifluoromethyl)benzyl)oxy)-1H-pyrrolo[2,3-c]pyridine-3-carboxamide |
| Hy5-4 | N-(4-(ethylsulfonyl)benzyl)-1-methyl-7-(((1r,4r)-4-(trifluoromethyl)cyclohexyl)methoxy)-1H-pyrrolo[2,3-c]pyridine-3-carboxamide |
| Hy5-5 | N-((R)-1-(4-(ethylsulfonyl)phenyl)-2-hydroxyethyl)-1-methyl-7-(((1r,4R)-4-(trifluoromethyl)cyclohexyl)methoxy)-1H-pyrrolo[2,3-c]pyridine-3-carboxamide |
| Hy6-1 | N-(4-(ethylsulfonyl)benzyl)-2,5-dimethyl-4-((4-(trifluoromethyl)benzyl)oxy)thieno[2,3-d]pyrimidine-6-carboxamide |
| Hy6-2 | N-(4-(ethylsulfonyl)benzyl)-2,5-dimethyl-4-(((1r,4r)-4-(trifluoromethyl)cyclohexyl)methoxy)thieno[2,3-d]pyrimidine-6-carboxamide |
| Hy6-3 | (R)-N-(1-(4-(ethylsulfonyl)phenyl)-2-hydroxyethyl)-2,5-dimethyl-4-((4-(trifluoromethyl)benzyl)oxy)thieno[2,3-d]pyrimidine-6-carboxamide |
| Hy6-4 | N-((R)-1-(4-(ethylsulfonyl)phenyl)-2-hydroxyethyl)-2,5-dimethyl-4-(((1r,4R)-4-(trifluoromethyl)cyclohexyl)methoxy)thieno[2,3-d]pyrimidine-6-carboxamide |
| Hy7-1.1[bb] | (S)-N-(4-(ethylsulfonyl)benzyl)-2-(5-fluoropyrimidin-2-yl)-4-isopropyl-1,2,3,4-tetrahydroisoquinoline-7-carboxamide |
| Hy7-1.2[bb] | (R)-N-(4-(ethylsulfonyl)benzyl)-2-(5-fluoropyrimidin-2-yl)-4-isopropyl-1,2,3,4-tetrahydroisoquinoline-7-carboxamide |
| Hy7-2.1[cc] | (S)-2-(5-cyanopyrimidin-2-yl)-N-(4-(ethylsulfonyl)benzyl)-4-isopropyl-1,2,3,4-tetrahydroisoquinoline-7-carboxamide |
| Hy7-2.2[cc] | (R)-2-(5-cyanopyrimidin-2-yl)-N-(4-(ethylsulfonyl)benzyl)-4-isopropyl-1,2,3,4-tetrahydroisoquinoline-7-carboxamide |
| Hy7-3.1[dd] | (S)-2-(5-chloropyrimidin-2-yl)-N-(4-(ethylsulfonyl)benzyl)-4-isopropyl-1,2,3,4-tetrahydroisoquinoline-7-carboxamide |
| Hy7-3.2[dd] | (R)-2-(5-chloropyrimidin-2-yl)-N-(4-(ethylsulfonyl)benzyl)-4-isopropyl-1,2,3,4-tetrahydroisoquinoline-7-carboxamide |
| Hy7-4.1[ee] | (S)-2-(5-cyclopropylpyrimidin-2-yl)-N-(4-(ethylsulfonyl)benzyl)-4-isopropyl-1,2,3,4-tetrahydroisoquinoline-7-carboxamide |
| Hy7-4.2[ee] | (R)-2-(5-cyclopropylpyrimidin-2-yl)-N-(4-(ethylsulfonyl)benzyl)-4-isopropyl-1,2,3,4-tetrahydroisoquinoline-7-carboxamide |
| Hy7-5.1[ff] | (S)-2-(5-ethoxypyrimidin-2-yl)-N-(4-(ethylsulfonyl)benzyl)-4-isopropyl-1,2,3,4-tetrahydroisoquinoline-7-carboxamide |
| Hy7-5.2[ff] | (R)-2-(5-ethoxypyrimidin-2-yl)-N-(4-(ethylsulfonyl)benzyl)-4-isopropyl-1,2,3,4-tetrahydroisoquinoline-7-carboxamide |
| Hy7-6.1[gg] | (S)-2-(5-chloropyrimidin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7-6.2[gg] | (R)-2-(5-chloropyrimidin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7-7.1[hh] | (S)-4-ethyl-N-(4-(ethylsulfonyl)benzyl)-2-(4-(trifluoromethyl)phenyl)-1,2,3,4-tetrahydroisoquinoline-7-carboxamide |
| Hy7-7.2[hh] | (R)-4-ethyl-N-(4-(ethylsulfonyl)benzyl)-2-(4-(trifluoromethyl)phenyl)-1,2,3,4-tetrahydroisoquinoline-7-carboxamide |
| Hy7-8.1[ii] | (S)-4-ethyl-N-(4-(ethylsulfonyl)benzyl)-2-(5-(trifluoromethyl)pyridin-2-yl)-1,2,3,4-tetrahydroisoquinoline-7-carboxamide |
| Hy7-8.2[ii] | (R)-4-ethyl-N-(4-(ethylsulfonyl)benzyl)-2-(5-(trifluoromethyl)pyridin-2-yl)-1,2,3,4-tetrahydroisoquinoline-7-carboxamide |
| Hy7-9.1[jj] | (S)-4-ethyl-N-(4-(ethylsulfonyl)benzyl)-2-(5-(trifluoromethyl)pyrimidin-2-yl)-1,2,3,4-tetrahydroisoquinoline-7-carboxamide |
| Hy7-9.2[jj] | (R)-4-ethyl-N-(4-(ethylsulfonyl)benzyl)-2-(5-(trifluoromethyl)pyrimidin-2-yl)-1,2,3,4-tetrahydroisoquinoline-7-carboxamide |
| Hy7-10.1[kk] | (R)-4-ethyl-N-((5-(ethylsulfonyl)pyridin-2-yl)methyl)-2-(5-(trifluoromethyl)pyrimidin-2-yl)-1,2,3,4-tetrahydroisoquinoline-7-carboxamide |

-continued

| Cpd No | Name |
|---|---|
| Hy7-10.2[kk] | (S)-4-ethyl-N-((5-(ethylsulfonyl)pyridin-2-yl)methyl)-2-(5-(trifluoromethyl)pyrimidin-2-yl)-1,2,3,4-tetrahydroisoquinoline-7-carboxamide |
| Hy7-11.1[ll] | (S)-2-(5-cyclopropylpyrimidin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7-11.2[ll] | (R)-2-(5-cyclopropylpyrimidin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7-12.1[mm] | (S)-4-ethyl-N-(4-(ethylsulfonyl)benzyl)-1-oxo-2-(4-(trifluoromethyl)phenyl)-1,2,3,4-tetrahydroisoquinoline-7-carboxamide |
| Hy7-12.2[mm] | (R)-4-ethyl-N-(4-(ethylsulfonyl)benzyl)-1-oxo-2-(4-(trifluoromethyl)phenyl)-1,2,3,4-tetrahydroisoquinoline-7-carboxamide |
| Hy7-13.1[nn] | (S)-4-ethyl-N-(4-(ethylsulfonyl)benzyl)-2-(3-methyl-5-(trifluoromethyl)pyridin-2-yl)-1,2,3,4-tetrahydroisoquinoline-7-carboxamide |
| Hy7-13.2[nn] | (R)-4-ethyl-N-(4-(ethylsulfonyl)benzyl)-2-(3-methyl-5-(trifluoromethyl)pyridin-2-yl)-1,2,3,4-tetrahydroisoquinoline-7-carboxamide |
| Hy7-14.1[oo] | (S)-N-(4-(ethylsulfonyl)benzyl)-4-isopropyl-2-(4-(trifluoromethyl)pyrimidin-2-yl)-1,2,3,4-tetrahydroisoquinoline-7-carboxamide |
| Hy7-14.2[oo] | (R)-N-(4-(ethylsulfonyl)benzyl)-4-isopropyl-2-(4-(trifluoromethyl)pyrimidin-2-yl)-1,2,3,4-tetrahydroisoquinoline-7-carboxamide |
| Hy7-15.1[pp] | (S)-N-(4-(ethylsulfonyl)benzyl)-4-isopropyl-2-(5-(trifluoromethyl)pyrimidin-2-yl)-1,2,3,4-tetrahydroisoquinoline-7-carboxamide |
| Hy7-15.2[pp] | (R)-N-(4-(ethylsulfonyl)benzyl)-4-isopropyl-2-(5-(trifluoromethyl)pyrimidin-2-yl)-1,2,3,4-tetrahydroisoquinoline-7-carboxamide |
| Hy7-16.1[qq] | ethyl (S)-2-(7-((4-(ethylsulfonyl)benzyl)carbamoyl)-4-isopropyl-3,4-dihydroisoquinolin-2(1H)-yl)pyrimidine-5-carboxylate |
| Hy7-16.2[qq] | ethyl (R)-2-(7-((4-(ethylsulfonyl)benzyl)carbamoyl)-4-isopropyl-3,4-dihydroisoquinolin-2(1H)-yl)pyrimidine-5-carboxylate |
| Hy7-17.1[rr] | (S)-4-ethyl-N-((R)-1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide |
| Hy7-17.2[rr] | (R)-4-ethyl-N-((R)-1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide |
| Hy7-18.1[ss] | (S)-4-ethyl-N-((R)-1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide |
| Hy7-18.2[ss] | (S)-4-ethyl-N-((S)-1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide |
| Hy7-18.3[ss] | (R)-4-ethyl-N-((R)-1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide |
| Hy7-18.4[ss] | (R)-4-ethyl-N-((S)-1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide |
| Hy7-19.1[tt] | (S)-N-(4-(ethylsulfonyl)benzyl)-4-isopropyl-2-(5-morpholinopyrimidin-2-yl)-1,2,3,4-tetrahydroisoquinoline-7-carboxamide |
| Hy7-19.2[tt] | (R)-N-(4-(ethylsulfonyl)benzyl)-4-isopropyl-2-(5-morpholinopyrimidin-2-yl)-1,2,3,4-tetrahydroisoquinoline-7-carboxamide |
| Hy7-20.1[uu] | (S)-4-ethyl-N-(4-(ethylsulfonyl)benzyl)-2-(5-(6-methoxypyridin-2-yl)pyrimidin-2-yl)-1,2,3,4-tetrahydroisoquinoline-7-carboxamide |
| Hy7-20.2[uu] | (R)-4-ethyl-N-(4-(ethylsulfonyl)benzyl)-2-(5-(6-methoxypyridin-2-yl)pyrimidin-2-yl)-1,2,3,4-tetrahydroisoquinoline-7-carboxamide |
| Hy7-21.1[vv] | (S)-N-(4-(ethylsulfonyl)benzyl)-4-isopropyl-2-(5-(6-oxo-1,6-dihydropyridin-3-yl)pyrimidin-2-yl)-1,2,3,4-tetrahydroisoquinoline-7-carboxamide |
| Hy7-21.2[vv] | (R)-N-(4-(ethylsulfonyl)benzyl)-4-isopropyl-2-(5-(6-oxo-1,6-dihydropyridin-3-yl)pyrimidin-2-yl)-1,2,3,4-tetrahydroisoquinoline-7-carboxamide |
| Hy7-22.1[ww] | (S)-4-ethyl-N-((R)-1-(4-(ethylsulfonyl)phenyl)-2-hydroxyethyl)-2-(3-methyl-5-(trifluoromethyl)pyridin-2-yl)-1,2,3,4-tetrahydroisoquinoline-7-carboxamide |
| Hy7-22.2[ww] | (R)-4-ethyl-N-((R)-1-(4-(ethylsulfonyl)phenyl)-2-hydroxyethyl)-2-(3-methyl-5-(trifluoromethyl)pyridin-2-yl)-1,2,3,4-tetrahydroisoquinoline-7-carboxamide |
| Hy7-23.1[xx] | (S)-N-(4-(ethylsulfonyl)benzyl)-4-isopropyl-2-(5-(2-methoxypyridin-4-yl)pyrimidin-2-yl)-1,2,3,4-tetrahydroisoquinoline-7-carboxamide |

| Cpd No | Name |
|---|---|
| Hy7-23.2[xx] | (R)-N-(4-(ethylsulfonyl)benzyl)-4-isopropyl-2-(5-(2-methoxypyridin-4-yl)pyrimidin-2-yl)-1,2,3,4-tetrahydroisoquinoline-7-carboxamide |
| Hy7-24.1[yy] | (S)-N-(4-(ethylsulfonyl)benzyl)-4-isopropyl-2-(5-(1-methyl-6-oxo-1,6-dihydropyridin-3-yl)pyrimidin-2-yl)-1,2,3,4-tetrahydroisoquinoline-7-carboxamide |
| Hy7-24.2[yy] | (R)-N-(4-(ethylsulfonyl)benzyl)-4-isopropyl-2-(5-(1-methyl-6-oxo-1,6-dihydropyridin-3-yl)pyrimidin-2-yl)-1,2,3,4-tetrahydroisoquinoline-7-carboxamide |
| Hy7-25.1[zz] | (S)-N-(4-(ethylsulfonyl)benzyl)-4-isopropyl-2-(5-(1-methyl-2-oxo-1,2-dihydropyridin-4-yl)pyrimidin-2-yl)-1,2,3,4-tetrahydroisoquinoline-7-carboxamide |
| Hy7-25.2[zz] | (R)-N-(4-(ethylsulfonyl)benzyl)-4-isopropyl-2-(5-(1-methyl-2-oxo-1,2-dihydropyridin-4-yl)pyrimidin-2-yl)-1,2,3,4-tetrahydroisoquinoline-7-carboxamide |
| Hy7-26.1[aaa] | ethyl (S)-2-(7-((4-(ethylsulfonyl)benzyl)carbamoyl)-4-isopropyl-3,4-dihydroisoquinolin-2(1H)-yl)-4-(trifluoromethyl)pyrimidine-5-carboxylate |
| Hy7-26.2[aaa] | ethyl (R)-2-(7-((4-(ethylsulfonyl)benzyl)carbamoyl)-4-isopropyl-3,4-dihydroisoquinolin-2(1H)-yl)-4-(trifluoromethyl)pyrimidine-5-carboxylate |
| Hy7-27.1[bbb] | (S)-N-(4-(ethylsulfonyl)benzyl)-2-(4-fluorobenzyl)-4-isopropyl-1,2,3,4-tetrahydroisoquinoline-7-carboxamide |
| Hy7-27.2[bbb] | (R)-N-(4-(ethylsulfonyl)benzyl)-2-(4-fluorobenzyl)-4-isopropyl-1,2,3,4-tetrahydroisoquinoline-7-carboxamide |
| Hy7-28.1[ccc] | (S)-2-(4-cyanobenzyl)-N-(4-(ethylsulfonyl)benzyl)-4-isopropyl-1,2,3,4-tetrahydroisoquinoline-7-carboxamide |
| Hy7-28.2[ccc] | (R)-2-(4-cyanobenzyl)-N-(4-(ethylsulfonyl)benzyl)-4-isopropyl-1,2,3,4-tetrahydroisoquinoline-7-carboxamide |
| Hy7-29.1[ddd] | (S)-2-(4-chlorobenzyl)-N-(4-(ethylsulfonyl)benzyl)-4-isopropyl-1,2,3,4-tetrahydroisoquinoline-7-carboxamide |
| Hy7-29.2[ddd] | (R)-2-(4-chlorobenzyl)-N-(4-(ethylsulfonyl)benzyl)-4-isopropyl-1,2,3,4-tetrahydroisoquinoline-7-carboxamide |
| Hy7-30.1[eee] | (S)-4-ethyl-N-((R)-1-(4-(ethylsulfonyl)phenyl)-2-hydroxyethyl)-2-(tetrahydro-2H-pyran-4-yl)-1,2,3,4-tetrahydroisoquinoline-7-carboxamide |
| Hy7-30.2[eee] | (R)-4-ethyl-N-((R)-1-(4-(ethylsulfonyl)phenyl)-2-hydroxyethyl)-2-(tetrahydro-2H-pyran-4-yl)-1,2,3,4-tetrahydroisoquinoline-7-carboxamide |
| Hy7-31.1[fff] | (S)-4-ethyl-N-(4-(ethylsulfonyl)benzyl)-2-(5-(oxazol-2-yl)pyrimidin-2-yl)-1,2,3,4-tetrahydroisoquinoline-7-carboxamide |
| Hy7-31.2[fff] | (R)-4-ethyl-N-(4-(ethylsulfonyl)benzyl)-2-(5-(oxazol-2-yl)pyrimidin-2-yl)-1,2,3,4-tetrahydroisoquinoline-7-carboxamide |
| Hy7-32.1[ggg] | (S)-2-(4,4-difluorocyclohexyl)-4-ethyl-N-((R)-1-(4-(ethylsulfonyl)phenyl)-2-hydroxyethyl)-1,2,3,4-tetrahydroisoquinoline-7-carboxamide |
| Hy7-32.2[ggg] | (R)-2-(4,4-difluorocyclohexyl)-4-ethyl-N-((R)-1-(4-(ethylsulfonyl)phenyl)-2-hydroxyethyl)-1,2,3,4-tetrahydroisoquinoline-7-carboxamide |
| Hy7-33.1[hhh] | (S)-4-ethyl-N-((R)-1-(4-(ethylsulfonyl)phenyl)-2-hydroxyethyl)-2-(5-(oxazol-2-yl)pyrimidin-2-yl)-1,2,3,4-tetrahydroisoquinoline-7-carboxamide and |
| Hy7-33.2[hhh] | (R)-4-ethyl-N-((R)-1-(4-(ethylsulfonyl)phenyl)-2-hydroxyethyl)-2-(5-(oxazol-2-yl)pyrimidin-2-yl)-1,2,3,4-tetrahydroisoquinoline-7-carboxamide |
| Hy7-34.1[iii] | ethyl 2-((S)-4-ethyl-7-(((R)-1-(4-(ethylsulfonyl)phenyl)-2-hydroxyethyl)carbamoyl)-3,4-dihydroisoquinolin-2(1H)-yl)pyrimidine-5-carboxylate |
| Hy7-34.2[iii] | ethyl 2-((R)-4-ethyl-7-(((R)-1-(4-(ethylsulfonyl)phenyl)-2-hydroxyethyl)carbamoyl)-3,4-dihydroisoquinolin-2(1H)-yl)pyrimidine-5-carboxylate |
| Hy7-35.1[jjj] | (S)-4-ethyl-N-((R)-1-(4-(ethylsulfonyl)phenyl)-2-hydroxyethyl)-2-((1r,4S)-4-(trifluoromethyl)cyclohexyl)-1,2,3,4-tetrahydroisoquinoline-7-carboxamide |
| Hy7-35.2[jjj] | (S)-4-ethyl-N-((R)-1-(4-(ethylsulfonyl)phenyl)-2-hydroxyethyl)-2-((1s,4R)-4-(trifluoromethyl)cyclohexyl)-1,2,3,4-tetrahydroisoquinoline-7-carboxamide |
| Hy7-35.3[jjj] | (R)-4-ethyl-N-((R)-1-(4-(ethylsulfonyl)phenyl)-2-hydroxyethyl)-2-((1r,4R)-4-(trifluoromethyl)cyclohexyl)-1,2,3,4-tetrahydroisoquinoline-7-carboxamide |
| Hy7-35.4[jjj] | (R)-4-ethyl-N-((R)-1-(4-(ethylsulfonyl)phenyl)-2-hydroxyethyl)-2-((1s,4S)-4-(trifluoromethyl)cyclohexyl)-1,2,3,4-tetrahydroisoquinoline-7-carboxamide |
| Hy7-36.1[kkk] | (S)-N-(4-(ethylsulfonyl)benzyl)-4-(trifluoromethyl)-2-(5-(trifluoromethyl)pyrimidin-2-yl)-1,2,3,4-tetrahydroisoquinoline-7-carboxamide |
| Hy7-36.2[kkk] | (R)-N-(4-(ethylsulfonyl)benzyl)-4-(trifluoromethyl)-2-(5-(trifluoromethyl)pyrimidin-2-yl)-1,2,3,4-tetrahydroisoquinoline-7-carboxamide |

-continued

Compounds Names[a]

| Cpd No | Name |
|---|---|
| Hy7-37.1[III] | (S)-2-(3-cyano-5-(trifluoromethyl)pyridin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7-37.2[III] | (R)-2-(3-cyano-5-(trifluoromethyl)pyridin-2-yl)-4-ethyl-N-((R)-1-(4-(ethylsulfonyl)phenyl)-2-hydroxyethyl)-1,2,3,4-tetrahydroisoquinoline-7-carboxamide |
| Hy7B-1 | N-(4-(ethylsulfonyl)benzyl)-8,8-dimethyl-6-(5-(trifluoromethyl)pyrimidin-2-yl)-5,6,7,8-tetrahydro-1,6-naphthyridine-3-carboxamide | a, b, c, d, e, f, g, h, i, j, k, l, m, n, o, p, q, r, s, t, u, v, w, x, y, z, aa, bb, cc, dd, ee, ff, gg, hh, ii, jj, kk, ll, mm, nn, oo, pp, qq, rr, ss, tt, uu, vv, ww, xx, yy, z, aaa, bbb, ccc, ddd, eee, fff, ggg, hhh, iii, jjj, kkk, ll=isomer mixtures were separated by chromatography. Unknown stereocenters were assigned arbitrarily when naming the compounds.

LC-MS Methods

Method 1

HPLC System: Waters ACQUITY

Column: Waters ACQUITY CSH™ C18 1.7 uM

Guard column: Waters Assy. Frit, 0.2 uM, 2.1 mm.

Column tem: 40° C.

Mobile Phase: A: TFA:Water (1:1000, v:v)

B: TFA:ACN (1:1000, v:v)

Gradient Program:

| Time (min) | B % |
|---|---|
| 0 | 5 |
| 1.9 | 95 |
| 2.20 | 95 |
| 2.21 | 5 |

Flow Rate: 0.65 mL/min

Mass Spectrometer Parameters

| Mass Spectrometer | Waters SQD | |
|---|---|---|
| Ionization | Positive Electrospray Ionization (ESI) | |
| Mode | Scan (100-1400 m/z in every 0.2 second) | |
| ES Capilary Voltage: | 3.5 kv | |
| ES Cone Voltage: | 25 v | |
| Source Temperature | 120° C. | |
| Disolvation Temperature: | 500° C. | |
| Desolvation Gas Flow: | Nitrogen | Setting 650 (L/hr) |
| Cone Gas Flow: | Nitrogen | Setting 50 (L/hr) |

Method 2

5-95AB_1.5MIN

| Column | MERCK, RP-18e 25-2 mm |
|---|---|
| Mobile Phase | A: water(4 L) + TFA(1.5 mL)<br>B: acetonitrile(4 L) + TFA(0.75 mL) |

| TIME(min) | B % |
|---|---|
| 0 | 5 |
| 0.7 | 95 |
| 1.1 | 95 |
| 1.11 | 5 |
| 1.5 | 5 |

5-95AB_1.5MIN

| Flow Rate | 1.5 mL/min |
|---|---|
| wavelength | UV 220 nm |
| Oven Temp | 50° C. |
| MS ionization | ESI |

10-80CD_3MIN

| Column | Xtimate C18 2.1*30 mm, 3 um |
|---|---|
| Mobile Phase | A: water(1 L) + NH3H2O(0.5 mL)<br>B: acetonitrile |

| TIME(min) | B % |
|---|---|
| 0 | 10 |
| 2 | 80 |
| 2.48 | 80 |
| 2.49 | 10 |
| 3 | 10 |

| Flow Rate | 1.0 mL/min |
|---|---|
| wavelength | UV 220 nm&254 nm |
| Oven Temp | 30° C. |
| MS ionization | ESI |

10-80AB_2MIN

| Column | Xtimate C18 2.1*30 mm, 3 um |
|---|---|
| Mobile Phase | A: water(4 L) + TFA(1.5 mL)<br>B: acetonitrile(4 L) + TFA(0.75 mL) |

| TIME(min) | B % |
|---|---|
| 0 | 10 |
| 0.9 | 80 |
| 1.5 | 80 |
| 1.51 | 10 |
| 2 | 10 |

| Flow Rate | 1.2 mL/min |
|---|---|
| wavelength | UV 220 nm |
| Oven Temp | 50° C. |

10-80AB_2MIN

| Column | XBridge Shield RP18 2.1*50 mm |
|---|---|
| Mobile Phase | A: water(4 L) + TFA(1.5 mL)<br>B: acetonitrile(4 L) + TFA(0.75 mL) |

| 10-80AB_2MIN | |
|---|---|
| TIME(min) | B % |
| 0 | 10 |
| 0.9 | 80 |
| 1.5 | 80 |
| 1.51 | 10 |
| 2 | 10 |
| Flow Rate | 1.2 mL/min |
| wavelength | UV 220 nm |
| Oven Temp | 50° C. |

| 5-95AB_1.5MIN | |
|---|---|
| Column | YMC-Pack ODS-AQ |
| Mobile Phase | A: water(4 L) + TFA(1.5 mL) |
| | B: acetonitrile(4 L) + TFA(0.75 mL) |
| TIME(min) | B % |
| 0 | 5 |
| 0.7 | 95 |
| 1.1 | 95 |
| 1.11 | 5 |
| 1.5 | 5 |
| Flow Rate | 1.5 mL/min |
| wavelength | UV 220 nm |
| Oven Temp | 50° C. |
| MS ionization | ESI |

Preparation of Intermediates

Preparation 1A: (R)-2-amino-2-(4-(ethylsulfonyl)phenyl)ethanol

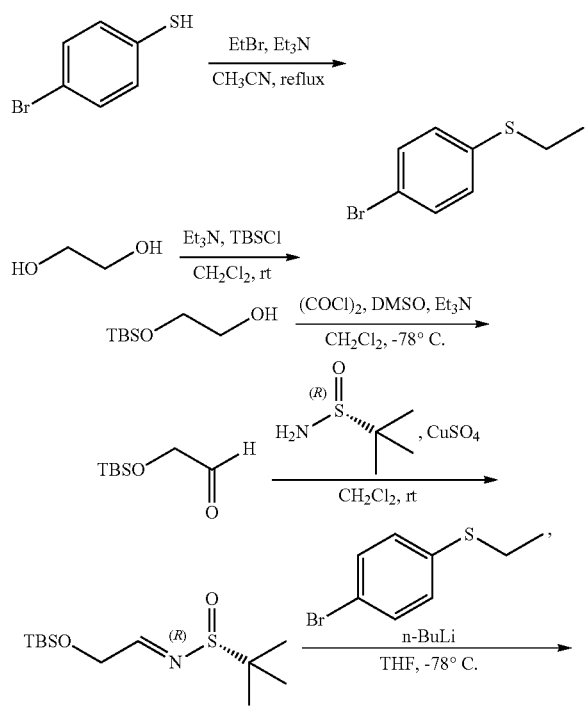

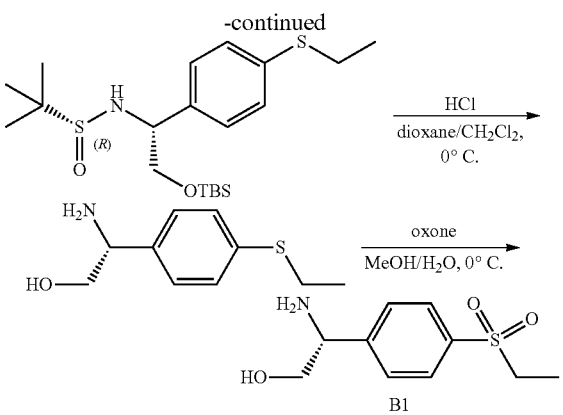

Step 1: (4-bromophenyl)(ethyl)sulfane

A mixture of 4-bromobenzenethiol (50 g, 0.26 mol), bromoethane (58 g, 0.53 mol) and triethylamine (78 g, 0.78 mol) in acetonitrile (1 L) was stirred at reflux for 17 h. The mixture was cooled to rt and filtered. The filtrate was concentrated under vacuum. The residue was purified by silica gel chromatography (eluting with petroleum ether) to give (4-bromophenyl)(ethyl)sulfane (55 g, 96%) as an oil. $^1$H NMR (CDCl$_3$, 400 MHz): δ 7.40-7.42 (dd, J=6.4, 2.0 Hz, 2H), 7.18-7.20 (dd, J=6.4, 2.0 Hz, 2H), 2.91-2.96 (q, J=7.2 Hz, 2H), 1.30-1.33 (t, J=7.2 Hz, 3H).

Step 2: 2-((tert-butyldimethylsilyl)oxy)ethanol

To a solution of ethane-1,2-diol (110 g, 1.77 mol) in anhydrous CH$_2$Cl$_2$ (1.1 L) was added triethylamine (215.2 g, 296 mL, 2.13 mol) at rt. The mixture was cooled to 0° C., then tert-butylchlorodimethylsilane (267.1 g, 1.77 mol) dissolved in CH$_2$Cl$_2$ (300 mL) was added dropwise over 1 h. The mixture was stirred at rt overnight. The reaction mixture was quenched with saturated aqueous NH$_4$Cl solution (400 mL) and separated. The aqueous phase was extracted with MTBE (2×400 mL). The combined organic layers were concentrated under vacuum and the residue was redissolved in MTBE (400 mL). The MTBE layer was washed with water (2×500 mL) and brine (500 mL), dried over anhydrous sodium sulfate, filtered and concentrated under vacuum to give 2-((tert-butyldimethylsilyl)oxy)ethanol (280 g, 90%) as a slight oil, which was used for the next step directly without further purification. $^1$H NMR (CDCl$_3$, 400 MHz): δ 3.64-3.66 (m, 2H), 3.57-3.60 (m, 2H), 0.85 (s, 9H), 0.02 (s, 6H).

Step 3: 2-((tert-butyldimethylsilyl)oxy)acetaldehyde

To a solution of CH$_2$Cl$_2$ (1.8 L) cooled to −30° C. was added oxalyl chloride (79.2 g, 52.8 mL, 624 mmol) dropwise. The mixture was cooled to −78° C., then DMSO (62.5 g, 88.5 mL, 1.25 mmol) was added dropwise. After addition, the mixture was stirred at −78° C. for 30 min. A solution of 2-((tert-butyldimethylsilyl)oxy)ethanol (100 g, 567 mmol) dissolved in CH$_2$Cl$_2$ (200 mL) was added slowly at −78° C. The reaction mixture was stirred at −78° C. for 1 h. Triethylamine (287 g, 395 mL, 2.84 mmol) was added dropwise at −78° C. The mixture was stirred at −78° C. for 30 min and then rt overnight. The reaction mixture was washed with water (1 L), 1 N HCl (2×1 L), saturated aqueous NaHCO$_3$ solution (1 L) and brine (1 L). The organic layer was dried over anhydrous sodium sulfate, filtered and concentrated under vacuum to give 2-((tert-butyldimethylsilyl)oxy)acetaldehyde (98.5 g, 99.8%) as a brown oil, which was used for the next step directly without further purification. 1H NMR (CDCl$_3$, 400 MHz): δ 9.70 (s, 1H), 4.22 (s, 2H), 0.93 (s, 9H), 0.11 (s, 6H).

Step 4: (R,E)-N-(2-((tert-butyldimethylsilyl)oxy)ethylidene)-2-methylpropane-2-sulfinamide A mixture of 2-((tert-butyldimethylsilyl)oxy)acetaldehyde (93.5 g, 0.54 mol), (R)-2-methylpropane-2-sulfinamide (78.8 g, 0.65 mol) and copper (II) sulfate (215 g, 1.35 mol) in anhydrous CH$_2$Cl$_2$ (1.5 L) was stirred at rt for 16 h. The mixture was quenched with H$_2$O (800 mL) and separated. The aqueous phase was extracted with CH$_2$Cl$_2$ (2×1 L). The combined organic layers were washed with water (1 L) and brine (1 L), dried over anhydrous sodium sulfate, filtered and concentrated under vacuum. The residue was purified by silica gel chromatography (eluting with petroleum ether: ethyl acetate=8:1) to give (R,E)-N-(2-((tert-butyldimethylsilyl)oxy)ethylidene)-2-methylpropane-2-sulfinamide (38.5 g, 26%) as a yellow oil. $^1$H NMR (CDCl$_3$, 400 MHz): δ 7.96-7.97 (t, J=3.2 Hz, 1H), 4.44-4.45 (d, J=2.8 Hz, 2H), 1.11 (s, 9H), 0.00 (s, 6H).

Step 5: (R)—N—((R)-2-((tert-butyldimethylsilyl)oxy)-1-(4-(ethylthio)phenyl)ethyl)-2-methylpropane-2-sulfinamide To a solution of (4-bromophenyl)(ethyl)sulfane (28.9 g, 133.1 mmol) in anhydrous THF (500 mL) was added dropwise n-butyllithium (73 mL, 181.5 mmol, 2.5 M in hexanes) at −78° C. The mixture was stirred at −78° C. for 30 min. A solution of (R,E)-N-(2-((tert-butyldimethylsilyl)oxy)ethylidene)-2-methylpropane-2-sulfinamide (33.5 g, 121 mmol) in anhydrous THF (100 mL) was added to the mixture at −78° C. The mixture was stirred at −78° C. for 2 h, then allowed to warm to rt and stirred for 2 h. The mixture was quenched with saturated aqueous NH$_4$Cl solution (200 mL) and extracted with ethyl acetate (3×300 mL). The combined organic layer was washed with water (200 mL) and brine (200 mL), dried over anhydrous Na$_2$SO$_4$, filtered and concentrated under vacuum. The residue was purified by silica gel chromatography (eluting with petroleum ether: ethyl acetate=15:1) three times to afford (R)—N—((R)-2-((tert-butyldimethylsilyl)oxy)-1-(4-(ethylthio)phenyl)ethyl)-2-methylpropane-2-sulfinamide (22 g, 44%) as a yellow oil. $^1$H NMR (CDCl$_3$, 400 MHz): δ 7.21-7.24 (d, J=7.2 Hz, 2H), 7.18-7.21 (d, J=8.4 Hz, 2H), 4.42-4.45 (dd, J=8.8, 2.4 Hz, 1H), 4.21 (brs, 1H), 3.69-3.73 (dd, J=10.4, 4.4 Hz, 1H), 3.51-3.56 (t, J=9.6 Hz, 1H), 2.87-2.92 (q, J=7.6 Hz, 2H), 1.25-1.29 (t, J=7.2 Hz, 3H), 1.18 (s, 9H), 0.88 (s, 9H), 0.02 (s, 6H). LCMS t$_R$=1.010 min in 5-95AB_1.5 min chromatography (MK RP18e 25-2 mm), MS (ESI) m/z 437.9 [M+Na]$^+$. Isomer SFC t$_R$=3.607 and 4.014 min in 12 min chromatography (AD-H_5_5_40_2.3 5 ML), ee= 90.85%.

Step 6: (R)-2-amino-2-(4-(ethylthio)phenyl)ethanol

To a solution of (R)—N—((R)-2-((tert-butyldimethylsilyl)oxy)-1-(4-(ethylthio)phenyl)ethyl)-2-methylpropane-2-sulfinamide (22 g, 52.9 mmol) in CH$_2$Cl$_2$ (250 mL) was added HCl (26.5 mL, 4 N in dioxane) at 0° C. The mixture was stirred at rt for 2 h. LCMS showed no starting material remaining. The mixture was concentrated under reduced pressure to afford crude (R)-2-amino-2-(4-(ethylthio)phenyl)ethanol HCl salt (12.3 g, 100%) as a brown solid, which was used for the next step directly without further purification. LCMS t$_R$=1.226 min in 0-30AB_2 min chromatography (Xtimate 3 um, C18, 2.1*30 mm), MS (ESI) m/z 180.9 [M-OH]$^+$.

Step 7: (R)-2-amino-2-(4-(ethylsulfonyl)phenyl)ethanol

To a mixture of (R)-2-amino-2-(4-(ethylthio)phenyl)ethanol (15.2 g, 65.0 mmol) in methanol (200 mL) was added dropwise a solution of oxone reagent (80.0 g, 130.0 mmol) in water (200 mL) at 0° C. The mixture was stirred at rt for 1.5 h; LCMS showed no starting material remaining. The mixture was filtered and methanol was removed under reduced pressure. The aqueous phase was extracted with EtOAc (2×80 mL), then the aqueous layer was basified to pH=8-9 with solid sodium carbonate portionwise at 0° C., then this solution was lyophilized (contained the Na$_2$CO$_3$). The solid was dissolved in CH$_2$Cl$_2$:MeOH (3:1, 600 mL) and stirred for 30 min, filtered, then concentrated under reduced pressure. The residue was purified by silica gel chromatography (eluting with CH$_2$Cl$_2$:MeOH=1:0 to 4:1) to give (R)-2-amino-2-(4-(ethylsulfonyl)phenyl)ethanol (11.5 g, 77%) as a white solid. LC-MS t$_R$=0.738 min in 0-30CD_POS chromatography (Xtimate ODS 2.1*30 mm, 3 um), MS (ESI) m/z 230.1 [M+H]$^+$. Isomer SFC t$_R$=6.99 min in 30 min chromatography (CD-PH_10-80_B_08 ML), ee=97.42%. $^1$H NMR (D$_2$O, 400 MHz): δ 7.82-7.84 (d, J=8.0 Hz, 2H), 7.54-7.56 (d, J=8.4 Hz, 2H), 4.33-4.35 (t, J=6.4 Hz, 1H), 3.72-3.78 (m, 2H), 3.19-3.25 (q, J=7.6 Hz, 2H), 1.03-1.07 (t, J=7.6 Hz, 3H).

Preparation 1B: (R)-2-amino-2-(4-(ethylsulfonyl)phenyl)ethanol

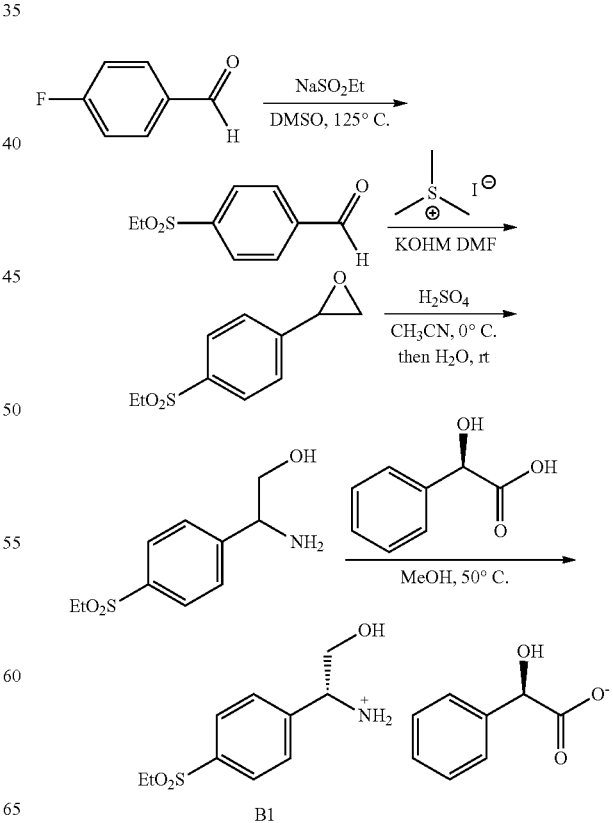

B1

Step 1: 4-(ethylsulfonyl)benzaldehyde

To a solution of 4-fluorobenzaldehyde (24.6 g, 198 mmol) in dimethylsulfoxide (60 mL) was added sodium ethanesulfinate (46 g, 396 mmol). The resulting mixture was stirred at 125° C. for 20 h. After cooling to rt, the reaction mixture was triturated with 350 mL of $H_2O$. The product was filtered, washed with two 10-mL portions of EtOH and dried under vacuum to afford 4-(ethylsulfonyl)benzaldehyde as a light yellow solid (31.2 g, 80% yield). LC-MS $t_R$=1.19 min in 2 min chromatography, MS (ESI) m/z 199.1 $[M+H]^+$. $^1H$ NMR ($CDCl_3$) δ 10.14 (s, 1H), 8.09 (s, 4H), 3.16 (q, J=7.2 Hz, 2H), 1.30 (t, J=7.2 Hz, 3H).

Step 2: 2-(4-(ethylsulfonyl)phenyl)oxirane

To a solution of 4-(ethylsulfonyl)benzaldehyde (10 g, 50.5 mmol) in DMF (85 mL) at rt was added trimethylsulfonium iodide (11.9 g, 58.1 mmol) followed by potassium hydroxide powder (5.66 g, 101 mmol). The reaction mixture was stirred at rt for 20 min before quenching with $H_2O$ (50 mL). The mixture was carefully neutralized with 1 N HCl solution (55 mL) and extracted with ethyl acetate (3×100 mL). The combined organic phase was washed with brine, dried over anhydrous $Na_2SO_4$, and passed through a pad of silica gel (eluting with ethyl acetate). It was concentrated under reduced pressure to afford crude 2-(4-(ethylsulfonyl)phenyl)oxirane as yellow oil, which was used directly for the next step without further purification. LC-MS $t_R$=1.13 min in 2 min chromatography, MS (ESI) m/z 213.2 $[M+H]^+$.

Step 3: 2-amino-2-(4-(ethylsulfonyl)phenyl)ethan-1-ol

To a solution of crude 2-(4-(ethylsulfonyl)phenyl)oxirane (50.5 mmol) in $CH_3CN$ (200 mL) at 0° C. was slowly added concentrated sulfuric acid (5.4 mL, 101 mmol). The mixture was allowed to stir at rt for 1.5 h. LCMS showed the starting material was consumed. $H_2O$ (15 mL) was added to the reaction mixture. Stirring continued at rt for 8 h, then at 45° C. for 10 h. After cooling to rt, the pH of the reaction mixture was adjusted to 3-4 by addition of 1 N NaOH solution (90 mL). The mixture was extracted with ethyl acetate (100 mL). The organic phase was then extracted with $H_2O$ (2×30 mL). The combined aqueous layers were then basified with 1 N NaOH solution (110 mL) to pH=9 and extracted with 1-butanol (5×60 mL). The combined organic layer (consisting of 1-butanol extracts) was dried over anhydrous $Na_2SO_4$, filtered and concentrated under reduced pressure. It was dried under high vacuum to afford crude 2-amino-2-(4-(ethylsulfonyl)phenyl)ethan-1-ol as an off-white solid. 4 g, 35% yield over 3 steps. Intermediate 4-(4-(ethylsulfonyl)phenyl)-2-methyl-4,5-dihydrooxazole: LC-MS $t_R$=0.77, 0.81 min in 2 min chromatography, MS (ESI) m/z 254.26 $[M+H]^+$. 2-amino-2-(4-(ethylsulfonyl)phenyl)ethan-1-ol: LC-MS $t_R$=0.61 min in 2 min chromatography, MS (ESI) m/z 230.21 $[M+H]^+$. $^1H$ NMR ($CD_3OD$): δ 7.88 (d, J=8.4 Hz, 2H), 7.64 (d, J=8.4 Hz, 2H), 4.16-4.12 (m, 1H), 3.76-3.72 (m, 1H), 3.66-3.61 (m, 1H), 3.17 (q, J=7.2 Hz, 2H), 1.19 (t, J=7.2 Hz, 3H).

Step 4: 2-amino-2-(4-(ethylsulfonyl)phenyl)ethan-1-ol mono-mandelate salt

To a solution of 2-amino-2-(4-(ethylsulfonyl)phenyl) ethan-1-ol (238 mg, 1.0 mmol) in MeOH (3 mL) at 50° C. was added a solution of (R)-Mandelic acid (76 mg, 0.5 mmol) in MeOH (1 mL). The resulting solution was allowed to cool down to ambient temperature slowly. After stirring for 1 day, the resulting crystals were collected by vacuum filtration and dried under high vacuum, providing the mono-mandelate salt as a white crystal, 107 mg (28% yield), 92.5% ee. $^1H$ NMR ($CD_3OD$): δ 7.97 (d, J=8.0 Hz, 2H), 7.71 (d, J=8.4 Hz, 2H), 7.46 (d, J=8.0 Hz, 2H), 7.46 (d, J=8.0 Hz, 2H), 7.31-7.27 (m, 2H), 7.25-7.22 (m, 1H), 4.42-4.42 (m, 1H), 3.92-3.89 (m, 1H), 3.81-3.77 (m, 1H), 3.21 (q, J=7.2 Hz, 2H), 1.21 (t, J=7.2 Hz, 3H).

Preparation 2: (R)-2-amino-2-(5-(ethyl sulfonyl) pyridin-2-yl)ethanol

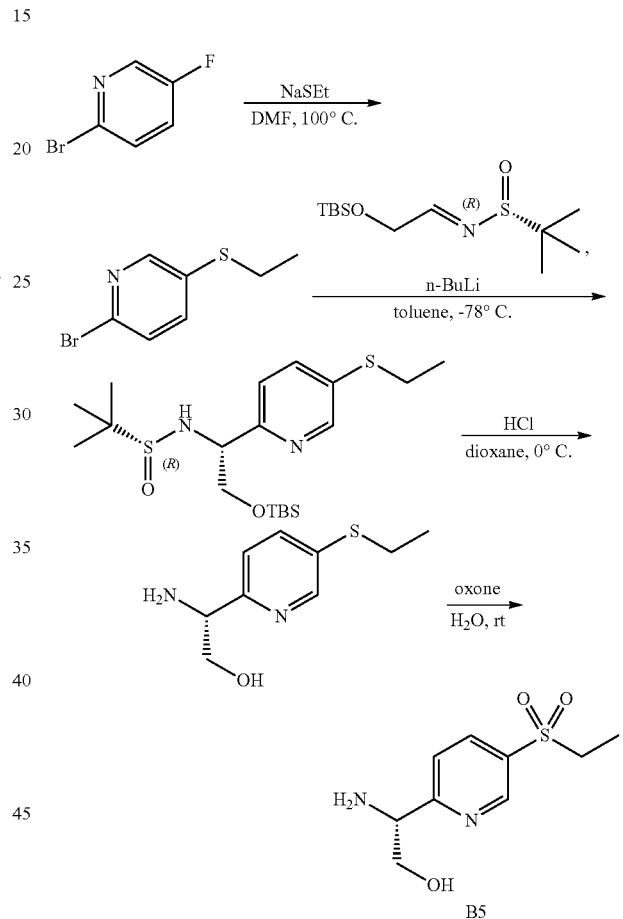

Step 1: 2-bromo-5-(ethylthio)pyridine

To a mixture of 2-bromo-5-fluoropyridine (6.28 g, 35.66 mmol) in anhydrous DMF (60 mL) was added sodium ethanethiolate (3 g, 35.66 mmol). The mixture was stirred at 100° C. for 3 h. TLC (petroleum ether/ethyl acetate 10/1) showed that the starting material was not consumed completely. Additional sodium ethanethiolate (0.9 g, 9.56 mmol) was added to the mixture. The mixture was stirred at 100° C. for 12 h. The mixture was quenched with $H_2O$ (150 mL) and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 80/1) to afford 2-bromo-5-(ethylthio)pyridine (7.0 g, 90%)

as a colorless oil. LC-MS $t_R$=0.717 min in 5-95AB_1.5 min chromatography (Welch Merck RP-18e 25-2 mm), MS (ESI) m/z 217.6 [M+H]$^+$.

Step 2: (R)—N—((R)-2-((tert-butyldimethylsilyl) oxy)-1-(5-(ethylthio)pyridin-2-yl)ethyl)-2-methyl-propane-2-sulfinamide To a solution of toluene (60 mL) was added n-BuLi (10.6 mL, 26.48 mmol, 2.5 M in hexanes) dropwise at −78° C.; the internal temperature did not exceed −50° C. A solution of 2-bromo-5-(ethylthio)pyridine (3.85 g, 17.65 mmol) in toluene (10 mL) was then added to the reaction mixture at −78° C.; the internal temperature did not exceed −65° C. The mixture was stirred at −78° C. for 1 h. A solution of (R,E)-N-(2-((tert-butyldimethylsilyl)oxy)ethylidene)-2-methylpropane-2-sulfinamide (4.90 g, 17.65 mmol) in toluene (10 mL) was added to the reaction mixture at −78° C.; the internal temperature did not exceed −60° C. The mixture was stirred at −78° C. for another 2 h. The mixture was quenched with brine (150 mL) at −78° C. and extracted with ethyl acetate (3×150 mL). The combined organic layers were washed with brine (400 mL), dried over anhydrous sodium sulfate, filtered and concentrated under reduced pressure. The residue was purified by silica gel chromatography (eluting with petroleum ether/ethyl acetate 10/1 to 3/1) to afford (R)—N—((R)-2-((tert-butyldimethylsilyl) oxy)-1-(5-(ethylthio)pyridin-2-yl)ethyl)-2-methylpropane-2-sulfinamide (3.0 g, 41%) as a pale yellow oil. LC-MS $t_R$=1.014 min in 5-95AB_1.5 min chromatography (Welch Merck RP-18e 25-2 mm), MS (ESI) m/z 417.2 [M+H]$^+$.

Step 3: (R)-2-amino-2-(5-(ethylthio)pyridin-2-yl)ethanol

Procedure same as that for (R)-2-amino-2-(4-(ethylthio) phenyl)ethanol with (R)—N—((R)-2-((tert-butyldimethylsilyl)oxy)-1-(5-(ethylthio)pyridin-2-yl)ethyl)-2-methylpropane-2-sulfinamide as the starting material.

Step 4: (R)-2-amino-2-(5-(ethyl sulfonyl)pyridin-2-yl)ethanol

Procedure same as that for (R)-2-amino-2-(4-(ethylsulfonyl)phenyl)ethanol with (R)-2-amino-2-(5-(ethylthio)pyridin-2-yl)ethanol as the starting material. $^1$H NMR (CD$_3$OD, 400 MHz): δ 9.08 (s, 1H), 8.35 (dd, J=2.0, 8.4 Hz, 1H), 7.79 (d, J=8.4 Hz, 1H), 4.70 (t, J=5.6 Hz, 1H), 4.03 (dd, J=4.8, 12.0 Hz, 1H), 3.91 (dd, J=4.8, 11.6 Hz, 1H), 3.29 (q, J=7.2 Hz, 2H), 1.25 (t, J=7.2 Hz, 3H).

Preparation 3: (R)-2-amino-2-(4-(methylsulfonyl) phenyl)ethanol

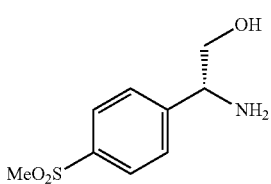

B6

The compound was prepared analogously to (R)-2-amino-2-(4-(methylsulfonyl)phenyl)ethanol (B1).

Preparation 4: (R)-2-amino-2-(5-(methylsulfonyl) pyridin-2-yl)ethanol

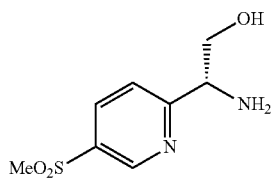

B7

The compound was prepared analogously to (R)-2-amino-2-(5-(ethyl sulfonyl)pyridin-2-yl)ethanol (B5).

Example 1

N—((R)-1-(4-(ethylsulfonyl)phenyl)-2-hydroxy-ethyl)-1-((trans-4-(trifluoromethyl)cyclohexyl) methoxy)isoquinoline-6-carboxamide (Cpd No Hy1A-5)

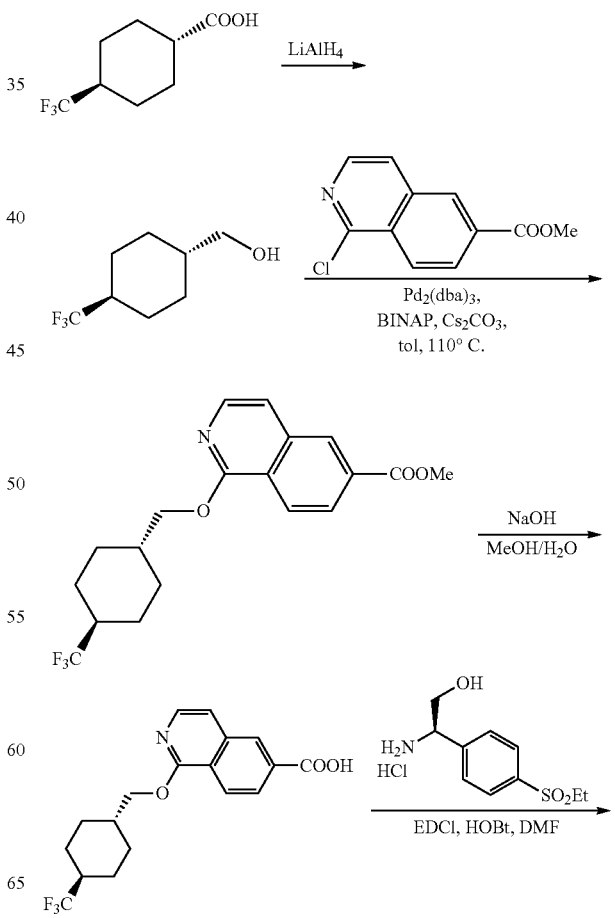

-continued

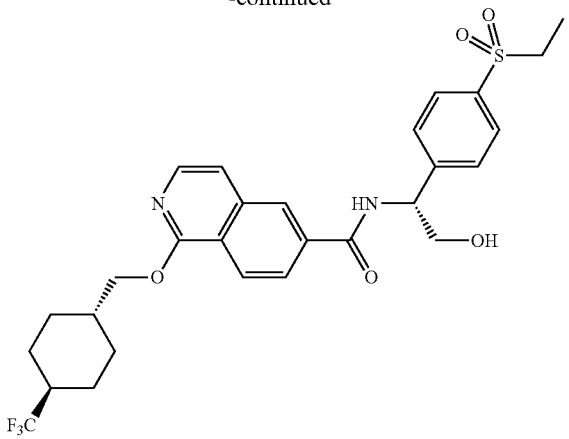

Step 1

To a mixture of trans-4-(trifluoromethyl)cyclohexanecarboxylic acid (200 mg, 1.02 mmol) in anhydrous THF (4 mL) was added dropwise LiAlH$_4$ (2 mL, 2.0 mmol, 1 M in THF) at 0° C. under N$_2$. The mixture was stirred at 0° C. for 2 h under N$_2$. TLC (petroleum ether/ethyl acetate=4/1) showed that the reaction was completed. The mixture was quenched with sat. Na$_2$SO$_4$ solution (1 mL) and diluted with CH$_2$Cl$_2$ (20 mL). The organic layer was dried over anhydrous sodium sulfate, filtered and concentrated under reduced pressure to afford crude trans-4-(trifluoromethyl)cyclohexyl)methanol (180 mg, 96%) as a yellow oil, which was used for the next step directly without further purification. $^1$H NMR (CDCl$_3$ 400 MHz): δ 3.41 (t, J=5.6 Hz, 2H), 2.00-1.80 (m, 4H), 1.35-1.15 (m, 4H), 1.03-0.88 (m, 2H).

Step 2

To a mixture of crude trans-4-(trifluoromethyl)cyclohexyl)methanol (80 mg, 0.439 mmol) in anhydrous toluene (5 mL) was added methyl 1-chloroisoquinoline-6-carboxylate (35 mg, 0.158 mmol), Pd$_2$(dba)$_3$ (35 mg, 0.038 mmol), BINAP (35 mg, 0.0553 mmol) and Cs$_2$CO$_3$ (103 mg, 0.316 mmol). The mixture was stirred at 110° C. for 5 h under N$_2$. The mixture diluted with ethyl acetate (30 mL) and washed with brine (80 mL). The organic layer was dried over anhydrous sodium sulfate, filtered and concentrated under reduced pressure. The residue was purified by preparative TLC with petroleum ether/ethyl acetate=6/1 to afford methyl 1-((trans-4-(trifluoromethyl)cyclohexyl)methoxy)isoquinoline-6-carboxylate (57 mg, 100%) as a yellow solid. LC-MS $t_R$=0.953 min in 5-95AB_1.5 min chromatography (Welch MK RP-18e, 25-2 mm), MS (ESI) m/z 368.0 [M+H]$^+$.

Step 3

To a mixture of methyl 1-((trans-4-(trifluoromethyl)cyclohexyl)methoxy)isoquinoline-6-carboxylate (57 mg, 0.155 mmol) in MeOH (5 mL) and H$_2$O (1 mL) was added NaOH (124 mg, 3.106 mmol). The mixture was stirred at rt for 1.5 h. The mixture was concentrated under reduced pressure. The residue was diluted with H$_2$O (20 mL) and adjusted to pH=4-5 with 1 N HCl solution. The aqueous layer was extracted with ethyl acetate (3×20 mL). The combined organic layers were dried over anhydrous sodium sulfate, filtered and concentrated under reduced pressure to afford crude 1-((trans-4-(trifluoromethyl)cyclohexyl)methoxy)isoquinoline-6-carboxylic acid (55 mg, 100%) as a yellow solid, which was used for the next step directly without further purification. LC-MS $t_R$=0.841 min in 5-95AB_1.5 min chromatography (Welch MK RP-18e, 25-2 mm), MS (ESI) m/z 353.9 [M+H]$^+$.

Step 4

To a mixture of crude 1-((trans-4-(trifluoromethyl)cyclohexyl)methoxy)isoquinoline-6-carboxylic acid (48 mg, 0.136 mmol) in CH$_2$Cl$_2$ (5 mL) was added (R)-2-amino-2-(4-(ethylsulfonyl)phenyl)ethanol HCl salt (36 mg, 0.136 mmol), EDCI (52 mg, 0.272 mmol), HOBt (37 mg, 0.272 mmol) and Et$_3$N (41 mg, 0.408 mmol). The mixture was stirred at rt for 16 h. The mixture was quenched with H$_2$O (20 mL) and extracted with CH$_2$Cl$_2$ (3×20 mL). The combined organic layers were dried over anhydrous Na$_2$SO$_4$, filtered and concentrated under reduced pressure. The residue was purified by preparative TLC with ethyl acetate, basic preparative HPLC separation, then dry-freezing directly to afford N—((R)-1-(4-(ethyl sulfonyl)phenyl)-2-hydroxyethyl)-1-((trans-4-(trifluoromethyl)cyclohexyl)methoxy)isoquinoline-6-carboxamide (11.10 mg, 14%) as a white solid. LC-MS $t_R$=0.810 min in 5-95AB_1.5 min chromatography (Welch MK RP-18e, 25-2 mm), MS (ESI) m/z 565.1 [M+H]$^+$. Isomer SFC $t_R$=3.834 min in 8 min chromatography (Column: AS-H; Method Name: AS-H_S__5_540_3ML_8MIN_15CM . . . M, ee=97%) $^1$H NMR (CDCl$_3$ 400 MHz): δ 8.26 (d, J=8.8 Hz, 1H), 8.14 (s, 1H), 7.98 (d, J=5.6 Hz, 1H), 7.93-7.83 (m, 3H), 7.56 (d, J=8.0 Hz, 2H), 7.25-7.18 (m, 2H), 5.35-5.27 (m, 1H), 4.28 (d, J=6.0 Hz, 2H), 4.15-3.95 (m, 2H), 3.04 (q, J=7.6 Hz, 2H), 2.15-1.90 (m, 6H), 1.45-1.32 (m, 2H), 1.28-1.15 (m, 5H).

Basic Preparative HPLC Method:
Mobile phase A: water with 0.05% ammonia hydroxide solution
Mobile phase B: MeCN
Flow rate: 25 mL/min.
Detection: UV 220 nm
Column: Phenomenex Gemini 150*25 mm*10 um
Column temperature: 40° C.

| Time in min | % A | % B |
|---|---|---|
| 0.00 | 49 | 51 |
| 10.00 | 19 | 81 |
| 10.20 | 0 | 100 |
| 13.00 | 0 | 100 |

The compounds listed below were prepared using analogous procedures:

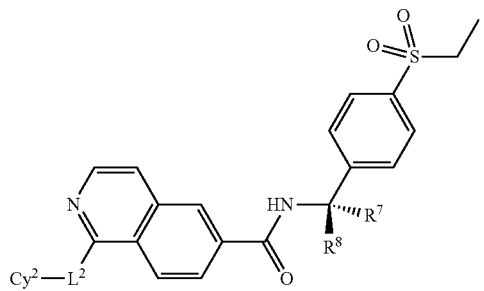

| Cpd No | Cy² | L² | R⁷ | R⁸ |
|---|---|---|---|---|
| Hy1A-1 | 4-tetrahydropyranyl | O | H | H |
| Hy1A-2 | 4-(trifluoromethyl)phenyl | O | H | H |
| Hy1A-3.1[a] | 4-(trifluoromethyl)cyclohexyl | O | H | H |
| Hy1A-3.2[a] | 4-(trifluoromethyl)cyclohexyl | O | H | H |
| Hy1A-4 | 4-(trifluoromethyl)phenyl | CH₂O | H | H |
| Hy1A-7 | 4-(trifluoromethyl)phenyl | CH₂O | CH₂OH | H |
| Hy1A-8 | trans-4-(trifluoromethyl)cyclohexyl | CH₂O | CH₂OH | H | a cis and trans isomers separated by chromatography.

Example 2

N—((R)-1-(4-(ethylsulfonyl)phenyl)-2-hydroxyethyl)-3-methyl-1-((trans-4-(trifluoromethyl)cyclohexyl)methoxy)isoquinoline-6-carboxamide (Cpd No Hy1A-9)

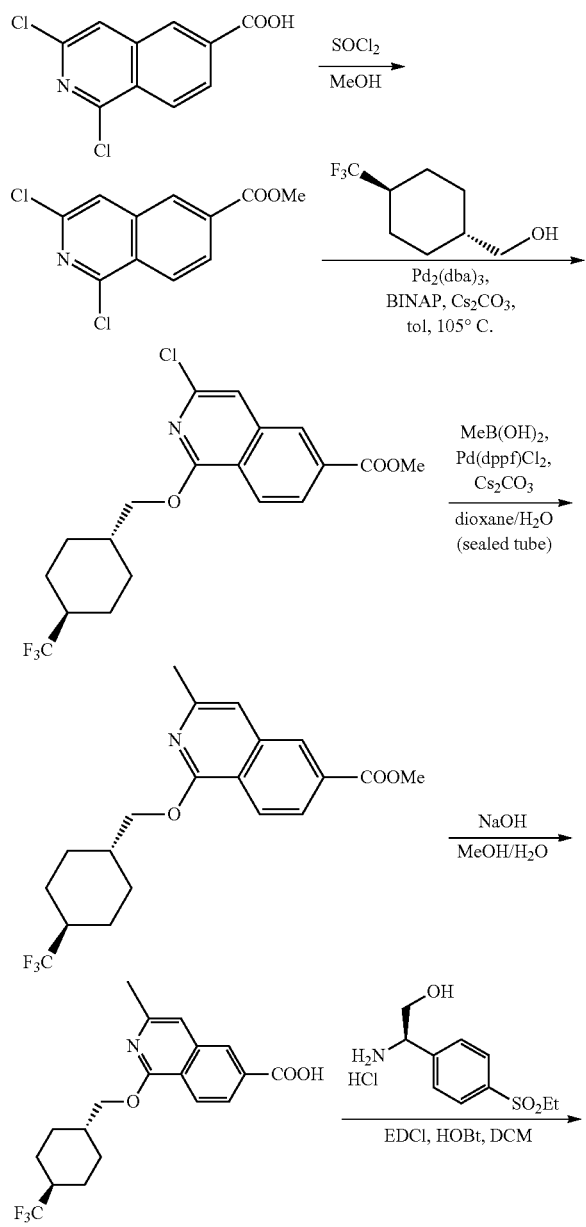

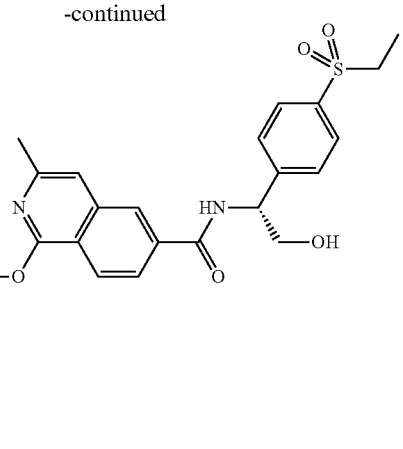

Step 1

To a solution of 1,3-dichloroisoquinoline-6-carboxylic acid (80 mg, 0.33 mmol) in MeOH (3 mL) was added SOCl₂ (1 mL) slowly at 0° C. The mixture was stirred at 40° C. for 1 h. LCMS showed that the reaction was completed. The reaction solution was concentrated under reduced pressure to afford crude methyl 1,3-dichloroisoquinoline-6-carboxylate (85 mg, 100%) as a white solid, which was used for the next step directly without further purification. LC-MS: $t_R$=0.796 min in 5-95 AB_1.5 MIN chromatography (MERCK RP-18e 25-2 mm), MS (ESI) m/z 255.7 [M+H]⁺.

Step 2

To a mixture of crude methyl 1,3-dichloroisoquinoline-6-carboxylate (50 mg, 0.2 mmol), Cs₂CO₃ (130 mg, 0.4 mmol), BINAP (7 mg, 0.01 mmol), and Pd₂dba₃ (10 mg, 0.01 mmol) was added a solution of (trans-4-(trifluoromethyl)cyclohexyl)methanol (36 mg, 0.2 mmol) in anhydrous toluene (4 mL) under N₂. The mixture was stirred at 105° C. under N₂ for 3 h. LCMS showed that the reaction was completed. The reaction mixture was filtered, the filtrate was concentrated under reduced pressure. The residue was purified by preparative TLC (petroleum ether:dichloromethane=2:1) to afford methyl 3-chloro-1-((trans-4-(trifluoromethyl)cyclohexyl)methoxy)isoquinoline-6-carboxylate (45 mg, 56%) as a white solid. LC-MS: $t_R$=1.007 min in 5-95 AB_1.5 MIN chromatography (MERCK RP-18e 25-2 mm), MS (ESI) m/z 402.0 [M+H]⁺. ¹H NMR (CDCl₃ 400 MHz): δ 8.38 (d, J=1.2 Hz, 1H), 8.25 (d, J=8.4 Hz, 1H), 8.09 (dd, J=8.4, 1.2 Hz, 1H), 7.34 (s, 1H), 4.37 (d, J=6.4 Hz, 2H), 4.00 (s, 3H), 2.15-1.90 (m, 5H), 1.45-1.35 (m, 2H), 1.25-1.17 (m, 3H). NOSEY confirmed structure.

Step 3

A mixture of methyl 3-chloro-1-((trans-4-(trifluoromethyl)cyclohexyl)methoxy)isoquinoline-6-carboxylate (140 mg, 0.35 mmol), CH₃B(OH)₂ (63 mg, 1.05 mmol), Cs₂CO₃ (228 mg, 0.70 mmol) and Pd(dppf)Cl₂ (26 mg, 0.035 mmol) in dioxane (0.5 mL) and H₂O (0.1 mL) was stirred at 100° C. in sealed tube for 8 h. TLC (petroleum ether:dichloromethane=2:1) showed that the reaction was completed. The reaction solution was filtered. The filtrate was added with water (30 mL), extracted with ethyl acetate (3×15 mL). The combined organic layers were washed with brine (30 mL), dried over anhydrous Na₂SO₄, filtered and concentrated under reduced pressure. The residue was purified by preparative TLC (petroleum ether:dichloromethane=2:1) to afford methyl 3-methyl-1-((trans-4-(trifluoromethyl)cyclohexyl)methoxy)isoquinoline-6-carboxylate (85 mg, 64%) as a colorless oil. LC-MS: $t_R$=1.017 min in 5-95 AB_1.5 MIN chromatography (MERCK RP-18e 25-2 mm), MS (ESI) m/z 382.0 [M+H]⁺.

Step 4

To a solution of methyl 3-methyl-1-((trans-4-(trifluoromethyl)cyclohexyl)methoxy)isoquinoline-6-carboxylate (80 mg, 0.21 mmol) in MeOH (5 mL) was added 2N aq. NaOH (1 mL). The mixture was stirred at 40° C. for 1.5 h. TLC (petroleum ether:dichloromethane=2:1) showed that the reaction was completed. The reaction solution was added with water (20 mL), concentrated under reduced pressure to remove MeOH. The residue was acidified by 4N HCl to pH=3, extracted with ethyl acetate (3×10 mL). The combined organic layers were dried over anhydrous $Na_2SO_4$, filtered and concentrated under reduced pressure to afford crude 3-methyl-1-((trans-4-(trifluoromethyl)cyclohexyl) methoxy)isoquinoline-6-carboxylic acid (77 mg, 100%) as a white solid, which was used for the next step directly without further purification.

Step 5

To a solution of crude 3-methyl-1-((trans-4-(trifluoromethyl)cyclohexyl)methoxy)isoquinoline-6-carboxylic acid (40 mg, 0.11 mmol) in $CH_2Cl_2$ (2 mL) was added (R)-2-amino-2-(4-(ethylsulfonyl)phenyl)ethanol hydrochloride salt (43 mg, 0.16 mmol), HATU (60 mg, 0.16 mmol) and $Et_3N$ (32 mg, 0.32 mmol). The mixture was stirred 25° C. for 15 h. LCMS showed that the reaction was completed. The reaction solution was concentrated under reduced pressure. The residue was purified by preparative TLC (petroleum ether:ethyl acetate=1:1), basic preparative HPLC separation and dry-freezing to afford N—((R)-1-(4-(ethyl sulfonyl) phenyl)-2-hydroxyethyl)-3-methyl-1-((trans-4-(trifluoromethyl)cyclohexyl)methoxy)isoquinoline-6-carboxamide (Hy1A-9, 13.70 mg, 22%) as a white solid. LC-MS: $t_R$=0.829 min in 5-95 AB_1.5 MIN chromatography (MERCK RP-18e 25-2 mm), MS (ESI) m/z 579.1 [M+H]⁺. ¹H NMR (CDCl₃ 400 MHz): δ 8.25 (d, J=8.4 Hz, 1H), 8.10 (d, J=1.2 Hz, 1H), 7.89 (d, J=8.4 Hz, 2H), 7.82 (d, J=6.8 Hz, 1H), 7.61 (d, J=8.4 Hz, 2H), 7.28 (s, 1H), 7.08 (s, 1H), 5.40-5.30 (m, 1H), 4.35 (d, J=6.0 Hz, 2H), 4.15-4.00 (m, 2H), 3.10 (q, J=7.6 Hz, 2H), 2.54 (s, 3H), 2.12-1.88 (m, 6H), 1.45-1.35 (m, 2H), 1.29 (t, J=7.6 Hz, 3H), 1.25-1.15 (m, 2H). Isomer SFC: $t_R$=1.661 min in 3 min chromatography (Column: AD-H; Method Name: AD-H_3UM_4_5_40_4ML_3MIN.M, ee=96.60%).

Basic Preparative HPLC Method
Instrument: DC
Mobile phase A: water (0.05% ammonia hydroxide v/v)
Mobile phase B: $CH_3CN$
Flow rate: 25 mL/min.
Detection: UV 220 nm/254 nm
Column: Phenomenex Gemini 150*25 mm*10 um
Column temperature: 30° C.

| Time in min | % A | % B |
|---|---|---|
| 0.00 | 38 | 62 |
| 10.00 | 18 | 82 |
| 10.20 | 0 | 100 |
| 13.00 | 0 | 100 |

The following compound was prepared using procedures analogous to those described above:

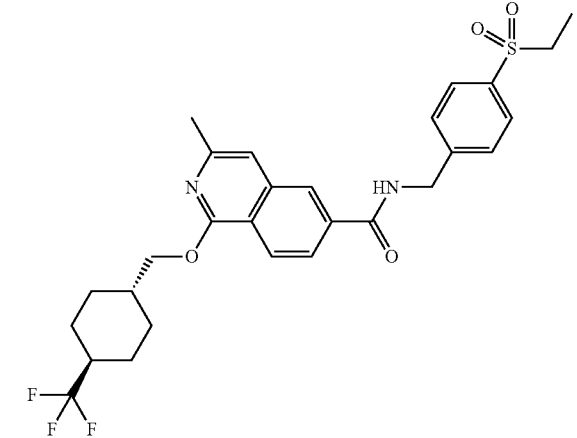

Cpd No Hy1A-6

The following compounds are prepared using procedures analogous to those described above;

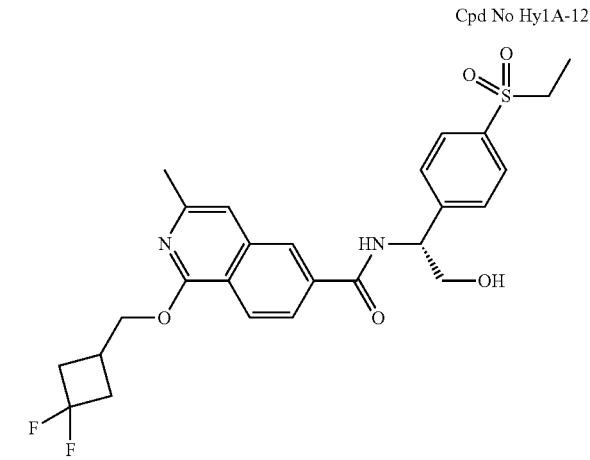

Cpd No Hy1A-12

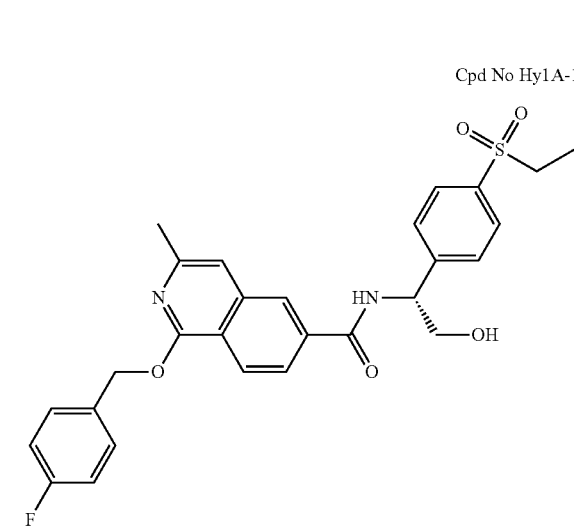

Cpd No Hy1A-13

Cpd No Hy1A-14
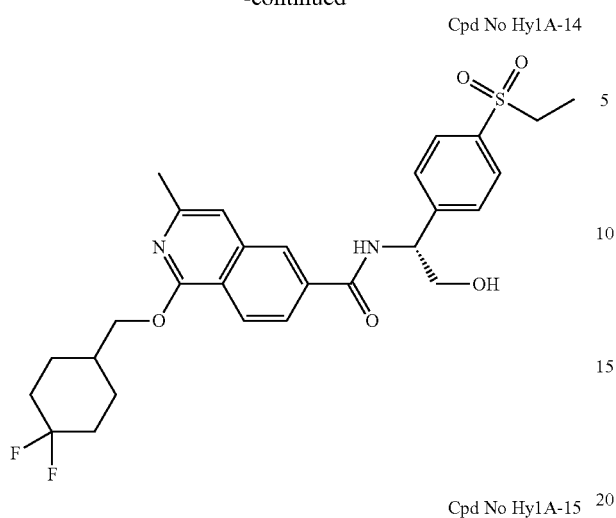
Cpd No Hy1A-15
Cpd No HY1A-16
Cpd No Hy1A-17
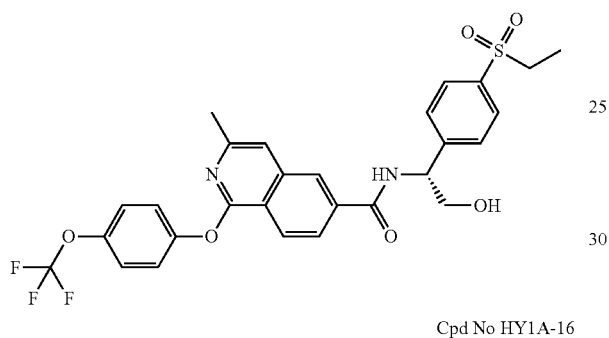
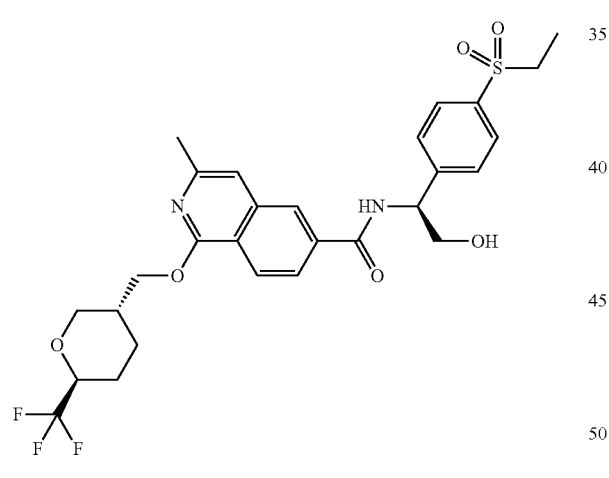
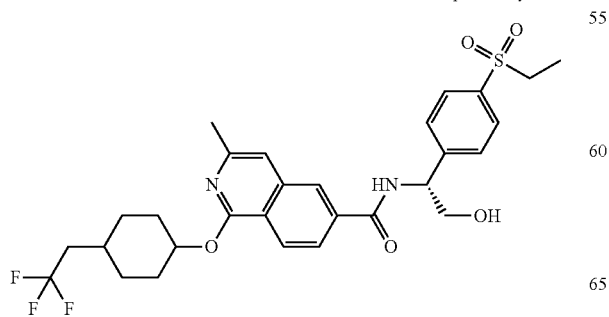
Cpd No Hy1A-18.1, -18.2, -18.3[a]
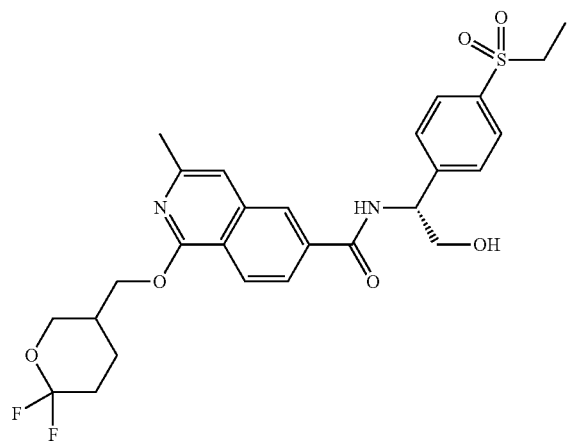
Cpd No Hy1A-19
[a] The four isomers were separated chromatographically into three fractions. Fraction 18.1 is one trans isomer. Fraction 18.2 is the other trans isomer. Fraction 18.3 is a mixture of two cis isomers.

The following compounds are prepared following procedures analogous to those described above, using the appropriate boronic acid in Step 3 in place of methyl boronic acid:

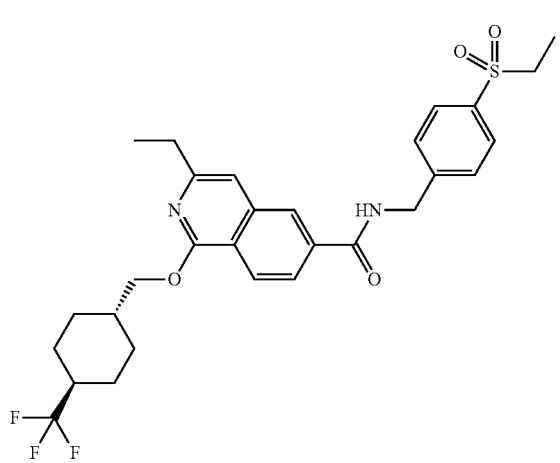

Cpd No Hy1A-20

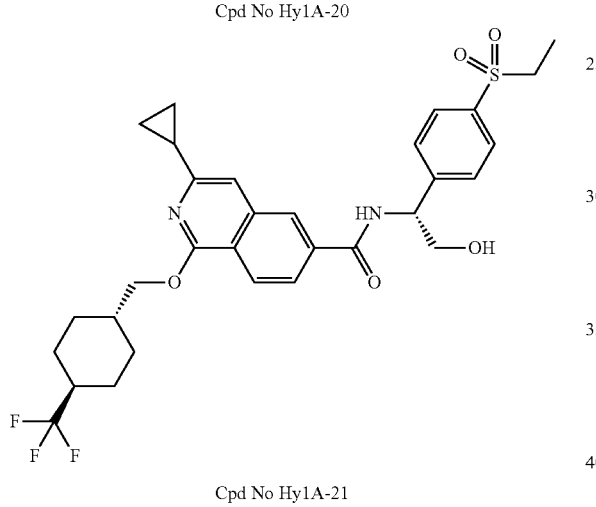

Cpd No Hy1A-21

The following compounds are prepared following procedures analogous to those described above, using 2-amino-2-(5-(ethyl sulfonyl)pyridin-2-yl)ethan-1-ol in Step 5:

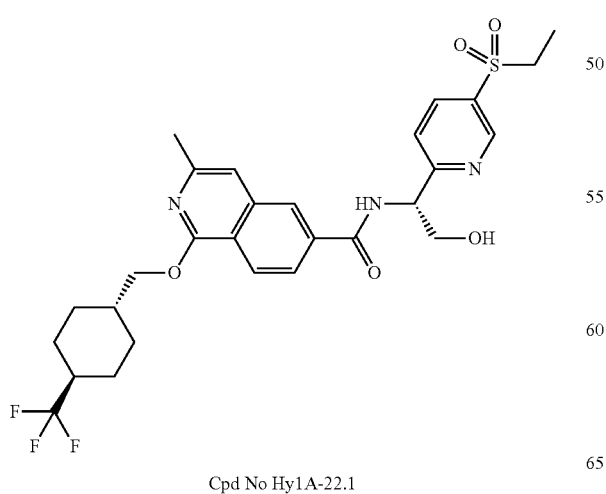

Cpd No Hy1A-22.1

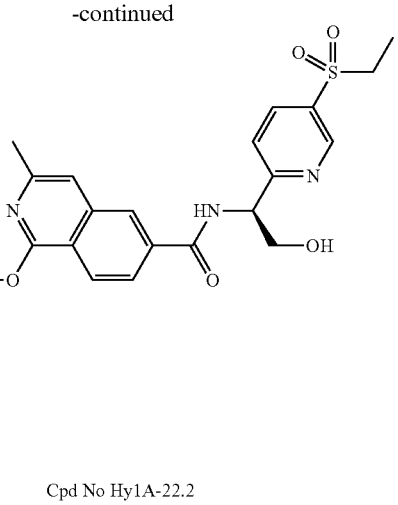

Cpd No Hy1A-22.2

The following compound is prepared following procedures analogous to those described above, using $Pd_2(dba)_3$, bippyphos, $Cs_2CO_3$, MeOH at 60° C. in Step 3:

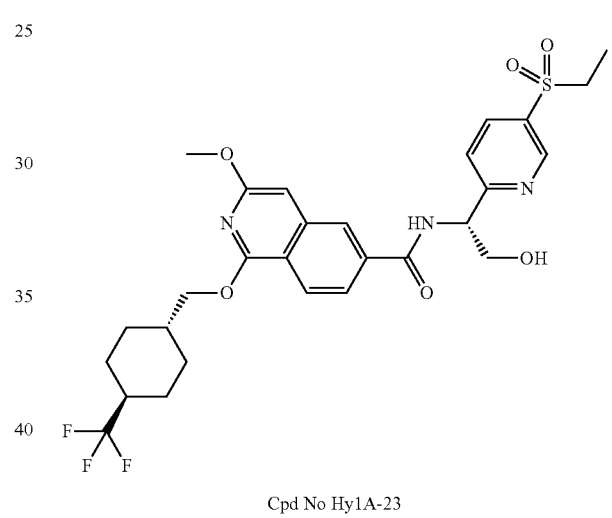

Cpd No Hy1A-23

The following compounds were prepared using procedures analogous to those described above, omitting Step 3:

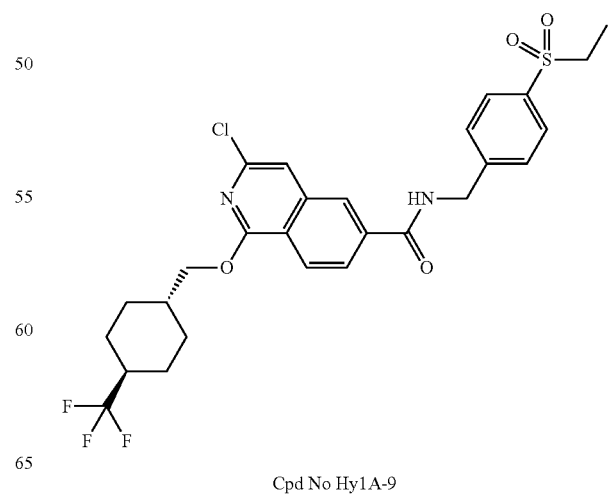

Cpd No Hy1A-9

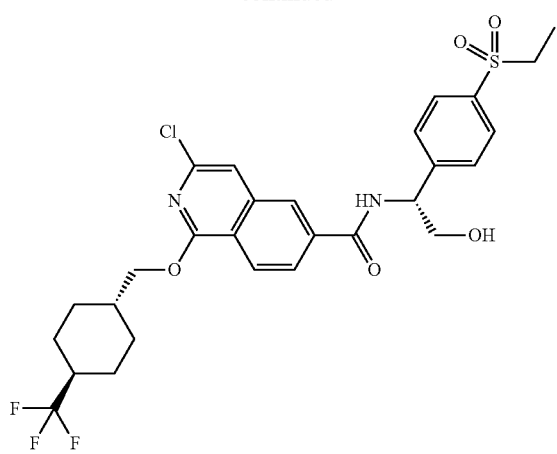

Cpd No Hy1A-11

Example 3

(R)—N-(1-(4-(ethylsulfonyl)phenyl)-2-hydroxyethyl)-2-methyl-4-((4-(trifluoromethyl)benzyl)oxy)quinoline-7-carboxamide (Cpd No Hy1B-3)

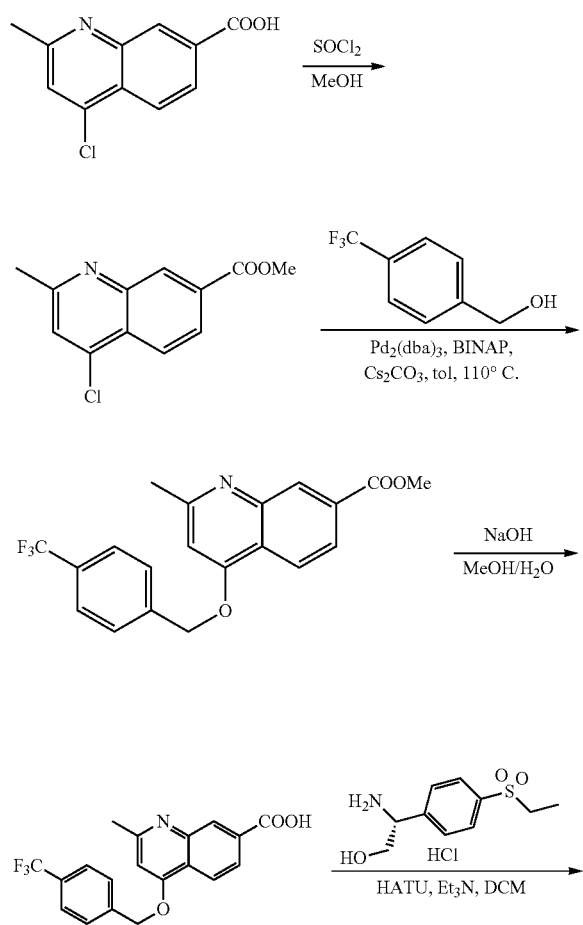

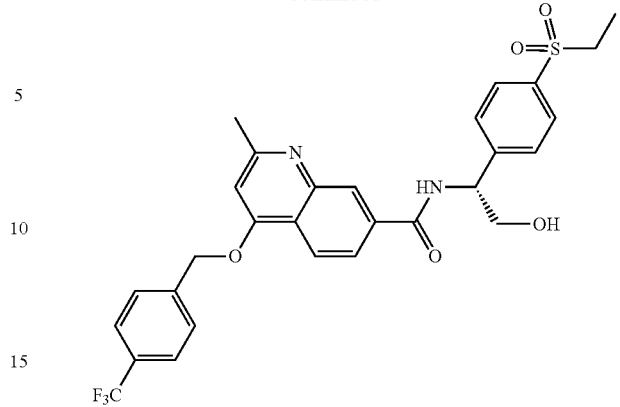

Step 1

To a solution of 4-chloro-2-methylquinoline-7-carboxylic acid (150 mg, 0.679 mmol) in MeOH (3 mL) was added $SOCl_2$ (3 mL). The mixture was stirred at 45° C. for 3 h. The mixture was concentrated under reduced pressure to afford crude methyl 4-chloro-2-methylquinoline-7-carboxylate (158 mg, 100%) as a white solid, which was used for next step directly without further purification. LC-MS $t_R$=0.673 min in 5-95AB_1.5 min chromatography (Welch MK RP-18e, 25-2 mm), MS (ESI) m/z 235.9 [M+H]$^+$.

Step 2

To a mixture of crude methyl 4-chloro-2-methylquinoline-7-carboxylate (70 mg, 0.3 mmol), (4-(trifluoromethyl)phenyl)methanol (79 mg, 0.45 mmol), BINAP (37 mg, 0.06 mmol), $Cs_2CO_3$ (291 mg, 0.9 mmol) in anhydrous toluene (2 mL) was added $Pd_2(dba)_3$ (55 mg, 0.06 mmol) under $N_2$. The mixture was stirred at 110° C. for 16 h under $N_2$. TLC (petroleum ether/ethyl acetate=3/1) showed that the reaction was completed. The mixture was filtered through celite and the filter cake was washed with $CH_2Cl_2$ (20 mL). The filtrate was concentrated under reduced pressure. The residue was purified by preparative TLC (petroleum ether/ethyl acetate=3/1) to afford methyl 2-methyl-4-((4-(trifluoromethyl)benzyl)oxy)quinoline-7-carboxylate (25 mg, 22.5%) as a white solid. LC-MS $t_R$=0.685 min in 5-95AB_1.5 min chromatography (Welch MK RP-18e, 25-2 mm), MS (ESI) m/z 375.9 [M+H]$^+$.

Step 3

A solution of methyl 2-methyl-4-((4-(trifluoromethyl)benzyl)oxy)quinoline-7-carboxylate (35 mg, 0.093 mmol), NaOH (186 mg, 4.6 mmol) in MeOH (2 mL) and $H_2O$ (1 mL) was stirred at rt for 4 h. LCMS showed that the reaction was completed. The mixture was adjusted to pH=3 with 1 N HCl solution. The mixture was added with water (5 mL) and extracted with $CH_2Cl_2$ (3×5 mL). The combined organic layers were washed with brine (10 mL), dried over anhydrous $Na_2SO_4$, filtered and concentrated under reduced pressure to afford crude 2-methyl-4-((4-(trifluoromethyl)benzyl)oxy)quinoline-7-carboxylic acid (35 mg, 100%) as a yellow oil, which was used for the next step directly without further purification. LC-MS $t_R$=0.653 min in 5-95AB_1.5 min chromatography (Welch MK RP-18e, 25-2 mm), MS (ESI) m/z 361.9 [M+H]$^+$.

Step 4

To a mixture of crude 2-methyl-4-((4-(trifluoromethyl)benzyl)oxy)quinoline-7-carboxylic acid (20 mg, 0.055 mmol), (R)-2-amino-2-(4-(ethylsulfonyl)phenyl)ethanol HCl salt (25 mg, 0.11 mmol), HATU (42 mg, 0.11 mmol) in anhydrous $CH_2Cl_2$ (1 mL) was added $Et_3N$ (11 mg, 0.11 mmol). LCMS showed that the reaction was completed. The mixture was stirred at rt for 4 h. The mixture was purified by preparative TLC (petroleum ether/ethyl acetate=1/4) to afford a crude product, which was separated by basic preparative HPLC separation and dry-freezing directly to afford (R)—N-(1-(4-(ethylsulfonyl)phenyl)-2-hydroxyethyl)-2-methyl-4-((4-(trifluoromethyl)benzyl)oxy)quinoline-7-carboxamide (Hy1B-3, 1.80 mg, 5%) as a white solid. LC-MS $t_R$=0.678 min in 5-95AB_1.5 min chromatography (Welch MK RP-18e, 25-2 mm), MS (ESI) m/z 573.0 [M+H]$^+$. $^1$H NMR (CDCl$_3$ 400 MHz): δ 8.97-8.95 (m, 1H), 8.81 (s, 1H), 8.18 (d, J=9.2 Hz, 1H), 7.99 (d, J=8.4 Hz, 1H), 7.68 (d, J=8.4 Hz, 1H), 7.67 (s, 1H) 7.59 (d, J=8.0 Hz, 4H), 7.50 (d, J=8.0 Hz, 2H), 6.85 (s, 1H), 5.44-5.40 (m, 2H), 5.30-5.20 (m, 1H), 4.09 (d, J=4.8 Hz, 2H), 2.96 (q, J=7.2 Hz, 2H), 2.82 (s, 3H), 1.16 (t, J=7.2 Hz, 3H). Isomer SFC $t_R$=6.814 min in 10 min chromatography (Column: AD-H; Method Name: AD-3_ETOH(DEA)_54025ML.M, ee=100%).

Basic Preparative HPLC Method:

Mobile phase A: water with 0.05% ammonia hydroxide solution

Mobile phase B: MeCN

Flow rate: 25 mL/min.

Detection: UV 220 nm

Column: Gemini 150*25 mm*10 um

Column temperature: 40° C.

| Time in min | % A | % B |
|---|---|---|
| 0.00 | 60 | 40 |
| 10.00 | 30 | 70 |
| 10.20 | 0 | 100 |
| 13.00 | 0 | 100 |

The compounds shown below are prepared following analogous procedures:

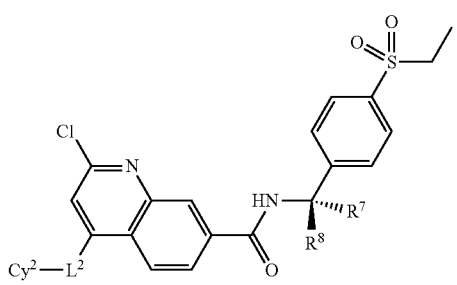

| Cpd No | Cy$^2$ | L$^2$ | R$^7$ | R$^8$ |
|---|---|---|---|---|
| Hy1B-1 | 4-(trifluoromethyl)phenyl | CH$_2$O | H | H |
| Hy1B-2 | trans-4-(trifluoromethyl)cyclohexyl | CH$_2$O | H | H |
| Hy1B-4 | trans-4-(trifluoromethyl)cyclohexyl | CH$_2$O | CH$_2$OH | H |

Example 4

N-(4-(ethylsulfonyl)benzyl)-4-(((1r,4r)-4-(trifluoromethyl)cyclohexyl)methoxy)quinazoline-7-carboxamide (Cpd No Hy1C-2)

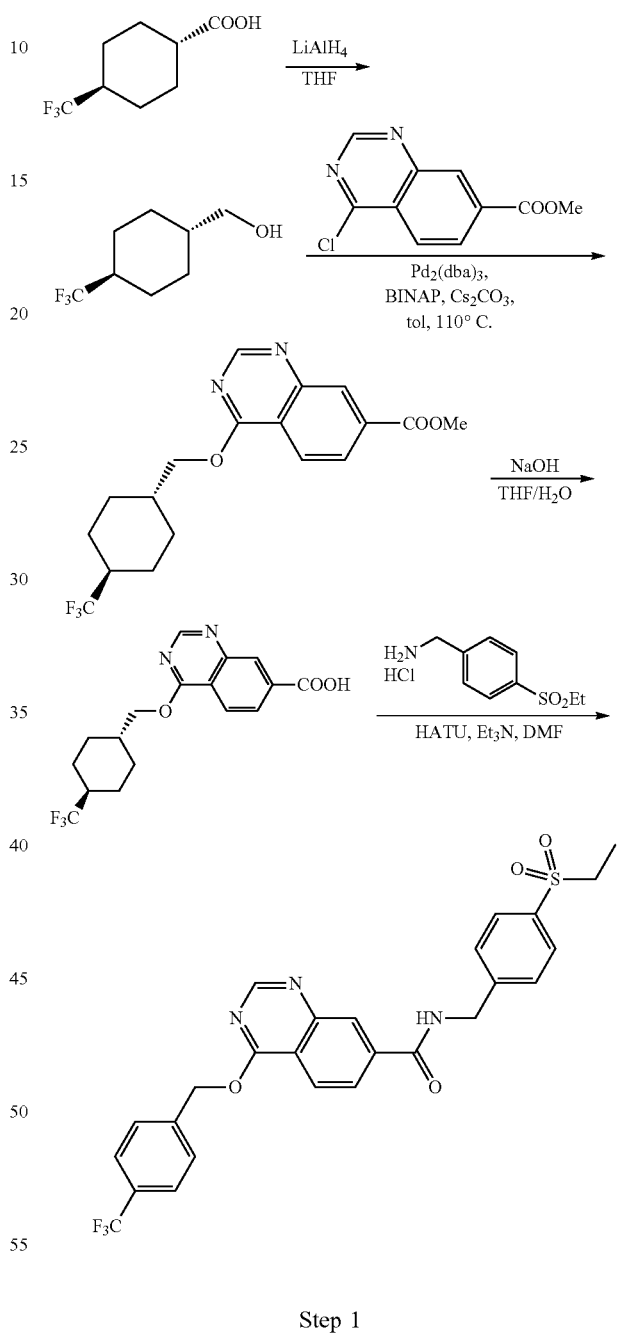

Step 1

To a solution of trans-4-(trifluoromethyl)cyclohexanecarboxylic acid (0.5 g, 2.6 mmol) in anhydrous THF (5 mL) was added LiAlH$_4$ (5.1 mL, 5.1 mmol, 1 M in THF) at 0° C. under N$_2$. The mixture was stirred at 0-25° C. under N$_2$ for 2 h. TLC (petroleum ether:ethyl acetate=2:1) showed the reaction was completed. The reaction solution was added with ice water (0.2 mL), 10% aq. NaOH (0.2 mL) and then water (0.1 mL) dropwise at 0° C. The mixture was stirred at 0-20° C. for 0.5 h. Solid Na$_2$SO$_4$ (1 g) was added and then the mixture was stirred at rt for 0.5 h. The mixture was filtered and washed with ethyl acetate (3×10 mL). The combined organic layers were concentrated under reduced pressure to afford crude trans-4-(trifluoromethyl)cyclohexyl)methanol (450 mg, 97%) as a colorless oil, which was used for the next step directly without further purification. $^1$H NMR (CDCl$_3$ 400 MHz): δ 3.48 (d, J=6.0 Hz, 2H), 2.01-1.90 (m, 4H), 1.35-1.30 (m, 3H), 1.02-0.94 (m, 2H).

Step 2

To a mixture of crude methyl 4-chloroquinazoline-7-carboxylate (100 mg, 0.45 mmol), trans-4-(trifluoromethyl) cyclohexyl)methanol (123 mg, 0.68 mmol), Cs$_2$CO$_3$ (293 mg, 0.90 mmol) and BINAP (112 mg, 0.18 mmol) in toluene (5 mL) was added Pd$_2$(dba)$_3$ (165 mg, 0.18 mmol). The resulting mixture was stirred at 110° C. under N$_2$ for 20 h. LCMS showed the reaction was completed. The reaction solution was filtered. The filtrate was added with water (30 mL), extracted with ethyl acetate (3×15 mL). The mixture was washed with brine (3×10 mL) and then dried over anhydrous Na$_2$SO$_4$, filtered and concentrated under reduced pressure. The residue was purified by preparative TLC (petroleum ether/ethyl acetate=5/1) to afford methyl 4-((trans-4-(trifluoromethyl)cyclohexyl)methoxy)quinazoline-7-carboxylate (110 mg, 66%) as a pale yellow solid. LC-MS $t_R$=0.880 min in 5-95AB_1.5 min chromatography (Merck RP-18e 25-2 mm), MS (ESI) m/z 369.0 [M+H]$^+$.

Step 3

To a solution of methyl 4-((trans-4-(trifluoromethyl)cyclohexyl)methoxy)quinazoline-7-carboxylate (70 mg, 0.19 mmol) in THF (3 mL) was added NaOH (76 mg, 1.9 mmol) and water (1.0 mL). The reaction mixture was stirred at rt for 5 h. LCMS showed the reaction was completed. The solvents were removed under reduced pressure. Water (10 mL) was added. The mixture was acidified with 1 N HCl solution to pH=5. The mixture was extracted with ethyl acetate (3×15 mL). The combined organic layers were washed with brine (10 mL), dried over anhydrous sodium sulfate, filtered and concentrated under reduced pressure to afford crude 4-((trans-4-(trifluoromethyl)cyclohexyl)methoxy)quinazoline-7-carboxylic acid (67 mg, 100% yield) as a white solid, which was used for the next step directly without further purification. LC-MS $t_R$=0.778 min in 5-95AB_1.5 min chromatography (Merck RP-18e 25-2 mm), MS (ESI) m/z 354.9 [M+H]$^+$.

Step 4

To a solution of 4-((trans-4-(trifluoromethyl)cyclohexyl) methoxy)quinazoline-7-carboxylic acid (20 mg, 0.056 mmol), (4-(ethylsulfonyl)phenyl)methanamine hydrochloride (16 mg, 0.068 mmol) and HATU (43 mg, 0.11 mmol) in dry DMF (2 mL) was added Et$_3$N (17 mg, 0.17 mmol). The mixture was stirred at rt for 2 h. LCMS showed the starting material was consumed completely. Ethyl acetate (10 mL) was added. The mixture was washed with brine (2×10 mL). The organic layer was dried over anhydrous sodium sulfate, filtered and concentrated under reduced pressure. The residue was purified by basic preparative HPLC separation to afford N-(4-(ethylsulfonyl)benzyl)-4-((trans-4-(trifluoromethyl)cyclohexyl)methoxy)quinazoline-7-carboxamide (Hy1C-2, 13.50 mg, 12%) as a white solid. LC-MS $t_R$=0.795 min in 5-95AB_1.5 min chromatography (MK RP-18e 25-2 mm), MS (ESI) m/z 536.1 [M+H]$^+$. $^1$H NMR (DMSO-d$_6$ 400 MHz): δ 9.59 (t, J=5.6 Hz, 1H), 8.87 (s, 1H), 8.47 (s, 1H), 8.29 (d, J=8.8 Hz, 1H), 8.13 (dd, J=1.2, 8.4 Hz, 1H), 7.87 (d, J=8.4 Hz, 2H), 7.64 (d, J=8.0 Hz, 2H), 4.65 (d, J=6.0 Hz, 2H), 4.43 (d, J=6.0 Hz, 2H), 3.29 (q, J=7.2 Hz, 2H), 2.34-2.28 (m, 1H), 2.04-1.90 (m, 5H), 1.40-1.24 (m, 4H), 1.10 (t, J=7.2 Hz, 3H). Isomer SFC $t_R$=1.792 min in 3 min chromatography (Column: AD-H; Method Name: AD-H_3UM_4_5_40_4ML_3MIN.M, ee=100%).

Basic Preparative HPLC Method

Mobile phase A: water with 0.05% NH$_3$.H$_2$O

Mobile phase B: CH$_3$CN

Flow rate: 25 mL/min.

Detection: UV 220 nm/254 nm

Column: Gemini 150*25 mm*5 um

Column temperature: 30° C.

| Time in min | % A | % B |
|---|---|---|
| 0.00 | 50 | 50 |
| 10.00 | 20 | 80 |
| 10.20 | 0 | 100 |
| 12.00 | 0 | 100 |

The compound shown below is prepared following analogous procedures:

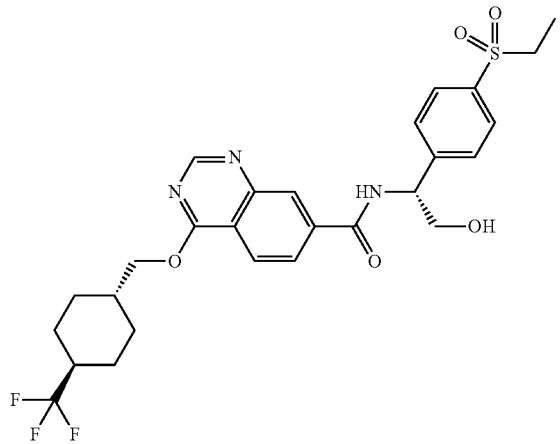

Cpd No Hy1C-1

Example 5
(S)-2-((6-(difluoromethoxy)pyridin-3-yl)methyl)-N-(4-(ethylsulfonyl)benzyl)-1-isopropyl-1,2,3,4-tetrahydroisoquinoline-6-carboxamide and (R)-2-((6-(difluoromethoxy)pyridin-3-yl)methyl)-N-(4-(ethylsulfonyl)benzyl)-1-isopropyl-1,2,3,4-tetrahydroisoquinoline-6-carboxamide (Cpd Nos Hy2A-25.1 and Hy2A-25.2)
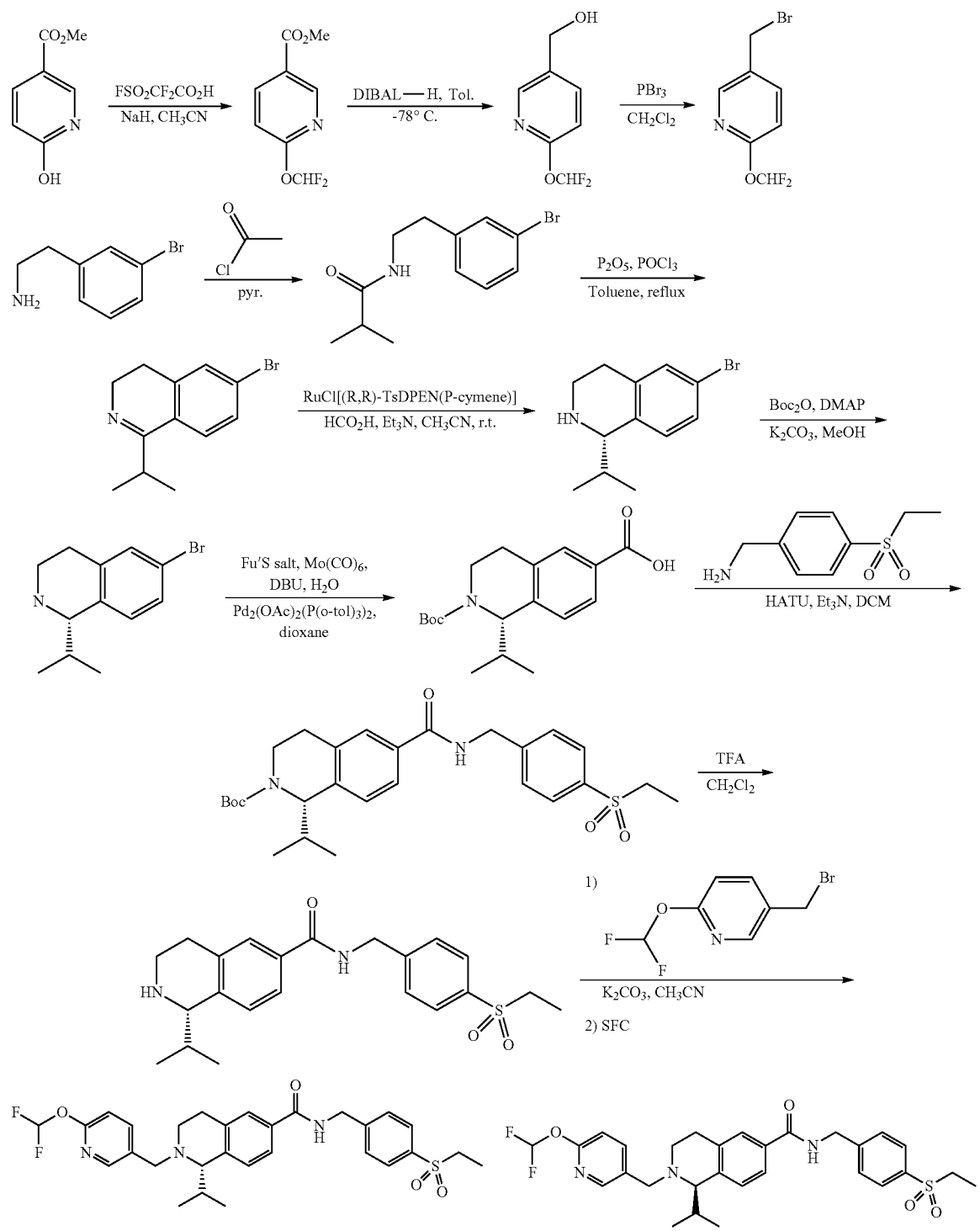

Step 1

To a solution of methyl 6-hydroxynicotinate (3.07 g, 20.0 mmol) in anhydrous acetonitrile (310 mL) was treated portionwise with NaH (60% dispersion in mineral oil, 2.16 g, 54.1 mmol) and the mixture was stirred at rt under a nitrogen atmosphere for 30 min. 2,2-difluoro-2-(fluorosulfonyl) acetic acid (6.07 g, 34.1 mmole) was then added dropwise and the resulting heterogeneous mixture was further stirred at rt under a nitrogen atmosphere for 30 min. Water (25 mL) was added slowly, and acetonitrile was removed under reduced pressure, water (150 mL) and ethyl acetate (150 mL) were added, and the separated layer was further extracted with ethyl acetate (3×100 mL). The combined organic layers were washed with brine (100 mL), dried over $Na_2SO_4$, concentrated to dryness under reduced pressure. The residue was purified by column chromatography on silica gel (eluting with petroleum ether:ethyl acetate=20:1 to 10:1) to afford methyl 6-(difluoromethoxy)nicotinate (3.0 g, 73%) as a yellow solid. $^1$H NMR: ($CDCl_3$ 400 MHz): δ 8.85 (s, 1H), 8.34 (d, J=8.0 Hz, 1H), 7.73-7.37 (m, 1H), 6.96 (d, J=7.6 Hz, 1H), 3.96 (s, 3H).

Step 2

To a solution of methyl 6-(difluoromethoxy)nicotinate (1.43 g, 7.0 mmol) in anhydrous toluene (40 mL) was treated dropwise with a solution of 1 M DIBAL-H in toluene (21.2 mL) and the resulting mixture was further stirred at −78° C. under a nitrogen atmosphere for 5 min, and then at 0° C. for 1.5 h. The mixture was treated successively with water (18.3 mL), sodium hydroxide (1 N, 4 mL) and sat. sodium bicarbonate (33 mL). The separated layer was further extracted with ethyl acetate (3×10 mL). The combined organic layers were dried over $Na_2SO_4$, filtered, concentrated to dryness under reduced pressure affording (6-(difluoromethoxy)pyridin-3-yl)methanol (1.0 g, 81%) as a colorless oil H NMR: ($CDCl_3$ 400 MHz): δ 8.18 (s, 1H), 7.78 (d, J=8.0 Hz, 1H), 7.66-7.37 (m, 1H), 6.92 (d, J=8.0 Hz, 1H), 4.71 (s, 2H).

Step 3

To a solution of (6-(difluoromethoxy)pyridin-3-yl)methanol (100.0 mg, 0.56 mmol) in anhydrous dichloromethane (5 mL) was cooled down with an ice-water bath under a nitrogen atmosphere. After stirring for 5 min, $PBr_3$ (168.0 mg, 0.62 mmol) in anhydrous dichloromethane (0.5 mL) was added dropwise under a nitrogen atmosphere. After addition, the reaction mixture was stirred for 1 h with an ice-water bath. TLC (petroleum ether:ethyl acetate=3:1) showed the starting material was consumed completely. The reaction mixture was quenched with sat. sodium bicarbonate (10 mL). The aqueous phase was extracted with dichloromethane (3×10 mL), washed with brine (20 mL), dried over anhydrous $Na_2SO_4$, filtered and concentrated by rotary evaporation under reduced pressure to afford 5-(bromomethyl)-2-(difluoromethoxy)pyridine (94 mg, 70%) as a colorless oil.

Step 4

To an ice-cooled solution of 2-(3-bromophenyl)ethanamine (30.0 g, 0.15 mol) in pyridine (100 mL) was added isobutyryl chloride (19.2 g, 0.18 mol) dropwise. Then the mixture was stirred at rt for 17 h. The mixture was poured into ice, filtered and dried in vacuum to give N-(3-bromophenethyl)isobutyramide (30.0 g, 74%) as a white solid. $^1$H NMR ($CDCl_3$ 400 MHz): δ 7.39-7.33 (m, 2H), 7.18 (t, J=7.6 Hz, 1H), 7.12 (d, J=7.6 Hz, 1H), 5.50 (brs, 1H), 3.52-3.45 (m, 2H), 2.80 (t, J=7.2 Hz, 2H), 2.32-2.28 (m, 1H), 1.12 (d, J=6.8 Hz, 6H).

Step 5

To a solution of N-(3-bromophenethyl)isobutyramide (500 mg, 1.9 mmol) in toluene (5 mL) was added $P_2O_5$ (657 mg, 4.6 mmol) and $POCl_3$ (2.7 g, 18 mmol). The mixture was refluxed for 16 h under $N_2$ atmosphere. TLC (petroleum ether:ethyl acetate=5:1) showed the starting material was consumed. The mixture was added into aq. NaOH solution (20%, 50 mL) slowly. The resulting mixture was extracted with ethyl acetate (3×20 mL). The combined organic layers were washed with brine (20 mL), dried over anhydrous $Na_2SO_4$, filtered and concentrated under reduced pressure. The residue was purified by column chromatography on silica gel (eluting with petroleum ether:ethyl acetate=10:1-3:1) to afford 6-bromo-1-isopropyl-3,4-dihydroisoquinoline (300 mg, 62%) as an oil. LCMS: $t_R$=1.078 min in 10-80AB_2 min chromatography (Durashell C18, XBrige Shield RP18 2.1*50 mm), MS (ESI) m/z 270.0 [M+19]$^+$. $^1$H NMR ($CD_3OD$ 400 MHz): δ 7.58 (d, J=8.4 Hz, 1H), 7.52 (d, J=8.4 Hz, 1H), 7.48 (s, 1H), 3.60-3.56 (m, 2H), 3.36-3.32 (m, 1H), 2.71-2.67 (m, 2H), 1.20 (d, J=6.8 Hz, 6H).

Step 6

To a solution of 6-bromo-1-isopropyl-3,4-dihydroisoquinoline (1.0 g, 4.0 mmol) in $CH_3CN$ (15 mL) was added $HCOOH$-$Et_3N$ azeotropic mixture (mole ratio 5:2, 3.5 mL) and RuCl[(R,R)-TsDPEN(P-cymene)] (30 mg, 0.05 mmol). Then the mixture was stirred at rt for 17 h under $N_2$ atmosphere. TLC (petroleum ether:ethyl acetate=5:1) showed the starting material was consumed. The mixture was quenched with sat. $NaHCO_3$ solution (15 mL) and then extracted with ethyl acetate (3×20 mL). The combined organic layers were washed with brine (20 mL), dried over anhydrous $Na_2SO_4$, filtered and concentrated under reduced pressure to afford (S)-6-bromo-1-isopropyl-1,2,3,4-tetrahydroisoquinoline (1.0 g, crude, 100%) as a red liquid, which was used in the next step directly. LCMS: $t_R$=0.650 min in 5-95AB_1.5 min chromatography (MK RP-18e 25-2 mm), MS (ESI) m/z 253.9 [M+H]$^+$.

Step 7

To a solution of (S)-6-bromo-1-isopropyl-1,2,3,4-tetrahydroisoquinoline (4.0 g, 16.0 mmol) in $CH_3OH$ (60 mL) was added $Boc_2O$ (5.2 g, 23.6 mmol), $K_2CO_3$ (6.4 g, 46.8 mmol) and DMAP (200 mg, 1.6 mmol). Then the mixture was stirred at rt for 16 h. TLC (petroleum ether:ethyl acetate=10:1) showed the starting material was consumed. The mixture was diluted with $H_2O$ (60 mL) and extracted with ethyl acetate (3×60 mL). The combined organic layers were washed with brine (60 mL), dried over anhydrous $Na_2SO_4$, filtered and concentrated under reduced pressure. The residue was purified by column chromatograph on silica gel (eluting with petroleum ether:ethyl acetate=20:1-10:1) to afford (S)-tert-butyl 6-bromo-1-isopropyl-3,4-dihydroisoquinoline-2(1H)-carboxylate (3.4 g, 60%) as an oil.

LCMS: $t_R$=1.018 min in 5-95AB_1.5 min chromatography (MK RP-18e 25-2 mm), MS (ESI) m/z 297.9 [M−55]$^+$.

SFC: $t_R$=8.34 and 10.09 min in 20 min chromatography (AD-H_5_B_05ML), ee=64.78%.

Step 8

A mixture of (S)-tert-butyl 6-bromo-1-isopropyl-3,4-dihydroisoquinoline-2(1H)-carboxylate (150 mg, 0.42 mmol), $H_2O$ (23 mg, 1.26 mmol), Fu's salt (24 mg, 0.08 mmol), $Mo(CO)_6$ (111 mg, 0.42 mmol), DBU (152 mg, 1.26 mmol) and $Pd_2(OAc)_2(P(o\text{-}tol)_3)_2$ (20 mg, 0.02 mmol) in dioxane (2 mL) was heated in microwave at 140° C. for 20 min. The mixture was basified to pH=10 with aq. NaOH (10%) and extracted with water (3×10 mL). The combined aqueous layer was acidified to pH=2 with HCl (1N) and extracted with $CH_2Cl_2$ (3×15 mL). The combined organic layers were washed with brine (10 mL), dried over anhydrous $Na_2SO_4$, filtered and concentrated under reduced pressure to afford (S)-2-(tert-butoxycarbonyl)-1-isopropyl-1,2,3,4-tetrahydroisoquinoline-6-carboxylic acid (135 mg, crude, 100%) as an oil, which was used for the next step directly. LCMS: $t_R$=0.848 min in 5-95AB_1.5 min chromatography (MK RP-18e 25-2 mm), MS (ESI) m/z 263.9 [M−55]+. SFC: $t_R$=3.839 and 4.184 min in 15 min chromatography (IC-3_3_5402, 35 mL), ee=65.46%.

Step 9

To a solution of (S)-2-(tert-butoxycarbonyl)-1-isopropyl-1,2,3,4-tetrahydroisoquinoline-6-carboxylic acid (540 mg, 1.7 mmol) in $CH_2Cl_2$ (20 mL) was added (4-(ethylsulfonyl)phenyl)methanamine (340 mg, 1.7 mmol), HATU (988 mg, 2.6 mmol) and $Et_3N$ (343 mg, 3.4 mmol). The mixture was stirred at rt overnight. TLC (petroleum ether:ethyl acetate=1:1) showed the starting material was consumed. The mixture was diluted with water (20 mL) and extracted with $CH_2Cl_2$ (3×20 mL). The combined organic layers were washed with brine (20 mL), dried over anhydrous $Na_2SO_4$, filtered and concentrated under reduced pressure. The residue was purified by preparative TLC (petroleum ether:ethyl acetate=1:1-2:1) to give (S)-tert-butyl 6-((4-(ethylsulfonyl)benzyl)carbamoyl)-1-isopropyl-3,4-dihydroisoquinoline-2(1H)-carboxylate (800 mg, 95%) as an oil. LCMS: $t_R$=1.189 min in 5-95AB_1.5 min chromatography (MK RP-18e 25-2 mm), MS (ESI) m/z 445.1 [M−55]+.

Step 10

To a solution of (S)-tert-butyl 6-((4-(ethylsulfonyl)benzyl)carbamoyl)-1-isopropyl-3,4-dihydroisoquinoline-2(1H)-carboxylate (0.8 g, 1.6 mmol) in dichloromethane (8.0 mL) was added TFA (1.6 mL) at 0° C. The mixture was stirred at rt overnight. The solution was adjusted to pH=8 with sat. $NaHCO_3$ solution. The mixture was extracted with dichloromethane (3×20 mL). The combined organic layers were washed with brine (20 mL), dried over anhydrous $Na_2SO_4$, filtered and concentrated under reduced pressure to afford (S)—N-(4-(ethylsulfonyl)benzyl)-1-isopropyl-1,2,3,4-tetrahydroisoquinoline-6-carboxamide (640 mg, 100%) as a yellow oil. LCMS: $t_R$=0.758 min in 5-95AB_1.5 min chromatography (MK RP-18e 25-2 mm), MS (ESI) m/z 401.1 [M+H]+.

Step 11

To a solution of (S)—N-(4-(ethylsulfonyl)benzyl)-1-isopropyl-1,2,3,4-tetrahydroisoquinoline-6-carboxamide (50 mg, 0.125 mmol) in $CH_3CN$ (5 mL) was added 5-(bromomethyl)-2-(difluoromethoxy)pyridine (29 mg, 0.125 mmol) and $K_2CO_3$ (51 mg, 0.375 mmole). The mixture was stirred at rt overnight. The mixture was diluted with ethyl acetate (10 mL) and water (10 mL), extracted with ethyl acetate (3×10 mL). The combined organic layers were washed with brine (20 mL), dried over $Na_2SO_4$, filtered and concentrated under reduced pressure. The residue was purified by column chromatography on silica gel (eluting with petroleum ether:ethyl acetate=10:1 to 1:1) to afford product which was purified by SFC and acidic preparative HPLC separation. After HPLC purification, the eluent was concentrated to remove organic solvent, the residue aqueous solution was lyophilized to give (S)-2-((6-(difluoromethoxy)pyridin-3-yl)methyl)-N-(4-(ethyl sulfonyl)benzyl)-1-isopropyl-1,2,3,4-tetrahydroisoquinoline-6-carboxamide (Hy2A-25.1) (22.40 mg, 74%) and (R)-2-((6-(difluoromethoxy)pyridin-3-yl)methyl)-N-(4-(ethyl sulfonyl)benzyl)-1-isopropyl-1,2,3,4-tetrahydroisoquinoline-6-carboxamide (Hy2A-25.2) (2.60 mg, 2%) as white solids. (Hy2A-25.1, 22.40 mg, 74%) as a white solid. LC-MS: $t_R$=0.765 min in 5-95AB_1.50 min chromatography (MK RP-18e 25-2 mm), MS (ESI) m/z 558.1 [M+H]+. $^1$H NMR ($CD_3OD$ 400 MHz): δ 8.52-8.51 (m, 1H), 8.05-7.91 (m, 1H), 7.90-7.84 (m, 4H), 7.66-7.61 (m, 3H), 7.35-7.33 (m, 1H), 7.14-7.12 (m, 1H), 4.72-4.70 (m, 2H), 4.45-4.14 (m, 2H), 3.93-3.90 (m, 1H), 3.50-3.33 (m, 4H), 3.23-3.19 (m, 2H), 1.30-1.15 (m, 6H), 0.82-0.80 (m, 2H), 0.66-0.64 (m, 2H). $^{19}$F NMR ($CD_3OD$ 400 MHz): δ−90.92. SFC: $t_R$=3.799 min in 8.0 min chromatography (Column: AS-H_S_5_5_40_3ML_8 MIN_15CM) ee=100%

Acid preparative HPLC Method:

Mobile phase A: water with 0.05% HCl solution

Mobile phase B: $CH_3CN$

Flow rate: 30 mL/min.

Detection: UV 220 nm

Column: Synergi Max-RP 150*30 mm*4 um

Column temperature: 30° C.

| Time in min | % A | % B |
| --- | --- | --- |
| 0.00 | 82 | 18 |
| 8.00 | 52 | 48 |
| 8.20 | 0 | 100 |
| 10.00 | 0 | 100 |

(Hy2A-25.2, 2.60 mg, 2%) as a white solid. LC-MS: $t_R$=0.765 min in 5-95AB_1.50 min chromatography (MK RP-18e 25-2 mm), MS (ESI) m/z 558.1 [M+H]$^+$. $^1$H NMR: (CD$_3$OD 400 MHz): δ 8.29 (s, 1H), 8.05-7.91 (m, 1H), 7.89-7.84 (m, 4H), 7.66-7.61 (m, 2H), 7.34 (d, J=8.0 Hz 1H), 7.13 (d, J=8.0 Hz 1H), 4.72 (s, 2H), 4.51-4.37 (m, 2H), 4.24-4.17 (m, 1H), 3.90-3.89 (m, 1H), 3.52-3.50 (m, 3H), 3.23-3.19 (m, 2H), 2.24-2.23 (m, 1H), 1.28-1.15 (m, 6H), 0.82-0.80 (m, 3H). $^{19}$F NMR: (CD$_3$OD 400 MHz): δ−90.80. SFC: $t_R$=4.388 min in 8.0 min chromatography (Column: AS-H_S_5_5_40_3ML_8 MIN_15CM) ee=100%

Acid preparative HPLC Method:
Mobile phase A: water with 0.05% HCl solution
Mobile phase B: CH$_3$CN
Flow rate: 30 mL/min.
Detection: UV 220 nm
Column: Synergi Max-RP 150*30 mm*4 um
Column temperature: 30° C.

| Time in min | % A | % B |
|---|---|---|
| 0.00 | 82 | 18 |
| 8.00 | 52 | 48 |
| 8.20 | 0 | 100 |
| 10.00 | 0 | 100 |

The following compounds prepared by analogous procedures

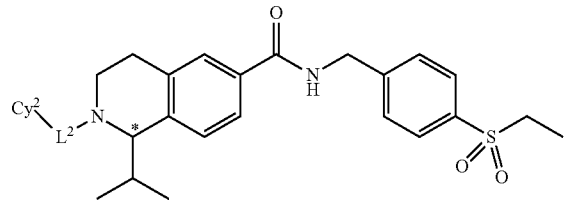

| Cpd No | Cy$^2$ | L$^2$ | * |
|---|---|---|---|
| Hy2A-1.1 | 5-cyano-2-pyrimidinyl | bond | a |
| Hy2A-1.2 | 5-cyano-2-pyrimidinyl | bond | a |
| Hy2A-2 | 5-(trifluoromethyl)-2-pyrimidinyl | bond | b |
| Hy2A-3 | 4-(trifluoromethyl)-2-pyrimidinyl | bond | b |
| Hy2A-4.1 | 5-(ethoxycarbonyl)-2-pyrimidinyl | bond | c |
| Hy2A-4.2 | 5-(ethoxycarbonyl)-2-pyrimidinyl | bond | c |
| Hy2A-5 | 5-(ethoxycarbonyl)-4-(trifluoromethyl)-2-pyrimidinyl | bond | d |
| Hy2A-5.1 | 5-(ethoxycarbonyl)-4-(trifluoromethyl)-2-pyrimidinyl | bond | e |
| Hy2A-5.2 | 5-(ethoxycarbonyl)-4-(trifluoromethyl)-2-pyrimidinyl | bond | e |
| Hy2A-12.1 | 5-methyl-2-pyrimidinyl | CH$_2$ | f |
| Hy2A-12.2 | 5-methyl-2-pyrimidinyl | CH$_2$ | f |
| Hy2A-13 | 4-fluorophenyl | CH$_2$ | g |
| Hy2A-14 | 4-cyanophenyl | CH$_2$ | h |
| Hy2A-15.1 | 4-cyanophenyl | CH$_2$ | i |
| Hy2A-15.2 | 4-cyanophenyl | CH$_2$ | i |
| Hy2A-16.1 | 5-cyano-2-pyridyl | CH$_2$ | j |
| Hy2A-16.2 | 5-cyano-2-pyridyl | CH$_2$ | j |
| Hy2A-17.1 | 6-cyano-3-pyridyl | CH$_2$ | k |
| Hy2A-17.2 | 6-cyano-3-pyridyl | CH$_2$ | k |
| Hy2A-18 | 5-methyl-2-pyrazinyl | CH$_2$ | l |
| Hy2A-19 | 4-chlorophenyl | CH$_2$ | m |
| Hy2A-20.1 | 4-chlorophenyl | CH$_2$ | n |
| Hy2A-20.2 | 4-chlorophenyl | CH$_2$ | n |
| Hy2A-21 | 5-chloro-2-pyridyl | CH$_2$ | o |
| Hy2A-24 | 1-methoxycarbonyl-4-piperidinyl | CH$_2$ | p |
| Hy2A-26.1 | 5-bromo-2-pyrimidinyl | CH$_2$ | q |
| Hy2A-26.2 | 5-bromo-2-pyrimidinyl | CH$_2$ | q | a, b, c, e, f, i, j, k, n, q=single isomers, separated by chromatography on chiral columns.

d, g, h, l, m, o, p=racemic compound.

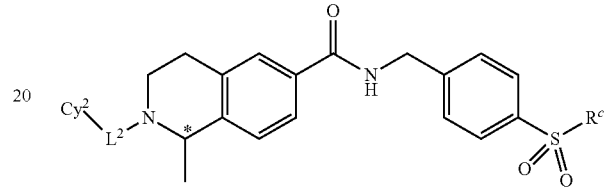

| Cpd No | Cy$^2$ | L$^2$ | R$^c$ | * |
|---|---|---|---|---|
| Hy2A-6 | 4-fluorophenyl | CH$_2$ | Me | a |
| Hy2A-7 | 4-cyanophenyl | CH$_2$ | Me | b |
| Hy2A-8 | 4-fluorophenyl | CH$_2$ | Et | c |
| Hy2A-9 | 4-chlorophenyl | CH$_2$ | Et | d |
| Hy2A-10 | 4-cyanophenyl | CH$_2$ | Et | e |
| Hy2A-11 | 4-chlorophenyl | CH$_2$ | Et | f | a, b, c, d, e, f=compounds are racemic.

The following compounds are prepared following procedures analogous to those described above except that Step 8 was replaced by reductive amination with trans-4-(trifluoromethyl)cyclohexane-1-carboxaldehyde mediated by NaCNBH$_3$ in the presence of HOAc, in MeOH solution at 70° C. for 1 h.

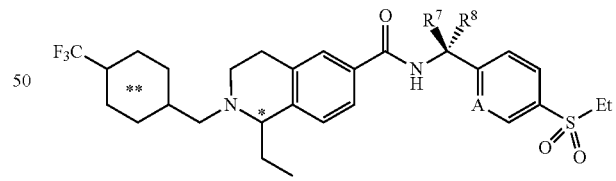

| Cpd No[a] | R$^7$ | R$^8$ | A | * | ** |
|---|---|---|---|---|---|
| Hy2A-27 | H | H | H | (S) | trans |
| Hy2A-28.1 | CH$_2$OH | H | CH | (S) | trans |
| Hy2A-28.2 | H | CH$_2$OH | CH | (S) | trans |
| Hy2A-28.3 | CH$_2$OH | H | CH | (R) | trans |
| Hy2A-29.1 | CH$_2$OH | H | N | (S) | trans |
| Hy2A-29.2 | H | CH$_2$OH | N | (S) | trans |
| Hy2A-29.3 | CH$_2$OH | H | N | (R) | trans |

[a]Isomers were separated by chromatography on a chiral column; stereochemistry was asssigned arbitrarily.

Example 6
(S)-2-(4-cyanobenzyl)-N-(4-(ethylsulfonyl)benzyl)-1-isopropyl-4,4-dimethyl-1,2,3,4-tetrahydroisoquinoline-6-carboxamide and (R)-2-(4-cyanobenzyl)-N-(4-(ethylsulfonyl)benzyl)-1-isopropyl-4,4-dimethyl-1-1,2,3,4-tetrahydroisoquinoline-6-carboxamide (Cpd Nos. Hy2A-23.1 and Hy2A-23.2)
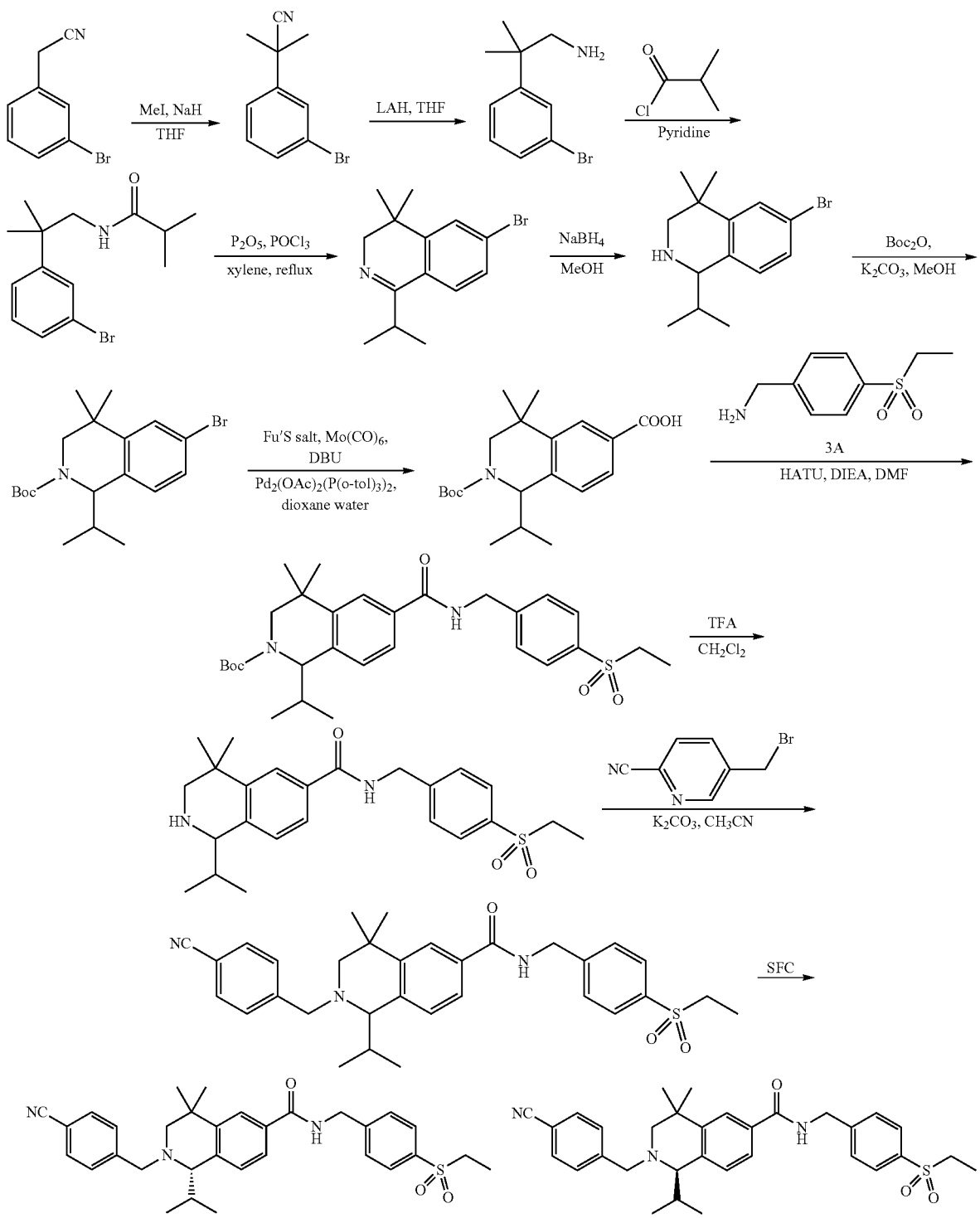

Step 1

To a solution of 2-(3-bromophenyl)acetonitrile (5.0 g, 24.38 mmol) in anhydrous THF (60 mL) was cooled down to 0-5° C. with an ice-water bath for 10 min. NaH (60% w/w in mineral oil, 2.6 g, 63.8 mmol) was added in portions and the mixture was stirred for 10 min. MeI (16.6 g, 116.9 mmol) was added dropwise via syringe over 5 min and the reaction was stirred at 0-5° C. with an ice-water bath until the starting material was consumed by TLC (petroleum ether:ethyl acetate=10:1, 2 hours). The reaction was quenched with water and partitioned between ethyl acetate (3×30 mL). The combined organics were washed with brine (2×50 mL), dried over anhydrous $Na_2SO_4$, filtered and concentrated by rotary evaporation under reduced pressure to give the residue, which was purified by column chromatography on silica gel (petroleum ether:ethyl acetate=50:1-15:1) to afford the 2-(3-bromophenyl)-2-methylpropanenitrile (4.8 g, 84%) as a flavescent oil. $^1$H NMR: (400 MHz): δ 7.61-7.58 (m, 1H), 7.47-7.39 (m, 2H), 7.29-7.24 (m, 1H), 1.71 (s, 6H).

Step 2

To a solution of $LiAlH_4$ (2.7 g, 71.40 mmol) in anhydrous THF (30 mL) was cooled down to 0-5° C. with an ice-water bath under a nitrogen atmosphere for 10 min. The 2-(3-bromophenyl)-2-methylpropanenitrile (4.0 g, 17.85 mmol) in anhydrous THF (20 mL) was added dropwise via syringe over 5 min. After addition, the reaction was stirred at rt for 2 h. The reaction mixture was checked by TLC. TLC (petroleum ether:ethyl acetate=10:1) showed the reaction was consumed completely. The reaction was cooled down to 0-5° C. with an ice-water bath for 10 min, quenched with water (30 mL). The mixture was filtered through a celite, washed with ethyl acetate (3×50 mL). The filtrate was concentrated by rotary evaporation under reduced pressure to give the residue, which was extracted with ethyl acetate (3×30 mL). The combined organics were washed with (2×50 mL), dried over anhydrous $Na_2SO_4$, filtered and concentrated by rotary evaporation under reduced pressure to afford the 2-(3-bromophenyl)-2-methylpropan-1-amine (3.2 g, 57%, crude) as a dark oil which was used for the next step directly. LC-MS: $t_R$=1.207 min in 10-80AB_2.0 min chromatography (Welch Xtimate C18, 2.1*30 mm, 3 um), MS (ESI) m/z 362.1 [M+Na]$^+$.

Step 3

To a solution of 2-(3-bromophenyl)-2-methylpropan-1-amine (21.0 g, 92.05 mmol) in pyridine (300 mL) was cooled down to 0-5° C. with an ice-water bath under a nitrogen atmosphere for 15 min. Isobutyryl chloride (11.6 mL, 110.46 mmol, d=1.017 g/mL) was added dropwise via syringe over 10 min. Then the reaction was stirred at rt overnight. The reaction was cooled down to 0-5° C. with an ice-water bath, quenched with water (200 mL) and diluted with ethyl acetate (800 mL). The organic layer was washed with brine (4×300 mL), concentrated by rotary evaporation under reduced pressure to afford the residue which was purified by basic preparative HPLC separation to afford the N-(2-(3-bromophenyl)-2-methylpropyl)isobutyramide (13.5 g, 49%) as a yellow oil.

Basic Preparative HPLC Method:
Mobile phase A: water with 0.05% ammonia hydroxide solution
Mobile phase B: MeCN
Flow rate: 80 mL/min.
Detection: UV 220 nm
Column: Phenomenex Gemini C18 250*250 mm*10 um
Column temperature: 30° C.

| Time in min | % A | % B |
|---|---|---|
| 0.00 | 55 | 45 |
| 25.00 | 30 | 70 |
| 25.20 | 0 | 100 |
| 30.00 | 0 | 100 |

$^1$H NMR: ($CDCl_3$ 400 MHz): δ 7.51-7.48 (m, 1H), 7.42-7.37 (m, 1H), 7.33-7.28 (m, 1H), 7.27-7.21 (m, 1H), 5.19-5.08 (m, 1H), 3.46 (d, J=6.0 Hz, 2H), 2.29-2.21 (m, 1H), 1.33 (s, 6H), 1.08 (d, J=6.8 Hz, 6H).

Step 4

To a solution of N-(2-(3-bromophenyl)-2-methylpropyl)isobutyramide (5.0 g, 16.76 mmol) in xylene (50 mL) was added $P_2O_5$ (5.9 g, 41.90 mmol) with an ice-water bath under a nitrogen atmosphere. After being stirred for 5 min, $POCl_3$ (27.5 g, 179.35 mmol) was added dropwise via syringe over 2 min. Then the reaction mixture was heated at reflux with a 120-125 OC oil bath overnight. The reaction was cooled down to rt, quenched with 15% wt sodium hydroxide solution (3×100 mL), dried over anhydrous $Na_2SO_4$, filtered and concentrated by rotary evaporation under reduced pressure to afford the residue which was purified by purified by column chromatography on silica gel (petroleum ether:ethyl acetate=50:1-20:1) to afford 6-bromo-1-isopropyl-4,4-dimethyl-3,4-dihydroisoquinoline (1.8 g, 38%) as a yellow oil. $^1$H NMR: ($CDCl_3$ 400 MHz): δ 7.48 (d, J=2.0 Hz, 1H), 7.43-7.36 (m, 2H), 3.50 (d, J=1.2 Hz, 1H), 3.29-3.19 (m, 1H), 1.22-1.16 (m, 12H).

Step 5

To a solution of 6-bromo-1-isopropyl-4,4-dimethyl-3,4-dihydroisoquinoline (500 mg, 1.78 mmol) in anhydrous MeOH (8 mL) was added $NaBH_4$ (136 mg, 3.56 mmol) under a nitrogen atmosphere. After addition, the reaction mixture was stirred at rt for 2 h. Then the reaction mixture was checked by TLC. TLC (petroleum ether:ethyl acetate=10:1) showed the starting material was consumed completely. Then the reaction was diluted with sat. $NH_4Cl$ solution (20 mL), extracted with ethyl acetate (3×10 mL). The combined organics were washed with brine (2×20 mL), dried over anhydrous $Na_2SO_4$, filtered and concentrated to afford the 6-bromo-1-isopropyl-4,4-dimethyl-1,2,3,4-tetrahydroisoquinoline (430 mg, 86%) as a white solid which was used for next step directly. $^1$H NMR: ($CDCl_3$ 400 MHz): δ 7.43 (d, J=2.0 Hz, 1H), 7.25-7.21 (m, 1H), 7.01 (d, J=8.4 Hz, 1H), 3.85 (d, J=4.0 Hz, 1H), 2.79 (dd, J=35.6, 12.4 Hz, 2H), 2.43-2.27 (m, 1H), 1.28 (s, 3H), 1.21 (s, 3H), 1.13 (d, J=7.2 Hz, 3H), 0.72 (d, J=6.8 Hz, 3H).

Step 6

To a solution of 6-bromo-1-isopropyl-4,4-dimethyl-1,2,3,4-tetrahydroisoquinoline (4.0 g, 14.17 mmol) in MeOH (50 mL) was added $(Boc)_2O$ (4.6 g, 21.26 mmol) and $K_2CO_3$ (4.9 g, 35.43 mmol) under a nitrogen atmosphere. The mixture was stirred at rt overnight. After, the reaction was checked by TLC. TLC (petroleum ether:ethyl acetate=5:1) showed the reaction was consumed completely. The reaction was diluted with water (80 mL) and extracted with ethyl acetate (3×30 mL). The combined organics were washed with brine (2×100 mL), dried over anhydrous $Na_2SO_4$, filtered and concentrated by rotary evaporation under reduced pressure to afford the residue which was purified by purified by column chromatography on silica gel (petroleum ether:ethyl acetate=50:1) to afford tert-butyl 6-bromo-1-isopropyl-4,4-dimethyl-3,4-dihydroisoquinoline-2(1H)-carboxylate (4.5 g, 38%) as a colorless oil. 1H NMR: ($CDCl_3$ 400 MHz): δ 7.46-7.39 (m, 1H), 7.26-7.21 (m, 1H), 7.00-6.95 (m, 1H), 4.92-4.86 (m, 0.5H), 4.79-4.72 (m, 0.5H), 4.11-4.05 (m, 0.5H), 3.90-3.83 (m, 0.5H), 3.12-3.04 (m, 0.5H), 2.99-2.92 (m, 0.5H), 2.11-1.96 (m, 1H), 1.49-1.42 (m, 9H), 1.32-1.25 (m, 3H), 1.16 (s, 3H), 1.08-1.03 (m, 3H), 0.94-0.86 (m, 3H).

Step 7

To a solution of tert-butyl 6-bromo-1-isopropyl-4,4-dimethyl-3,4-dihydroisoquinoline-2(1H)-carboxylate (400 mg, 1.05 mmol) in 1,4-dioxane (2.0 mL) and $H_2O$ (2.0 mL) was added Fu's salt (61 mg, 0.21 mmol), $Mo(CO)_6$ (277 mg, 1.05 mmol), DBU (480 mg, 3.15 mmol) and $Pd_2(OAc)_2(P(o-tol)_3)_2$ (103 mg, 0.11 mmol) under a nitrogen atmosphere. After addition, the reaction mixture was heated at 140° C. in microwave for 20 min. The reaction mixture was cooled down to rt, filtered through celite, washed with ethyl acetate (3×20 mL). The combined organics were washed with brine (2×30 mL), dried over anhydrous $Na_2SO_4$, concentrated by rotary evaporation under reduced pressure to afford the residue, which was purified by preparative HPLC (TFA) to afford the 2-(tert-butoxycarbonyl)-1-isopropyl-4,4-dimethyl-1,2,3,4-tetrahydroisoquinoline-6-carboxylic acid (300 mg, 60% purity, 49%) as a white solid. LC-MS: $t_R$=1.217 min in 10-80AB_2.0 min chromatography (Welch Xtimate C18, 2.1*30 mm, 3 um), MS (ESI) m/z 292.1 [M−55]$^+$.

Step 8

To a solution of 2-(tert-butoxycarbonyl)-1-isopropyl-4,4-dimethyl-1,2,3,4-tetrahydroisoquinoline-6-carboxylic acid (300 mg, 0.518 mmol, 60% purity) in anhydrous DMF (8 ml) was added (4-(ethylsulfonyl)phenyl)methanamine (103 mg, 0.518 mmol), HATU (295 mg, 0.777 mmol) and DIPEA (134 mg, 1.036 mmol) under a nitrogen atmosphere. After addition, the reaction mixture was stirred at rt overnight. The reaction mixture was diluted with ethyl acetate (40 mL). The organic layer was washed with brine (3×20 mL), concentrated by rotary evaporation under reduced pressure to afford the residue which was purified by column chromatography on silica gel (petroleum ether:ethyl acetate=5:1-1:2) to afford tert-butyl 6-((4-(ethylsulfonyl)benzyl)carbamoyl)-1-isopropyl-4,4-dimethyl-3,4-dihydroisoquinoline-2(1H)-carboxylate (220 mg, 80%) as a yellow oil. LC-MS: $t_R$=1.242 min in 10-80AB_2.0 min chromatography (Welch Xtimate C18, 2.1*30 mm, 3 um), MS (ESI) m/z 529.2 [M+H]$^+$.

Step 9

To a solution of tert-butyl 6-((4-(ethylsulfonyl)benzyl)carbamoyl)-1-isopropyl-4,4-dimethyl-3,4-dihydroisoquinoline-2(1H)-carboxylate (220 mg, 0.416 mmol) in $CH_2Cl_2$ (3 mL) was added TFA (1 mL) under a nitrogen atmosphere. After addition, the reaction was stirred at rt overnight. The reaction mixture was checked by TLC. TLC (petroleum ether:ethyl acetate=10:1) showed the starting material was consumed completely. The reaction was basified with sat. $NaHCO_3$ solution to pH=10-11, extracted with ethyl acetate (3×10 mL). The combined organic layers were dried over anhydrous $Na_2SO_4$, filtered and concentrated by rotary evaporation under reduced pressure to afford the N-(4-(ethylsulfonyl)benzyl)-1-isopropyl-4,4-dimethyl-1,2,3,4-tetrahydroisoquinoline-6-carboxamide (160 mg, 90%) as a brown solid. LC-MS: $t_R$=0.816 min in 10-80AB_2.0 min chromatography (Welch Xtimate C18, 2.1*30 mm, 3 um), MS (ESI) m/z 429.2 [M+H]$^+$.

Step 10

To a solution of N-(4-(ethylsulfonyl)benzyl)-1-isopropyl-4,4-dimethyl-1,2,3,4-tetrahydroisoquinoline-6-carboxamide (60 mg, 0.14 mmol) in $CH_3CN$ (2 mL) was added 4-(bromomethyl)benzonitrile (33 mg, 0.17 mmol) and $K_2CO_3$ (39 mg, 0.28 mmol) under a nitrogen atmosphere. After addition, the reaction mixture was stirred at rt overnight. The reaction mixture was diluted with ethyl acetate (20 mL) and water (10 mL). The aqueous phase was extracted with ethyl acetate (2×10 mL). The combined organics were washed with brine (2×20 mL), dried over anhydrous $Na_2SO_4$, filtered and the filtrate was concentrated by rotary evaporation under reduced pressure to afford the residue which was purified by column chromatography on silica gel (petroleum ether:ethyl acetate=5:1-1:1) to afford 2-(4-cyanobenzyl)-N-(4-(ethylsulfonyl)benzyl)-1-isopropyl-4,4-dimethyl-1,2,3,4-tetrahydroisoquinoline-6-carboxamide (60 mg, 79%) as a colorless solid. LC-MS: $t_R$=0.769 min in 5-95AB_1.5 min chromatography (Welch Xtimate C18, 2.1*30 mm, 3 um), MS (ESI) m/z 566.1 [M+Na]$^+$.

Step 11

The 2-(4-cyanobenzyl)-N-(4-(ethylsulfonyl)benzyl)-1-isopropyl-4,4-dimethyl-1,2,3,4-tetrahydroisoquinoline-6-carboxamide (60 mg, 0.11 mmol) was separated with SFC, purified by preparative HPLC (HCl). After preparative HPLC purification, the eluent was concentrated by rotary evaporation under reduced pressure to remove organic solvents. The residual aqueous solution was lyophilized to give the two enantiomers of 2-(4-cyanobenzyl)-N-(4-(ethylsulfonyl)benzyl)-1-isopropyl-4,4-dimethyl-1,2,3,4-tetrahydroisoquinoline-6-carboxamide as white solids. (Hy2A-23.1, 21.50 mg, 99.79% purity, 36%) as a white solid. LC-MS: $t_R$=0.976 min in 10-80AB_2.0 min chromatography (Welch Xtimate C18, 2.1*30 mm, 3 um), MS (ESI) m/z 544.2 [M+H]$^+$. $^1$H NMR: ($CD_3OD$ 400 MHz): δ 8.12 (s, 1H), 7.96-7.59 (m, 9H), 7.27 (d, J=8.4 Hz, 1H), 4.75-4.18 (m, 4H), 4.08-3.39 (m, 2H), 3.28-2.07 (m, 4H), 1.80-1.40 (m, 6H), 1.27-1.05 (m, 6H), 0.76 (s, 3H). SFC: $t_R$=1.490 min in 3.0 min chromatography (AD-H_3UM_5_5_40_4 mL.ee=100%).

HCl Preparative HPLC Method:
Mobile phase A: water with 0.05% HCl solution (v/v)
Mobile phase B: MeCN
Flow rate: 30 mL/min.
Detection: UV 220 nm
Column: Synergi Ma-RP C18 150*30*4 um
Column temperature: 30° C.

| Time in min | % A | % B |
|---|---|---|
| 0.00 | 76 | 24 |
| 8.00 | 46 | 54 |
| 8.20 | 0 | 100 |
| 10.00 | 0 | 100 |

(Hy2A-23.2, 22.50 mg, 99.83% purity, 38%) as a white solid. LC-MS: $t_R$=0.976 min in 10-80AB_2.0 min chromatography (Welch Xtimate C18, 2.1*30 mm, 3 um), MS (ESI) m/z 544.2 [M+H]$^+$. $^1$H NMR: (CD$_3$OD 400 MHz): δ 7.87 (m, 6.5H), 7.64 (d, J=8.0 Hz, 3.5H), 7.26 (d, J=6.0 Hz, 1H), 4.73 (s, 3H), 3.22 (dd, J=14.8, 7.2 Hz, 3H), 1.50 (s, 3H), 1.39-1.28 (m, 3H), 1.25-1.18 (m, 5H), 0.77 (s, 1H). SFC: $t_R$=1.636 min in 8.0 min chromatography (AD-H_3UM_5_5_40_4 mL.ee=99.38%).

HCl Preparative HPLC Method:

Mobile phase A: water with 0.05% HCl solution (v/v)

Mobile phase B: MeCN

Flow rate: 30 mL/min.

Detection: UV 220 nm

Column: Synergi Ma-RP C18 150*30*4 um

Column temperature: 30° C.

| Time in min | % A | % B |
|---|---|---|
| 0.00 | 76 | 24 |
| 8.00 | 46 | 54 |
| 8.20 | 0 | 100 |
| 10.00 | 0 | 100 |

The following compounds are prepared using analogous procedures:

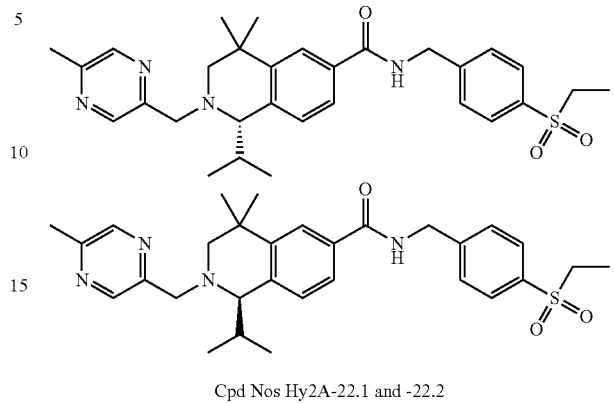

Cpd Nos Hy2A-22.1 and -22.2

Example 7

(S)-7-(4-chlorobenzyl)-N-(4-(ethylsulfonyl)benzyl)-8-isopropyl-5,6,7,8-tetrahydro-1,7-naphthyridine-3-carboxamide and (R)-7-(4-chlorobenzyl)-N-(4-(ethylsulfonyl)benzyl)-8-isopropyl-5,6,7,8-tetrahydro-1,7-naphthyridine-3-carboxamide (Cpd Nos Hy2B-8.1 and Hy2B-8.2)

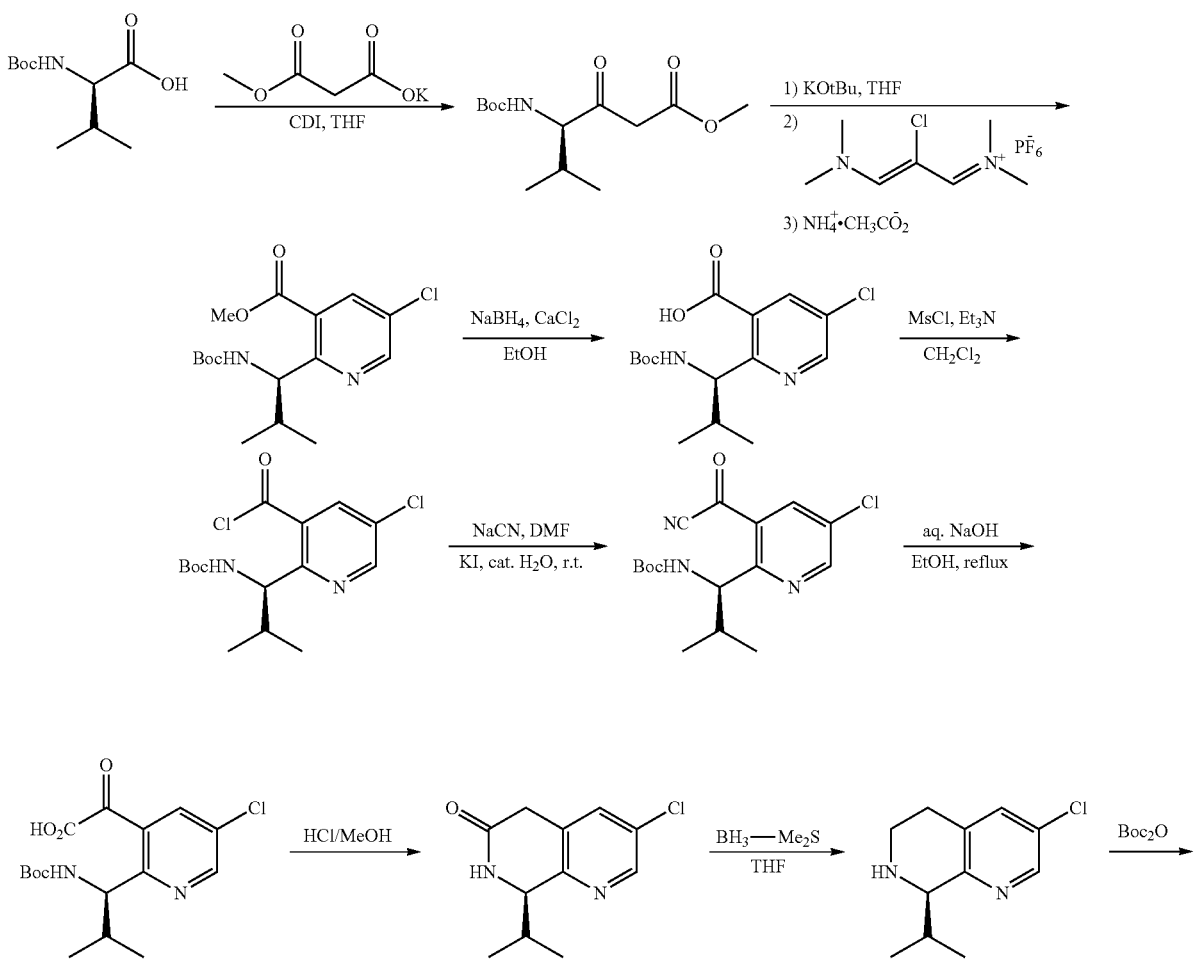

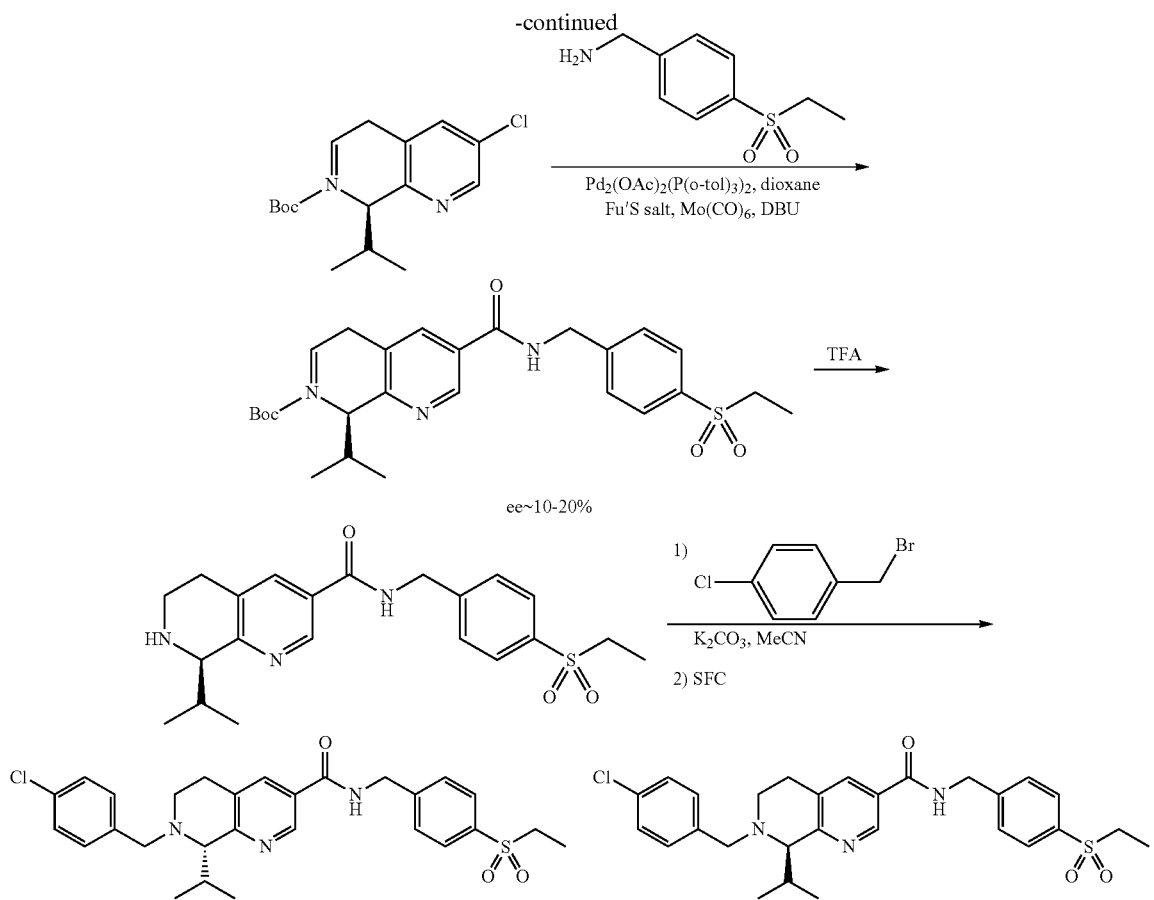

Step 1

A mixture of (R)-2-((tert-butoxycarbonyl)amino)-3-methylbutanoic acid (19.6 g, 90.0 mmol) and CDI (15.3 g, 95.6 mmol) in THF (300 mL) was stirred at rt for 1 h. Then potassium 3-methoxy-3-oxopropanoate (15.5 g, 99.0 mmol) and MgCl$_2$ (9.5 g, 95.0 mmol) were added. After addition, the mixture was stirred at 50° C. for 18 h. TLC (petroleum ether:ethyl acetate=5:1) showed the starting material was consumed. The mixture was quenched with water (500 mL), extracted with ethyl acetate (3×500 mL). The combined organic layers were washed with sat. aq. NaHCO$_3$ solution (200 mL), brine (200 mL), dried over anhydrous sodium sulfate, filtered and concentrated under reduced pressure to give crude (R)-methyl 4-((tert-butoxycarbonyl) amino)-5-methyl-3-oxohexanoate (25 g, 100%) as a yellow oil.

Step 2

To a solution of (R)-methyl 4-((tert-butoxycarbonyl)amino)-5-methyl-3-oxohexanoate (25 g, 91.5 mmol) in anhydrous THF (400 mL) was added KO$^t$Bu (10.8 g, 96.0 mmol) at 0° C. under N$_2$. After stirred for 45 min, to the mixture was added DABCO (10.8 g, 96.0 mmol) and 2-chloro-1,3-bis(dimethylamino)trimethinium hexafluorophosphate (29.4 g, 96.0 mmol), and then the mixture was stirred at rt for 3 h under N$_2$. CH$_3$CO$_2$NH$_4$ (21.2 g, 275 mmol) was added to the above solution, and the resulting mixture was stirred at rt overnight. TLC (petroleum ether:ethyl acetate=5:1) showed the starting material was consumed. The mixture was diluted with ethyl acetate (1000 mL), washed with water (3×300 mL), brine (300 mL), dried over anhydrous sodium sulfate, filtered and concentrated under reduced pressure. The residue was purified by column chromatograph on silica gel (eluting with petroleum ether:ethyl acetate=5:1) to give (R)-methyl 2-(1-((tert-butoxycarbonyl)amino)-2-methylpropyl)-5-chloronicotinate (11.4 g, 36%) as a colorless oil. LC-MS: $t_R$=0.913 min in 5-95AB_1.5 min chromatography (MK RP18e 25-2 mm), MS (ESI) m/z 342.9 [M+H]$^+$.

Step 3

To a solution of (R)-methyl 2-(1-((tert-butoxycarbonyl)amino)-2-methylpropyl)-5-chloronicotinate (11.4 g, 33.3 mmol) in ethanol (250 mL) was added NaBH$_4$ (2.5 g, 66.6 mmol) and CaCl$_2$ (3.6 g, 33.3 mmol) at 0° C. under N$_2$. The mixture was stirred at the same temperature for 2 h. TLC (petroleum ether:ethyl acetate=5:1) showed the starting material was consumed. The mixture was poured into sat. aq. NH$_4$Cl solution (150 mL), extracted with ethyl acetate (3×200 mL). The combined organic layers were washed with brine (200 mL), dried over anhydrous sodium sulfate, filtered and concentrated under reduced pressure to give (R)-tert-butyl (1-(5-chloro-3-(hydroxymethyl) pyridin-2-yl)-2-methylpropyl)carbamate (7.3 g, 70%) as a colorless oil, which was used for the next step directly without further purification.

Step 4

To a solution of (R)-tert-butyl (1-(5-chloro-3-(hydroxymethyl)pyridin-2-yl)-2-methylpropyl)carbamate (7.3 g, 22.2 mmol) and Et₃N (11.3 mL, 81.4 mmol, 0.726 g/mL) in CH₂Cl₂ (100 mL) was added MsCl (3.4 g, 29.6 mmol) at 0° C. under N₂. The mixture was stirred at 0° C. for 16 h. The mixture was diluted with CH₂Cl₂ (100 mL), washed with brine (100 mL), dried over anhydrous Na₂SO₄, filtered and concentrated under reduced pressure. The residue was purified by column chromatograph on silica gel (eluting with petroleum ether:ethyl acetate=5:1) to give (R)-tert-butyl (1-(5-chloro-3-(chloromethyl)pyridin-2-yl)-2-methylpropyl)carbamate (4.2 g, 58%) as a white solid. LC-MS: $t_R$=0.940 min in 5-95AB_1.5 min chromatography (MK RP18e 25-2 mm), MS (ESI) m/z 332.9 [M+H]⁺.

Step 5

A mixture of (R)-tert-butyl (1-(5-chloro-3-(chloromethyl)pyridin-2-yl)-2-methylpropyl)carbamate (4.2 g, 12.7 mmol), NaCN (1.8 g, 36.7 mmol), and KI (0.2 g, 1.27 mmol) in DMF (50 mL) and water (5 mL) was stirred at rt overnight. TLC (petroleum ether:ethyl acetate=5:1) showed the starting material was consumed completely. The mixture was poured into water (300 mL), extracted with ethyl acetate (3×300 mL). The combined organic layers were washed with brine (100 mL), dried over anhydrous sodium sulfate, filtered and concentrated under reduced pressure to give (R)-tert-butyl (1-(5-chloro-3-(cyanomethyl)pyridin-2-yl)-2-methylpropyl)carbamate (4.0 g, 100%) as a yellow oil. LC-MS: $t_R$=0.873 min in 5-95AB_1.5 min chromatography (MK RP18e 25-2 mm), MS (ESI) m/z 267.9 [M−55]⁺.

Step 6

To a solution of (R)-tert-butyl (1-(5-chloro-3-(cyanomethyl)pyridin-2-yl)-2-methylpropyl)carbamate (4.0 g, 12.4 mol) in ethanol (50 mL) was added dropwise a solution of NaOH (1.5 g, 10% wt in water, 37.2 mmol). The mixture was stirred at 90° C. for 16 h. The mixture was cooled to rt, poured into water (100 mL) and adjusted to pH=3 with 1 N HCl solution. The mixture was extracted with ethyl acetate (3×50 mL) and the combined organic layers were washed with brine, dried over anhydrous Na₂SO₄, filtered and concentrated under reduced pressure to give (R)-2-(2-(1-((tert-butoxycarbonyl)amino)-2-methylpropyl)-5-chloropyridin-3-yl)acetic acid (2.6 g, 62%) as a colorless oil. LC-MS: $t_R$=1.125 min in 5-95AB_1.5 min chromatography (MK RP18e 25-2 mm), MS (ESI) m/z 342.9 [M+H]⁺.

Step 7

A mixture of (R)-2-(2-(1-((tert-butoxycarbonyl)amino)-2-methylpropyl)-5-chloropyridin-3-yl)acetic acid (2.6 g, 7.6 mmol) in HCl/MeOH (100 mL, 4 N) was stirred at rt overnight. The mixture was concentrated under reduced pressure. The residue was diluted with ethyl acetate (200 mL), washed with sat. aq. NaHCO₃ solution (100 mL), brine (100 mL), dried over Na₂SO₄, filtered and concentrated under reduced pressure. The residue was purified by column chromatography on silica gel (eluting with petroleum ether:ethyl acetate=1:1) to give (R)-3-chloro-8-isopropyl-7,8-dihydro-1,7-naphthyridin-6(5H)-one (900 mg, 53%) as a colorless oil. LC-MS: $t_R$=0.677 min in 5-95AB_1.5 min chromatography (MK RP18e 25-2 mm), MS (ESI) m/z 224.9 [M+H]⁺. ¹H NMR (CDCl₃ 400 MHz): δ 8.41 (d, J=2.0 Hz, 1H), 7.44 (d, J=1.6 Hz, 1H), 4.43 (brs, 1H), 3.76-3.61 (m, 1H), 3.58-3.43 (m, 1H), 2.41-2.27 (m, 1H), 1.12-0.96 (m, 3H), 0.73 (d, J=6.8 Hz, 3H).

Step 8

To a solution of (R)-3-chloro-8-isopropyl-7,8-dihydro-1,7-naphthyridin-6(5H)-one (900 mg, 4.0 mmol) in THF (40 mL) was added BH₃·Me₂S (2.5 mL, 20.0 mmol) at 0° C. under N₂. The mixture was stirred at reflux for 3 h. TLC (petroleum ether:ethyl acetate=1:1) showed the starting material was consumed. The mixture was cooled to 0° C., and quenched with sat. NH₄Cl solution (50 mL), diluted with water (100 mL), extracted with ethyl acetate (3×100 mL). The combined organic layers were washed with brine (100 mL), dried over anhydrous sodium sulfate, filtered and concentrated under reduced pressure to give (R)-3-chloro-8-isopropyl-5,6,7,8-tetrahydro-1,7-naphthyridine (1.3 g, 100%) as a yellow oil, which was used for the next step directly without further purification. LC-MS: $t_R$=0.790 min in 5-95AB_1.5 min chromatography (MK RP18e 25-2 mm), MS (ESI) m/z 210.9 [M+H]⁺.

Step 9

A mixture of (R)-3-chloro-8-isopropyl-5,6,7,8-tetrahydro-1,7-naphthyridine (1.3 g, 6.2 mol), Boc₂O (3.4 g, 15.5 mmol), and Et₃N (3.1 g, 30.9 mmol) in CH₂Cl₂ (50 mL) was stirred at rt overnight. The mixture was concentrated under reduced pressure. The residue was purified by column chromatograph on silica gel (eluting with petroleum ether:ethyl acetate=5:1) to give (R)-tert-butyl 3-chloro-8-isopropyl-5,6-dihydro-1,7-naphthyridine-7(8H)-carboxylate (276 m g, 15%) as a colorless oil. LC-MS: $t_R$=0.935 min in 5-95AB_1.5 min chromatography (MK RP18e 25-2 mm), MS (ESI) m/z 311.0 [M+H]⁺.

Step 10

A mixture of (R)-tert-butyl 3-chloro-8-isopropyl-5,6-dihydro-1,7-naphthyridine-7(8H)-carboxylate (315 mg, 1.01 mmol), (4-(ethylsulfonyl)phenyl)methanamine (600 mg, 3.0 mmol), Fu's salt (29 mg, 0.1 mmol), Mo(CO)₆ (264 mg, 1.01 mmol), DBU (456 mg, 3.0 mmol), and Pd₂(OAc)₂(P(o-tol)₃)₂(33 mg, 0.035 mmol) in dioxane (5 mL) was stirred at 160° C. for 20 min under N₂ in microwave. The mixture was concentrated under reduced pressure. The residue was purified by preparative TLC (petroleum ether:ethyl acetate=1:1) to give (R)-tert-butyl 3-((4-(ethylsulfonyl)benzyl)carbamoyl)-8-isopropyl-5,6-dihydro-1,7-naphthyridine-7(8H)-carboxylate (240 mg, 47%) as a colorless oil.

Step 11

A mixture of (R)-tert-butyl 3-((4-(ethylsulfonyl)benzyl)carbamoyl)-8-isopropyl-5,6-dihydro-1,7-naphthyridine-7(8H)-carboxylate (240 mg, 0.478 mmol) and TFA (1.0 mL) in dichloromethane (5 mL) was stirred at 25° C. for 2 h. TLC (petroleum ether:ethyl acetate=1:2) showed the starting material was consumed completely. The mixture was concentrated under reduced pressure to afford crude (R)—N-(4-(ethyl sulfonyl)benzyl)-8-isopropyl-5,6,7,8-tetrahydro-1,7-naphthyridine-3-carboxamide (200 mg, 100%) as a red oil, which was used for the next step directly without further purification.

Step 12

A mixture of (R)—N-(4-(ethylsulfonyl)benzyl)-8-isopropyl-5,6,7,8-tetrahydro-1,7-naphthyridine-3-carboxamide (50 mg, 0.124 mmol), 1-(bromomethyl)-4-chlorobenzene (25 mg, 0.124 mmol), and K₂CO₃ (51 mg, 0.372 mmol) in CH₃CN (2 mL) was stirred at 25° C. for 3 h. TLC (petroleum ether:ethyl acetate=1:2) showed the starting material was consumed completely. The mixture was filtered. The filtrate was concentrated under reduced pressure to give the crude product. The residue was purified by preparative TLC (petroleum ether:ethyl acetate=1:2) to give about 30 mg of the product. The product was purified by SFC separation and basic preparative HPLC to give the two enantiomers of 7-(4-chlorobenzyl)-N-(4-(ethylsulfonyl)benzyl)-8-isopropyl-5,6,7,8-tetrahydro-1,7-naphthyridine-3-carboxamide as white solids. (Hy2B-8.1, 10.2 mg, 20%) as a white solid. LCMS: $t_R$=0.700 min in 5-95AB_1.5 min chromatography (MK RP18e 25-2 mm, MS (ESI) m/z 526.1 [M+H]⁺. ¹H NMR (CDCl₃ 400 MHz): δ 8.82 (d, J=2.0 Hz, 1H), 7.89 (m, 3H), 7.57 (d, J=8.0 Hz, 2H), 7.30-7.29 (m, 4H), 6.68-6.65 (m, 1H), 4.80-4.78 (m, 2H), 3.77-3.62 (m, 2H), 3.51 (d, J=6.0 Hz, 1H), 3.22-3.20 (m, 2H), 3.13 (q, J=7.2 Hz, 2H), 2.79-2.78 (m, 1H), 2.77-2.70 (m, 2H), 2.20-2.15 (m, 1H), 1.30 (t, J=7.6 Hz, 3H), 1.06 (d, J=6.8 Hz, 3H), 0.92 (d, J=6.8 Hz, 3H). SFC: $t_R$=0.946 min in 3 min chromatography (AD-H_3UM_3_40_4ML_3MIN.M), ee=100%.

(Hy2B-8.2, 28.5 mg, 57%) as a white solid. LCMS: $t_R$=0.703 min in 5-95AB_1.5 min chromatography (MK RP18e 25-2 mm, MS (ESI) m/z 526.1 [M+H]⁺. ¹H NMR (CDCl₃ 400 MHz): δ 8.82 (d, J=2.0 Hz, 1H), 7.89 (d, J=8.4 Hz, 3H), 7.57 (d, J=8.4 Hz, 2H), 7.30-7.28 (m, 4H), 6.68-6.66 (m, 1H), 4.80-4.78 (m, 2H), 3.77-3.62 (m, 2H), 3.51 (d, J=6.0 Hz, 1H), 3.22-3.20 (m, 2H), 3.13 (q, J=7.2 Hz, 2H), 2.79-2.78 (m, 1H), 2.77-2.70 (m, 2H), 2.20-2.15 (m, 1H), 1.30 (t, J=7.2 Hz, 3H), 1.06 (d, J=6.8 Hz, 3H), 0.92 (d, J=6.8 Hz, 3H). SFC: $t_R$=1.288 min in 3 min chromatography (AD-H_3UM_3_404ML_3MIN.M), ee=100%.

Example 8

(S)-7-(4-cyanobenzyl)-N-(4-(ethylsulfonyl)benzyl)-8-isopropyl-5,6,7,8-tetrahydro-1,7-naphthyridine-3-carboxamide and (R)-7-(4-cyanobenzyl)-N-(4-(ethylsulfonyl)benzyl)-8-isopropyl-5,6,7,8-tetrahydro-1,7-naphthyridine-3-carboxamide (Cpd Nos Hy2B-9.1 and Hy2B-9.2)

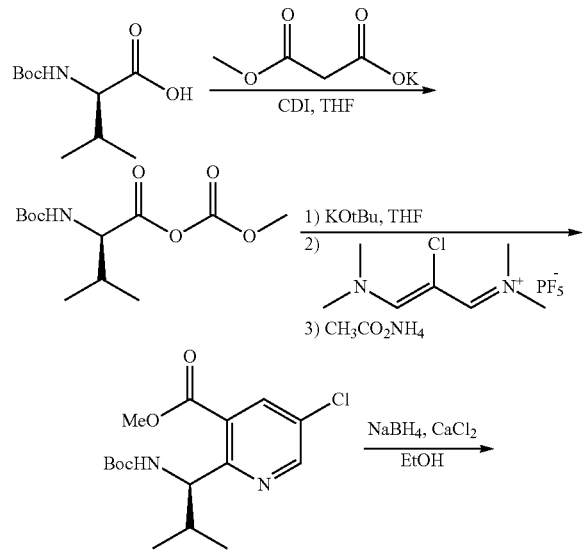

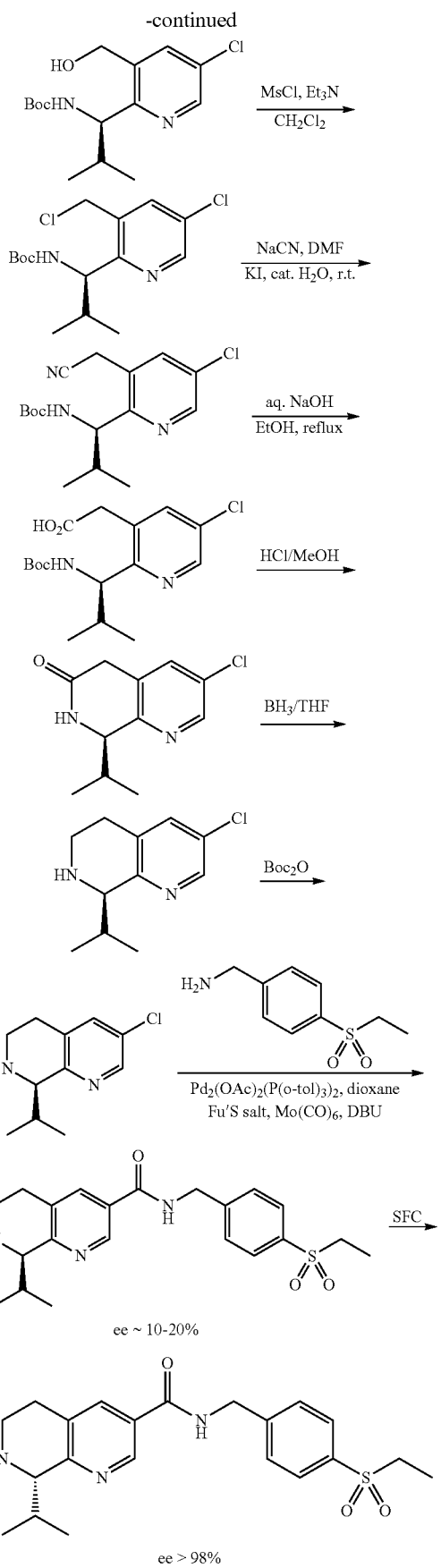

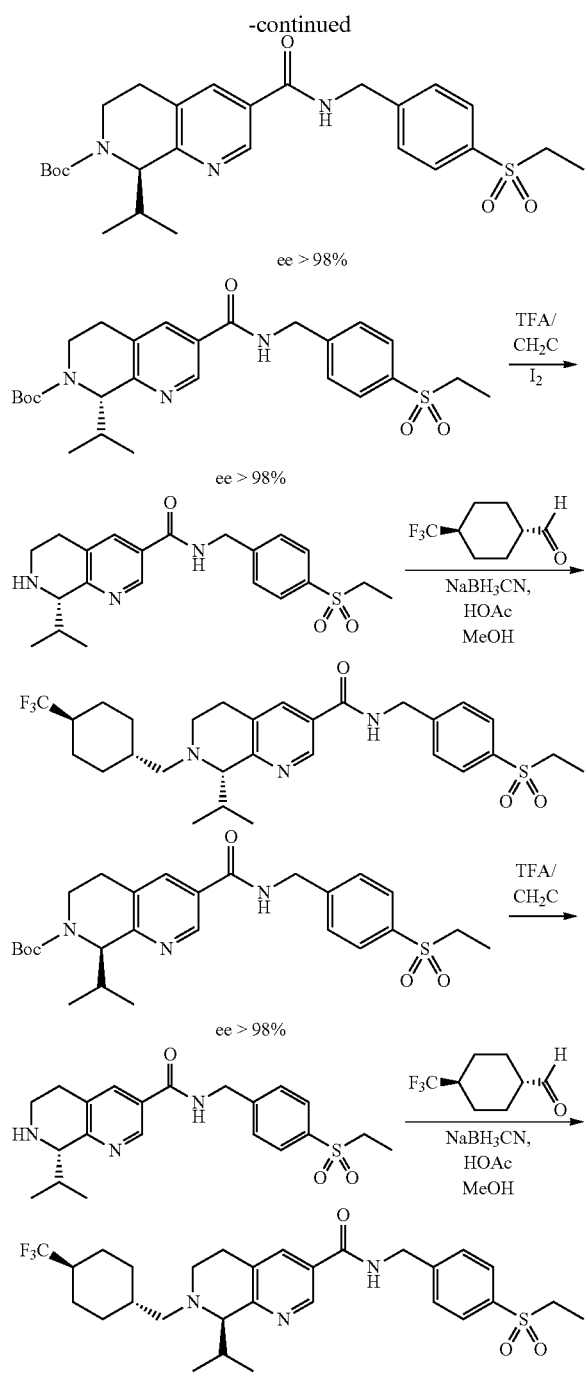

Step 1

A mixture of (R)-2-((tert-butoxycarbonyl)amino)-3-methylbutanoic acid (19.6 g, 90.0 mmol) and CDI (15.3 g, 95.6 mmol) in THF (300 mL) was stirred at rt for 1 h. Then potassium 3-methoxy-3-oxopropanoate (15.5 g, 99.0 mmol) and $MgCl_2$ (9.5 g, 95.0 mmol) were added. After addition, the mixture was stirred at 50° C. for 18 h. TLC (petroleum ether:ethyl acetate=5:1) showed the starting material was consumed. The mixture was quenched with water (500 mL), extracted with ethyl acetate (3×500 mL). The combined organic layers were washed with sat. aq. $NaHCO_3$ solution (200 mL), brine (200 mL), dried over anhydrous sodium sulfate, filtered and concentrated under reduced pressure to give crude (R)-methyl 4-((tert-butoxycarbonyl) amino)-5-methyl-3-oxohexanoate (25 g, 100%) as a yellow oil.

Step 2

To a solution of (R)-methyl 4-((tert-butoxycarbonyl) amino)-5-methyl-3-oxohexanoate (25 g, 91.5 mmol) in THF (400 mL) was added $KO^tBu$ (10.8 g, 96.0 mmol) at 0° C. under $N_2$. After stirred for 45 min, the mixture was added DABCO (10.8 g, 96.0 mmol) and 2-chloro-1,3-bis(dimethylamino)trimethinium hexafluorophosphate (29.4 g, 96.0 mmol), and then the mixture was stirred at rt for 3 h under $N_2$. $CH_3CO_2NH_4$ (21.2 g, 275 mmol) was added to the above solution, and the resulting mixture was stirred at rt overnight. TLC (petroleum ether:ethyl acetate=5:1) showed the starting material was consumed. The mixture was diluted with ethyl acetate (1000 mL), washed with water (3×300 mL), brine (300 mL), dried over anhydrous sodium sulfate, filtered and concentrated under reduced pressure. The residue was purified by column chromatograph on silica gel (eluting with petroleum ether:ethyl acetate=5:1) to give (R)-methyl 2-(1-((tert-butoxycarbonyl)amino)-2-methylpropyl)-5-chloronicotinate (11.4 g, 36%) as a colorless oil. LC-MS: $t_R$=0.913 min in 5-95AB_1.5 min chromatography (MK RP18e 25-2 mm), MS (ESI) m/z 342.9 [M+H]$^+$.

Step 3

To a solution of (R)-methyl 2-(1-((tert-butoxycarbonyl) amino)-2-methylpropyl)-5-chloronicotinate (11.4 g, 33.3 mmol) in ethanol (250 mL) was added $NaBH_4$ (2.5 g, 66.6 mmol) and $CaCl_2$ (3.6 g, 33.3 mmol) at 0° C. under $N_2$. The mixture was stirred at the same temperature for 2 h. TLC (petroleum ether:ethyl acetate=5:1) showed the starting material was consumed. The mixture was poured into sat. aq. $NH_4Cl$ solution (150 mL), extracted with ethyl acetate (3×200 mL). The combined organic layers were washed with brine (200 mL), dried over anhydrous sodium sulfate, filtered and concentrated under reduced pressure to give (R)-tert-butyl (1-(5-chloro-3-(hydroxymethyl) pyridin-2-yl)-2-methylpropyl)carbamate (7.3 g, 70%) as a colorless oil, which was used directly for the next step without further purification.

Step 4

To a solution of (R)-tert-butyl (1-(5-chloro-3-(hydroxymethyl)pyridin-2-yl)-2-methylpropyl)carbamate (7.3 g, 22.2 mmol) and $Et_3N$ (11.3 mL, 81.4 mmol, 0.726 g/mL) in $CH_2Cl_2$ (100 mL) was added MsCl (3.4 g, 29.6 mmol) at 0° C. under $N_2$. The mixture was stirred at the same temperature for 16 h. The mixture was diluted with $CH_2Cl_2$ (100 mL), washed with brine, dried over anhydrous $Na_2SO_4$, filtered and concentrated under reduced pressure. The residue was purified by column chromatograph on silica gel (eluting with petroleum ether:ethyl acetate=5:1) to give (R)-tert-butyl (1-(5-chloro-3-(chloromethyl)pyridin-2-yl)-2-methylpropyl)carbamate (4.2 g, 58%) as a white solid. LC-MS: $t_R$=0.940 min in 5-95AB_1.5 min chromatography (MK RP18e 25-2 mm), MS (ESI) m/z 332.9 [M+H]$^+$.

Step 5

A mixture of (R)-tert-butyl (1-(5-chloro-3-(chloromethyl) pyridin-2-yl)-2-methylpropyl)carbamate (4.2 g, 12.7 mmol), NaCN (1.8 g, 36.7 mmol), and KI (0.2 g, 1.27 mmol) in DMF (50 mL) and water (5 mL) was stirred at rt overnight. TLC (petroleum ether:ethyl acetate=5:1) showed the starting material was consumed completely. The mixture was poured into water (300 mL), extracted with ethyl acetate (3×300 mL). The combined organic layers were washed with brine (100 mL), dried over anhydrous sodium sulfate, filtered and concentrated under reduced pressure to give (R)-tert-butyl (1-(5-chloro-3-(cyanomethyl)pyridin-2-yl)-2-methylpropyl)carbamate (4.0 g, 100%) as a yellow oil. LC-MS: $t_R$=0.873 min in 5-95AB_1.5 min chromatography (MK RP18e 25-2 mm), MS (ESI) m/z 267.9 [M−55]$^+$.

Step 6

To a solution of (R)-tert-butyl (1-(5-chloro-3-(cyanomethyl)pyridin-2-yl)-2-methylpropyl)carbamate (4.0 g, 12.4 mol) in ethanol (50 mL) was added dropwise a solution of NaOH (1.5 g, 10% wt in water, 37.2 mmol). The mixture was stirred at 90° C. for 16 h. The mixture was cooled to rt, poured into water (100 mL) and adjusted to pH=3 with 1N HCl solution. The mixture was extracted with ethyl acetate (3×50 mL) and the combined organic layers were washed with brine, dried over anhydrous $Na_2SO_4$, filtered and concentrated under reduced pressure to give (R)-2-(2-(1-((tert-butoxycarbonyl)amino)-2-methylpropyl)-5-chloropyridin-3-yl)acetic acid (2.6 g, 62%) as a colorless oil. LC-MS: $t_R$=1.125 min in 5-95AB_1.5 min chromatography (MK RP18e 25-2 mm), MS (ESI) m/z 342.9 [M+H]$^+$.

Step 7

A mixture of (R)-2-(2-(1-((tert-butoxycarbonyl)amino)-2-methylpropyl)-5-chloropyridin-3-yl)acetic acid (2.6 g, 7.6 mmol) in HCl/MeOH (100 mL, 4N) was stirred at rt overnight. The mixture was concentrated under reduced pressure. The residue was diluted with ethyl acetate (200 mL), washed with sat. aq. $NaHCO_3$ solution (100 mL), brine (100 mL), dried over $Na_2SO_4$, filtered and concentrated under reduced pressure. The residue was purified by column chromatography on silica gel (petroleum ether:ethyl acetate=1:1) to give (R)-3-chloro-8-isopropyl-7,8-dihydro-1,7-naphthyridin-6(5H)-one (900 mg, 53%) as a colorless oil. LC-MS: $t_R$=0.677 min in 5-95AB_1.5 min chromatography (MK RP18e 25-2 mm), MS (ESI) m/z 224.9 [M+H]$^+$. H NMR ($CDCl_3$ 400 MHz): δ 8.41 (d, J=2.0 Hz, 1H), 7.44 (d, J=1.5 Hz, 1H), 4.43 (brs, 1H), 3.76-3.61 (m, 1H), 3.58-3.43 (m, 1H), 2.41-2.27 (m, 1H), 1.12-0.96 (m, 3H), 0.73 (d, J=6.8 Hz, 3H).

Step 8

To a solution of (R)-3-chloro-8-isopropyl-7,8-dihydro-1,7-naphthyridin-6(5H)-one (900 mg, 4.0 mmol) in THF (40 mL) was added $BH_3$-$Me_2S$ (2.5 mL, 20.0 mmol) at 0° C. under $N_2$. The mixture was stirred at 80° C. for 3 h. TLC (petroleum ether:ethyl acetate=1:1) showed the starting material was consumed. The mixture was cooled to 0° C., and quenched with sat. $NH_4Cl$ solution (50 mL), diluted with water (100 mL), extracted with ethyl acetate (3×100 mL). The combined organic layers were washed with brine (100 mL), dried over anhydrous sodium sulfate, filtered and concentrated under reduced pressure to give (R)-3-chloro-8-isopropyl-5,6,7,8-tetrahydro-1,7-naphthyridine (1.3 g, 100%) as a yellow oil, which was used directly for the next step without further purification. LC-MS: $t_R$=0.790 min in 5-95AB_1.5 min chromatography (MK RP18e 25-2 mm), MS (ESI) m/z 210.9 [M+H]$^+$.

Step 9

A mixture of (R)-3-chloro-8-isopropyl-5,6,7,8-tetrahydro-1,7-naphthyridine (1.3 g, 6.2 mol), $Boc_2O$ (3.4 g, 15.5 mmol), and $Et_3N$ (3.1 g, 30.9 mmol) in $CH_2Cl_2$ (50 mL) was stirred at rt overnight. The mixture was concentrated under reduced pressure. The residue was purified by column chromatograph on silica gel (eluting with petroleum ether:ethyl acetate=5:1) to give (R)-tert-butyl 3-chloro-8-isopropyl-5,6-dihydro-1,7-naphthyridine-7(8H)-carboxylate (276 m g, 15%) as a colorless oil. LC-MS: $t_R$=0.935 min in 5-95AB_1.5 min chromatography (MK RP18e 25-2 mm), MS (ESI) m/z 311.0 [M+H]$^+$.

Step 10

A mixture of (R)-tert-butyl 3-chloro-8-isopropyl-5,6-dihydro-1,7-naphthyridine-7(8H)-carboxylate (200 mg, 0.65 mmol), (4-(ethylsulfonyl)phenyl)methanamine (386 mg, 1.94 mmol), Fu's salt (18.8 mg, 0.065 mmol), $Mo(CO)_6$ (170 mg, 0.65 mmol), DBU (294 mg, 1.94 mmol), and $Pd_2(OAc)_2(P(o-tol)_3)_2$ (21.2 mg, 0.0225 mmol) in dioxane (5 mL) was stirred at 160° C. for 20 min under $N_2$ in microwave. The mixture was concentrated under reduced pressure. The residue was purified by preparative TLC (eluting with petroleum ether:ethyl acetate=1:1), SFC separation to give (S)-tert-butyl 3-((4-(ethylsulfonyl)benzyl)carbamoyl)-8-isopropyl-5,6-dihydro-1,7-naphthyridine-7(8H)-carboxylate (38 mg, 58%) and (R)-tert-butyl 3-((4-(ethylsulfonyl)benzyl)carbamoyl)-8-isopropyl-5,6-dihydro-1,7-naphthyridine-7(8H)-carboxylate (48 mg, 73%) as a colorless oil. LC-MS: $t_R$=0.835 min in 5-95AB_1.5 min chromatography (MK RP18e 25-2 mm), MS (ESI) m/z 502.0 [M+H]$^+$.
Before SFC Separation
Isomer SFC $t_R$=6.334, 6.511 in 12 min chromatography (Column: OJ-H, Method Name: OJ-H_5_5_40_2, 35ML.M, ee=0.604%).
SFC Separation Condition:
Instrument: Thar 80
Column: OJ 250 mm*30 mm, 5 um
Mobile phase: A: Supercritical $CO_2$, B: EtOH (0.05% $NH_3H_2O$), A:B=80:20 at 60 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm

Step 11

A mixture of (S)-tert-butyl 3-((4-(ethylsulfonyl)benzyl)carbamoyl)-8-isopropyl-5,6-dihydro-1,7-naphthyridine-7(8H)-carboxylate (38 mg, 0.076 mmol) and TFA (1.0 mL) in dichloromethane (5 mL) was stirred at rt for 2 h. TLC (petroleum ether:ethyl acetate=1:2) showed the starting material was consumed completely. The mixture was concentrated under reduced pressure to afford crude (S)—N-(4-(ethyl sulfonyl)benzyl)-8-isopropyl-5,6,7,8-tetrahydro-1,7-naphthyridine-3-carboxamide (crude, 100%) as a red-brown oil, which was used directly for the next step without further purification.

Step 12 (Hy2B-9.1)

A mixture of (S)—N-(4-(ethylsulfonyl)benzyl)-8-isopropyl-5,6,7,8-tetrahydro-1,7-naphthyridine-3-carboxamide (20 mg, 0.05 mmol), trans-4-(trifluoromethyl)cyclohexanecarbaldehyde (27 mg, 0.15 mmol), HOAc (0.23 mg) and NaBH$_3$CN (7.5 mg, 0.15 mmol) in MeOH (1.5 mL) was stirred at 70° C. for 2 h. TLC (petroleum ether:ethyl acetate=1:1) showed the starting material was consumed completely. The mixture was concentrated under reduced pressure and diluted with H$_2$O (15 mL) and extracted with EtOAc (3×40 mL). The combined organic layer were washed with brine (40 mL), dried over anhydrous Na$_2$SO$_4$, filtered and concentrated to give the crude product. The crude product was purified by preparative TLC (CH$_2$Cl$_2$: MeOH=20:1) and acid preparative HPLC to give (S)—N-(4-(ethyl sulfonyl)benzyl)-8-isopropyl-7-((trans-4-(trifluoromethyl)cyclohexyl)methyl)-5,6,7,8-tetrahydro-1,7-naphthyridine-3-carboxamide (Hy2B-9.1, 6.8 mg, 34%) as a white solid. LCMS: t$_R$=0.935 min in 10-80AB_2.0 min chromatography (A: Xtimate C18, 2.1*30 mm, 3 um), MS (ESI) m/z 566.2 [M+H]$^+$. $^1$H NMR (CD$_3$OD 400 MHz): δ 9.00 (s, 1H), 8.21 (s, 1H), 7.90 (d, J=8.4 Hz, 2H), 7.66 (d, J=8.4 Hz, 2H), 4.73 (s, 2H), 4.42-4.40 (m, 1H), 3.95-3.90 (m, 1H), 3.68-3.58 (m, 1H), 3.23-3.19 (m, 2H), 3.14-3.12 (m, 2H), 2.49-2.35 (m, 1H), 2.06-1.91 (m, 6H), 1.48-1.34 (m, 6H), 1.24-1.20 (m, 6H), 0.92-0.89 (m, 3H). $^{19}$F NMR (CD$_3$OD 400 MHz): δ−75.40. Isomer SFC: t$_R$=1.636 min in 3 min chromatography (AD-H_3UM_3_5_40_4ML_3MIN.M), ee=100%.

Step 13

A mixture of (R)-tert-butyl 3-((4-(ethylsulfonyl)benzyl)carbamoyl)-8-isopropyl-5,6-dihydro-1,7-naphthyridine-7(8H)-carboxylate (48 mg, 0.096 mmol) and TFA (1.0 mL) in dichloromethane (5 mL) was stirred at rt for 2 h. TLC (petroleum ether:ethyl acetate=1:2) showed the starting material was consumed completely. The mixture was concentrated under reduced pressure to afford crude (R)—N-(4-(ethylsulfonyl)benzyl)-8-isopropyl-5,6,7,8-tetrahydro-1,7-naphthyridine-3-carboxamide (crude, 100%) as a red-brown oil, which was used directly for the next step without further purification.

Step 14 (Hy2B-9.2)

A mixture of (R)—N-(4-(ethylsulfonyl)benzyl)-8-isopropyl-5,6,7,8-tetrahydro-1,7-naphthyridine-3-carboxamide (12 mg, 0.03 mmol), trans-4-(trifluoromethyl) cyclohexanecarbaldehyde (16.2 mg, 0.09 mmol), HOAc (0.18 mg) and NaBH$_3$CN (5.6 mg, 0.09 mmol) in MeOH (1 mL) was stirred at 70° C. for 2 h. TLC (petroleum ether:ethyl acetate=1:1) showed the starting material was consumed completely. The mixture was concentrated under reduced pressure, diluted with H$_2$O (15 mL), extracted with EtOAc (3×40 mL). The combined organic layers were washed with brine (40 mL), dried, filtered and concentrated to give the crude product. The crude product was purified by preparative TLC (DCM:MeOH=20:1) and acid preparative HPLC to give (R)—N-(4-(ethylsulfonyl)benzyl)-8-isopropyl-7-((trans-4-(trifluoromethyl)cyclohexyl) methyl)-5,6,7,8-tetrahydro-1,7-naphthyridine-3-carboxamide (Hy2B-9.2, 4 mg, 80%) as a white solid. LCMS: t$_R$=0.929 min in 10-80AB_2.0 min chromatography (A: Xtimate C18, 2.1*30 mm, 3 um), MS (ESI) m/z 566.2 [M+H]$^+$. $^1$H NMR (CD$_3$OD 400 MHz): δ 9.41-9.38 (m, 1H), 9.00 (s, 1H), 8.20 (s, 1H), 7.91 (d, J=8.4 Hz, 2H), 7.66 (d, J=8.4 Hz, 2H), 4.84 (s, 2H), 4.42-4.40 (m, 1H), 3.97-3.89 (m, 1H), 3.59-3.55 (m, 1H), 3.25-3.20 (m, 2H), 3.14-3.12 (m, 2H), 2.49-2.45 (m, 1H), 2.07-1.90 (m, 6H), 1.49-1.34 (m, 6H), 1.24-1.14 (m, 6H), 0.92-0.90 (m, 3H). $^{19}$F NMR (CD$_3$OD 400 MHz): δ−75.417. Isomer SFC: t$_R$=1.634 min in 3 min chromatography (AD-H_3UM 3_5_40_4ML_3MIN.M), ee=100%.

The following compounds are prepared using procedures analogous to those described in Examples 7 and 8.

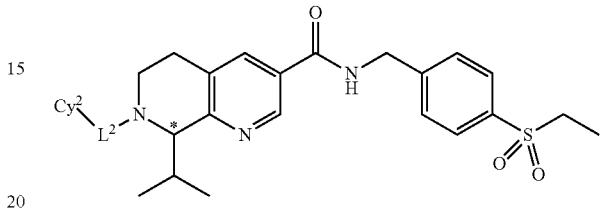

| Cpd No | Cy$^2$ | L$^2$ | * |
|---|---|---|---|
| Hy2B-1.1 | 5-cyano-2-pyrimidinyl | bond | a |
| Hy2B-1.2 | 5-cyano-2-pyrimidinyl | bond | a |
| Hy2B-2.1 | 5-chloro-2-pyrimidinyl | bond | b |
| Hy2B-2.2 | 5-chloro-2-pyrimidinyl | bond | b |
| Hy2B-3.1 | 5-(trifluoromethyl)-2-pyrimidinyl | bond | c |
| Hy2B-3.2 | 5-(trifluoromethyl)-2-pyrimidinyl | bond | c |
| Hy2B-4.1 | 5-(ethoxycarbonyl)-2-pyrimidinyl | bond | d |
| Hy2B-4.2 | 5-(ethoxycarbonyl)-2-pyrimidinyl | bond | d |
| Hy2B-5.1 | 5-(ethoxycarbonyl)-4-(trifluoromethyl)-2-pyrimidinyl | bond | e |
| Hy2B-5.2 | 5-(ethoxycarbonyl)-4-(trifluoromethyl)-2-pyrimidinyl | bond | e |
| Hy2B-6.1 | 4-fluorophenyl | CH$_2$ | f |
| Hy2B-6.2 | 4-fluorophenyl | CH$_2$ | f |
| Hy2B-7.1 | 4-cyanophenyl | CH$_2$ | g |
| Hy2B-7.2 | 4-cyanophenyl | CH$_2$ | g |
| Hy2B-10.1 | 4-chlorophenyl | CH$_2$ | h |
| Hy2B-10.2 | 4-chlorophenyl | CH$_2$ | h | a, b, c, d, e, f, g, h=single isomers, separated by chromatography on chiral columns.

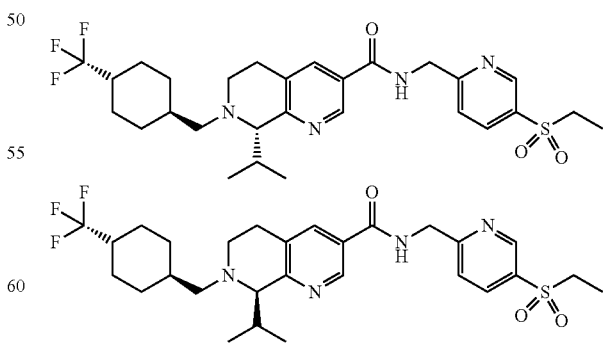

Cpd Nos Hy2B-10.1 and -10.2$^a$

[a] Isomers were separated by chromatography on a chiral column.

Example 9

3-cyclopropyl-N—((R)-1-(4-(ethylsulfonyl)phenyl)-2-hydroxyethyl)-2-((trans-4-(trifluoromethyl)cyclohexyl)methyl)-2H-indazole-6-carboxamide (Cpd No Hy3A-1)

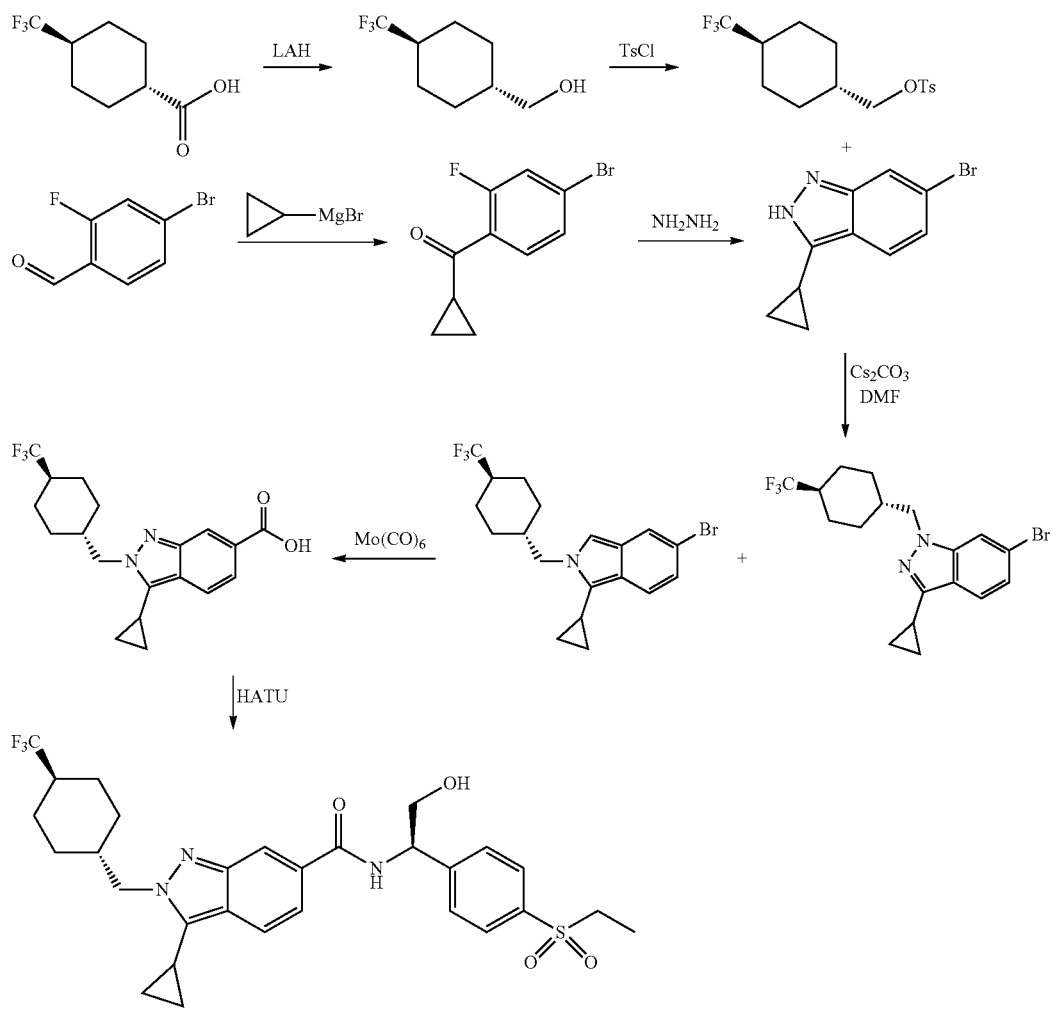

Step 1. (trans-4-(trifluoromethyl)cyclohexyl)methanol

To a solution of trans-4-(trifluoromethyl)cyclohexanecarboxylic acid (5.2074 g, 26.5 mmol) in THF (100 mL) was added 20 mL (40 mmol) of 2.0 M LiAlH$_4$ in THF at 0° C. (ice bath). The resulting reaction mixture was allowed to stir at rt for 20 h and then carefully quenched with 30 g of sodium sulfate decahydrate (Glauber's salt). After vigorously stirred at rt for 2 h, the solid was filtered and washed with DCM. The combined filtrate was evaporated under reduced pressure to afford (trans-4-(trifluoromethyl)cyclohexyl)methanol as a colorless liquid, which was used in the next step without further purification. $^1$H NMR (CDCl$_3$, 400 MHz) δ 3.47 (d, J=6.15 Hz, 2H), 2.02-1.89 (m, 5H), 1.57 (s, 1H), 1.52-1.44 (m, 1H), 1.38-1.27 (m, 2H), 1.04-0.94 (m, 2H); $^{19}$F NMR (CDCl$_3$, 376 MHz) δ −73.82 (d, J=7.89 Hz).

Step 2. (trans-4-(trifluoromethyl)cyclohexyl)methyl 4-methylbenzenesulfonate To a solution of (trans-4-(trifluoromethyl)cyclohexyl)methanol, obtained as described above, in THF (50 mL) was added 1.1350 g (28.4 mmol) of 60% NaH at 0° C. (ice bath). The resulting reaction mixture was allowed to stir at rt for 0.5 h and then 5.4140 g (28.4 mmol) of TsCl was added in portion over 10 min. The reaction mixture was stirred at rt for 17 h and then quenched with saturated NaHCO$_3$, extracted twice with ethyl acetate, and dried over Na$_2$SO$_4$. After the solvent was evaporated under reduced pressure, the residue was purified by chromatography on silica gel (120 g column eluted with 0-5% MeOH/DCM over 30 min) to give 5.7950 g (65% in two steps) of (trans-4-(trifluoromethyl)cyclohexyl)methyl 4-methylbenzenesulfonate as a solid. LC-MS t$_R$=1.85 min in 2.5 min chromatography, m/z 165 (M$^+$-OTs); $^1$H NMR (CDCl$_3$, 400 MHz) δ 7.78 (d, J=8.49 Hz, 2H), 7.35 (d, J=8.49 Hz, 2H), 3.84 (d, J=6.15 Hz, 2H), 2.46 (s, 3H), 1.98-1.90 (m, 3H), 1.86-1.82 (m, 2H), 1.69-1.62 (m, 1H), 1.33-1.23 (m, 2H), 1.03-0.93 (m, 2H); $^{19}$F NMR (CDCl$_3$, 376 MHz) δ −73.86 (d, J=7.89 Hz).

Step 3. (4-bromo-2-fluorophenyl)(cyclopropyl)methanone and (4-bromo-2-fluorophenyl)(cyclopropyl)methanol To a solution of 4-bromo-2-fluorobenzaldehyde (7.0400 g, 34.7 mmol) in THF (50 mL) was added 84 mL of 0.5 M cyclopropylmagnesium bromide in THF at −78° C. under nitrogen. The reaction mixture was allowed to slowly warm to 12° C. over 17 h and then quenched with saturated NH$_4$Cl, extracted twice with ethyl acetate, and dried over Na$_2$SO$_4$. After the solvent was evaporated under reduced pressure, the residue was purified by chromatography on silica gel (120 g column eluted with 0-60% ethyl acetate/hexanes over 40 min) to afford 3.0050 g (36%) of (4-bromo-2-fluorophenyl)(cyclopropyl)methanone, LC-MS $t_R$=1.68 min in 2.5 min chromatography, m/z 243, 245 (MH$^+$); $^1$H NMR (CDCl$_3$, 400 MHz) δ 7.65 (t, J=8.20 Hz, 1H), 7.39-7.34 (m, 2H), 2.64-2.57 (m, 1H), 1.30-1.26 (m, 2H), 1.11-1.06 (m, 2H); $^{19}$F NMR (CDCl$_3$, 376 MHz) δ−108.96 (m) and 0.7856 g (9%) of (4-bromo-2-fluorophenyl)(cyclopropyl)methanol, LC-MS $t_R$=1.51 min in 2.5 min chromatography, m/z 227, 229 (M$^+$-OH); $^1$H NMR (CDCl$_3$, 400 MHz) δ 7.45-7.41 (m, 1H), 7.30 (d, J=8.20 Hz, 1H), 7.22 (d, J=9.67 Hz, 1H), 4.33 (d, J=8.20 Hz, 1H), 2.09 (m, 1H), 1.22-1.19 (m, 1H), 0.64-0.63 (m, 1H), 0.54-0.43 (m, 2H); $^{19}$F NMR (CDCl$_3$, 376 MHz) δ−116.28 (m).

Step 4. 6-bromo-3-cyclopropyl-2H-indazole

A mixture of (4-bromo-2-fluorophenyl)(cyclopropyl)methanone (0.5216 g, 2.15 mmol) and hydrazine hydrate (1.5360 g) in dioxane (3 mL) was heated in microwave at 160° C. for 2 h. The reaction mixture was quenched with saturated NH$_4$Cl, extracted twice with ethyl acetate, and dried over Na$_2$SO$_4$. After the solvent was evaporated under reduced pressure, the crude product was used in the next step without further purification. LC-MS $t_R$=1.53 min in 2.5 min chromatography, m/z 237, 239 (MH$^+$); $^1$H NMR (CDCl$_3$, 400 MHz) δ 7.63-7.59 (m, 2H), 7.26-7.22 (m, 1H), 2.24-2.18 (m, 1H), 1.08-1.05 (m, 4H).

Step 5. 6-bromo-3-cyclopropyl-1-((trans-4-(trifluoromethyl)cyclohexyl)methyl)-1H-indazole and 6-bromo-3-cyclopropyl-2-((trans-4-(trifluoromethyl)cyclohexyl)methyl)-2H-indazole A mixture of 6-bromo-3-cyclopropyl-2H-indazole, obtained as described above, (trans-4-(trifluoromethyl)cyclohexyl)methyl 4-methylbenzenesulfonate (0.8160 g, 2.42 mmol), and Cs$_2$CO$_3$ (3.1140 g) in DMF (10 mL) was heated at 80° C. for 15 h. The reaction mixture was cooled to rt and then quenched with saturated NH$_4$Cl, extracted twice with ethyl acetate, and dried over Na$_2$SO$_4$. After the solvent was evaporated under reduced pressure, the residue was purified by chromatography on silica gel (40 g column eluted with 0-50% ethyl acetate/hexanes over 30 min) to afford 0.4044 g (47%) of 6-bromo-3-cyclopropyl-1-((trans-4-(trifluoromethyl)cyclohexyl)methyl)-1H-indazole, LC-MS $t_R$=2.16 min in 2.5 min chromatography, m/z 401, 403 (MH$^+$); $^1$H NMR (CDCl$_3$, 400 MHz) D 7.57 (d, J=8.50 Hz, 1H), 7.46 (s, 1H), 7.20-7.17 (m, 1H), 4.06 (d, J=7.03 Hz, 2H), 2.18-2.13 (m, 1H), 2.00-1.92 (m, 4H), 1.71 (d, J=12.89 Hz, 2H), 1.32-1.22 (m, 2H), 1.11-1.01 (m, 6H); 19F NMR (CDCl$_3$, 376 MHz) δ −73.80 (d, J=7.89 Hz) and 0.0852 g (10%) of 6-bromo-3-cyclopropyl-2-((trans-4-(trifluoromethyl)cyclohexyl)methyl)-2H-indazole, LC-MS $t_R$=2.05 min in 2.5 min chromatography, m/z 401, 403 (MH$^+$); $^1$H NMR (CDCl$_3$, 400 MHz) δ 7.79 (s, 1H), 7.53 (d, J=8.78 Hz, 1H), 7.07 (d, J=8.78 Hz, 1H), 4.33 (d, J=7.32 Hz, 2H), 2.19-2.13 (m, 1H), 2.04-1.94 (m, 4H), 1.78 (d, J=12.89 Hz, 2H), 1.37-1.26 (m, 2H), 1.19-1.08 (m, 4H), 0.97-0.93 (m, 2H); $^{19}$F NMR (CDCl$_3$, 376 MHz) δ−73.80 (d, J=9.21 Hz).

Step 6. 3-cyclopropyl-2-((trans-4-(trifluoromethyl)cyclohexyl)methyl)-2H-indazole-6-carboxylic acid A mixture of 6-bromo-3-cyclopropyl-2-((trans-4-(trifluoromethyl)cyclohexyl)methyl)-2H-indazole (0.0852 g, 0.21 mmol), Molybdenumhexacarbonyl (0.1190 g), Herrmann's palladacycle (0.0579 g), Tri-tert-butylphosphonium tetrafluoroborate (0.0573 g), water (0.1 mL), and DBU (0.1 mL) in dioxane (2 mL) was heated in microwave at 150° C. for 20 min. The reaction mixture was purified by reverse-phase HPLC (Phenomenex® Luna 5 L C$_{18}$ (2) 250×21.20 mm column, 10% CH$_3$CN/H$_2$O, 0.1% CF$_3$COOH over 1.5 min, 10%-90% CH$_3$CN/H$_2$O, 0.1% CF$_3$COOH over 8 min, and then 90% CH$_3$CN/H$_2$O, 0.1% CF$_3$COOH over 4 min, flow rate 25 mL/min) to yield 0.0624 g (80%) of 3-cyclopropyl-2-((trans-4-(trifluoromethyl)cyclohexyl)methyl)-2H-indazole-6-carboxylic acid. LC-MS $t_R$=1.70 min in 2.5 min chromatography, m/z 367 (MH$^+$).

Step 7. 3-cyclopropyl-N—((R)-1-(4-(ethylsulfonyl)phenyl)-2-hydroxyethyl)-2-((trans-4-(trifluoromethyl)cyclohexyl)methyl)-2H-indazole-6-carboxamide A mixture of 3-cyclopropyl-2-((trans-4-(trifluoromethyl)cyclohexyl)methyl)-2H-indazole-6-carboxylic acid (0.0208 g, 0.0567 mmol), HATU (0.0359 g), TEA (0.1 mL), and (R)-2-amino-2-(4-(ethylsulfonyl)phenyl)ethan-1-ol (0.0176 g, 0.0767 mmol) in DMF (2 mL) was stirred at rt for 2 h. The reaction mixture was purified by reverse-phase HPLC (Phenomenex® Luna 5 t C$_{18}$ (2) 250×21.20 mm column, 10% CH$_3$CN/H$_2$O, 0.1% CF$_3$COOH over 1.5 min, 10%-90% CH$_3$CN/H$_2$O, 0.1% CF$_3$COOH over 8 min, and then 90% CH$_3$CN/H$_2$O, 0.1% CF$_3$COOH over 4 min, flow rate 25 mL/min) and the fractions were then lyophilized to afford 3-cyclopropyl-N—((R)-1-(4-(ethylsulfonyl)phenyl)-2-hydroxyethyl)-2-((trans-4-(trifluoromethyl)cyclohexyl)methyl)-2H-indazole-6-carboxamide as a white fluffy solid. LC-MS $t_R$=1.59 min in 2.5 min chromatography, m/z 578 (MH$^+$); $^1$H NMR (DMSO-d$_6$, 400 MHz) δ 8.82 (d, J=8.20 Hz, 1H), 8.21 (s, 1H), 7.84 (d, J=8.20 Hz, 2H), 7.70-7.66 (m, 3H), 7.41 (d, J=9.08 Hz, 1H), 5.16-5.14 (m, 1H), 4.38 (d, J=7.33 Hz, 2H), 3.78-3.67 (m, 2H), 3.26 (q, J=7.32 Hz, 2H), 2.20-2.09 (m, 3H), 1.85 (m, 2H), 1.66 (m, 2H), 1.24-1.14 (m, 6H), 1.09 (t, J=7.32 Hz, 3H), 0.97-0.96 (m, 2H); $^{19}$F NMR (DMSO-d$_6$, 376 MHz) δ−72.25 (d, J=9.21 Hz).

The following compounds are prepared using analogous procedures:
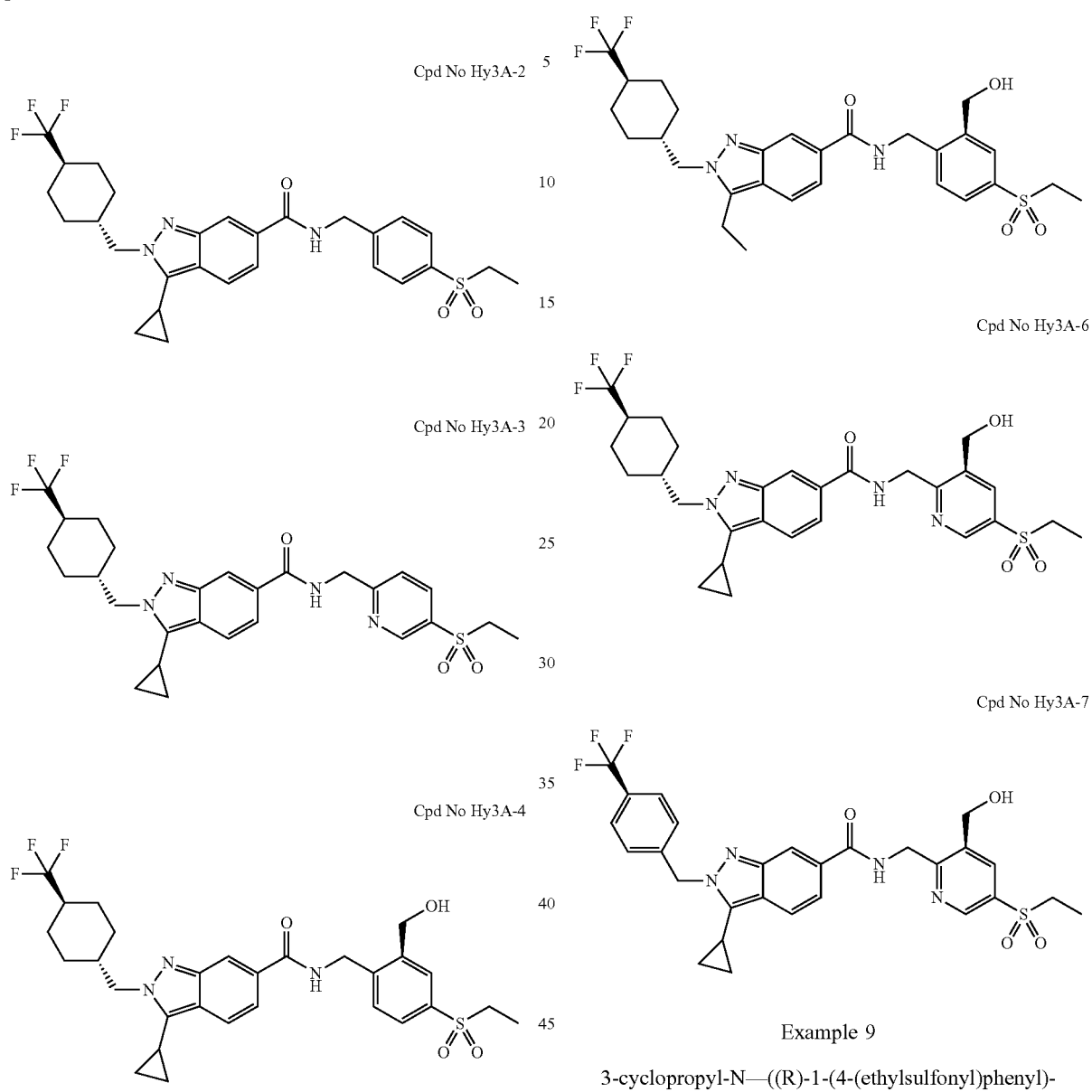
Example 9
3-cyclopropyl-N—((R)-1-(4-(ethylsulfonyl)phenyl)-2-hydroxyethyl)-2-(((1r,4R)-4-(trifluoromethyl)cyclohexyl)methyl)-2H-pyrazolo[4,3-b]pyridine-6-carboxamide (Cpd No Hy3B-1)
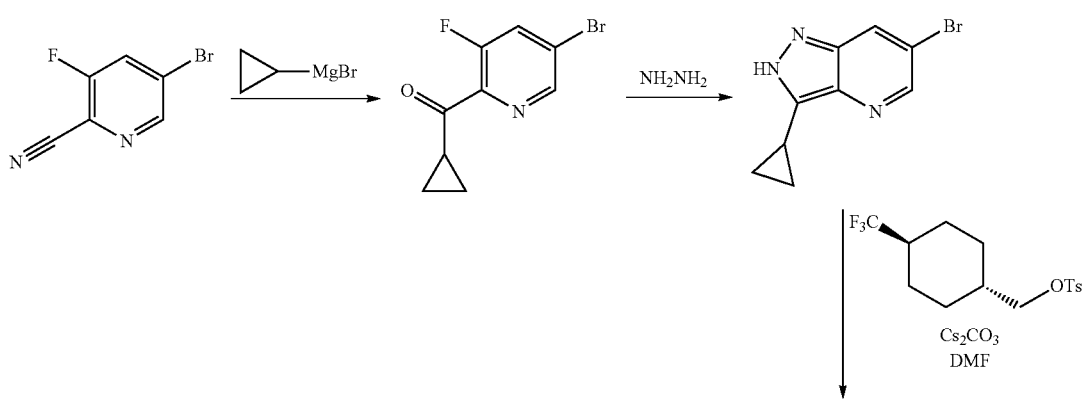

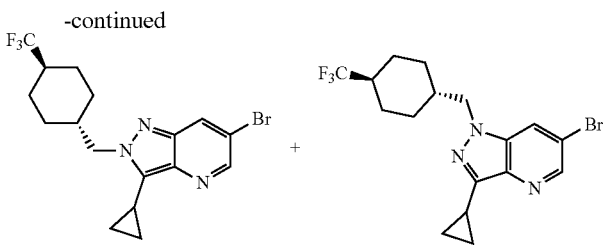

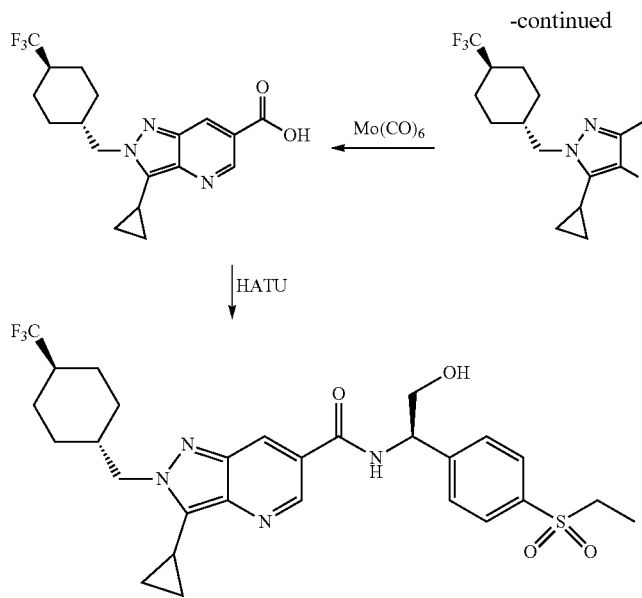

Compound Hy3B-1 was prepared as shown in the Scheme above. (5-Bromo-3-fluoropyridin-2-yl)(cyclopropyl)methanone was prepared by addition of cyclopropylmagnesium bromide to 5-bromo-3-fluoropicolinonitrile. (5-Bromo-3-fluoropyridin-2-yl)(cyclopropyl)methanone was converted to Compound Hy3B-1 using procedures analogous to those described in Example 8 Steps 4-7.

The following compounds are prepared using analogous procedures:

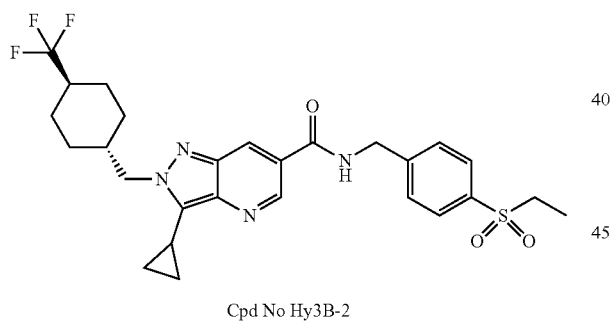

Cpd No Hy3B-2

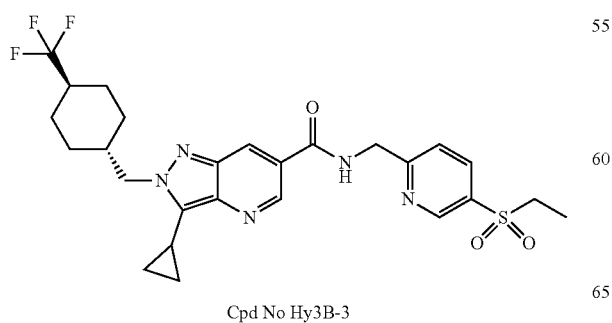

Cpd No Hy3B-3

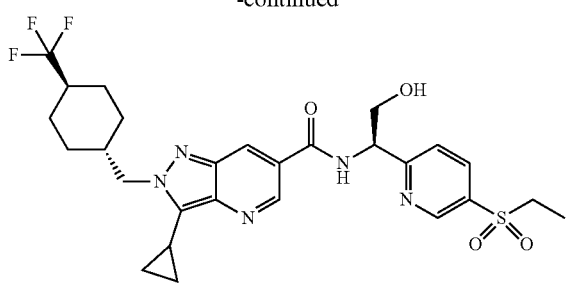

Cpd No Hy3B-4

Example 10

N-(4-(ethylsulfonyl)benzyl)-1-methyl-7-(((1r,4r)-4-(trifluoromethyl)cyclohexyl)methoxy)-1H-pyrrolo[2,3-c]pyridine-2-carboxamide (Cpd No Hy4-1)

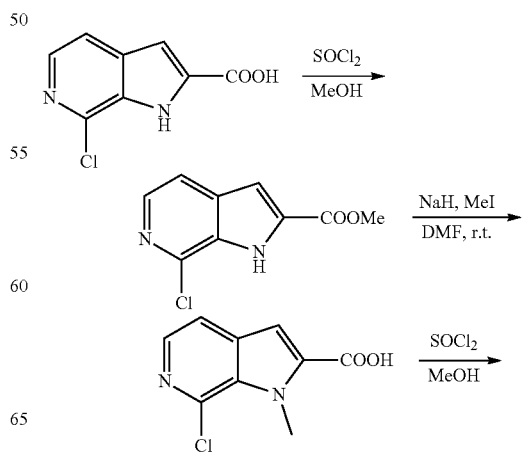

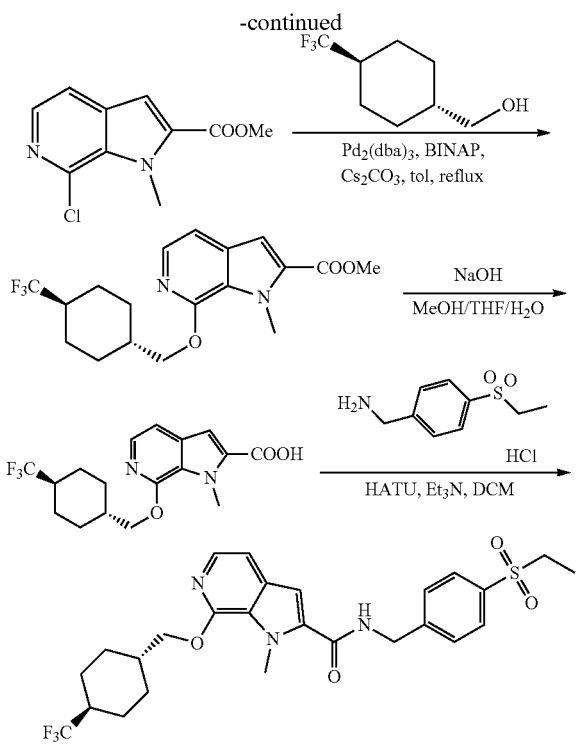

Step 1

To a mixture of 7-chloro-1H-pyrrolo[2,3-c]pyridine-2-carboxylic acid (200 mg, 1.02 mmol) in anhydrous MeOH (5 mL) was added dropwise $SOCl_2$ (2 mL). The mixture was stirred at 60° C. for 6 h under $N_2$. LCMS showed that the reaction was completed. The mixture was concentrated under reduced pressure and dry-freezing directly to give crude methyl 7-chloro-1H-pyrrolo[2,3-c]pyridine-2-carboxylate (214 mg, 100%) as a white solid, which was used for the next step directly without further purification. LC-MS $t_R$=0.675 min in 5-95AB_1.5 min chromatography (Welch MK RP-18e, 25-2 mm), MS (ESI) m/z 210.9 [M+H]$^+$.

Step 2

To a mixture of crude methyl 7-chloro-1H-pyrrolo[2,3-c]pyridine-2-carboxylate (90 mg, 0.429 mmol) in anhydrous DMF (3 mL) was added NaH (34 mg, 0.857 mmol, 60% in mineral oil). The mixture was stirred at rt for 0.5 h under $N_2$. MeI (183 mg, 1.29 mmol) was added to the mixture and the mixture was stirred at rt for 3 h under $N_2$. TLC (petroleum ether/ethyl acetate=4/1) showed that the starting material was consumed completely. The mixture was adjusted to pH=4-5 with 1 M HCl solution. The mixture was concentrated under reduced pressure and dry-freezing directly to give crude 7-chloro-1-methyl-1H-pyrrolo[2,3-c]pyridine-2-carboxylic acid (150 mg, >100%, contain some salts) as a yellow solid, which was used for the next step directly without further purification. LC-MS $t_R$=0.551 min in 5-95AB_1.5 min chromatography (Welch MK RP-18e, 25-2 mm), MS (ESI) m/z 210.9 [M+H]$^+$.

Step 3

To a mixture of crude 7-chloro-1-methyl-1H-pyrrolo[2,3-c]pyridine-2-carboxylic acid (crude 150 mg, 0.429 mmol) in anhydrous MeOH (3 mL) was added dropwise $SOCl_2$ (0.8 mL). The mixture was stirred at 50° C. for 1 h under $N_2$. LCMS showed that the reaction was completed. The mixture was concentrated under reduced pressure. The residue was diluted with $H_2O$ (20 mL) and adjusted to pH=7-8 with aq. $NaHCO_3$ solution. The aqueous layer was extracted with ethyl acetate (3×20 mL). The combined organic layers were dried over anhydrous sodium sulfate, filtered and concentrated under reduced pressure. The residue was purified by column chromatography on silica gel eluting with petroleum ether/ethyl acetate=1/0-5/1 to give methyl 7-chloro-1-methyl-1H-pyrrolo[2,3-c]pyridine-2-carboxylate (50 mg, 52%) as a white solid. LC-MS $t_R$=0.758 min in 5-95AB_1.5 min chromatography (Welch MK RP-18e, 25-2 mm), MS (ESI) m/z 225.0 [M+H]$^+$.

Step 4

To a mixture of methyl 7-chloro-1-methyl-1H-pyrrolo[2,3-c]pyridine-2-carboxylate (20 mg, 0.0893 mmol) in dry toluene (2 mL) was added (trans-4-(trifluoromethyl)cyclohexyl)methanol (32 mg, 0.1786 mmol), $Pd_2(dba)_3$ (20 mg, 0.0219 mmol), BINAP (20 mg, 0.032 mmol) and $Cs_2CO_3$ (60 mg, 0.1786 mmol). The mixture was stirred at 110° C. for 7 h under $N_2$. LCMS showed that the reaction was completed. The mixture was quenched with water (15 mL) and extracted with ethyl acetate (3×15 mL). The combined organic layers were dried over anhydrous sodium sulfate, filtered and concentrated under reduced pressure. The residue was purified by preparative TLC with petroleum ether/ethyl acetate=7/1 to afford methyl 1-methyl-7-((trans-4-(trifluoromethyl)cyclohexyl)methoxy)-1H-pyrrolo[2,3-c]pyridine-2-carboxylate (33 mg, 100%) as a yellow solid. LC-MS $t_R$=1.308 min in 5-95AB_1.5 min chromatography (Welch Xtimate C18, 2.1*30 mm), MS (ESI) m/z 371.1 [M+H]$^+$.

Step 5

To a mixture of methyl 1-methyl-7-((trans-4-(trifluoromethyl)cyclohexyl)methoxy)-1H-pyrrolo[2,3-c]pyridine-2-carboxylate (17 mg, 0.0447 mmol) in MeOH/THF/$H_2O$ (3 mL/1 mL/0.8 mL) was added NaOH (36 mg, 0.893 mmol). The mixture was stirred at 45° C. for 2 h under $N_2$. LCMS showed that the reaction was completed. The mixture was concentrated under reduced pressure. The residue was diluted with $H_2O$ (10 mL) and adjusted to pH=5-6 with 1 M HCl solution. The aqueous layer was extracted with ethyl acetate (3×10 mL). The combined organic layers were dried over anhydrous sodium sulfate, filtered and concentrated under reduced pressure to afford crude 1-methyl-7-((trans-4-(trifluoromethyl)cyclohexyl)methoxy)-1H-pyrrolo[2,3-c]pyridine-2-carboxylic acid (16 mg, 100%) as a yellow solid, which was used for the next step directly without further purification. LC-MS $t_R$=0.836 min in 5-95AB_1.5 min chromatography (Welch MK RP-18e, 25-2 mm), MS (ESI) m/z 357.1 [M+H]$^+$.

Step 6

To a mixture of crude 1-methyl-7-((trans-4-(trifluoromethyl)cyclohexyl)methoxy)-1H-pyrrolo[2,3-c]pyridine-2-carboxylic acid (16 mg, 0.0447 mmol) in $CH_2Cl_2$ (1 mL) was added (4-(ethylsulfonyl)phenyl)methanamine HCl salt (18 mg, 0.0894 mmol), HATU (34 mg, 0.0894 mmol) and $Et_3N$ (9 mg, 0.0894 mmol). The mixture was stirred at rt for 2 h under $N_2$. LCMS showed that the reaction was completed. The mixture was diluted with water (10 mL) and extracted with DCM (3×10 mL). The combined organic layers were dried over anhydrous sodium sulfate, filtered and concentrated under reduced pressure. The residue was purified by preparative TLC with petroleum ether/ethyl acetate=2/3 and basic preparative HPLC separation, then dry-freezing directly to afford N-(4-(ethylsulfonyl)benzyl)-1-methyl-7-((trans-4-(trifluoromethyl)cyclohexyl)methoxy)-1H-pyrrolo[2,3-c]pyridine-2-carboxamide (Hy4-1, 8.10 mg, 34%) as a white solid. LC-MS $t_R$=0.778 min in 5-95AB_1.5 min chromatography (Welch MK RP-18e, 25-2 mm), MS (ESI) m/z 538.1 [M+H]$^+$. $^1$H NMR (CDCl$_3$ 400 MHz): δ 7.88 (d, J=8.0 Hz, 2H), 7.70 (d, J=6.0 Hz, 1H), 7.54 (d, J=8.0 Hz, 2H), 7.07 (d, J=5.6 Hz, 1H), 6.79 (s, 1H), 6.72-6.65 (m, 1H), 4.73 (d, J=6.0 Hz, 2H), 4.34 (s, 3H), 4.32 (d, J=6.4 Hz, 2H), 3.10 (q, J=7.6 Hz, 2H), 2.14-1.85 (m, 6H), 1.49-1.35 (m, 2H), 1.27 (t, J=7.6 Hz, 3H), 1.24-1.10 (m, 2H). Isomer SFC $t_R$=1.644 min in 3 min chromatography (Column: OD-H; Method Name: OD-H_3UM_5_5_40_4ML_3MIN.M, ee=99%).

Basic Preparative HPLC Method:

Mobile phase A: water with 0.05% ammonia hydroxide solution

Mobile phase B: MeCN

Flow rate: 25 mL/min.

Detection: UV 220 nm

Column: Gemini 150*25 5 u

Column temperature: 40° C.

| Time in min | % A | % B |
|---|---|---|
| 0.00 | 43 | 57 |
| 10.00 | 13 | 87 |
| 10.20 | 0 | 100 |
| 12.00 | 0 | 100 |

The following compounds are prepared following analogous procedures:

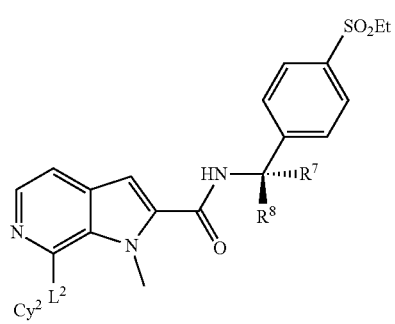

| Cpd No | Cy$^2$ | L$^2$ | R$^7$ | R$^8$ |
|---|---|---|---|---|
| Hy4-2 | trans-4-(trifluoromethyl)cyclohexyl | CH$_2$O | CH$_2$OH | H |
| Hy4-3 | 4-(trifluoromethyl)phenyl | CH$_2$O | H | H |
| Hy4-4 | 4-(trifluoromethyl)phenyl | CH$_2$O | CH$_2$OH | H |

The following compound is prepared by a similar procedure using SEM protection of the indole NH.

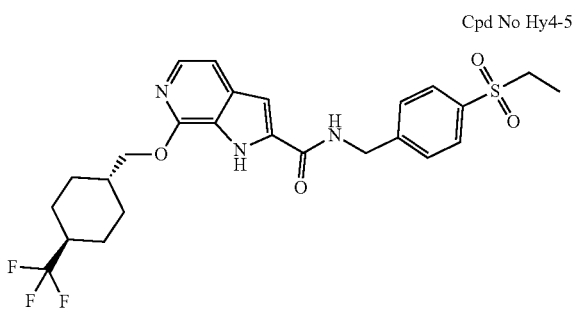 [SMILES: CCS(=O)(=O)c1ccc(CNC(=O)c2cc3ccnc(OC[C@H]4CC[C@H](C(F)(F)F)CC4)c3[nH]2)cc1]

Cpd No Hy4-5

Example 11

N-(4-(ethylsulfonyl)benzyl)-1-methyl-7-((4-(trifluoromethyl)benzyl)oxy)-1H-pyrrolo[2,3-c]pyridine-3-carboxamide (Cpd No Hy5-3)

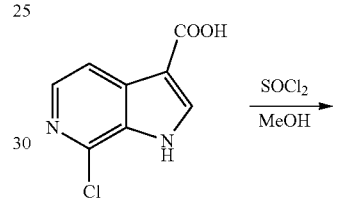

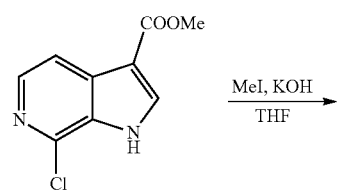

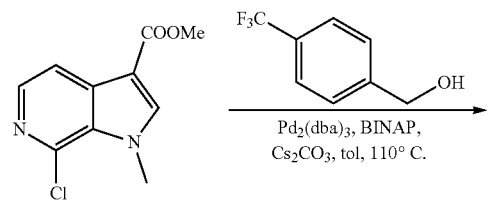

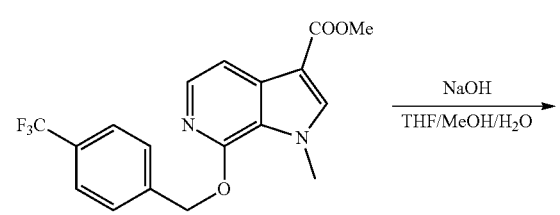

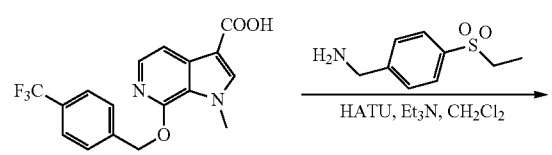

-continued

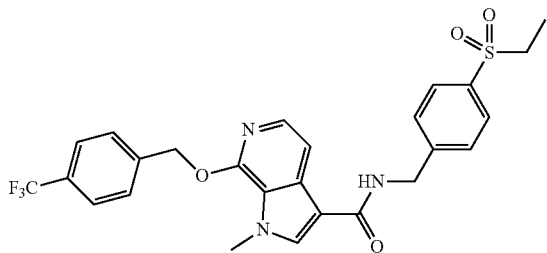

Step 1

To a solution of methyl 7-chloro-1H-pyrrolo[2,3-c]pyridine-3-carboxylate (100 mg, 0.51 mmol) in anhydrous MeOH (3 mL) was added SOCl$_2$ (1 mL) dropwise. The mixture was stirred at 40° C. for 16 h. LCMS showed that the reaction was completed. The mixture was concentrated under reduced pressure to afford crude methyl 7-chloro-1-methyl-1H-pyrrolo[2,3-c]pyridine-3-carboxylate (107 mg, 100%) as a yellow solid, which was used for the next step directly without further purification. LC-MS: $t_R$=0.581 min in 5-95AB_1.5 min chromatography (Welch MK RP-18e, 25-2 mm), MS (ESI) m/z 210.7 [M+H]$^+$.

Step 2

To a solution of crude methyl 7-chloro-1H-pyrrolo[2,3-c]pyridine-3-carboxylate (100 mg, 0.48 mmol) in anhydrous THF (5 mL) was added KOH (67 mg, 1.20 mmol) and MeI (224 mg, 1.6 mmol). The mixture was stirred at 50° C. for 4 h. LCMS showed that the reaction was completed. The mixture was added with water (5 mL) and extracted with CH$_2$Cl$_2$ (3×5 mL). The combined organic layers were dried over anhydrous Na$_2$SO$_4$, filtered and concentrated under reduced pressure to afford crude methyl 7-chloro-1-methyl-1H-pyrrolo[2,3-c]pyridine-3-carboxylate (110 mg, 103%) as a yellow solid, which was used for the next step directly without further purification. LC-MS: $t_R$=0.742 min in 5-95AB_1.5 min chromatography (RP-18e, 25-2 mm), MS (ESI) m/z 224.8 [M+H]$^+$.

Step 3

The mixture of crude methyl 7-chloro-1-methyl-1H-pyrrolo[2,3-c]pyridine-3-carboxylate (20 mg, 0.09 mmol), (4-(trifluoromethyl)phenyl)methanol (32 mg, 0.18 mmol), Pd$_2$(dba)$_3$ (16 mg, 0.018 mmol), BINAP (11 mg, 0.018 mmol), Cs$_2$CO$_3$ (88 mg, 0.27 mmol) in anhydrous toluene (1 mL) was stirred at 110° C. for 16 h under N$_2$. TLC (petroleum ether/ethyl acetate=5/1) showed that the reaction was completed. The mixture wad filtered through celite and the filter cake was washed with CH$_2$Cl$_2$ (15 mL). The filtrate was concentrated under reduced pressure. The residue was purified by preparative TLC (petroleum ether/ethyl acetate=5/1) to afford methyl 1-methyl-7-((4-(trifluoromethyl)benzyl)oxy)-1H-pyrrolo[2,3-c]pyridine-3-carboxylate (11 mg, 34%) as a colorless oil. LC-MS $t_R$=0.968 min in 5-95AB_1.5 min chromatography (Welch MK RP-18e, 25-2 mm), MS (ESI) m/z 365.0 [M+H]$^+$.

Step 4

A mixture of methyl 1-methyl-7-((4-(trifluoromethyl)benzyl)oxy)-1H-pyrrolo[2,3-c]pyridine-3-carboxylate (16 mg, 0.044 mmol), NaOH (88 mg, 2.2 mmol) in THF/MeOH/H$_2$O (6 mL, v/v=1/4/1) was stirred at 40° C. for 16 h. TLC (petroleum ether/ethyl acetate=5/1) showed that the most of starting material was consumed. The mixture was adjusted to pH=3 with 1 N HCl solution and extracted with CH$_2$Cl$_2$ (3×10 mL). The combined organic layers were washed with brine (15 mL), dried over anhydrous Na$_2$SO$_4$, filtered and concentrated under reduced pressure to give crude 1-methyl-7-((4-(trifluoromethyl)benzyl)oxy)-1H-pyrrolo[2,3-c]pyridine-3-carboxylic acid (10 mg, 62.5%) as a white solid, which was used for next step directly without further purification.

Step 5

To a mixture of crude 1-methyl-7-((4-(trifluoromethyl)benzyl)oxy)-1H-pyrrolo[2,3-c]pyridine-3-carboxylic acid (10 mg, 0.029 mmol), (4-(ethylsulfonyl)phenyl)methanamine hydrochloride HCl salt (14 mg, 0.58 mmol) and HATU (22 mg, 0.058 mmol) in anhydrous CH$_2$Cl$_2$ (1 mL) was added with Et$_3$N (6 mg, 0.058 mmol). The mixture was stirred at rt for 3 h. The mixture was added water (10 mL) and extracted with CH$_2$Cl$_2$ (3×10 mL). The combined organic layers were washed with brine (20 mL), dried over anhydrous Na$_2$SO$_4$, filtered and concentrated under reduced pressure to give crude product (15 mg, 100%), which was purified by basic preparative HPLC separation and dry-freezing directly to afford N-(4-(ethylsulfonyl)benzyl)-1-methyl-7-((4-(trifluoromethyl)benzyl)oxy)-1H-pyrrolo[2,3-c]pyridine-3-carboxamide (Hy5-3, 7.10 mg, 45%) as a white solid. LC-MS $t_R$=0.776 min in 5-95AB_1.5 min chromatography (Welch MK RP-18e, 25-2 mm), MS (ESI) m/z 532.0 [M+H]$^+$. $^1$H NMR (CDCl$_3$ 400 MHz): δ 7.90-7.80 (m, 3H), 7.65-7.62 (m, 3H), 7.60-7.55 (m, 2H), 7.52 (d, J=8.0 Hz. 2H), 7.46 (d, J=5.6 Hz, 1H), 6.39 (t, J=6.0 Hz, 1H), 5.61 (s, 2H), 4.75 (d, J=6.4 Hz, 2H), 4.08 (s, 3H), 3.09 (q, J=7.2 Hz, 2H), 1.25 (t, J=7.2 Hz, 3H).

Basic Preparative HPLC Method:

Mobile phase A: water with 0.05% ammonia hydroxide solution

Mobile phase B: MeCN

Flow rate: 25 mL/min.

Detection: UV 220 nm

Column: Phenomenex Gemini 150*25 mm*10 um

Column temperature: 40° C.

| Time in min | % A | % B |
|---|---|---|
| 0.00 | 55 | 45 |
| 10.00 | 25 | 75 |
| 10.20 | 0 | 100 |
| 13.00 | 0 | 100 |

The following compounds are prepared using analogous procedures:

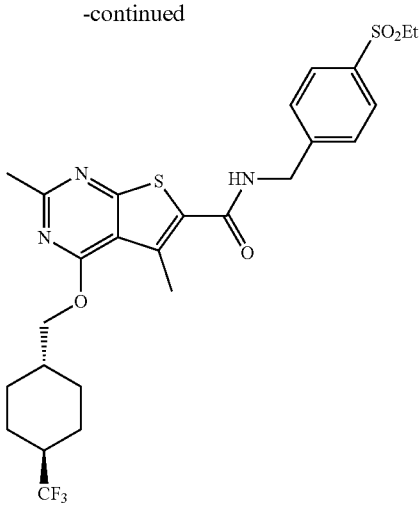

| Cpd No | Cy² | L² | R²ᵃ | R⁷ | R⁸ |
|---|---|---|---|---|---|
| Hy5-1 | 4-(trifluoromethyl)phenyl | O | Me | H | H |
| Hy5-2 | trans-4-(trifluoromethyl)cyclohexyl | CH₂O | H | H | H |
| Hy5-4 | trans-4-(trifluoromethyl)cyclohexyl | CH₂O | Me | H | H |
| Hy5-5 | trans-4-(trifluoromethyl)cyclohexyl | CH₂O | Me | CH₂OH | H |

Example 12

N-(4-(ethylsulfonyl)benzyl)-2,5-dimethyl-4-(((1r,4r)-4-(trifluoromethyl)cyclohexyl)methoxy)thieno[2,3-d]pyrimidine-6-carboxamide (Cpd No Hy6-2)

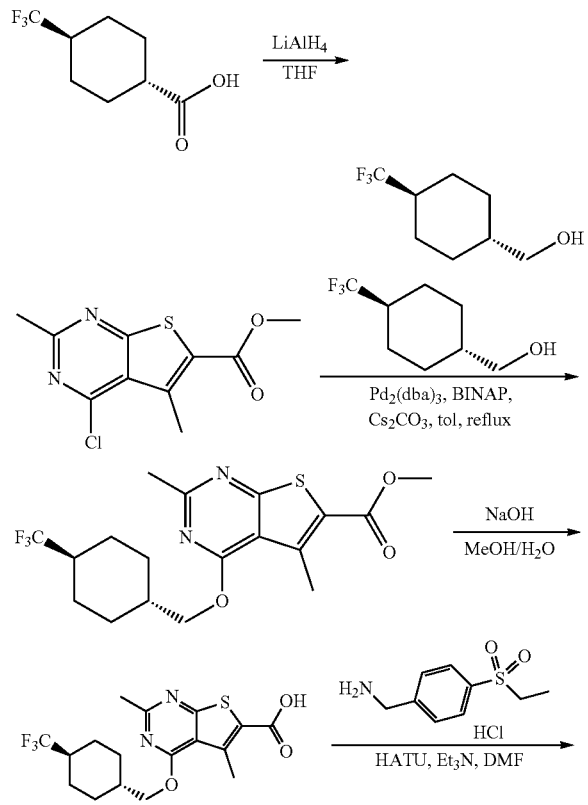

Step 1

To a solution of trans-4-(trifluoromethyl)cyclohexanecarboxylic acid (2.0 g, 11.4 mmol) in anhydrous THF (50 mL) was added LiAlH₄ (20 mL, 0.02 mmol, 1 M in THF) dropwise at 0° C. under N₂. The mixture was stirred at 0° C. for 4 h. TLC (petroleum ether/ethyl acetate=3/1) showed that the reaction was completed. The mixture was quenched with water (0.76 mL) and 10% aq. NaOH solution (0.76 mL) at 0° C. The mixture was filtered. The filtrate was dried over anhydrous Na₂SO₄, filtered, concentrated under reduced pressure to give crude (trans-4-(trifluoromethyl)cyclohexyl)methanol (1.73 g, 93%) as a pale yellow solid, which was used for the next step directly without further purification.

Step 2

To a solution of crude methyl 4-chloro-2,5-dimethylthieno[2,3-d]pyrimidine-6-carboxylate (100 mg, 0.39 mmol) in anhydrous toluene (6 mL) was added (trans-4-(trifluoromethyl)cyclohexyl)methanol (71 mg, 0.39 mmol), BINAP (24 mg, 0.04 mmol), Cs₂CO₃ (380 mg, 1.17 mmol) and Pd₂dba₃ (36 mg, 0.04 mmol) under N₂. The mixture was stirred at 110° C. for 2 h. LCMS showed that the reaction was completed. The mixture was diluted with water (10 mL) and extracted with ethyl acetate (3×10 mL). The combined organic layers were washed with brine (20 mL), dried over anhydrous Na₂SO₄, filtered, concentrated under reduced pressure. The residue was purified by preparative TLC with petroleum ether/ethyl acetate=3/1 to afford methyl 2,5-dimethyl-4-((trans-4-(trifluoromethyl)cyclohexyl)methoxy)thieno[2,3-d]pyrimidine-6-carboxylate (59 mg, 38%) as a pale yellow solid. LC-MS t$_R$=4.931 min in 10-80AB_7 min chromatography (Welch Xtimate 3 um, C18, 2.1*30 mm), MS (ESI) m/z 403.1 [M+H]⁺.

Step 3

To a solution of methyl 2,5-dimethyl-4-((trans-4-(trifluoromethyl)cyclohexyl)methoxy)thieno[2,3-d]pyrimidine-6-carboxylate (50 mg, 0.12 mmol) in MeOH/H₂O (3 mL, v/v=1/1) was added NaOH (99 mg, 2.49 mmol). The mixture was stirred at rt for 2 h. LCMS showed that the reaction was completed. The mixture was concentrated under reduced pressure. The mixture was added with water (10 mL). The aqueous layer was adjusted to pH=3-4 with 1 N HCl solution and extracted with ethyl acetate (3×10 mL). The combined organic layers were dried over anhydrous $Na_2SO_4$, filtered and concentrated under reduced pressure to afford crude 2,5-dimethyl-4-((trans-4-(trifluoromethyl)cyclohexyl) methoxy)thieno[2,3-d]pyrimidine-6-carboxylic acid (48 mg, 99%) as a pale yellow solid, which was used for the next step directly without further purification. LC-MS $t_R$=0.844 min in 5-95 AB_1.5 min chromatography (Welch MK RP-18e 25-2 mm), MS (ESI) m/z 389.0 $[M+H]^+$.

Step 4

To a solution of crude 2,5-dimethyl-4-((trans-4-(trifluoromethyl)cyclohexyl)methoxy)thieno[2,3-d]pyrimidine-6-carboxylic acid (48 mg, 0.12 mmol) in anhydrous DMF (6 mL) was added (4-(ethylsulfonyl)phenyl)methanamine hydrochloride HCl salt (35 mg, 0.15 mmol), HATU (56 mg, 0.15 mmol) and $Et_3N$ (37 mg, 0.37 mmol) under $N_2$. The mixture was stirred at rt for 2 h. LCMS showed that the reaction was completed. The mixture was added with water (10 mL) and extracted with ethyl acetate (3×10 mL). The combined organic layers were washed with $H_2O$ (3×10 mL) and brine (10 mL), dried over anhydrous $Na_2SO_4$, filtered and concentrated under reduced pressure. The residue was purified by preparative TLC with petroleum ether/ethyl acetate=1/3 to give the crude product, which was purified by SFC (OJ) and basic preparative HPLC separation, then lyophilized directly to afford N-(4-(ethylsulfonyl)benzyl)-2,5-dimethyl-4-((trans-4-(trifluoromethyl)cyclohexyl) methoxy)thieno[2,3-d]pyrimidine-6-carboxamide (Hy6-2, 30.60 mg, 38%) as a white solid.

Before Separation:
Isomer SFC: $t_R$=1.556 and 1.636 min in 3 min chromatography (Column: OJ-H; Method Name: OJ-H_3UM_5_5_40_4ML_3MIN.M, ee=95%).
SFC separation method:
Instrument: Berger MultiGram™ SFC, Mettler Toledo Co, Ltd
Column: OJ (250 mm*30 mm, 5 um)
Mobile phase: A: Supercritical $CO_2$, B: EtOH (0.05% $NH_4OH$), A:B=65:35 at 60 mL/min
Column Temp: 38° C.
Nozzle Pressure: 100 Bar
Nozzle Temp: 60° C.
Evaporator Temp: 20° C.
Trimmer Temp: 25° C.
Wavelength: 220 nm
LC-MS $t_R$=0.985 min in 5-95 AB chromatography (Welch MK RP-18e 25-2 mm), MS (ESI) m/z 570.1 $[M+H]^+$. Isomer SFC: $t_R$=1.566 min in 3 min chromatography (Column: OJ-H; Method Name: OJ-H_3UM_5_5_40_4ML_3MIN.M, ee=100%). $^1H$ NMR ($CDCl_3$ 400 MHz): δ 7.90 (d, J=8.4 Hz, 2H), 7.55 (d, J=7.6 Hz, 2H), 6.33-6.26 (m, 1H), 4.73 (d, J=6.4 Hz, 2H), 4.37 (d, J=6.8 Hz, 2H), 3.10 (q, J=7.6 Hz, 2H), 2.84 (s, 3H), 2.27 (s, 3H), 2.08-1.98 (m, 5H), 1.94-1.86 (m, 1H), 1.45-1.32 (m, 2H), 1.28 (t, J=7.6 Hz, 3H), 1.21-1.11 (m, 2H).

Basic Preparative HPLC Method:
Mobile phase A: water with 0.05% ammonia hydroxide v/v solution
Mobile phase B: MeCN
Flow rate: 25 mL/min.
Detection: UV 220 nm
Column: Phenomenex Synergi C18 150*25*10 um
Column temperature: 30° C.

| Time in min | % A | % B |
|---|---|---|
| 0.00 | 40 | 60 |
| 10.00 | 10 | 90 |
| 10.20 | 0 | 100 |
| 13.00 | 0 | 100 |

The compounds shown below are prepared following analogous procedures:

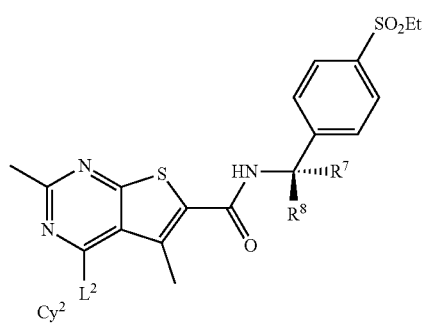

| Cpd No | $Cy^2$ | $L^2$ | $R^7$ | $R^8$ |
|---|---|---|---|---|
| Hy6-1 | 4-(trifluoromethyl)phenyl | $CH_2O$ | H | H |
| Hy6-3 | 4-(trifluoromethyl)phenyl | $CH_2O$ | $CH_2OH$ | H |
| Hy6-4 | trans-4-(trifluoromethyl)cyclohexyl | $CH_2O$ | $CH_2OH$ | H |

Example 13

(S)-4-ethyl-N—((R)-1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide and (R)-4-ethyl-N—((R)-1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide (Cpd Nos Hy7-17.1 and Hy7-17.2)

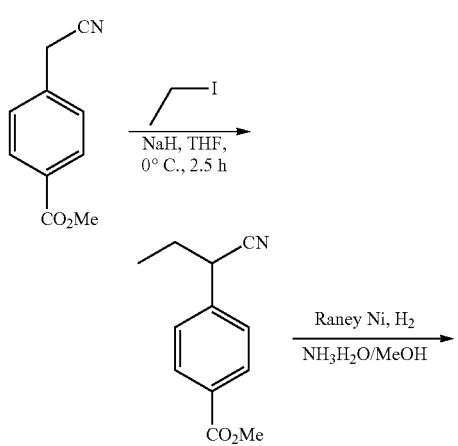

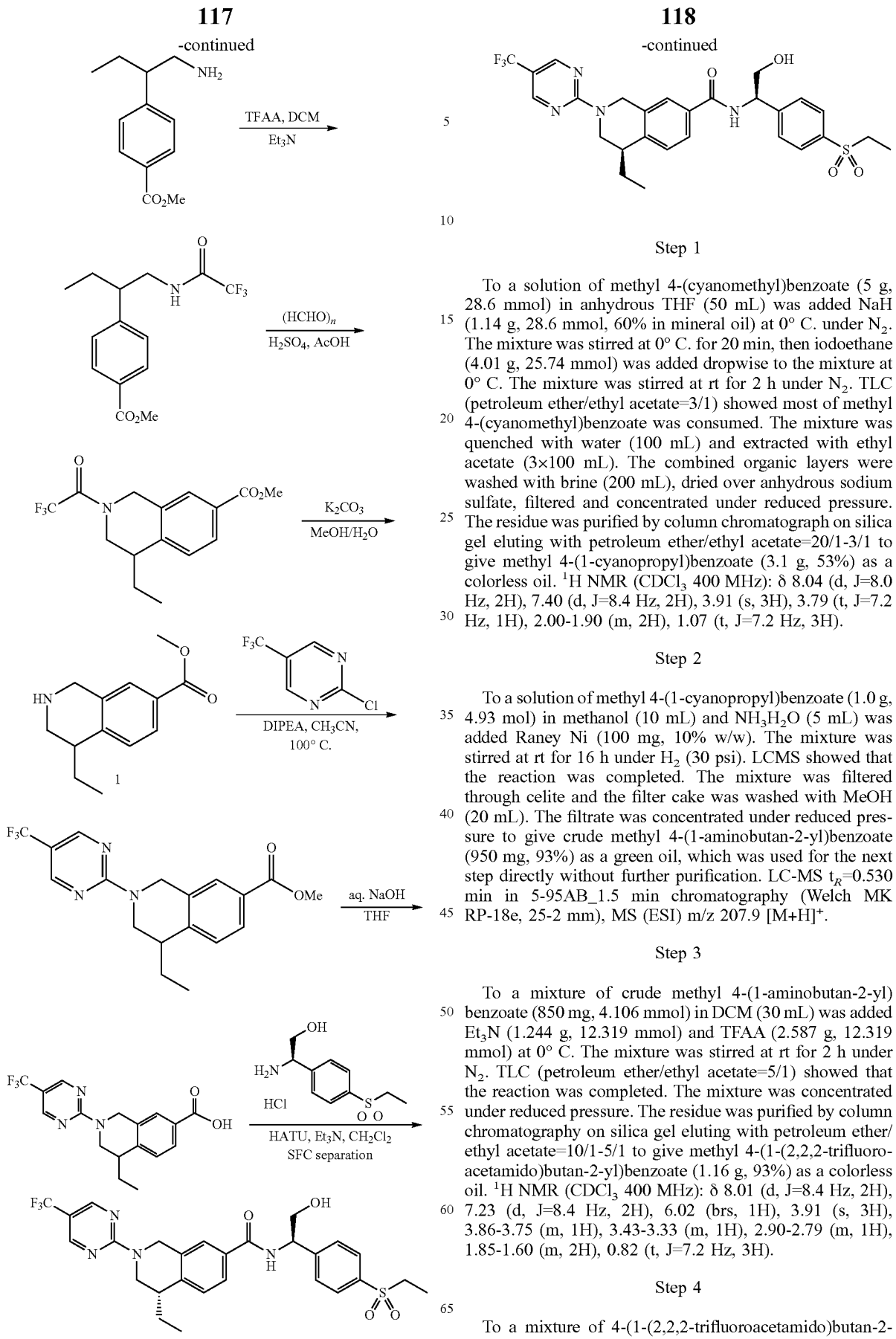

Step 1

To a solution of methyl 4-(cyanomethyl)benzoate (5 g, 28.6 mmol) in anhydrous THF (50 mL) was added NaH (1.14 g, 28.6 mmol, 60% in mineral oil) at 0° C. under $N_2$. The mixture was stirred at 0° C. for 20 min, then iodoethane (4.01 g, 25.74 mmol) was added dropwise to the mixture at 0° C. The mixture was stirred at rt for 2 h under $N_2$. TLC (petroleum ether/ethyl acetate=3/1) showed most of methyl 4-(cyanomethyl)benzoate was consumed. The mixture was quenched with water (100 mL) and extracted with ethyl acetate (3×100 mL). The combined organic layers were washed with brine (200 mL), dried over anhydrous sodium sulfate, filtered and concentrated under reduced pressure. The residue was purified by column chromatograph on silica gel eluting with petroleum ether/ethyl acetate=20/1-3/1 to give methyl 4-(1-cyanopropyl)benzoate (3.1 g, 53%) as a colorless oil. $^1$H NMR (CDCl$_3$ 400 MHz): δ 8.04 (d, J=8.0 Hz, 2H), 7.40 (d, J=8.4 Hz, 2H), 3.91 (s, 3H), 3.79 (t, J=7.2 Hz, 1H), 2.00-1.90 (m, 2H), 1.07 (t, J=7.2 Hz, 3H).

Step 2

To a solution of methyl 4-(1-cyanopropyl)benzoate (1.0 g, 4.93 mol) in methanol (10 mL) and NH$_3$H$_2$O (5 mL) was added Raney Ni (100 mg, 10% w/w). The mixture was stirred at rt for 16 h under H$_2$ (30 psi). LCMS showed that the reaction was completed. The mixture was filtered through celite and the filter cake was washed with MeOH (20 mL). The filtrate was concentrated under reduced pressure to give crude methyl 4-(1-aminobutan-2-yl)benzoate (950 mg, 93%) as a green oil, which was used for the next step directly without further purification. LC-MS $t_R$=0.530 min in 5-95AB_1.5 min chromatography (Welch MK RP-18e, 25-2 mm), MS (ESI) m/z 207.9 [M+H]$^+$.

Step 3

To a mixture of crude methyl 4-(1-aminobutan-2-yl) benzoate (850 mg, 4.106 mmol) in DCM (30 mL) was added Et$_3$N (1.244 g, 12.319 mmol) and TFAA (2.587 g, 12.319 mmol) at 0° C. The mixture was stirred at rt for 2 h under N$_2$. TLC (petroleum ether/ethyl acetate=5/1) showed that the reaction was completed. The mixture was concentrated under reduced pressure. The residue was purified by column chromatography on silica gel eluting with petroleum ether/ ethyl acetate=10/1-5/1 to give methyl 4-(1-(2,2,2-trifluoroacetamido)butan-2-yl)benzoate (1.16 g, 93%) as a colorless oil. $^1$H NMR (CDCl$_3$ 400 MHz): δ 8.01 (d, J=8.4 Hz, 2H), 7.23 (d, J=8.4 Hz, 2H), 6.02 (brs, 1H), 3.91 (s, 3H), 3.86-3.75 (m, 1H), 3.43-3.33 (m, 1H), 2.90-2.79 (m, 1H), 1.85-1.60 (m, 2H), 0.82 (t, J=7.2 Hz, 3H).

Step 4

To a mixture of 4-(1-(2,2,2-trifluoroacetamido)butan-2-yl)benzoate (800 mg, 2.64 mmol) and (HCHO)$_n$ (675 mg, 22.5 mmol) was added conc. H$_2$SO$_4$ (6 mL) and acetic acid (4 mL). The mixture was stirred at rt for 16 h. TLC (petroleum ether/ethyl acetate=10/1) showed that the reaction was completed. The mixture was poured into ice-water (50 mL) and extracted with ethyl acetate (3×50 mL). The combined organic layers were washed with brine (100 mL), dried over anhydrous sodium sulfate, filtered and concentrated under reduced pressure. The residue was purified by column chromatograph on silica gel eluting with petroleum ether/ethyl acetate=1/0-5/1 to give methyl 4-ethyl-2-(2,2,2-trifluoroacetyl)-1,2,3,4-tetrahydroisoquinoline-7-carboxylate (832 mg, 100%) as a colorless oil. $^1$H NMR (CDCl$_3$ 400 MHz): δ 7.91-7.75 (m, 2H), 7.25-7.20 (m, 1H), 4.87-4.80 (m, 1.5H), 4.66-4.56 (m, 1H), 4.32-4.31 (m, 0.5H), 3.85 (s, 3H), 3.66-3.61 (m, 0.5H), 3.40-3.33 (m, 0.5H), 2.82-2.78 (m, 1H), 1.70-1.58 (m, 2H), 1.06-0.92 (m, 3H).

Step 5

To a mixture of methyl 4-ethyl-2-(2,2,2-trifluoroacetyl)-1,2,3,4-tetrahydroisoquinoline-7-carboxylate (832 mg, 2.64 mmol) in methanol (2 mL) and water (0.4 mL) was added K$_2$CO$_3$ (729 mg, 5.28 mmol). The mixture was stirred at rt for 16 h. LCMS showed that the reaction was completed. The mixture was quenched with water (50 mL) and extracted with ethyl acetate (3×50 mL). The combined organic layers were dried over anhydrous anhydrous sodium sulfate, filtered and concentrated under reduced pressure to give crude methyl 4-ethyl-1,2,3,4-tetrahydroisoquinoline-7-carboxylate (470 mg, 81%) as a pale yellow solid, which was used directly for the next step without further purification.

Crude methyl 4-ethyl-1,2,3,4-tetrahydroisoquinoline-7-carboxylate (180 mg, 0.82 mmol) was purified by column chromatography on silica gel eluting with petroleum ether/ethyl acetate=1/0-4/1 to give methyl 4-ethyl-1,2,3,4-tetrahydroisoquinoline-7-carboxylate (1, 133.50 mg, 74%) as a pale yellow solid. LC-MS $t_R$=0.520 min in 5-95AB_1.5 min chromatography (Welch MK RP-18e, 25-2 mm), MS (ESI) m/z 220.0 [M+H]$^+$. $^1$H NMR (CDCl$_3$ 400 MHz): δ 7.81 (d, J=8.0 Hz, 1H), 7.72 (s, 1H), 7.26 (d, J=8.0 Hz, 1H), 3.95-3.87 (m, 1H), 3.92 (s, 3H), 3.61-3.53 (m, 1H), 3.30-3.18 (m, 1H), 2.96-2.86 (m, 1H), 2.81-2.70 (m, 2H), 1.83-1.72 (m, 2H), 0.98 (q, J=7.2 Hz, 3H).

Step 6

A mixture of crude methyl 4-ethyl-1,2,3,4-tetrahydroisoquinoline-7-carboxylate (100 mg, 0.46 mmol), 2-chloro-5-(trifluoromethyl)pyrimidine (99 mg, 0.55 mmol) and DIPEA (178 mg, 1.38 mmol) in CH$_3$CN (1 mL) was stirred at 100° C. for 2 h in a sealed tube. LCMS showed that the reaction was completed. The mixture was concentrated under reduced pressure. The residue was purified by preparative TLC with petroleum ether/ethyl acetate=8/1 to afford methyl 4-ethyl-2-(5-(trifluoromethyl)pyrimidin-2-yl)-1,2,3,4-tetrahydroisoquinoline-7-carboxylate (140 mg, 81.8%) as a yellow oil. LC-MS $t_R$=0.911 min in 5-95AB_1.5 min chromatography (Welch MK RP-18e, 25-2 mm), MS (ESI) m/z 366.0 [M+H]$^+$.

Step 7

To a mixture of methyl 4-ethyl-2-(5-(trifluoromethyl)pyrimidin-2-yl)-1,2,3,4-tetrahydroisoquinoline-7-carboxylate (140 mg, 0.38 mmol) in THF (4 mL) was added 2 N aq. NaOH (2 mL) solution. The mixture was stirred at 40° C. for 3 h. LCMS showed that the reaction was completed. The reaction solution was added with water (10 mL) and concentrated under reduced pressure to remove THF. The residue was acidified by 1 N HCl to pH=3, and then extracted with ethyl acetate (3×10 mL). The combined organic layers were dried over anhydrous Na$_2$SO$_4$, filtered and concentrated under reduced pressure to afford crude 4-ethyl-2-(5-(trifluoromethyl)pyrimidin-2-yl)-1,2,3,4-tetrahydroisoquinoline-7-carboxylic acid (115 mg, 85.8%) as a light yellow solid, which was used for the next step without further purification. LC-MS $t_R$=0.824 min in 5-95AB_1.5 min chromatography (Welch MK RP-18e, 25-2 mm), MS (ESI) m/z 351.8 [M+H]$^+$.

Step 8

To a mixture of crude 4-ethyl-2-(5-(trifluoromethyl)pyrimidin-2-yl)-1,2,3,4-tetrahydroisoquinoline-7-carboxylic acid (108 mg, 0.31 mmol), (R)-2-amino-2-(4-(ethylsulfonyl)phenyl)ethanol hydrochloride (110 mg, 0.40 mmol) and HATU (190 mg, 0.50 mmol) in dry CH$_2$Cl$_2$ (2 mL) was added Et$_3$N (94 mg, 0.93 mmol). The mixture was stirred at rt for 2 h. LCMS showed that the reaction was completed. The mixture was filtered and the filtrate was concentrated under reduced pressure to give the crude product. The crude product was purified by preparative TLC with petroleum ether/ethyl acetate=1/1, SFC separation (AD-H) and HCl preparative HPLC separation, then dry-freezing directly to give the two enantiomers of 4-ethyl-N—((R)-1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide as white solids.

Before SFC Separation:
Isomer SFC $t_R$=1.029 and 1.524 min in 5 min chromatography (Column: AD-H; Method
Name: AD-H_3UM_5_40_4ML_5MIN.M, ee=0.32%).
SFC Separation Condition:
Instrument: SFC-80-(8)
Column: AD 250 mm*30 mm*10 um
Mobile phase: A: Supercritical CO$_2$, B: $^i$PrOH (0.05% NH$_4$OH), A:B=50:50 at 80 mL/min
Column Temp: 40° C.
Nozzle Pressure: 100 Bar
Nozzle Temp: 60° C.
Evaporator Temp: 20° C.
Trimmer Temp: 25° C.
Wavelength: 220 nm
(Hy7-17.2, 20.80 mg, 21.4%) as a white solid. LC-MS $t_R$=0.909 min in 5-95AB_1.5 min chromatography (Welch MK RP-18e, 25-2 mm), MS (ESI) m/z 563.1 [M+H]$^+$. $^1$H NMR (CDCl$_3$ 400 MHz): δ 8.57 (s, 2H), 7.88 (d, J=8.0 Hz, 2H), 7.73 (s, 1H), 7.67 (d, J=8.0 Hz, 1H), 7.59 (d, J=8.4 Hz, 2H), 7.29 (d, J=8.0 Hz, 1H), 7.18 (d, J=6.8 Hz, 1H), 5.33-5.27 (m, 2H), 4.79-4.67 (m, 2H), 4.11-4.00 (m, 2H), 3.56 (dd, J=3.6, 13.2 Hz, 1H), 3.10 (q, J=7.6 Hz, 2H), 2.91-2.88 (m, 1H), 1.65-1.56 (m, 2H), 1.28 (t, J=7.6 Hz, 3H), 1.02 (t, J=7.6 Hz, 3H).
Isomer SFC $t_R$=0.697 min in 3 min chromatography (Column: AD-H; Method Name: AD-H_3UM_4_40_4ML_3MIN.M, ee=100%).
HCl preparative HPLC Method:
Mobile phase A: water (0.05% HCl)-ACN
Mobile phase B: MeCN
Flow rate: 25 mL/min.
Detection: UV 220 nm
Column: Phenomenex Synergi C18 150*25*10 um
Column temperature: 40° C.

| Time in min | % A | % B |
|---|---|---|
| 0.00 | 45 | 55 |
| 10.00 | 15 | 85 |
| 10.20 | 0 | 100 |
| 13.00 | 0 | 100 |

(Hy7-17.1, 24.40 mg, 25.2%) as a white solid. LC-MS $t_R$=0.909 min in 5-95AB_1.5 min chromatography (Welch MK RP-18e, 25-2 mm), MS (ESI) m/z 563.1 [M+H]$^+$. $^1$H NMR (CDCl$_3$ 400 MHz): δ 8.57 (s, 2H), 7.87 (d, J=8.4 Hz, 2H), 7.73 (s, 1H), 7.67 (d, J=8.0 Hz, 1H), 7.59 (d, J=8.0 Hz, 2H), 7.29 (d, J=7.6 Hz, 1H), 7.22 (d, J=6.4 Hz, 1H), 5.33-5.25 (m, 2H), 4.77-4.68 (m, 2H), 4.09-3.98 (m, 2H), 3.57 (dd, J=3.6, 12.8 Hz, 1H), 3.10 (q, J=7.6 Hz, 2H), 2.90-2.88 (m, 1H), 1.68-1.56 (m, 2H), 1.29 (t, J=7.6 Hz, 3H), 1.05 (t, J=7.6 Hz, 3H).

Isomer SFC $t_R$=1.035 min in 3 min chromatography (Column: AD-H; Method Name: AD-H_3UM_4_40_4ML_3MIN.M, ee=100%).

HCl Preparative HPLC Method:
Mobile phase A: water (0.05% HCl)-ACN
Mobile phase B: MeCN
Flow rate: 25 mL/min.
Detection: UV 220 nm
Column: Phenomenex Synergi C18 150*25*10 um
Column temperature: 40° C.

| Time in min | % A | % B |
|---|---|---|
| 0.00 | 45 | 55 |
| 10.00 | 15 | 85 |
| 10.20 | 0 | 100 |
| 13.00 | 0 | 100 |

The following compounds are prepared using procedures analogous to those described above:

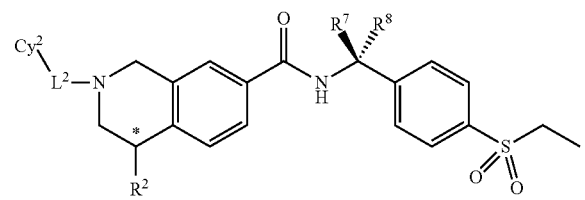

| Cpd No$^a$ | Cy$^2$ | L$^2$ | R$^2$ | R$^7$ | R$^8$ |
|---|---|---|---|---|---|
| Hy7-1.1 | 5-fluoro-2-pyrimidinyl | bond | i-Pr | H | H |
| Hy7-1.2 | 5-fluoro-2-pyrimidinyl | bond | i-Pr | H | H |
| Hy7-2.1 | 5-cyano-2-pyrimidinyl | bond | i-Pr | H | H |
| Hy7-2.2 | 5-cyano-2-pyrimidinyl | bond | i-Pr | H | H |
| Hy7-3.1 | 5-chloro-2-pyrimidinyl | bond | i-Pr | H | H |
| Hy7-3.2 | 5-chloro-2-pyrimidinyl | bond | i-Pr | H | H |
| Hy7-4.1 | 5-cyclopropyl-2-pyrimidinyl | bond | i-Pr | H | H |
| Hy7-4.2 | 5-cyclopropyl-2-pyrimidinyl | bond | i-Pr | H | H |
| Hy7-5.1 | 5-ethoxy-2-pyrimidinyl | bond | i-Pr | H | H |
| Hy7-5.2 | 5-ethoxy-2-pyrimidinyl | bond | i-Pr | H | H |
| Hy7-6.1 | 5-chloro-2-pyrimidinyl | bond | Et | CH$_2$OH | H |
| Hy7-6.2 | 5-chloro-2-pyrimidinyl | bond | Et | CH$_2$OH | H |
| Hy7-7.1 | 4-(trifluoromethyl)phenyl | bond | Et | H | H |
| Hy7-7.2 | 4-(trifluoromethyl)phenyl | bond | Et | H | H |
| Hy7-8.1 | 5-(trifluoromethyl)-2-pyridyl | bond | Et | H | H |
| Hy7-8.2 | 5-(trifluoromethyl)-2-pyridyl | bond | Et | H | H |
| Hy7-9.1 | 5-(trifluoromethyl)-2-pyrimidinyl | bond | Et | H | H |
| Hy7-9.2 | 5-(trifluoromethyl)-2-pyrimidinyl | bond | Et | H | H |
| Hy7-11.1 | 5-cyclopropyl-2-pyrimidinyl | bond | Et | CH$_2$OH | H |
| Hy7-11.2 | 5-cyclopropyl-2-pyrimidinyl | bond | Et | CH$_2$OH | H |
| Hy7-13.1 | 5-(trifluoromethyl)-3-methyl-2-pyridyl | bond | Et | H | H |
| Hy7-13.2 | 5-(trifluoromethyl)-3-methyl-2-pyridyl | bond | Et | H | H |
| Hy7-14.1 | 4-(trifluoromethyl)-2-pyrimidinyl | bond | i-Pr | H | H |
| Hy7-14.2 | 4-(trifluoromethyl)-2-pyrimidinyl | bond | i-Pr | H | H |
| Hy7-15.1 | 5-(trifluoromethyl)-2-pyrimidinyl | bond | i-Pr | H | H |
| Hy7-15.2 | 5-(trifluoromethyl)-2-pyrimidinyl | bond | i-Pr | H | H |
| Hy7-16.1 | 5-(ethoxycarbonyl)-2-pyrimidinyl | bond | i-Pr | H | H |
| Hy7-16.2 | 5-(ethoxycarbonyl)-2-pyrimidinyl | bond | i-Pr | H | H |
| Hy7-19.1 | 5-(4-morpholinyl)-2-pyrimidinyl | bond | i-Pr | H | H |
| Hy7-19.2 | 5-(4-morpholinyl)-2-pyrimidinyl | bond | i-Pr | H | H |
| Hy7-20.1 | 5-(6-methoxy-2-pyridyl)-2-pyrimidinyl | bond | Et | H | H |
| Hy7-20.2 | 5-(6-methoxy-2-pyridyl)-2-pyrimidinyl | bond | Et | H | H |
| Hy7-21.1 | (structure) | bond | i-Pr | H | H |
| Hy7-21.2 | (structure) | bond | i-Pr | H | H |
| Hy7-22.1 | 5-(trifluoromethyl)-3-methyl-2-pyridyl | bond | Et | CH$_2$OH | H |
| Hy7-22.2 | 5-(trifluoromethyl)-3-methyl-2-pyridyl | bond | Et | CH$_2$OH | H |
| Hy7-23.1 | 5-(2-methoxy-4-pyridyl)-2-pyrimidinyl | bond | i-Pr | H | H |
| Hy7-23.2 | 5-(2-methoxy-4-pyridyl)-2-pyrimidinyl | bond | i-Pr | H | H |
| Hy7-24.1 | (structure) | bond | i-Pr | H | H |
| Hy7-24.2 | (structure) | bond | i-Pr | H | H |
| Hy7-25.1 | (structure) | bond | i-Pr | H | H |

-continued

| Cpd No[a] | Cy² | L² | R² | R⁷ | R⁸ |
|---|---|---|---|---|---|
| Hy7-25.2 | (1-methyl-2-oxo-pyridin-4-yl)-pyrimidin-2-yl | bond | i-Pr | H | H |
| Hy7-26.1 | 5-(ethoxycarbonyl)-4-(trifluoromethyl)-2-pyrimidinyl | bond | i-Pr | H | H |
| Hy7-26.2 | 5-(ethoxycarbonyl)-4-(trifluoromethyl)-2-pyrimidinyl | bond | i-Pr | H | H |
| Hy7-27.1 | 4-fluorophenyl | CH₂ | i-Pr | H | H |
| Hy7-27.2 | 4-fluorophenyl | CH₂ | i-Pr | H | H |
| Hy7-28.1 | 4-cyanophenyl | CH₂ | i-Pr | H | H |
| Hy7-28.2 | 4-cyanophenyl | CH₂ | i-Pr | H | H |
| Hy7-29.1 | 4-chlorophenyl | CH₂ | i-Pr | H | H |
| Hy7-29.2 | 4-chlorophenyl | CH₂ | i-Pr | H | H |
| Hy7-30.1 | 4-tetrahydropyranyl | bond | Et | CH₂OH | H |
| Hy7-30.2 | 4-tetrahydropyranyl | bond | Et | CH₂OH | H |
| Hy7-31.1 | 5-(2-oxazolyl)-2-pyrimidinyl | bond | Et | H | H |
| Hy7-31.2 | 5-(2-oxazolyl)-2-pyrimidinyl | bond | Et | H | H |
| Hy7-32.1 | 4,4-difluorocyclohexyl | bond | Et | CH₂OH | H |
| Hy7-32.2 | 4,4-difluorocyclohexyl | bond | Et | CH₂OH | H |
| Hy7-33.1 | 5-(2-oxazolyl)-2-pyrimidinyl | bond | Et | CH₂OH | H |
| Hy7-33.2 | 5-(2-oxazolyl)-2-pyrimidinyl | bond | Et | CH₂OH | H |
| Hy7-34.1 | 5-(ethoxycarbonyl)-2-pyrimidinyl | bond | Et | CH₂OH | H |
| Hy7-34.2 | 5-(ethoxycarbonyl)-2-pyrimidinyl | bond | Et | CH₂OH | H |
| Hy7-35.1 | 4-(trifluoromethyl)cyclohexyl | bond | Et | CH₂OH | H |
| Hy7-35.2 | 4-(trifluoromethyl)cyclohexyl | bond | Et | CH₂OH | H |
| Hy7-35.3 | 4-(trifluoromethyl)cyclohexyl | bond | Et | CH₂OH | H |
| Hy7-35.4 | 4-(trifluoromethyl)cyclohexyl | bond | Et | CH₂OH | H |
| Hy7-36.1 | 5-(trifluoromethyl)-2-pyrimidinyl | bond | CF₃ | H | H |
| Hy7-36.2 | 5-(trifluoromethyl)-2-pyrimidinyl | bond | CF₃ | H | H |
| Hy7-37.1 | 3-cyano-5-(trifluoromethyl)-2-pyridyl | bond | Et | CH₂OH | H |
| Hy7-37.2 | 3-cyano-5-(trifluoromethyl)-2-pyridyl | bond | Et | CH₂OH | H |

[a]Isomer were separated by chromatography on chiral columns.

The following compounds are prepared by procedures analogous to those described above:

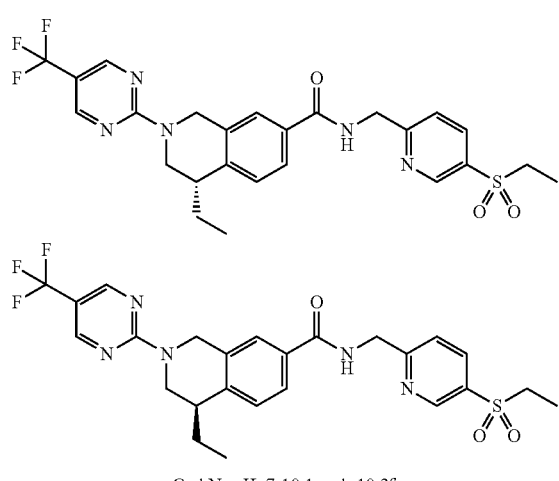

Cpd Nos Hy7-10.1 and -10.2[a]

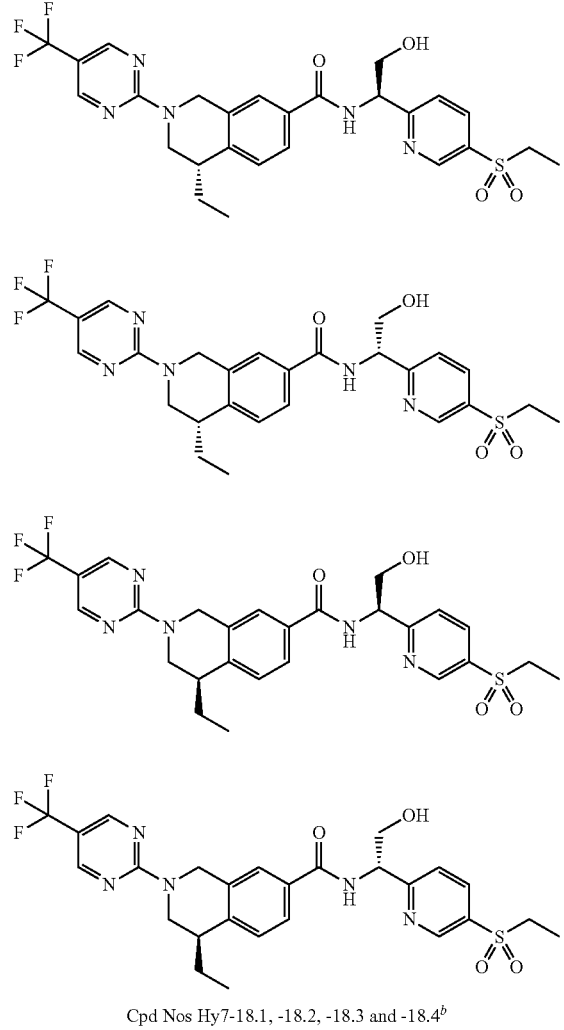

Cpd Nos Hy7-18.1, -18.2, -18.3 and -18.4[b]

The following compounds were byproducts in the preparation of Hy7-7.1 and Hy7-7.2

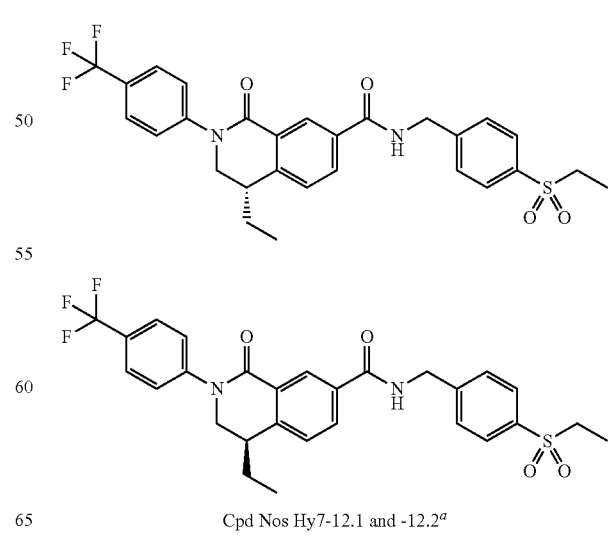

Cpd Nos Hy7-12.1 and -12.2[a]

Example 14
N-(4-(ethylsulfonyl)benzyl)-8,8-dimethyl-6-(5-(trifluoromethyl)pyrimidin-2-yl)-5,6,7,8-tetrahydro-1,6-naphthyridine-3-carboxamide (Hy7B-1)
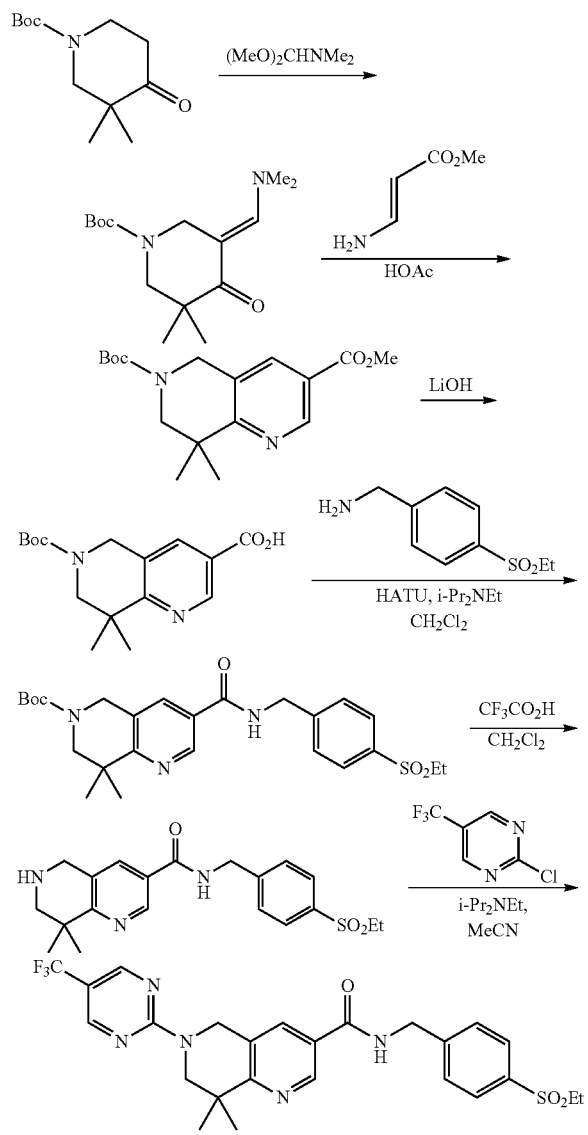
Example 15
(R)—N-(1-(4-(ethylsulfonyl)phenyl)-2-hydroxyethyl)-1-((4-(trifluoromethyl)phenoxy)methyl)isoquinoline-6-carboxamide (Hy1A-24)
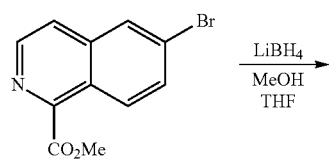
-continued
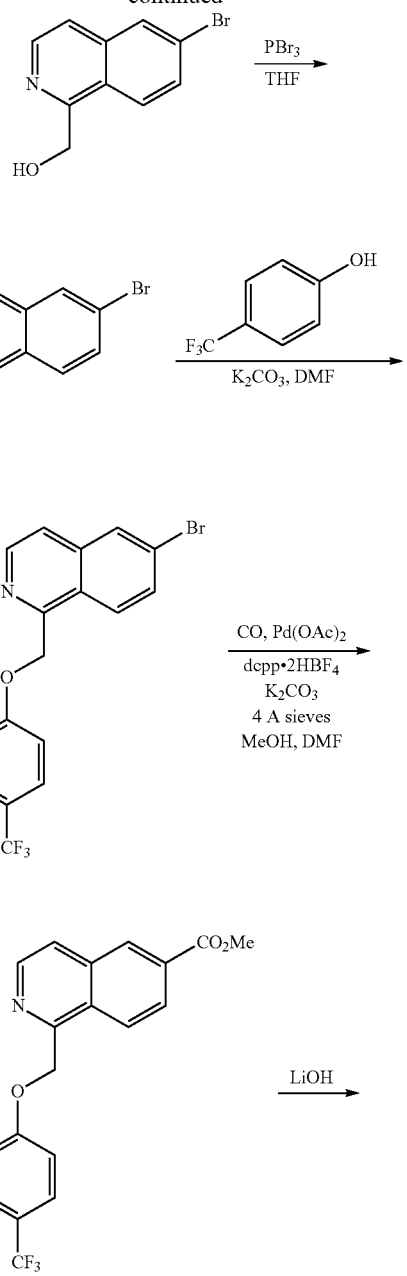
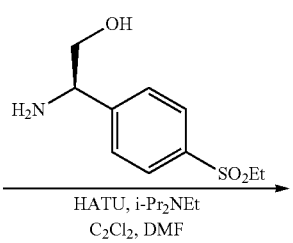

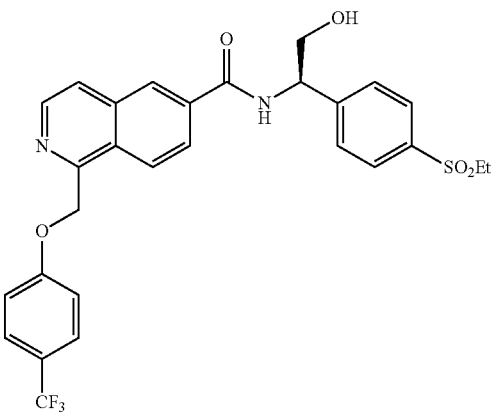

LC-MS Data is presented in the following tables.

TABLE 1

| Cpd No | LC-MS Method | tR (min) | Mass Observed |
| --- | --- | --- | --- |
| Hy1A-1 | 4 | 1.023 | 513.1 (M + H) |
| Hy1A-2 | 2 | 0.921 | 515.1 (M + H) |
| Hy1A-3.1 | 2 | 0.937 | 521.1 (M + H) |
| Hy1A-3.2 | 2 | 0.819 | 521.1 (M + H) |
| Hy1A-4 | 2 | 0.962 | 529.1 (M + H) |
| Hy1A-5 | 2 | 0.856 | 535.0 (M + H) |
| Hy1A-6 | 2 | 0.881 | 549.1 (M + H) |
| Hy1A-7 | 2 | 0.923 | 559.1 (M + H) |
| Hy1A-8 | 2 | 0.81 | 565.1 (M + H) |
| Hy1A-9 | 2 | 0.898 | 569.1 (M + H) |
| Hy1A-10 | 2 | 0.829 | 579.1 (M + H) |
| Hy1A-11 | 2 | 0.855 | 599.1 (M + H) |
| Hy1A-12 | 2 | 0.762 | 519.1 (M + H) |
| Hy1A-13 | 2 | 0.912 | 523.1 (M + H) |
| Hy1A-14 | 2 | 0.79 | 547.0 (M + H) |
| Hy1A-15 | 2 | 0.809 | 575.1 (M + H) |
| Hy1A-16 | 2 | 0.869 | 579.1 (M + H) |
| Hy1A-17 | 2 | 0.686 | 580.1 (M + H) |
| Hy1A-18.1 | 2 | 0.798 | 581.1 (M + H) |
| Hy1A-18.2 | 2 | 0.806 | 581.1 (M + H) |
| Hy1A-18.3 | 2 | 0.782 | 581.1 (M + H) |
| Hy1A-19 | 2 | 0.655 | 594.1 (M + H) |
| Hy1A-20 | 2 | 0.945 | 563.1 (M + H) |
| Hy1A-21 | 2 | 0.900 | 605.1 (M + H) |
| Hy1A-22.1 | 2 | 0.859 | 580.1 (M + H) |
| Hy1A-22.2 | 2 | 0.857 | 580.1 (M + H) |
| Hy1A-23 | 2 | 0.833 | 595.1 (M + H) |
| Hy1A-24 | 1 | 1.69 | 559.5 (M + H) |

TABLE 2

| Cpd No | LC-MS Method | tR (min) | Mass Observed |
| --- | --- | --- | --- |
| Hy1B-1 | 2 | 0.803 | 543.1 (M + H) |
| Hy1B-2 | 2 | 0.686 | 549.1 (M + H) |
| Hy1B-3 | 2 | 0.678 | 573.0 (M + H) |
| Hy1B-4 | 2 | 0.665 | 579.1 (M + H) |

TABLE 3

| Cpd No | LC-MS Method | tR (min) | Mass Observed |
| --- | --- | --- | --- |
| Hy1C-1 | 2 | 0.758 | m/z 566.1 (M + H) |
| Hy1C-2 | 2 | 0.795 | m/z 536.1 (M + H) |

TABLE 4

| Cpd No | LC-MS Method | tR (min) | Mass Observed |
| --- | --- | --- | --- |
| Hy2A-1.1 | 1 | 1.80 | 504 |
| Hy2A-1.2 | 1 | 1.80 | 504 |
| Hy2A-2 | 1 | 1.79 | 547 |
| Hy2A-3 | 1 | 1.79 | 547 |
| Hy2A-4.1 | 2 | 0.917 | 551.1 (M + H) |
| Hy2A-4.2 | 2 | 0.915 | 551.2 (M + H) |
| Hy2A-5 | 1 | 1.86 | 619 |
| Hy2A-5.1 | 2 | 0.977 | 619.1 (M + H) |
| Hy2A-5.2 | 2 | 0.983 | 619.1 (M + H) |
| Hy2A-6 | 1 | 0.79 | 467 |
| Hy2A-7 | 1 | 0.75 | 474 |
| Hy2A-8 | 1 | 0.84 | 481 |
| Hy2A-9 | 1 | 0.87 | 483 |
| Hy2A-10 | 1 | 0.8 | 488 |
| Hy2A-11 | 1 | 0.91 | 497 |
| Hy2A-12.1 | 2 | 0.736 | 507.2 (M + H) |
| Hy2A-12.2 | 2 | 0.742 | 507.2 (M + H) |
| Hy2A-13 | 1 | 0.95 | 509 |
| Hy2A-14 | 1 | 0.94 | 516 |
| Hy2A-15.1 | 5 | 0.934 | 516.2 (M + H) |
| Hy2A-15.2 | 2 | 0.682 | 516.1 (M + H) |
| Hy2A-16.1 | 2 | 0.734 | 517.1 (M + H) |
| Hy2A-16.2 | 2 | 0.727 | 517.1 (M + H) |
| Hy2A-17.1 | 2 | 0.745 | 517.1 (M + H) |
| Hy2A-17.2 | 2 | 0.749 | 517.1 (M + H) |
| Hy2A-18 | 2 | 0.738 | 521.2 (M + H) |
| Hy2A-19 | 1 | 1.03 | 525 |
| Hy2A-20.1 | 2 | 0.777 | 525.1 (M + H) |
| Hy2A-20.2 | 5 | 1.002 | 525.2 (M + H) |
| Hy2A-21 | 1 | 0.94 | 526 |
| Hy2A-22.1 | 5 | 0.894 | 535.2 (M + H) |
| Hy2A-22.2 | 5 | 0.904 | 535.2 (M + H) |
| Hy2A-23.1 | 4 | 0.976 | 544.2 (M + H) |
| Hy2A-23.2 | 4 | 0.976 | 544.2 (M + H) |
| Hy2A-24 | 3 | 2.077 | 556.3 (M + H) |
| Hy2A-25.1 | 2 | 0.765 | 558.1 (M + H) |
| Hy2A-25.2 | 2 | 0.768 | 558.1 (M + H) |
| Hy2A-26.1 | 4 | 0.874 | 571.1 (M + H) |
| Hy2A-26.2 | 4 | 0.882 | 571.1 (M + H) |
| Hy2A-27 | 2 | 0.662 | 551.1 (M + H) |
| Hy2A-28.1 | 2 | 0.644 | 581.1 (M + H) |
| Hy2A-28.2 | 2 | 0.635 | 581.1 (M + H) |
| Hy2A-28.3 | 2 | 0.639 | 581.2 (M + H) |
| Hy2A-29.1 | 2 | 0.635 | 582.1 (M + H) |
| Hy2A-29.2 | 2 | 0.645 | 582.1 (M + H) |
| Hy2A-29.3 | 2 | 0.631 | 582.1 (M + H) |

TABLE 5

| Cpd No | LC-MS Method | tR (min) | Mass Observed |
| --- | --- | --- | --- |
| Hy2B-1.1 | 2 | 0.792 | 505.2 (M + H) |
| Hy2B-1.2 | 2 | 0.788 | 505.1 (M + H) |
| Hy2B-2.1 | 2 | 0.840 | 514.1 (M + H) |
| Hy2B-2.2 | 2 | 0.841 | 514.1 (M + H) |
| Hy2B-3.1 | 2 | 0.862 | 548.0 (M + H) |
| Hy2B-3.2 | 2 | 0.861 | 548.1 (M + H) |
| Hy2B-4.1 | 2 | 0.841 | 552.2 (M + H) |
| Hy2B-4.2 | 2 | 0.836 | 552.1 (M + H) |
| Hy2B-5.1 | 2 | 0.908 | 620.1 (M + H) |
| Hy2B-5.2 | 2 | 0.903 | 620.1 (M + H) |
| Hy2B-6.1 | 2 | 0.757 | 510.2 (M + H) |
| Hy2B-6.2 | 2 | 0.751 | 510.1 (M + H) |
| Hy2B-7.1 | 2 | 0.762 | 517.1 (M + H) |
| Hy2B-7.2 | 2 | 0.678 | 517.1 (M + H) |
| Hy2B-8.1 | 2 | 0.700 | 526.1 (M + H) |
| Hy2B-8.2 | 2 | 0.703 | 526.1 (M + H) |
| Hy2B-9.1 | 4 | 0.935 | 566.2 (M + H) |
| Hy2B-9.2 | 4 | 0.929 | 566.2 (M + H) |
| Hy2B-10.1 | 3 | 0.701 | 567.2 (M + H) |
| Hy2B-10.2 | 2 | 0.708 | 567.1 (M + H) |

TABLE 6

| Compound | LC-MS Method | tR (min) | Mass observed |
| --- | --- | --- | --- |
| Hy3A-1 | 1 | 1.59 | 578 |
| Hy3A-2 | 1 | 1.67 | 548 |
| Hy3A-3 | 1 | 1.63 | 549 |
| Hy3A-4 | 1 | 1.52 | 572 |
| Hy3A-5 | 1 | 1.61 | 566 |
| Hy3A-6 | 1 | 1.49 | 579.6 |
| Hy3A-7 | 1 | 1.80 | 573.6 |
| Hy3B-1 | 1 | 1.54 | 579 |
| Hy3B-2 | 1 | 1.65 | 549 |
| Hy3B-3 | 1 | 1.57 | 550 |
| Hy3B-4 | 1 | 1.77 | 580.6 |

TABLE 7

| Compound | LC-MS Method | tR (min) | Mass observed |
| --- | --- | --- | --- |
| Hy4A-1 | 2 | 0.78 | 538 |
| Hy4A-2 | 2 | 0.74 | 568 |
| Hy4A-3 | 2 | 0.82 | 532 |
| Hy4A-4 | 2 | 0.76 | 562 |
| Hy4A-5 | 2 | 0.76 | 524 |

TABLE 8

| Cpd No | LC-MS Method | tR (min) | Mass Observed |
| --- | --- | --- | --- |
| Hy5-1 | 2 | 0.764 | 518.0 (M + H) |
| Hy5-2 | 2 | 0.712 | 524.1 (M + H) |
| Hy5-3 | 2 | 0.776 | 532.0 (M + H) |
| Hy5-4 | 2 | 0.752 | 538.1 (M + H) |
| Hy5-5 | 2 | 0.721 | 568.1 (M + H) |

TABLE 9

| Cpd No | LC-MS Method | tR (min) | Mass Observed |
| --- | --- | --- | --- |
| Hy6-1 | 2 | 0.975 | 564.1 (M + H) |
| Hy6-2 | 2 | 0.985 | 570.1 (M + H) |
| Hy6-3 | 2 | 0.794 | 594.1 (M + H) |
| Hy6-4 | 6 | 0.951 | 600.2 (M + H) |

TABLE 10

| Cpd No | LC-MS Method | tR (min) | Mass observed |
| --- | --- | --- | --- |
| Hy7-1.1 | 2 | 0.885 | 497.2 (M + H) |
| Hy7-1.2 | 2 | 0.874 | 497.1 (M + H) |
| Hy7-2.1 | 2 | 0.894 | 504.1 (M + H) |
| Hy7-2.2 | 2 | 0.888 | 504.0 (M + H) |
| Hy7-3.1 | 2 | 0.902 | 513.0 (M + H) |
| Hy7-3.2 | 2 | 0.898 | 513.0 (M + H) |
| Hy7-4.1 | 2 | 0.843 | 519.2 (M + H) |
| Hy7-4.2 | 2 | 0.842 | 519.1 (M + H) |
| Hy7-5.1 | 2 | 0.915 | 523.1 (M + H) |
| Hy7-5.2 | 2 | 0.910 | 523.1 (M + H) |
| Hy7-6.1 | 2 | 0.879 | 529.1 (M + H) |
| Hy7-6.2 | 2 | 0.887 | 529.1 (M + H) |
| Hy7-7.1 | 2 | 0.986 | 531.1 (M + H) |
| Hy7-7.2 | 2 | 0.983 | 531.1 (M + H) |
| Hy7-8.1 | 2 | 0.806 | 532.1 (M + H) |
| Hy7-8.2 | 2 | 0.807 | 532.1 (M + H) |
| Hy7-9.1 | 2 | 0.834 | 533.1 (M + H) |
| Hy7-9.2 | 2 | 0.823 | 533.1 (M + H) |
| Hy7-10.1 | 2 | 0.935 | 534.1 (M + H) |
| Hy7-10.2 | 2 | 0.937 | 534.1 (M + H) |
| Hy7-11.1 | 2 | 0.722 | 535.1 (M + H) |
| Hy7-11.2 | 2 | 0.727 | 535.1 (M + H) |
| Hy7-12.1 | 2 | 0.656 | 545.1 (M + H) |
| Hy7-12.2 | 2 | 0.651 | 545.1 (M + H) |
| Hy7-13.1 | 2 | 0.834 | 546.1 (M + H) |
| Hy7-13.2 | 2 | 0.837 | 546.1 (M + H) |
| Hy7-14.1 | 2 | 0.856 | 547.1 (M + H) |
| Hy7-14.2 | 2 | 0.934 | 547.0 (M + H) |
| Hy7-15.1 | 2 | 0.931 | 547.1 (M + H) |
| Hy7-15.2 | 2 | 0.918 | 547.1 (M + H) |
| Hy7-16.1 | 2 | 0.932 | 551.1 (M + H) |
| Hy7-16.2 | 2 | 0.930 | 551.1 (M + H) |
| Hy7-17.1 | 2 | 0.909 | 563.1 (M + H) |
| Hy7-17.2 | 2 | 0.909 | 563.1 (M + H) |
| Hy7-18.1 | 2 | 0.797 | 564.1 (M + H) |
| Hy7-18.2 | 2 | 0.793 | 564.2 (M + H) |
| Hy7-18.3 | 2 | 0.776 | 564.1 (M + H) |
| Hy7-18.4 | 2 | 0.780 | 564.1 (M + H) |
| Hy7-19.1 | 4 | 1.081 | 564.3 (M + H) |
| Hy7-19.2 | 4 | 1.081 | 564.2 (M + H) |
| Hy7-20.1 | 2 | 0.873 | 572.1 (M + H) |
| Hy7-20.2 | 2 | 0.769 | 572.1 (M + H) |
| Hy7-21.1 | 2 | 0.687 | 572.1 (M + H) |
| Hy7-21.2 | 2 | 0.685 | 572.0 (M + H) |
| Hy7-22.1 | 2 | 0.926 | 576.2 (M + H) |
| Hy7-22.2 | 2 | 0.931 | 576.2 (M + H) |
| Hy7-23.1 | 2 | 0.811 | 586.0 (M + H) |
| Hy7-23.2 | 2 | 0.803 | 586.0 (M + H) |
| Hy7-24.1 | 2 | 0.721 | 586.0 (M + H) |
| Hy7-24.2 | 2 | 0.720 | 586.0 (M + H) |
| Hy7-25.1 | 2 | 0.709 | 586.0 (M + H) |
| Hy7-25.2 | 4 | 1.828 | 586.2 (M + H) |
| Hy7-26.1 | 2 | 0.985 | 619.1 (M + H) |
| Hy7-26.2 | 2 | 0.981 | 619.1 (M + H) |
| Hy7-27.1 | 2 | 0.704 | 509.2 (M + H) |
| Hy7-27.2 | 2 | 0.706 | 509.1 (M + H) |
| Hy7-28.1 | 2 | 0.695 | 516.1 (M + H) |
| Hy7-28.2 | 2 | 0.703 | 516.1 (M + H) |
| Hy7-29.1 | 2 | 0.724 | 525.1 (M + H) |
| Hy7-29.2 | 2 | 0.715 | 525.1 (M + H) |
| Hy7-30.1 | 2 | 0.561 | 501.2 (M + H) |
| Hy7-30.2 | 2 | 0.548 | 501.2 (M + H) |
| Hy7-31.1 | 2 | 0.771 | 532.0 (M + H) |
| Hy7-31.2 | 2 | 0.771 | 532.1 (M + H) |
| Hy7-32.1 | 2 | 0.701 | 535.3 (M + H) |
| Hy7-32.2 | 2 | 0.710 | 535.2 (M + H) |
| Hy7-33.1 | 2 | 0.747 | 562.1 (M + H) |
| Hy7-33.2 | 2 | 0.749 | 562.3 (M + H) |
| Hy7-34.1 | 2 | 0.764 | 567.1 (M + H) |
| Hy7-34.2 | 2 | 0.769 | 567.1 (M + H) |
| Hy7-35.1 | 2 | 0.639 | 567.1 (M + H) |
| Hy7-35.2 | 2 | 0.734 | 567.1 (M + H) |
| Hy7-35.3 | 2 | 0.736 | 567.2 (M + H) |
| Hy7-35.4 | 2 | 0.637 | 567.1 (M + H) |
| Hy7-36.1 | 2 | 0.919 | 573.1 (M + H) |
| Hy7-36.2 | 2 | 0.795 | 573.0 (M + H) |
| Hy7-37.1 | 2 | 0.797 | 587.1 (M + H) |
| Hy7-37.2 | 2 | 0.793 | 587.1 (M + H) |
| Hy7B-1 | 1 | 1.89 | 534.5 (M + H) |

Biological Assays

Radio-Ligand RORγ Binding Assay (Assay 1)

Compounds described herein were tested for ability to bind to RORγ in a cell-free competition assay with commercially available radio-ligand (RL), 25-hydroxy [26, 27-$^3$H]-cholesterol (PerkinElmer, Cat. #NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM 3-octylglucopyranoside and 5 mM DTT. Tested compounds were dissolved in DMSO, and semi-log (3.162×) serial dilutions of the compounds were prepared in the same solvent. Two µL of the DMSO solutions were mixed with 28

μL of 8.6 nM 25-hydroxy [26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. #RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. #T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and $K_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds described herein were tested for RORγ inverse agonist activity in a cell-based, transcriptional activity assay. Secreted Nanoluc" luciferase was used as a reporter for transcriptional activity of the full-length RORγt in Jurkat cells (ATCC, Cat. #TIB-152). A reporter plasmid was constructed by inserting 5 repeats of the ROR Response Element (RORE) AAAGTAGGTCA (SEQ ID NO: 1) into a commercially available promoterless plasmid pNL1.3 [secNluc] (Promega, Cat. #N1021) using KpnI and HindIII restriction sites. The expression plasmid for RORγt was purchased (Geneocopoeia, Cat. #EX-T6988-M02). Jurkat cells (30 million cells) were transfected with 11 μg of EX-T6988-MO2 and 26 μg of the reporter plasmid in OptiMEM® media using Lipofectamine LTX and Plus™ reagents (Life Technologies, Cat. #15338-100). After 5-6 hrs of incubation at 37° C./5% $CO_2$, the cells were collected, resuspended in phenol-red free RPMI media containing 10% (v/v) delipidated FBS (Hyclone, Cat. #SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% $CO_2$ for 16-18 hrs. Luciferase activity in the conditioned supernatants was determined with NanoGlo® assay reagents (Promega, Cat. #N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Tables 11-20.

TABLE 11

| Cpd No | Avg ROR Bind Ki (nM) | Avg ROR γt/5x IC50 (nM) |
|---|---|---|
| Hy1A-1 | +++ | + |
| Hy1A-2 | ++ | |
| Hy1A-3.1 | +++ | + |
| Hy1A-3.2 | +++ | + |
| Hy1A-4 | +++ | ++ |
| Hy1A-5 | +++ | ++ |
| Hy1A-6 | +++ | +++ |
| Hy1A-7 | +++ | ++ |
| Hy1A-8 | +++ | ++ |
| Hy1A-9 | +++ | +++ |
| Hy1A-10 | +++ | +++ |
| Hy1A-11 | +++ | +++ |
| Hy1A-12 | +++ | + |
| Hy1A-13 | +++ | ++ |
| Hy1A-14 | +++ | +++ |
| Hy1A-15 | +++ | ++ |
| Hy1A-16 | +++ | +++ |
| Hy1A-17 | +++ | + |
| Hy1A-18.1 | +++ | +++ |
| Hy1A-18.2 | +++ | +++ |
| Hy1A-18.3 | +++ | + |
| Hy1A-19 | +++ | ++ |
| Hy1A-20 | +++ | +++ |
| Hy1A-21 | +++ | +++ |
| Hy1A-22.1 | +++ | +++ |
| Hy1A-22.2 | +++ | ++ |
| Hy1A-23 | +++ | +++ |
| Hy1A-24 | +++ | ++ |

TABLE 12

| Cpd No | Avg ROR Bind Ki (nM) | Avg ROR γt/5x IC50 (nM) |
|---|---|---|
| Hy1B-1 | ++ | |
| Hy1B-2 | ++ | |
| Hy1B-3 | +++ | ++ |
| Hy1B-4 | ++ | |

TABLE 13

| Cpd No | Avg ROR Bind Ki (nM) | Avg ROR γt/5x IC50 (nM) |
|---|---|---|
| Hy1C-1 | ++ | |
| Hy1C-2 | ++ | |

TABLE 14

| Cpd No | Avg ROR Bind Ki (nM) | Avg ROR γt/5x IC50 (nM) |
|---|---|---|
| Hy2A-1.1 | ++ | |
| Hy2A-1.2 | ++ | |
| Hy2A-2 | ++ | + |
| Hy2A-3 | +++ | + |
| Hy2A-4.1 | ++ | |
| Hy2A-4.2 | ++ | |
| Hy2A-5 | ++ | ++ |
| Hy2A-5.1 | +++ | ++ |
| Hy2A-5.2 | ++ | |
| Hy2A-6 | + | |
| Hy2A-7 | + | |
| Hy2A-8 | ++ | |
| Hy2A-9 | ++ | |
| Hy2A-10 | ++ | |
| Hy2A-11 | +++ | ++ |
| Hy2A-12.1 | ++ | ++ |
| Hy2A-12.2 | + | |
| Hy2A-13 | +++ | +++ |
| Hy2A-14 | +++ | +++ |
| Hy2A-15.1 | +++ | +++ |
| Hy2A-15.2 | +++ | |
| Hy2A-16.1 | +++ | +++ |

TABLE 14-continued

| Cpd No | Avg ROR Bind Ki (nM) | Avg ROR γt/5x IC50 (nM) |
|---|---|---|
| Hy2A-16.2 | ++ | |
| Hy2A-17.1 | +++ | +++ |
| Hy2A-17.2 | ++ | |
| Hy2A-18 | +++ | ++ |
| Hy2A-19 | +++ | +++ |
| Hy2A-20.1 | +++ | +++ |
| Hy2A-20.2 | +++ | ++ |
| Hy2A-21 | +++ | +++ |
| Hy2A-22.1 | +++ | ++ |
| Hy2A-22.2 | ++ | |
| Hy2A-23.1 | +++ | +++ |
| Hy2A-23.2 | +++ | ++ |
| Hy2A-24 | ++ | ++ |
| Hy2A-25.1 | +++ | +++ |
| Hy2A-25.2 | ++ | |
| Hy2A-26.1 | +++ | ++ |
| Hy2A-26.2 | ++ | |
| Hy2A-27 | +++ | +++ |
| Hy2A-28.1 | +++ | +++ |
| Hy2A-28.2 | +++ | ++ |
| Hy2A-28.3 | ++ | |
| Hy2A-29.1 | ++ | |
| Hy2A-29.2 | ++ | |
| Hy2A-29.3 | ++ | |

TABLE 15

| Cpd No | Avg ROR Bind Ki | Avg ROR γt/5x IC50 |
|---|---|---|
| Hy2B-1.1 | + | |
| Hy2B-1.2 | + | |
| Hy2B-2.1 | ++ | |
| Hy2B-2.2 | + | |
| Hy2B-3.1 | ++ | |
| Hy2B-3.2 | ++ | |
| Hy2B-4.1 | + | |
| Hy2B-4.2 | + | |
| Hy2B-5.1 | ++ | |
| Hy2B-5.2 | ++ | |
| Hy2B-6.1 | +++ | + |
| Hy2B-6.2 | ++ | |
| Hy2B-7.1 | +++ | ++ |
| Hy2B-7.2 | + | |
| Hy2B-8.1 | +++ | ++ |
| Hy2B-8.2 | ++ | |
| Hy2B-9.1 | +++ | ++ |
| Hy2B-9.2 | ++ | |
| Hy2B-10.1 | ++ | ++ |
| Hy2B-10.2 | ++ | |

TABLE 16

| Compound | Avg ROR Bind Ki (nM) | Avg ROR γt/5x IC50 (nM) |
|---|---|---|
| Hy3A-1 | +++ | +++ |
| Hy3A-2 | +++ | +++ |
| Hy3A-3 | +++ | +++ |
| Hy3A-4 | +++ | +++ |
| Hy3A-5 | +++ | +++ |
| Hy3A-6 | +++ | +++ |
| Hy3A-7 | +++ | +++ |
| Hy3B-1 | +++ | +++ |
| Hy3B-2 | +++ | +++ |
| Hy3B-3 | ++ | |
| Hy3B-4 | +++ | |

TABLE 17

| Cpd No | Avg ROR Bind Ki | Avg ROR γt/5x IC50 |
|---|---|---|
| Hy4-1 | +++ | ++ |
| Hy4-2 | +++ | +++ |
| Hy4-3 | +++ | ++ |
| Hy4-4 | +++ | ++ |
| Hy4-5 | ++ | |

TABLE 18

| Cpd No | Avg ROR Bind Ki (nM) | Avg ROR γt/5x IC50 (nM) |
|---|---|---|
| Hy5-1 | ++ | |
| Hy5-2 | ++ | |
| Hy5-3 | +++ | +++ |
| Hy5-4 | ++ | |
| Hy5-5 | ++ | |

TABLE 19

| Cpd No | Avg ROR Bind Ki (nM) | Avg ROR γt/5x IC50 (nM) |
|---|---|---|
| Hy6-1 | +++ | ++ |
| Hy6-2 | +++ | ++ |
| Hy6-3 | +++ | +++ |
| Hy6-4 | +++ | +++ |

TABLE 20

| Cpd No | Avg ROR Bind Ki (nM) | Avg ROR γt/5x IC5 (nM) |
|---|---|---|
| Hy7-1.1 | +++ | + |
| Hy7-1.2 | +++ | + |
| Hy7-2.1 | +++ | ++ |
| Hy7-2.2 | ++ | |
| Hy7-3.1 | +++ | ++ |
| Hy7-3.2 | +++ | + |
| Hy7-4.1 | +++ | ++ |
| Hy7-4.2 | +++ | + |
| Hy7-5.1 | +++ | ++ |
| Hy7-5.2 | ++ | |
| Hy7-6.1 | +++ | + |
| Hy7-6.2 | +++ | + |
| Hy7-7.1 | +++ | +++ |
| Hy7-7.2 | +++ | ++ |
| Hy7-8.1 | +++ | +++ |
| Hy7-8.2 | +++ | ++ |
| Hy7-9.1 | +++ | +++ |
| Hy7-9.2 | +++ | + |
| Hy7-10.1 | +++ | +++ |
| Hy7-10.2 | ++ | |
| Hy7-11.1 | +++ | ++ |
| Hy7-11.2 | +++ | + |
| Hy7-12.1 | +++ | ++ |
| Hy7-12.2 | +++ | ++ |
| Hy7-13.1 | +++ | +++ |
| Hy7-13.2 | +++ | ++ |
| Hy7-14.1 | +++ | + |
| Hy7-14.2 | +++ | + |
| Hy7-15.1 | +++ | ++ |
| Hy7-15.2 | +++ | |
| Hy7-16.1 | +++ | +++ |
| Hy7-16.2 | ++ | |
| Hy7-17.1 | +++ | +++ |
| Hy7-17.2 | +++ | + |
| Hy7-18.1 | +++ | +++ |
| Hy7-18.2 | +++ | + |
| Hy7-18.3 | ++ | |
| Hy7-18.4 | | |

TABLE 20-continued

| Cpd No | Avg ROR Bind Ki (nM) | Avg ROR γt/5x IC5 (nM) |
|---|---|---|
| Hy7-19.1 | ++ | |
| Hy7-19.2 | + | |
| Hy7-20.1 | +++ | +++ |
| Hy7-20.2 | ++ | |
| Hy7-21.1 | +++ | ++ |
| Hy7-21.2 | + | |
| Hy7-22.1 | +++ | +++ |

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaagtaggtc a                                                          11
```

TABLE 20-continued

| Cpd No | Avg ROR Bind Ki (nM) | Avg ROR γt/5x IC5 (nM) |
|---|---|---|
| Hy7-22.2 | +++ | ++ |
| Hy7-23.1 | +++ | +++ |
| Hy7-23.2 | ++ | |
| Hy7-24.1 | +++ | +++ |
| Hy7-24.2 | + | |
| Hy7-25.1 | +++ | ++ |
| Hy7-25.2 | + | |
| Hy7-26.1 | +++ | +++ |
| Hy7-26.2 | +++ | ++ |
| Hy7-27.1 | +++ | + |
| Hy7-27.2 | +++ | +++ |
| Hy7-28.1 | +++ | ++ |
| Hy7-28.2 | +++ | +++ |
| Hy7-29.1 | +++ | + |
| Hy7-29.2 | +++ | ++ |
| Hy7-30.1 | ++ | |
| Hy7-30.2 | | |
| Hy7-31.1 | +++ | +++ |
| Hy7-31.2 | +++ | + |
| Hy7-32.1 | +++ | + |
| Hy7-32.2 | ++ | |
| Hy7-33.1 | +++ | +++ |
| Hy7-33.2 | +++ | ++ |
| Hy7-34.1 | +++ | +++ |
| Hy7-34.2 | +++ | |
| Hy7-35.1 | +++ | +++ |
| Hy7-35.2 | +++ | + |
| Hy7-35.3 | +++ | |
| Hy7-35.4 | ++ | |
| Hy7-36.1 | +++ | +++ |
| Hy7-36.2 | +++ | + |
| Hy7-37.1 | +++ | +++ |
| Hy7-37.2 | +++ | |
| Hy7B-1 | ++ | |

"nt" or no value presented = not tested; + means >1000 nM; ++ means 100 nM-1000 nM; +++ means <100 nM.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound having the Formula IIIa, IVa, Va', VIa', VIIa'', VIIb'', VIIc'', VIIIa'', VIIIb'', or IXa':

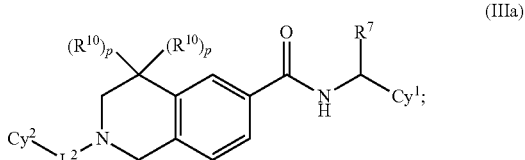

(IIIa)

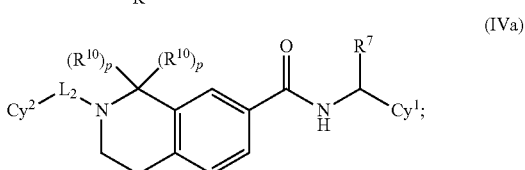

(IVa)

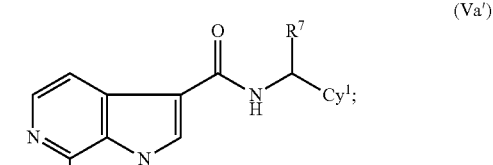

(Va')

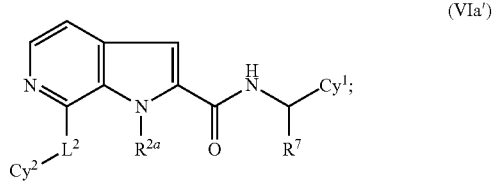

(VIa')

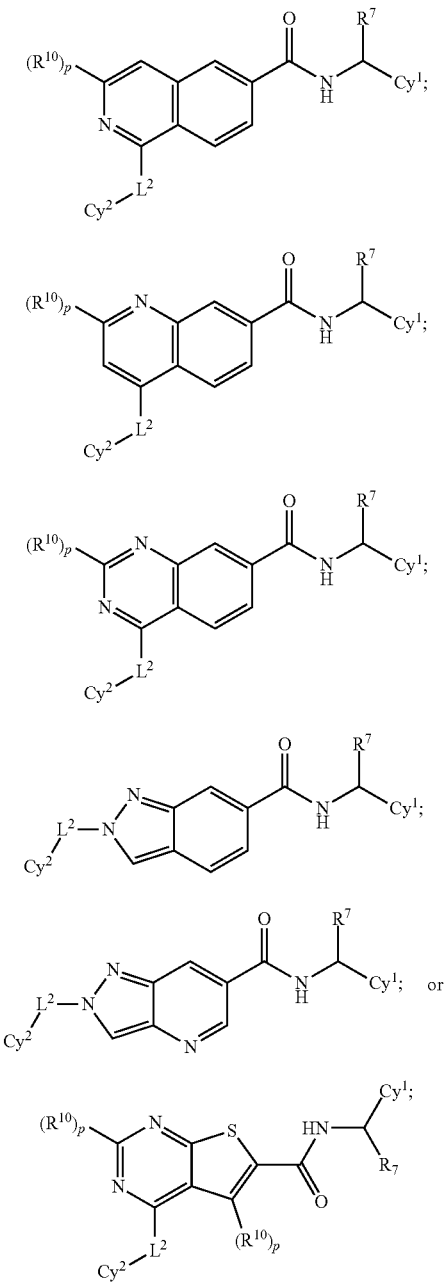

or a pharmaceutically acceptable salt thereof, wherein
p is independently 0 or 1;
$L^2$ is a bond or is selected from $CH_2$, $CH_2CH_2$, CHMe, O, C(=O), CH(OH), and $CH_2O$, wherein the oxygen or carbon atom in $CH_2O$ can be attached to $Cy^2$;
$Cy^1$ is selected from aryl, heteroaryl, heterocyclyl, and cycloalkyl, wherein the aryl, heteroaryl, heterocyclyl, and cycloalkyl are each substituted with 1 to 3 groups independently selected from $R^5$, wherein at least one $R^5$ is $-SO_2-(C_1-C_3)$alkyl;
$Cy^2$ is selected from aryl, heteroaryl, monocyclic cycloalkyl, and monocyclic heterocyclyl, wherein the aryl, heteroaryl, monocyclic cycloalkyl, and monocyclic heterocyclyl are each optionally substituted with 1 to 3 groups independently selected from $R^6$;

$R^{2a}$ is H, $(C_1-C_4)$alkyl, $(C_2-C_4)$alkenyl, $(C_1-C_4)$haloalkyl, or monocyclic cycloalkyl;
$R^5$ and $R^6$ are each independently selected from halogen, —CN, —$OR^c$, —$NR^dR^e$, —$S(O)_kR^c$, —$NR^cS(O)_2R^c$, —$S(O)_2NR^dR^e$, —C(=O)$OR^c$, —OC(=O)$OR^c$, —OC(=O)$R^c$, —OC(=S)$OR^c$, —C(=S)$OR^c$, —OC(=S)$R^c$, —C(=O)$NR^dR^e$, —$NR^cC(=O)R^c$, —C(=S)$NR^dR^e$, —$NR^cC(=S)R^c$, —$NR^cC(=O)OR^c$, —OC(=O)$NR^dR^e$, —$NR^c(C=S)OR^c$, —OC(=S)$NR^dR^e$, —$NR^cC(=O)NR^dR^e$, —$NR^c(C=S)NR^dR^e$, —C(=S)$R^c$, —C(=O)$R^c$, $(C_1-C_6)$alkyl, cycloalkyl, —$(CH_2)_{1-4}$-cycloalkyl, heterocyclyl, —$(CH_2)_{1-4}$-heterocyclyl, aryl, —NHC(=O)-heterocyclyl, —NHC(=O)-cycloalkyl, —$(CH_2)_{1-4}$-aryl, heteroaryl and —$(CH_2)_{1-4}$-heteroaryl,
wherein the alkyl, cycloalkyl, heterocyclyl, aryl or heteroaryl portion present in each of said $(C_1-C_6)$alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl substituent for $R^6$ are optionally substituted with halogen, $OR^c$, —$NO_2$, —CN, —$NR^cC(=O)R^c$, —$NR^dR^e$, —$S(O)_kR^c$, —C(=O)$OR^c$, —C(=O)$NR^dR^e$, —C(=O)$R^c$, $(C_1-C_3)$alkyl, halo$(C_1-C_3)$alkyl, $(C_1-C_3)$alkoxy$(C_1-C_3)$alkyl, $(C_1-C_3)$alkoxy, or halo$(C_1-C_3)$alkoxy;
each $R^c$ is independently selected from hydrogen and $(C_1-C_6)$alkyl optionally substituted with hydroxy, $(C_1-C_2)$alkoxy, —C(O)$NH_2$, —C(O)O$(C_1-C_3)$alkyl, or 1 to 3 halogen;
each $R^d$ and $R^e$ is independently selected from hydrogen and $(C_1-C_6)$alkyl;
k is 0, 1 or 2;
any heterocyclyl or heteroaryl portion of $Cy^1$ or $Cy^2$ is further optionally substituted with =O;
$R^7$ is hydrogen, $OR^c$, or $(C_1-C_3)$alkyl, wherein the $(C_1-C_3)$alkyl is optionally substituted with $OR^c$ or —$NR^dR^e$; and
$R^{10}$ is $(C_1-C_4)$alkyl, $(C_1-C_4)$haloalkyl, $(C_1-C_4)$alkoxy, $(C_1-C_4)$haloalkoxy, halo, cyano, or monocyclic cycloalkyl.

2. The compound of claim 1, wherein $R^{10}$ is $(C_1-C_4)$alkyl; and $L^2$ is $CH_2O$, wherein the methylene portion of $CH_2O$ is attached to $Cy^2$.

3. The compound of claim 1, wherein $R^2$ is $(C_1-C_4)$alkyl or cyclopropyl.

4. The compound of claim 1, wherein $R^7$ is hydrogen, —O$(C_1-C_3)$alkyl, or $(C_1-C_3)$alkyl, wherein the $(C_1-C_3)$alkyl is optionally substituted with OH, $NH_2$ or N$(C_1-C_3$alkyl$)_2$.

5. The compound of claim 1, wherein $Cy^1$ is aryl or heteroaryl, each substituted with 1 to 3 groups independently selected from $R^5$.

6. The compound of claim 1, wherein $Cy^1$ is phenyl or pyridinyl, each substituted with 1 to 3 groups independently selected from $R^5$.

7. The compound of claim 1, wherein $Cy^2$ is phenyl, pyrimidinyl, cyclohexyl, pyridinyl, tetrahydropyranyl, or piperidinyl, each optionally substituted with 1 to 3 groups independently selected from $R^6$.

8. The compound of claim 1, wherein $Cy^2$ is phenyl or cyclohexyl, each substituted with 1 to 3 groups independently selected from $R^6$.

9. The compound of claim 1, wherein
$R^5$ is selected from halogen, —CN, —$OR^c$, —$NR^dR^e$, —$NR^cS(O)_2R^c$, —$S(O)_2NR^dR^e$, —C(=O)$OR^c$, —C(=O)$NR^dR^e$, —$NR^cC(=O)R^c$, —$NR^cC(=O)$ OR$^c$, —OC(=S)NR$^d$R$^e$, —C(=O)R$^c$, —SO$_2$—(C$_1$-C$_3$)alkyl, and (C$_1$-C$_4$)alkyl optionally substituted with halogen; and R$^6$ is selected from halogen, —CN, —OR$^c$, —NR$^d$R$^e$, —NR$^c$S(O)$_2$R$^c$, —S(O)$_2$NR$^d$R$^e$, —C(=O)OR$^c$, —OC(=O)OR$^c$, —OC(=O)R$^c$, —C(=O)NR$^d$R$^e$, —NR$^c$C(=O)R$^c$, —C(=S)NR$^d$R$^e$, —NR$^c$C(=S)R$^c$, —NR$^c$C(=O)OR$^c$, —OC(=O)NR$^d$R$^e$, —NR$^c$(C=S)OR$^c$, —OC(=S)NR$^d$R$^e$, —NR$^c$C(=O)NR$^d$R$^e$, —NR$^c$(C=S)NR$^d$R$^e$, —C(=S)R$^c$, —C(=O)R$^c$, —SO$_2$—(C$_1$-C$_3$)alkyl, and (C$_1$-C$_4$)alkyl optionally substituted with halogen.

10. The compound of claim 1, wherein
R$^5$ is —SO$_2$—(C$_1$-C$_3$)alkyl;
R$^6$ is selected from CN, halo, —C(=O)OR$^c$, OR$^c$, and (C$_1$-C$_4$)alkyl optionally substituted with halogen; and
R$^c$ is (C$_1$-C$_4$)alkyl optionally substituted with halogen.

11. The compound of claim 1, wherein R$^{10}$ is (C$_1$-C$_4$)alkyl or halo.

12. The compound of claim 1, wherein L$^2$ is a bond or is selected from CH$_2$, O, and CH$_2$O, wherein the carbon atom in CH$_2$O is attached to a carbon atom on Cy$^2$.

13. A compound selected from one of the following or a pharmaceutically acceptable salt thereof:

N-(1-(4-(ethylsulfonyl)phenyl)-2-hydroxyethyl)-3-methyl-1 ((tetrahydro-2H-pyran-4-yl)methoxy)isoquinoline-6-carboxamide;
N-(4-(ethylsulfonyl)benzyl)-1-((4-(trifluoromethyl)phenoxy)isoquinoline-6-carboxamide;
N-(4-(ethylsulfonyl)benzyl)-1-((4-(trifluoromethyl)cyclohexyl)oxy)isoquinoline-6-carboxamide;
N-(4-(ethylsulfonyl)benzyl)-1-((4-(trifluoromethyl)cyclohexyl)oxy)isoquinoline-6-carboxamide;
N-(4-(ethylsulfonyl)benzyl)-1-((4-(trifluoromethyl)benzyl)oxy)isoquinoline-6-carboxamide;
N-(4-(ethylsulfonyl)benzyl)-1-((4-(trifluoromethyl)cyclohexyl)methoxy)isoquinoline-6-carboxamide;
N-(4-(ethylsulfonyl)benzyl)-3-methyl-1-((4-(trifluoromethyl)cyclohexyl)methoxy)isoquinoline-6-carboxamide;
N-(1-(4-(ethylsulfonyl)phenyl)-2-hydroxyethyl)-1-((4-(trifluoromethyl)benzyl)oxy)isoquinoline-6-carboxamide;
N-(1-(4-(ethylsulfonyl)phenyl)-2-hydroxyethyl)-1-((4-(trifluoromethyl)cyclohexyl)methoxy)isoquinoline-6-carboxamide;
3-chloro-N-(4-(ethylsulfonyl)benzyl)-1-((4-(trifluoromethyl)cyclohexyl)methoxy)isoquinoline-6-carboxamide;
N-(1-(4-(ethylsulfonyl)phenyl)-2-hydroxyethyl)-3-methyl-1-((4-(trifluoromethyl)cyclohexyl)methoxy)isoquinoline-6-carboxamide;
3-chloro-N-(1-(4-(ethylsulfonyl)phenyl)-2-hydroxyethyl)-1-((-4-(trifluoromethyl)cyclohexyl)methoxy)isoquinoline-6-carboxamide;
1-((3,3-difluorocyclobutyl)methoxy)-N-(1-(4-(ethylsulfonyl)phenyl)-2-hydroxyethyl)-3-methylisoquinoline-6-carboxamide;
N-(1-(4-(ethylsulfonyl)phenyl)-2-hydroxyethyl)-1-((4-fluorobenzyl)oxy)-3-methylisoquinoline-6-carboxamide;
1-((4,4-difluorocyclohexyl)methoxy)-N-(1-(4-(ethylsulfonyl)phenyl)-2-hydroxyethyl)-3-methylisoquinoline-6-carboxamide;
N-(1-(4-(ethylsulfonyl)phenyl)-2-hydroxyethyl)-3-methyl-1-(4-(trifluoromethoxy)phenoxy)isoquinoline-6-carboxamide;
N-(1-(4-(ethylsulfonyl)phenyl)-2-hydroxyethyl)-3-methyl-1-((-4-(trifluoromethyl)cyclohexyl)methoxy)isoquinoline-6-carboxamide;
N-(1-(4-(ethylsulfonyl)phenyl)-2-hydroxyethyl)-3-methyl-1-((1-(2,2,2-trifluoroethyl)piperidin-4-yl)oxy)isoquinoline-6-carboxamide;
N-(1-(4-(ethylsulfonyl)phenyl)-2-hydroxyethyl)-3-methyl-1-((6-(trifluoromethyl)tetrahydro-2H-pyran-3-yl)methoxy)isoquinoline-6-carboxamide;
N-(1-(4-(ethylsulfonyl)phenyl)-2-hydroxyethyl)-3-methyl-1-((6-(trifluoromethyl)tetrahydro-2H-pyran-3-yl)methoxy)isoquinoline-6-carboxamide;
N-(1-(4-(ethylsulfonyl)phenyl)-2-hydroxyethyl)-3-methyl-1-((-6-(trifluoromethyl)tetrahydro-2H-pyran-3-yl)methoxy)isoquinoline-6-carboxamide;
N-(1-(4-(ethylsulfonyl)phenyl)-2-hydroxyethyl)-3-methyl-1-((1-(2,2,2-trifluoroethyl)piperidin-4-yl)methoxy)isoquinoline-6-carboxamide;
3-ethyl-N-(4-(ethylsulfonyl)benzyl)-1-((4-(trifluoromethyl)cyclohexyl)methoxy)isoquinoline-6-carboxamide;
3-cyclopropyl-N-(1-(4-(ethylsulfonyl)phenyl)-2-hydroxyethyl)-1-((4-(trifluoromethyl)cyclohexyl)methoxy)isoquinoline-6-carboxamide;
N-(1-(5-(ethylsulfonyl)pyridin-2-yl)-2-hydroxyethyl)-3-methyl-1-((4-(trifluoromethyl)cyclohexyl)methoxy)isoquinoline-6-carboxamide;
N-(1-(5-(ethylsulfonyl)pyridin-2-yl)-2-hydroxyethyl)-3-methyl-1-((4-(trifluoromethyl)cyclohexyl)methoxy)isoquinoline-6-carboxamide;
N-(1-(4-(ethylsulfonyl)phenyl)-2-hydroxyethyl)-3-methoxy-1-((-4-(trifluoromethyl)cyclohexyl)methoxy)isoquinoline-6-carboxamide;
N-(1-(4-(ethylsulfonyl)phenyl)-2-hydroxyethyl)-1-((4-(trifluoromethyl)phenoxy)methyl)isoquinoline-6-carboxamide;
N-(4-(ethylsulfonyl)benzyl)-2-methyl-4-((4-(trifluoromethyl)benzyl)oxy)quinoline-7-carboxamide;
N-(4-(ethylsulfonyl)benzyl)-2-methyl-4-((4-(trifluoromethyl)cyclohexyl)methoxy)quinoline-7-carboxamide;
N-(1-(4-(ethylsulfonyl)phenyl)-2-hydroxyethyl)-2-methyl-4-((4-(trifluoromethyl)benzyl)oxy)quinoline-7-carboxamide;
N-(1-(4-(ethylsulfonyl)phenyl)-2-hydroxyethyl)-2-methyl-4-((4-(trifluoromethyl)cyclohexyl)methoxy)quinoline-7-carboxamide;
N-(1-(4-(ethylsulfonyl)phenyl)-2-hydroxyethyl)-4-((4-(trifluoromethyl)cyclohexyl)methoxy)quinazoline-7-carboxamide;
N-(4-(ethylsulfonyl)benzyl)-4-((4-(trifluoromethyl)cyclohexyl)methoxy)quinazoline-7-carboxamide;
2-(5-cyanopyrimidin-2-yl)-N-(4-(ethylsulfonyl)benzyl)-1-isopropyl-1,2,3,4-tetrahydroisoquinoline-6-carboxamide;
2-(5-cyanopyrimidin-2-yl)-N-(4-(ethylsulfonyl)benzyl)-1-isopropyl-1,2,3,4-tetrahydroisoquinoline-6-carboxamide;
N-(4-(ethylsulfonyl)benzyl)-1-isopropyl-2-(5-(trifluoromethyl)pyrimidin-2-yl)-1,2,3,4-tetrahydroisoquinoline-6-carboxamide;
N-(4-(ethylsulfonyl)benzyl)-1-isopropyl-2-(4-(trifluoromethyl)pyrimidin-2-yl)-1,2,3,4-tetrahydroisoquinoline-6-carboxamide;
ethyl (S)-2-(6-(((4-(ethylsulfonyl)benzyl)carbamoyl)-1-isopropyl-3,4-dihydroisoquinolin-2(1H)-yl)pyrimidine-5-carboxylate;

ethyl 2-(6-((4-(ethylsulfonyl)benzyl)carbamoyl)-1-isopropyl-3,4-dihydroisoquinolin-2(1H)-yl)pyrimidine-5-carboxylate;
ethyl 2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate;
ethyl 2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate;
ethyl 2-(6-((4-(ethylsulfonyl)benzyl)carbamoyl)-1-isopropyl-3,4-dihydroisoquinolin-2(1H)-yl)-4-(trifluoromethyl)pyrimidine-5-carboxylate;
2-(4-fluorobenzyl)-1-methyl-N-(4-(methylsulfonyl)benzyl)-1,2,3,4-tetrahydroisoquinoline-6-carboxamide;
2-(4-cyanobenzyl)-1-methyl-N-(4-(methylsulfonyl)benzyl)-1,2,3,4-tetrahydroisoquinoline-6-carboxamide;
N-(4-(ethylsulfonyl)benzyl)-2-(4-fluorobenzyl)-1-methyl-1,2,3,4-tetrahydroisoquinoline-6-carboxamide;
2-(4-chlorobenzyl)-1-methyl-N-(4-(methylsulfonyl)benzyl)-1,2,3,4-tetrahydroisoquinoline-6-carboxamide;
2-(4-cyanobenzyl)-N-(4-(ethylsulfonyl)benzyl)-1-methyl-1,2,3,4-tetrahydroisoquinoline-6-carboxamide;
2-(4-chlorobenzyl)-N-(4-(ethylsulfonyl)benzyl)-1-methyl-1,2,3,4-tetrahydroisoquinoline-6-carboxamide;
N-(4-(ethylsulfonyl)benzyl)-1-isopropyl-2-((5-methylpyrimidin-2-yl)methyl)-1,2,3,4-tetrahydroisoquinoline-6-carboxamide;
N-(4-(ethylsulfonyl)benzyl)-1-isopropyl-2-((5-methylpyrimidin-2-yl)methyl)-1,2,3,4-tetrahydroisoquinoline-6-carboxamide;
N-(4-(ethylsulfonyl)benzyl)-2-(4-fluorobenzyl)-1-isopropyl-1,2,3,4-tetrahydroisoquinoline-6-carboxamide;
2-(4-cyanobenzyl)-N-(4-(ethylsulfonyl)benzyl)-1-isopropyl-1,2,3,4-tetrahydroisoquinoline-6-carboxamide;
2-(4-cyanobenzyl)-N-(4-(ethylsulfonyl)benzyl)-1-isopropyl-1,2,3,4-tetrahydroisoquinoline-6-carboxamide;
2-(4-cyanobenzyl)-N-(4-(ethylsulfonyl)benzyl)-1-isopropyl-1,2,3,4-tetrahydroisoquinoline-6-carboxamide;
2-((5-cyanopyridin-2-yl)methyl)-N-(4-(ethylsulfonyl)benzyl)-1-isopropyl-1,2,3,4-tetrahydroisoquinoline-6-carboxamide;
2-((5-cyanopyridin-2-yl)methyl)-N-(4-(ethylsulfonyl)benzyl)-1-isopropyl-1,2,3,4-tetrahydroisoquinoline-6-carboxamide;
2-((6-cyanopyridin-3-yl)methyl)-N-(4-(ethylsulfonyl)benzyl)-1-isopropyl-1,2,3,4-tetrahydroisoquinoline-6-carboxamide;
2-((6-cyanopyridin-3-yl)methyl)-N-(4-(ethylsulfonyl)benzyl)-1-isopropyl-1,2,3,4-tetrahydroisoquinoline-6-carboxamide;
N-(1-(4-(ethylsulfonyl)phenyl)ethyl)-1-isopropyl-2-((5-methylpyrazin-2-yl)methyl)-1,2,3,4-tetrahydroisoquinoline-6-carboxamide 2-(4-chlorobenzyl)-N-(4-(ethylsulfonyl)benzyl)-1-isopropyl-1,2,3,4-tetrahydroisoquinoline-6-carboxamide;
2-(4-chlorobenzyl)-N-(4-(ethylsulfonyl)benzyl)-1-isopropyl-1,2,3,4-tetrahydroisoquinoline-6-carboxamide;
2-(4-chlorobenzyl)-N-(4-(ethylsulfonyl)benzyl)-1-isopropyl-1,2,3,4-tetrahydroisoquinoline-6-carboxamide;
2-((5-chloropyridin-2-yl)methyl)-N-(4-(ethylsulfonyl)benzyl)-1-isopropyl-1,2,3,4-tetrahydroisoquinoline-6-carboxamide;
N-(4-(ethylsulfonyl)benzyl)-1-isopropyl-4,4-dimethyl-2-((5-methylpyrazin-2-yl)methyl)-1,2,3,4-tetrahydroisoquinoline-6-carboxamide;
N-(4-(ethylsulfonyl)benzyl)-1-isopropyl-4,4-dimethyl-2-((5-methylpyrazin-2-yl)methyl)-1,2,3,4-tetrahydroisoquinoline-6-carboxamide;
2-(4-cyanobenzyl)-N-(4-(ethylsulfonyl)benzyl)-1-isopropyl-4,4-dimethyl-1,2,3,4-tetrahydroisoquinoline-6-carboxamide;
2-(4-cyanobenzyl)-N-(4-(ethylsulfonyl)benzyl)-1-isopropyl-4,4-dimethyl-1,2,3,4-tetrahydroisoquinoline-6-carboxamide;
methyl 4-((6-((4-(ethylsulfonyl)benzyl)carbamoyl)-1-isopropyl-3,4-dihydroisoquinolin-2(1H)-yl)methyl)piperidine-1-carboxylate;
2-((6-(difluoromethoxy)pyridin-3-yl)methyl)-N-(4-(ethylsulfonyl)benzyl)-1-isopropyl-1,2,3,4-tetrahydroisoquinoline-6-carboxamide;
2-((6-(difluoromethoxy)pyridin-3-yl)methyl)-N-(4-(ethylsulfonyl)benzyl)-1-isopropyl-1,2,3,4-tetrahydroisoquinoline-6-carboxamide;
2-((5-bromopyrimidin-2-yl)methyl)-N-(4-(ethylsulfonyl)benzyl)-1-isopropyl-1,2,3,4-tetrahydroisoquinoline-6-carboxamide;
2-((5-bromopyrimidin-2-yl)methyl)-N-(4-(ethylsulfonyl)benzyl)-1-isopropyl-1,2,3,4-tetrahydroisoquinoline-6-carboxamide;
1-ethyl-N-(4-(ethylsulfonyl)benzyl)-2-((4-(trifluoromethyl)cyclohexyl)methyl)-1,2,3,4-tetrahydroisoquinoline-6-carboxamide;
1-ethyl-N-(1-(4-(ethylsulfonyl)phenyl)-2-hydroxyethyl)-2-((4-(trifluoromethyl)cyclohexyl)methyl)-1,2,3,4-tetrahydroisoquinoline-6-carboxamide;
1-ethyl-N-(1-(4-(ethylsulfonyl)phenyl)-2-hydroxyethyl)-2-((4-(trifluoromethyl)cyclohexyl)methyl)-1,2,3,4-tetrahydroisoquinoline-6-carboxamide;
1-ethyl-N-(1-(4-(ethylsulfonyl)phenyl)-2-hydroxyethyl)-2-((4-(trifluoromethyl)cyclohexyl)methyl)-1,2,3,4-tetrahydroisoquinoline-6-carboxamide;
1-ethyl-N-(1-(5-(ethylsulfonyl)pyridin-2-yl)-2-hydroxyethyl)-2-((4-(trifluoromethyl)cyclohexyl)methyl)-1,2,3,4-tetrahydroisoquinoline-6-carboxamide;
1-ethyl-N-(1-(5-(ethylsulfonyl)pyridin-2-yl)-2-hydroxyethyl)-2-((4-(trifluoromethyl)cyclohexyl)methyl)-1,2,3,4-tetrahydroisoquinoline-6-carboxamide;
1-ethyl-N-(1-(5-(ethylsulfonyl)pyridin-2-yl)-2-hydroxyethyl)-2-((4-(trifluoromethyl)cyclohexyl)methyl)-1,2,3,4-tetrahydroisoquinoline-6-carboxamide;
7-(5-cyanopyrimidin-2-yl)-N-(4-(ethylsulfonyl)benzyl)-8-isopropyl-5,6,7,8-tetrahydro-1,7-naphthyridine-3-carboxamide;
7-(5-cyanopyrimidin-2-yl)-N-(4-(ethylsulfonyl)benzyl)-8-isopropyl-5,6,7,8-tetrahydro-1,7-naphthyridine-3-carboxamide;
7-(5-chloropyrimidin-2-yl)-N-(4-(ethylsulfonyl)benzyl)-8-isopropyl-5,6,7,8-tetrahydro-1,7-naphthyridine-3-carboxamide;
7-(5-chloropyrimidin-2-yl)-N-(4-(ethylsulfonyl)benzyl)-8-isopropyl-5,6,7,8-tetrahydro-1,7-naphthyridine-3-carboxamide;
N-(4-(ethylsulfonyl)benzyl)-8-isopropyl-7-(5-(trifluoromethyl)pyrimidin-2-yl)-5,6,7,8-tetrahydro-1,7-naphthyridine-3-carboxamide;
N-(4-(ethylsulfonyl)benzyl)-8-isopropyl-7-(5-(trifluoromethyl)pyrimidin-2-yl)-5,6,7,8-tetrahydro-1,7-naphthyridine-3-carboxamide;
ethyl 2-(3-((4-(ethylsulfonyl)benzyl)carbamoyl)-8-isopropyl-5,8-dihydro-1,7-naphthyridin-7(6H)-yl)pyrimidine-5-carboxylate;

ethyl 2-(3-((4-(ethylsulfonyl)benzyl)carbamoyl)-8-isopropyl-5,8-dihydro-1,7-naphthyridin-7(6H)-yl)pyrimidine-5-carboxylate;
ethyl 2-(3-((4-(ethylsulfonyl)benzyl)carbamoyl)-8-isopropyl-5,8-dihydro-1,7-naphthyridin-7(6H)-yl)-4-(trifluoromethyl)pyrimidine-5-carboxylate;
ethyl 2-(3-((4-(ethylsulfonyl)benzyl)carbamoyl)-8-isopropyl-5,8-dihydro-1,7-naphthyridin-7(6H)-yl)-4-(trifluoromethyl)pyrimidine-5-carboxylate;
N-(4-(ethylsulfonyl)benzyl)-7-(4-fluorobenzyl)-8-isopropyl-5,6,7,8-tetrahydro-1,7-naphthyridine-3-carboxamide;
N-(4-(ethylsulfonyl)benzyl)-7-(4-fluorobenzyl)-8-isopropyl-5,6,7,8-tetrahydro-1,7-naphthyridine-3-carboxamide;
7-(4-cyanobenzyl)-N-(4-(ethylsulfonyl)benzyl)-8-isopropyl-5,6,7,8-tetrahydro-1,7-naphthyridine-3-carboxamide;
7-(4-cyanobenzyl)-N-(4-(ethylsulfonyl)benzyl)-8-isopropyl-5,6,7,8-tetrahydro-1,7-naphthyridine-3-carboxamide;
7-(4-chlorobenzyl)-N-(4-(ethylsulfonyl)benzyl)-8-isopropyl-5,6,7,8-tetrahydro-1,7-naphthyridine-3-carboxamide;
7-(4-chlorobenzyl)-N-(4-(ethylsulfonyl)benzyl)-8-isopropyl-5,6,7,8-tetrahydro-1,7-naphthyridine-3-carboxamide;
N-(4-(ethylsulfonyl)benzyl)-8-isopropyl-7-((4-(trifluoromethyl)cyclohexyl)methyl)-5,6,7,8-tetrahydro-1,7-naphthyridine-3-carboxamide;
N-(4-(ethylsulfonyl)benzyl)-8-isopropyl-7-((4-(trifluoromethyl)cyclohexyl)methyl)-5,6,7,8-tetrahydro-1,7-naphthyridine-3-carboxamide;
N-((5-(ethylsulfonyl)pyridin-2-yl)methyl)-8-isopropyl-7-((4-(trifluoromethyl)cyclohexyl)methyl)-5,6,7,8-tetrahydro-1,7-naphthyridine-3-carboxamide;
N-((5-(ethylsulfonyl)pyridin-2-yl)methyl)-8-isopropyl-7-((4-(trifluoromethyl)cyclohexyl)methyl)-5,6,7,8-tetrahydro-1,7-naphthyridine-3-carboxamide;
3-cyclopropyl-N-1-(4-(ethylsulfonyl)phenyl)-2-hydroxyethyl)-2-((4-(trifluoromethyl)cyclohexyl)methyl)-2H-indazole-6-carboxamide;
3-cyclopropyl-N-(4-(ethylsulfonyl)benzyl)-2-((4-(trifluoromethyl)cyclohexyl)methyl)-2H-indazole-6-carboxamide;
3-cyclopropyl-N-((5-(ethylsulfonyl)pyridin-2-yl)methyl)-2-((4-(trifluoromethyl)cyclohexyl)methyl)-2H-indazole-6-carboxamide;
3-cyclopropyl-N-(1-(4-(ethylsulfonyl)phenyl)-2-hydroxyethyl)-2-(4-(trifluoromethyl)benzyl)-2H-indazole-6-carboxamide;
3-ethyl-N-(1-(4-(ethylsulfonyl)phenyl)-2-hydroxyethyl)-2-((4-(trifluoromethyl)cyclohexyl)methyl)-2H-indazole-6-carboxamide;
3-cyclopropyl-N-(1-(5-(ethylsulfonyl)pyridin-2-yl)-2-hydroxyethyl)-2-((4-(trifluoromethyl)cyclohexyl)methyl)-2H-indazole-6-carboxamide;
3-cyclopropyl-N-(1-(5-(ethylsulfonyl)pyridin-2-yl)-2-hydroxyethyl)-2-(4-(trifluoromethyl)benzyl)-2H-indazole-6-carboxamide;
3-cyclopropyl-N-(1-(4-(ethylsulfonyl)phenyl)-2-hydroxyethyl)-2-((4-(trifluoromethyl)cyclohexyl)methyl)-2H-pyrazolo[4,3-b]pyridine-6-carboxamide;
3-cyclopropyl-N-(4-(ethylsulfonyl)benzyl)-2-((4-(trifluoromethyl)cyclohexyl)methyl)-2H-pyrazolo[4,3-b]pyridine-6-carboxamide;
3-cyclopropyl-N-((5-(ethylsulfonyl)pyridin-2-yl)methyl)-2-((4-(trifluoromethyl)cyclohexyl)methyl)-2H-pyrazolo[4,3-b]pyridine-6-carboxamide;
3-cyclopropyl-N-(1-(5-(ethylsulfonyl)pyridin-2-yl)-2-hydroxyethyl)-2-((4-(trifluoromethyl)cyclohexyl)methyl)-2H-pyrazolo[4,3-b]pyridine-6-carboxamide;
N-(4-(ethylsulfonyl)benzyl)-1-methyl-7-((4-(trifluoromethyl)cyclohexyl)methoxy)-1H-pyrrolo[2,3-c]pyridine-2-carboxamide;
N-(1-(4-(ethylsulfonyl)phenyl)-2-hydroxyethyl)-1-methyl-7-((4-(trifluoromethyl)cyclohexyl)methoxy)-1H-pyrrolo[2,3-c]pyridine-2-carboxamide;
N-(4-(ethylsulfonyl)benzyl)-1-methyl-7-((4-(trifluoromethyl)benzyl)oxy)-1H-pyrrolo[2,3-c]pyridine-2-carboxamide;
N-(1-(4-(ethylsulfonyl)phenyl)-2-hydroxyethyl)-1-methyl-7-((4-(trifluoromethyl)benzyl)oxy)-1H-pyrrolo[2,3-c]pyridine-2-carboxamide;
N-(4-(ethylsulfonyl)benzyl)-7-((4-(trifluoromethyl)cyclohexyl)methoxy)-1H-pyrrolo[2,3-c]pyridine-2-carboxamide;
N-(4-(ethylsulfonyl)benzyl)-1-methyl-7-(4-(trifluoromethyl)phenoxy)-1H-pyrrolo[2,3-c]pyridine-3-carboxamide;
N-(4-(ethylsulfonyl)benzyl)-7-((4-(trifluoromethyl)cyclohexyl)methoxy)-1H-pyrrolo[2,3-c]pyridine-3-carboxamide;
N-(4-(ethylsulfonyl)benzyl)-1-methyl-7-((4-(trifluoromethyl)benzyl)oxy)-1H-pyrrolo[2,3-c]pyridine-3-carboxamide;
N-(4-(ethylsulfonyl)benzyl)-1-methyl-7-((4-(trifluoromethyl)cyclohexyl)methoxy)-1H-pyrrolo[2,3-c]pyridine-3-carboxamide;
N—((R)-1-(4-(ethylsulfonyl)phenyl)-2-hydroxyethyl)-1-methyl-7-((4-(trifluoromethyl)cyclohexyl)methoxy)-1H-pyrrolo[2,3-c]pyridine-3-carboxamide;
N-(4-(ethylsulfonyl)benzyl)-2,5-dimethyl-4-((4-(trifluoromethyl)benzyl)oxy)thieno[2,3-d]pyrimidine-6-carboxamide
N-(4-(ethylsulfonyl)benzyl)-2,5-dimethyl-4-((4-(trifluoromethyl)cyclohexyl)methoxy)thieno[2,3-d]pyrimidine-6-carboxamide;
N-(1-(4-(ethylsulfonyl)phenyl)-2-hydroxyethyl)-2,5-dimethyl-4-((4-(trifluoromethyl)benzyl)oxy)thieno[2,3-d]pyrimidine-6-carboxamide;
N-(1-(4-(ethylsulfonyl)phenyl)-2-hydroxyethyl)-2,5-dimethyl-4-((4-(trifluoromethyl)cyclohexyl)methoxy)thieno[2,3-d]pyrimidine-6-carboxamide;
N-(4-(ethylsulfonyl)benzyl)-2-(5-fluoropyrimidin-2-yl)-4-isopropyl-1,2,3,4-tetrahydroisoquinoline-7-carboxamide;
N-(4-(ethylsulfonyl)benzyl)-2-(5-fluoropyrimidin-2-yl)-4-isopropyl-1,2,3,4-tetrahydroisoquinoline-7-carboxamide;
2-(5-cyanopyrimidin-2-yl)-N-(4-(ethylsulfonyl)benzyl)-4-isopropyl-1,2,3,4-tetrahydroisoquinoline-7-carboxamide;
2-(5-cyanopyrimidin-2-yl)-N-(4-(ethylsulfonyl)benzyl)-4-isopropyl-1,2,3,4-tetrahydroisoquinoline-7-carboxamide;
2-(5-chloropyrimidin-2-yl)-N-(4-(ethylsulfonyl)benzyl)-4-isopropyl-1,2,3,4-tetrahydroisoquinoline-7-carboxamide;
2-(5-chloropyrimidin-2-yl)-N-(4-(ethylsulfonyl)benzyl)-4-isopropyl-1,2,3,4-tetrahydroisoquinoline-7-carboxamide;

2-(5-cyclopropylpyrimidin-2-yl)-N-(4-(ethylsulfonyl)benzyl)-4-isopropyl-1,2,3,4-tetrahydroisoquinoline-7-carboxamide;

2-(5-cyclopropylpyrimidin-2-yl)-N-(4-(ethylsulfonyl)benzyl)-4-isopropyl-1,2,3,4-tetrahydroisoquinoline-7-carboxamide;

2-(5-ethoxypyrimidin-2-yl)-N-(4-(ethylsulfonyl)benzyl)-4-isopropyl-1,2,3,4-tetrahydroisoquinoline-7-carboxamide;

2-(5-ethoxypyrimidin-2-yl)-N-(4-(ethylsulfonyl)benzyl)-4-isopropyl-1,2,3,4-tetrahydroisoquinoline-7-carboxamide;

2-(5-chloropyrimidin-2-yl)-4-ethyl-N-(1-(4-(ethylsulfonyl)phenyl)-2-hydroxyethyl)-1,2,3,4-tetrahydroisoquinoline-7-carboxamide;

2-(5-chloropyrimidin-2-yl)-4-ethyl-N-(1-(4-(ethylsulfonyl)phenyl)-2-hydroxyethyl)-1,2,3,4-tetrahydroisoquinoline-7-carboxamide;

4-ethyl-N-(4-(ethylsulfonyl)benzyl)-2-(4-(trifluoromethyl)phenyl)-1,2,3,4-tetrahydroisoquinoline-7-carboxamide;

4-ethyl-N-(4-(ethylsulfonyl)benzyl)-2-(4-(trifluoromethyl)phenyl)-1,2,3,4-tetrahydroisoquinoline-7-carboxamide;

4-ethyl-N-(4-(ethylsulfonyl)benzyl)-2-(5-(trifluoromethyl)pyridin-2-yl)-1,2,3,4-tetrahydroisoquinoline-7-carboxamide;

4-ethyl-N-(4-(ethylsulfonyl)benzyl)-2-(5-(trifluoromethyl)pyridin-2-yl)-1,2,3,4-tetrahydroisoquinoline-7-carboxamide;

4-ethyl-N-(4-(ethylsulfonyl)benzyl)-2-(5-(trifluoromethyl)pyrimidin-2-yl)-1,2,3,4-tetrahydroisoquinoline-7-carboxamide;

4-ethyl-N-(4-(ethylsulfonyl)benzyl)-2-(5-(trifluoromethyl)pyrimidin-2-yl)-1,2,3,4-tetrahydroisoquinoline-7-carboxamide;

4-ethyl-N-((5-(ethylsulfonyl)pyridin-2-yl)methyl)-2-(5-(trifluoromethyl)pyrimidin-2-yl)-1,2,3,4-tetrahydroisoquinoline-7-carboxamide;

4-ethyl-N-((5-(ethylsulfonyl)pyridin-2-yl)methyl)-2-(5-(trifluoromethyl)pyrimidin-2-yl)-1,2,3,4-tetrahydroisoquinoline-7-carboxamide;

2-(5-cyclopropylpyrimidin-2-yl)-4-ethyl-N-(1-(4-(ethylsulfonyl)phenyl)-2-hydroxyethyl)-1,2,3,4-tetrahydroisoquinoline-7-carboxamide;

2-(5-cyclopropylpyrimidin-2-yl)-4-ethyl-N-(1-(4-(ethylsulfonyl)phenyl)-2-hydroxyethyl)-1,2,3,4-tetrahydroisoquinoline-7-carboxamide;

4-ethyl-N-(4-(ethylsulfonyl)benzyl)-1-oxo-2-(4-(trifluoromethyl)phenyl)-1,2,3,4-tetrahydroisoquinoline-7-carboxamide;

4-ethyl-N-(4-(ethylsulfonyl)benzyl)-1-oxo-2-(4-(trifluoromethyl)phenyl)-1,2,3,4-tetrahydroisoquinoline-7-carboxamide;

4-ethyl-N-(4-(ethylsulfonyl)benzyl)-2-(3-methyl-5-(trifluoromethyl)pyridin-2-yl)-1,2,3,4-tetrahydroisoquinoline-7-carboxamide;

4-ethyl-N-(4-(ethylsulfonyl)benzyl)-2-(3-methyl-5-(trifluoromethyl)pyridin-2-yl)-1,2,3,4-tetrahydroisoquinoline-7-carboxamide;

N-(4-(ethylsulfonyl)benzyl)-4-isopropyl-2-(4-(trifluoromethyl)pyrimidin-2-yl)-1,2,3,4-tetrahydroisoquinoline-7-carboxamide;

N-(4-(ethylsulfonyl)benzyl)-4-isopropyl-2-(4-(trifluoromethyl)pyrimidin-2-yl)-1,2,3,4-tetrahydroisoquinoline-7-carboxamide;

N-(4-(ethylsulfonyl)benzyl)-4-isopropyl-2-(5-(trifluoromethyl)pyrimidin-2-yl)-1,2,3,4-tetrahydroisoquinoline-7-carboxamide;

N-(4-(ethylsulfonyl)benzyl)-4-isopropyl-2-(5-(trifluoromethyl)pyrimidin-2-yl)-1,2,3,4-tetrahydroisoquinoline-7-carboxamide;

ethyl 2-(7-((4-(ethylsulfonyl)benzyl)carbamoyl)-4-isopropyl-3,4-dihydroisoquinolin-2(1H)-yl)pyrimidine-5-carboxylate;

ethyl 2-(7-((4-(ethylsulfonyl)benzyl)carbamoyl)-4-isopropyl-3,4-dihydroisoquinolin-2(1H)-yl)pyrimidine-5-carboxylate;

4-ethyl-N-(1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide;

4-ethyl-N-(1-(4-(ethylsulfonyl)phenyl)-2-hydroxyethyl)-2-(5-(trifluoromethyl)pyrimidin-2-yl)-1,2,3,4-tetrahydroisoquinoline-7-carboxamide;

4-ethyl-N-(1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide;

4-ethyl-N-(1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide;

4-ethyl-N-(1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide;

4-ethyl-N-(1-(5-(ethylsulfonyl)pyridin-2-yl)-2-hydroxyethyl)-2-(5-(trifluoromethyl)pyrimidin-2-yl)-1,2,3,4-tetrahydroisoquinoline-7-carboxamide;

N-(4-(ethylsulfonyl)benzyl)-4-isopropyl-2-(5-morpholinopyrimidin-2-yl)-1,2,3,4-tetrahydroisoquinoline-7-carboxamide;

N-(4-(ethylsulfonyl)benzyl)-4-isopropyl-2-(5-morpholinopyrimidin-2-yl)-1,2,3,4-tetrahydroisoquinoline-7-carboxamide;

4-ethyl-N-(4-(ethylsulfonyl)benzyl)-2-(5-(6-methoxypyridin-2-yl)pyrimidin-2-yl)-1,2,3,4-tetrahydroisoquinoline-7-carboxamide;

4-ethyl-N-(4-(ethylsulfonyl)benzyl)-2-(5-(6-methoxypyridin-2-yl)pyrimidin-2-yl)-1,2,3,4-tetrahydroisoquinoline-7-carboxamide;

N-(4-(ethylsulfonyl)benzyl)-4-isopropyl-2-(5-(6-oxo-1,6-dihydropyridin-3-yl)pyrimidin-2-yl)-1,2,3,4-tetrahydroisoquinoline-7-carboxamide;

N-(4-(ethylsulfonyl)benzyl)-4-isopropyl-2-(5-(6-oxo-1,6-dihydropyridin-3-yl)pyrimidin-2-yl)-1,2,3,4-tetrahydroisoquinoline-7-carboxamide;

4-ethyl-N-(1-(4-(ethylsulfonyl)phenyl)-2-hydroxyethyl)-2-(3-methyl-5-(trifluoromethyl)pyridin-2-yl)-1,2,3,4-tetrahydroisoquinoline-7-carboxamide;

4-ethyl-N-(1-(4-(ethylsulfonyl)phenyl)-2-hydroxyethyl)-2-(3-methyl-5-(trifluoromethyl)pyridin-2-yl)-1,2,3,4-tetrahydroisoquinoline-7-carboxamide;

N-(4-(ethylsulfonyl)benzyl)-4-isopropyl-2-(5-(2-methoxypyridin-4-yl)pyrimidin-2-yl)-1,2,3,4-tetrahydroisoquinoline-7-carboxamide;

N-(4-(ethylsulfonyl)benzyl)-4-isopropyl-2-(5-(2-methoxypyridin-4-yl)pyrimidin-2-yl)-1,2,3,4-tetrahydroisoquinoline-7-carboxamide;

N-(4-(ethylsulfonyl)benzyl)-4-isopropyl-2-(5-(1-methyl-6-oxo-1,6-dihydropyridin-3-yl)pyrimidin-2-yl)-1,2,3,4-tetrahydroisoquinoline-7-carboxamide;

N-(4-(ethylsulfonyl)benzyl)-4-isopropyl-2-(5-(1-methyl-6-oxo-1,6-dihydropyridin-3-yl)pyrimidin-2-yl)-1,2,3,4-tetrahydroisoquinoline-7-carboxamide;

N-(4-(ethylsulfonyl)benzyl)-4-isopropyl-2-(5-(1-methyl-2-oxo-1,2-dihydropyridin-4-yl)pyrimidin-2-yl)-1,2,3,4-tetrahydroisoquinoline-7-carboxamide;

N-(4-(ethylsulfonyl)benzyl)-4-isopropyl-2-(5-(1-methyl-2-oxo-1,2-dihydropyridin-4-yl)pyrimidin-2-yl)-1,2,3,4-tetrahydroisoquinoline-7-carboxamide;

ethyl 2-(7-((4-(ethylsulfonyl)benzyl)carbamoyl)-4-isopropyl-3,4-dihydroisoquinolin-2(1H)-yl)-4-(trifluoromethyl)pyrimidine-5-carboxylate;

ethyl 2-(7-((4-(ethylsulfonyl)benzyl)carbamoyl)-4-isopropyl-3,4-dihydroisoquinolin-2(1H)-yl)-4-(trifluoromethyl)pyrimidine-5-carboxylate;

N-(4-(ethylsulfonyl)benzyl)-2-(4-fluorobenzyl)-4-isopropyl-1,2,3,4-tetrahydroisoquinoline-7-carboxamide;

N-(4-(ethylsulfonyl)benzyl)-2-(4-fluorobenzyl)-4-isopropyl-1,2,3,4-tetrahydroisoquinoline-7-carboxamide;

2-(4-cyanobenzyl)-N-(4-(ethylsulfonyl)benzyl)-4-isopropyl-1,2,3,4-tetrahydroisoquinoline-7-carboxamide;

2-(4-cyanobenzyl)-N-(4-(ethylsulfonyl)benzyl)-4-isopropyl-1,2,3,4-tetrahydroisoquinoline-7-carboxamide;

2-(4-chlorobenzyl)-N-(4-(ethylsulfonyl)benzyl)-4-isopropyl-1,2,3,4-tetrahydroisoquinoline-7-carboxamide;

2-(4-chlorobenzyl)-N-(4-(ethylsulfonyl)benzyl)-4-isopropyl-1,2,3,4-tetrahydroisoquinoline-7-carboxamide;

4-ethyl-N-(1-(4-(ethylsulfonyl)phenyl)-2-hydroxyethyl)-2-(tetrahydro-2H-pyran-4-yl)-1,2,3,4-tetrahydroisoquinoline-7-carboxamide;

4-ethyl-N-(1-(4-(ethylsulfonyl)phenyl)-2-hydroxyethyl)-2-(tetrahydro-2H-pyran-4-yl)-1,2,3,4-tetrahydroisoquinoline-7-carboxamide;

4-ethyl-N-(4-(ethylsulfonyl)benzyl)-2-(5-(oxazol-2-yl)pyrimidin-2-yl)-1,2,3,4-tetrahydroisoquinoline-7-carboxamide;

4-ethyl-N-(4-(ethylsulfonyl)benzyl)-2-(5-(oxazol-2-yl)pyrimidin-2-yl)-1,2,3,4-tetrahydroisoquinoline-7-carboxamide;

2-(4,4-difluorocyclohexyl)-4-ethyl-N-(1-(4-(ethylsulfonyl)phenyl)-2-hydroxyethyl)-1,2,3,4-tetrahydroisoquinoline-7-carboxamide;

2-(4,4-difluorocyclohexyl)-4-ethyl-N-(1-(4-(ethylsulfonyl)phenyl)-2-hydroxyethyl)-1,2,3,4-tetrahydroisoquinoline-7-carboxamide;

4-ethyl-N-(1-(4-(ethylsulfonyl)phenyl)-2-hydroxyethyl)-2-(5-(oxazol-2-yl)pyrimidin-2-yl)-1,2,3,4-tetrahydroisoquinoline-7-carboxamide; and 4-ethyl-N-(1-(4-(ethylsulfonyl)phenyl)-2-hydroxyethyl)-2-(5-(oxazol-2-yl)pyrimidin-2-yl)-1,2,3,4-tetrahydroisoquinoline-7-carboxamide;

ethyl 2-(4-ethyl-7-((1-(4-(ethylsulfonyl)phenyl)-2-hydroxyethyl)carbamoyl)-3,4-dihydroisoquinolin-2(1H)-yl)pyrimidine-5-carboxylate;

ethyl 2-(4-ethyl-7-((1-(4-(ethylsulfonyl)phenyl)-2-hydroxyethyl)carbamoyl)-3,4-dihydroisoquinolin-2(1H)-yl)pyrimidine-5-carboxylate;

4-ethyl-N-(1-(4-(ethylsulfonyl)phenyl)-2-hydroxyethyl)-2-(4-(trifluoromethyl)cyclohexyl)-1,2,3,4-tetrahydroisoquinoline-7-carboxamide;

4-ethyl-N-(1-(4-(ethylsulfonyl)phenyl)-2-hydroxyethyl)-2-(4-(trifluoromethyl)cyclohexyl)-1,2,3,4-tetrahydroisoquinoline-7-carboxamide;

4-ethyl-N-(1-(4-(ethylsulfonyl)phenyl)-2-hydroxyethyl)-2-(4-(trifluoromethyl)cyclohexyl)-1,2,3,4-tetrahydroisoquinoline-7-carboxamide;

4-ethyl-N-(1-(4-(ethylsulfonyl)phenyl)-2-hydroxyethyl)-2-(4-(trifluoromethyl)cyclohexyl)-1,2,3,4-tetrahydroisoquinoline-7-carboxamide;

N-(4-(ethylsulfonyl)benzyl)-4-(trifluoromethyl)-2-(5-(trifluoromethyl)pyrimidin-2-yl)-1,2,3,4-tetrahydroisoquinoline-7-carboxamide;

N-(4-(ethylsulfonyl)benzyl)-4-(trifluoromethyl)-2-(5-(trifluoromethyl)pyrimidin-2-yl)-1,2,3,4-tetrahydroisoquinoline-7-carboxamide;

2-(3-cyano-5-(trifluoromethyl)pyridin-2-yl)-4-ethyl-N-(1-(4-(ethylsulfonyl)phenyl)-2-hydroxyethyl)-1,2,3,4-tetrahydroisoquinoline-7-carboxamide;

2-(3-cyano-5-(trifluoromethyl)pyridin-2-yl)-4-ethyl-N-(1-(4-(ethylsulfonyl)phenyl)-2-hydroxyethyl)-1,2,3,4-tetrahydroisoquinoline-7-carboxamide; and N-(4-(ethylsulfonyl)benzyl)-8,8-dimethyl-6-(5-(trifluoromethyl)pyrimidin-2-yl)-5,6,7,8-tetrahydro-1,6-naphthyridine-3-carboxamide.

14. A pharmaceutical composition comprising a compound of claim 1, or a pharmaceutically acceptable salt thereof, and a pharmaceutically acceptable carrier.

\* \* \* \* \*